United States Patent [19]

Capet et al.

[11] Patent Number: 5,610,144
[45] Date of Patent: Mar. 11, 1997

[54] PYRROLIDINE AND THIAZOLIDINE DERIVATIVES, THEIR PREPARATION AND MEDICAMENTS CONTAINING THEM

[75] Inventors: Marc Capet, Thiais; Claude Cotrel, Paris; Claude Guyon, Saint Maur des Fosses; Michel Joannic, Neuilly Sur Marne; Franco Manfre, Limeil-Brevannes; Gérard Roussel, Soisy Sur Seine; Marie-Christine Dubroeuco, Enghein Les Bains; Michel Cheve, Soisy Sur Seine; Gilles Dutruc-Rosset, Paris, all of France

[73] Assignee: Rhone-Poulenc Rorer S.A., Antony, France

[21] Appl. No.: 175,381

[22] PCT Filed: Jul. 3, 1992

[86] PCT No.: PCT/FR92/00626

§ 371 Date: Jun. 27, 1994

§ 102(e) Date: Jun. 27, 1994

[87] PCT Pub. No.: WO93/01167

PCT Pub. Date: Jan. 21, 1993

[30] Foreign Application Priority Data

Jul. 10, 1991 [FR] France .................................. 91 08675

[51] Int. Cl.⁶ .......................... C07D 207/06; A61K 38/00
[52] U.S. Cl. ........................... 514/19; 546/245; 548/200; 548/201; 548/533
[58] Field of Search ................................ 548/533, 200, 548/201; 546/245; 514/19

[56] References Cited

U.S. PATENT DOCUMENTS 5,126,483  6/1992  Sekiya ........................................ 504/48
5,420,348  5/1995  Ito .............................................. 564/48

*Primary Examiner*—Robert Gerstl
*Attorney, Agent, or Firm*—Finnegan, Henderson, Farabow, Garrett & Dunner, L.L.P.

[57] ABSTRACT

This invention relates to compositions of formula:

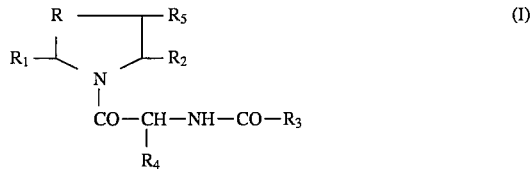

and their salts, their preparation and the medicaments containing them.

7 Claims, No Drawings

PYRROLIDINE AND THIAZOLIDINE DERIVATIVES, THEIR PREPARATION AND MEDICAMENTS CONTAINING THEM

This application is a 371 of PCT/FR 92/00626 filed Jul. 3, 1992.

DESCRIPTION OF THE INVENTION

The present invention relates to derivatives of formula:

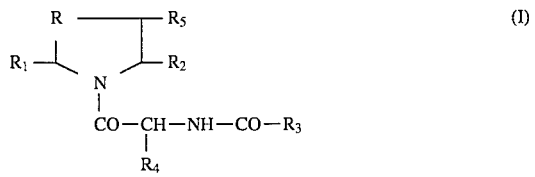

their salts, their preparation and medicaments containing them.

In the formula (I), either R represents a methylene, ethylene, SO, $SO_2$ or CHOH radical or a sulphur atom, $R_1$ represents a pyridyl radical optionally substituted by one or more alkyl radicals, a furyl radical optionally substituted by one or more alkyl radicals, a thienyl radical optionally substituted by one or more alkyl radicals, a quinolyl radical optionally substituted by one or more alkyl radicals, a naphthyl radical optionally substituted by one or more alkyl radicals, an indolyl radical optionally substituted by one or more alkyl radicals, or a phenyl radical optionally substituted by one or more substituents chosen from among the halogen atoms and the alkyl, alkoxy, hydroxyl, nitro, amino, monoalkylamino, dialkylamino, alkoxycarbonyl, —CO—$NR_7R_8$, —NH—CO—$CH_3$, trifluoromethyl or trifluoromethoxy radicals, and $R_5$ represents a hydrogen atom, or R represents a methylene radical, $R_1$ represents a hydrogen atom and $R_5$ represents a phenyl radical, or R represents a radical $CHR_6$ and $R_1$ and $R_5$ each represent a hydrogen atom, $R_2$ represents an alkoxycarbonyl, cycloalkyloxycarbonyl, cycloalkylalkyloxycarbonyl, —$CONR_9R_{10}$ or phenyl radical optionally substituted by one or more substituents chosen from among the alkyl, alkoxy or hydroxyl radicals, $R_3$ represents a phenyl radical (optionally substituted by one or more substituents chosen from among the halogen atoms and the alkyl, alkoxy and alkylthio radicals), a naphthyl, indolyl, quinolyl or phenylamino radical, the phenyl ring of which is optionally substituted by one or more substituents chosen from among the halogen atoms and the alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyamino-carbonyl, alkoxyaminocarbonyl, 5-tetrazolyl, 5-tetrazolylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O-alk-COOX, —CH=CH—COOX, —CO—COOX, -alk-$SO_3H$, in the form of a salt, —CH=CH-alk', —C(=NOH)—COOX, —S-alk-COOX, —O—$CH_2$-alk'-COOX, —CX=N—O-alk-COOX, -alk-N(OH)—CO-alk or 2,2-dimethyl-4,6-dioxo-1,3-dioxan-5-yl radicals, $R_4$ represents a hydrogen atom or an alkyl radical,
$R_6$ represents a phenyl radical,
$R_7$ represents a hydrogen atom or an alkyl, phenylalkyl or phenyl radical optionally substituted by one or more substituents chosen from among the halogen atoms and the alkyl, alkoxy and alkylthio radicals, $R_8$ represents an alkyl, phenylalkyl or phenyl radical optionally substituted by one or more substituents chosen from among the halogen atoms and the alkyl, alkoxy and alkylthio radicals, or $R_7$ and $R_8$ form with the nitrogen atom to which they are attached a mono- or polycyclic saturated or unsaturated heterocycle containing 4 to 9 carbon atoms and one or more hetero atoms (O, N) and optionally substituted by one or more alkyl radicals, $R_9$ represents a hydrogen atom or an alkyl, cycloalkylalkyl, cycloalkyl, phenylalkyl or phenyl radical optionally substituted by one or more substituents chosen from among the halogen atoms and the alkyl, alkoxy and alkylthio radicals, $R_{10}$ represents an alkyl, cycloalkylalkyl, cycloalkyl, phenylalkyl or phenyl radical optionally substituted by one or more substituents chosen from among the halogen atoms and the alkyl, alkoxy and alkylthio radicals, or $R_9$ and $R_{10}$ form together with the nitrogen atom to which they are attached a mono- or polycyclic saturated or unsaturated heterocycle containing 4 to 9 carbon atoms and one or more hetero atoms (O, N, S) and optionally substituted by one or more alkyl radicals, X represents a hydrogen atom, an alkyl or phenylalkyl radical, alk represents an alkyl or alkylene radical, alk' represents a hydroxyalkyl, hydroxyalkylene, alkoxyalkyl or alkoxyalkylene radical.

In the preceding definitions and in those cited below, unless otherwise mentioned, the alkyl, alkylene and alkoxy radicals and the alkyl, alkylene and alkoxy moieties contain 1 to 4 carbon atoms in a straight or branched chain, the acyl radicals or moieties contain 2 to 4 carbon atoms and the cycloalkyl radicals and moieties contain 3 to 6 carbon atoms.

When $R_7$ and $R_8$ form a heterocycle with the nitrogen atom to which they are attached, the latter is preferably a piperidino cycle optionally substituted by one or more alkyl radicals or a 1,2,3,4-tetrahydroquinoline cycle.

When $R_9$ and $R_{10}$ form a heterocycle with the nitrogen atom to which they are attached, the latter is preferably a piperidino cycle or a 1-perhydroazepinyl, 1,2,3,6-tetrahydro, 1-pyridyl, 1,2,3,4-tetrahydro-1-quinolyl, 1-pyrrolidinyl, 1,2,3,4-tetrahydro-2-isoquinolyl, thiomorpholino or 1-indolyl cycle, these cycles being optionally substituted by at least one alkyl radical.

The compounds of formula (I) having one or more asymmetric centres display isomer forms. The racemic mixtures and the enantiomers of these compounds also belong to the invention.

The compounds of formula (I) for which R represents a methylene, ethylene, CHOH or $CHR_6$ radical or a sulphur atom and $R_3$ represents a phenylamino radical, the phenyl ring of which is optionally substituted, may be prepared by the action of a reactive derivative of carbamic acid, obtained optionally in situ by the action of a reactive derivative of carbonic acid chosen from among N,N'-carbonyldiimidazole, phosgene, diphosgene and p-nitrophenyl chloroformate on a derivative of formula:

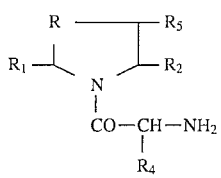

in which R represents a methylene, ethylene, CHOH or $CHR_6$ radical or a sulphur atom and $R_1$, $R_2$, $R_4$, $R_5$ and $R_6$ have the same meanings as in formula (I), on an aniline of which the phenyl ring is optionally substituted by one or more substituents chosen from among the halogen atoms and the alkyl, alkoxy, alkylthio, trifluoro- methyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O-alk-COOX, —CH=CH—COOX, —CO—COOX, -alk-$SO_3H$, —CH=CH-alk', —C(=NOH)—COOX, —S-alk-COOX, —O—$CH_2$-alk'-COOX, —CX=N—O-alk-COOX or -alk-N(OH)—CO-alk or 2,2-dimethyl-4,6-dioxo-1,3-dioxan-5-yl radicals.

This reaction is generally carried out in an inert solvent such as tetrahydrofuran, dimethylformamide, a chlorinated solvent (chloroform, 1,2-dichloroethane for example) or an aromatic solvent (benzene, toluene for example), at a temperature between 20° C. and the boiling point of the solvent.

The reactive derivative of carbamic acid may be obtained under the same solvent and temperature conditions.

The derivatives of formula (II) may be obtained by deprotection of a derivative of formula:

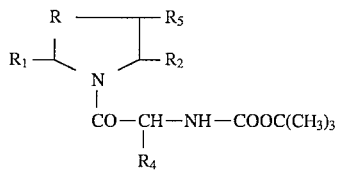

in which R represents a methylene, ethylene, CHOH or $CHR_6$ radical or a sulphur atom and $R_1$, $R_2$, $R_4$, $R_5$ and $R_6$ have the same meanings as in formula (I).

This deprotection is preferably carried out using iodotrimethylsilane in an inert solvent such as a chlorinated solvent (chloroform, 1,2-dichloroethane for example), at a temperature between 15° and 40° C.

The derivatives of formula (III) may be obtained by the action of a derivative of formula:

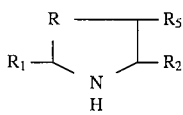

in which R represents a methylene, ethylene, CHOH or $CHR_6$ radical or a sulphur atom and $R_1$, $R_2$, $R_5$ and $R_6$ have the same meanings as in formula (I), on an acid of formula:

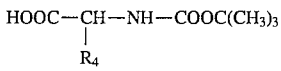

in which $R_4$ is defined as in formula (I).

This reaction is carried out in an inert solvent such as acetonitrile, tetrahydrofuran or a chlorinated solvent, in the presence of a condensation agent used in peptide chemistry such as carbodiimide (for example N,N'-dicyclohexylcarbodiimide) or an alkyl chloroformate, at a temperature between 10° and 40° C.

The derivatives of formula (V) may be obtained by the usual methods of aminoacid protection.

The derivatives of formula (IV) may be prepared by application or adaptation of the methods described in the literature and of the methods described below.

The derivatives of formula (IV) for which $R_2$ represents an alkoxycarbonyl, cycloalkyloxycarbonyl or cycloalkylalkyloxycarbonyl radical may be obtained by esterification of an acid of formula:

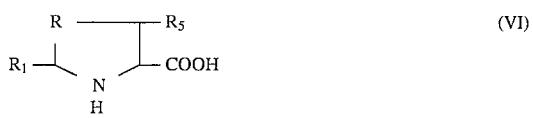

in which R represents a methylene, ethylene, CHOH or $CHR_6$ radical or a sulphur atom and $R_1$, $R_5$ and $R_6$ have the same meanings as in formula (I).

This esterification is generally carried out using an $R_{13}$—OH alcohol in which $R_{13}$ represents an alkyl, cycloalkyl or cycloalkylalkyl radical, in acid medium, at the boiling point of the reaction mixture. For compounds of formula (IV) for which $R_2$ represents a tert-butoxycarbonyl radical, isobutene is reacted with a product of formula (VI) in an inert solvent such as a chlorinated solvent, in the presence of an acid such as sulphuric acid, at a temperature in the vicinity of 20° C.

The derivatives of formula (VI) for which R represents a methylene radical and $R_1$ and $R_5$ are defined as in formula (I) may be prepared by application or adaptation of the method described by H. GERSHON et al., J. Org. Chem., 26, 2347 (1961).

The derivatives of formula (VI) for which R represents a $CHR_6$ radical and $R_1$, $R_5$ and $R_6$ are defined as in formula (I) may be prepared by application or adaptation of the method described by J. K. THOTTATHIL et al., Tetrahedron Letters, 27, 151 (1986), and D. R. KRONENTHAL et al., Tetrahedron Letters, 31, 1241 (1990).

The derivatives of formula (VI) for which R represents a methylene radical, $R_1$ represents a hydrogen atom and $R_5$ represents a phenyl radical may be prepared by application or adaptation of the method described by Y. N. BELOKON et al., J. Chem. Soc. Perkin Trans 1, 2075 (1988)and J. RIVIER and G. R. MARSHALL, Peptides, Chemistry, Structure and Biology, Proceedings of the Eleventh American Peptide Symposium, Jul. 9–14, 1989—La Jolla Calif. U.S.A.—ESCOM Leiden 1990.

The derivatives of formula (VI) for which R represents a sulphur atom, $R_1$ is defined as in formula (I) and $R_5$ represents a hydrogen atom may be obtained by the action of a derivative of formula:

in which $R_5$ represents a hydrogen atom, on an aldehyde of formula:

in which $R_1$ has the same meaning as in formula (I).

This reaction is preferably carried out in an alcohol, at the boiling point of the reaction mixture.

The derivatives of formula (VI) for which R represents an ethylene radical, $R_1$ is defined as in formula (I) and $R_5$ represents a hydrogen atom may be prepared by reduction of the derivatives of formula:

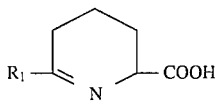

in which $R_1$ has the same meaning as in formula (I).

This reduction is generally carried out using hydrogen, in an inert solvent such as an alcohol, in the presence of a catalyst such as platinum oxide, at a temperature between 20° and 100° C. optionally under pressure or using sodium borohydride and potassium carbonate in the water-alcohol mixture (preferably ethanol), at a temperature between 0° and 20° C.

The derivatives of formula (IX) may be obtained by the action of an alkyl acetamidomalonate on a derivative of formula:

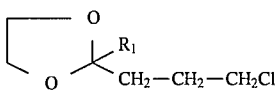

in which $R_1$ has the same meaning as in formula (I), followed by hydrolysis, decarboxylation and dehydration of the product obtained by heating in aqueous hydrochloric acid, the action of the alkyl acetamidomalonate on the product of formula (X) being carried out in an alcohol, in the presence of a base such as an alkali metal alkoxide, at the boiling point of the solvent.

The derivatives of formula (X) may be obtained by application or adaptation of the method described by M. T. WILLS et al., J. Org. Chem., 45 (12), 2495 (1980).

The derivatives of formula (IV) may also be obtained by deprotection of a derivative of formula:

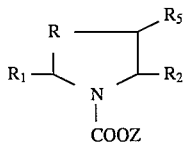

in which R represents a methylene, ethylene, CHOH or $CHR_6$ radical or a sulphur atom, $R_1$, $R_2$, $R_5$ and $R_6$ have the same meanings as in formula (I) and Z represents an alkyl radical and preferably tert-butyl, it being understood that when $R_2$ represents a tert-butoxycarbonyl radical, Z cannot be a methyl or an ethyl radical.

This reaction is carried out in an inert solvent such as a chlorinated solvent, using iodotrimethylsilane, at a temperature between 15° C. and the boiling point of the reaction mixture.

The derivatives of formula (XI) for which R represents a methylene radical, $R_1$ represents a phenyl, optionally substituted 2-thienyl, optionally substituted 2-furyl or optionally substituted 3-indolyl radical, $R_2$ represents an alkoxycarbonyl, cycloalkyloxycarbonyl, cycloalkylalkyloxycarbonyl radical and $R_5$ represents a hydrogen atom may be obtained by the action of a derivative of formula:

$$R_1H \quad\quad (XII)$$

in which $R_1$ represents a phenyl, optionally substituted 2-thienyl, optionally substituted 2-furyl or optionally substituted 3-indolyl radical, on a derivative of formula:

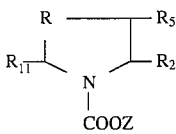

in which R represents a methylene radical, $R_2$ and $R_5$ have the same meanings as above, $R_{11}$ represents an alkoxy radical containing 1 or 2 carbon atoms and Z represents an alkyl radical.

This reaction is generally carried out in the presence of a strong acid such as p-toluenesulphonic acid or a Lewis acid such as aluminium trichloride, optionally in an inert solvent such as an aromatic solvent, at a temperature between 20° C. and the boiling point of the reaction mixture.

The derivatives of formula (XIII) may be prepared by application or adaptation of the method described by T. SHONO et al., J. Am. Chem. Soc., 104, 6697 (1982).

The derivatives of formula (XI) for which $R_2$ represents an alkoxycarbonyl, cycloalkyloxycarbonyl or cycloalkylalkyloxyaarbonyl radical and Z represents a tert-butyl radical may be prepared by esterification of an acid of formula:

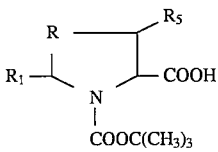

in which R represents a methylene, ethylene, CHOH or $CHR_6$ radical or a sulphur atom and $R_1$, $R_5$ and $R_6$ have the same meanings as in formula (I).

This esterification is carried out under the conditions described above for the esterification of the acids of formula (VI) or using an alcohol, in the presence of tosyl chloride, in pyridine.

The acids of formula (XIV) may be obtained by action of ditert-butyl dicarbonate on an acid of formula (VI).

This reaction is carried out in an inert solvent such as water, dioxan or a mixture of these solvents, in the presence of an alkali metal carbonate, at a temperature in the vicinity of 20° C.

The derivatives of formula (XI) for which $R_2$ represents a $-CONR_9R_{10}$ group and Z represents a tert-butyl radical may be obtained by reaction of an acid of formula (XIV) or a reactive derivative of this acid with an amine of formula:

$$HNR_9R_{10} \quad\quad (XV)$$

in which $R_9$ and $R_{10}$ have the same meanings as in formula

When using the acid, the operation is carried out in the presence of a condensation agent used in peptide chemistry such as a carbodiimide (for example N,N'-dicyclohexylcarbodiimide) or N,N'-carbonyldiimidazole, in an inert solvent such as an ether (tetrahydrofuran, dioxan for example), an amide (dimethylformamide) or a chlorinated solvent (methylene chloride, 1,2-dichloroethane, chloroform for example) at a temperature between 0° C. and the reflux temperature of the reaction mixture.

When using a reactive derivative of the acid, it is possible to react the anhydride, a mixed anhydride or an ester (which may be chosen from among the activated or nonactivated esters of the acid).

The operation is then carried out either in an organic mediums-optionally in the presence of an acid acceptor such as a nitrogen-containing organic base (trialkylamine, pyridine, 1,8-diazabicyclo[5.4.0]-7-undecene or 1,5-diazabicyclo[4.3.0]-5-nonene for example), in a solvent such as mentioned above, or in a mixture of these solvents, at a temperature between 0° C. and the reflux temperature of the reaction mixture, either in a two-phase water/organic medium in the presence of an alkaline or alkaline earth base (sodium hydroxide, potassium hydroxide) or of an alkali metal or alkaline earth metal carbonate or bicarbonate at a temperature between 0 and 40° C.

The derivatives of formula (IV) for which R represents a methylene radical, $R_1$ is defined as in the general formula (I) with the exception of radicals or substituents which may have been altered during a reduction (for example the quinolyl radical or the nitro substituent), $R_2$ represents a phenyl radical optionally substituted by one or more radicals chosen from among the alkyl, alkoxy and hydroxyl radicals and $R_5$ represents a hydrogen atom may be obtained by application or adaptation of the methods described by C. G. OVERBERGER et al., J. Amer. Chem. Soc., 91 887 (1969). This method involves pyrrole reductions which may be obtained by application or adaptation of the methods described in Synthesis, 613 (1991), Tetrahedron Letters 4407–4410 (1986).

The derivatives of formula (IV) for which R represents a methylene radical, $R_1$ represents a phenyl radical optionally substituted by one or more radicals chosen from among the alkyl, alkoxy and hydroxyl radicals or the optionally substituted naphthyl radical and $R_2$ represents a phenyl radical optionally substituted by one or more radicals chosen from among the alkyl, alkoxy and hydroxyl radicals and $R_5$ represents a hydrogen atom may also be obtained by reaction of ethylene with a derivative of formula:

$$R_1\text{---}CH\text{=}N\text{---}CH_2\text{---}R_2 \quad \text{(XVI)}$$

in which $R_1$ and $R_2$ have the same meanings as above.

Ethylene may be formed in situ by decomposition of tetrahydrofuran in the presence of a base such as butyllithium, at a temperature between 0° and 25° C. Ethylene may also be added, in the presence of lithium diisopropylamide, in tetrahydrofuran at a temperature in the vicinity of 20° C.

The derivatives of formula (XVI) may be obtained by the action of an aldehyde of formula (VIII) in which $R_1$ has the same meaning as above on an amine of formula:

$$R_2\text{---}CH_2\text{---}NH_2 \quad \text{(XVII)}$$

in which $R_2$ has the same meaning as above.

This reaction is generally carried out in an inert solvent such as a hydrocarbon (benzene, toluene for example), a chlorinated solvent (dichloromethane, chloroform for example), optionally in the presence of p-toluenesulphonic acid, at the boiling point of the reaction mixture.

The compounds of formula (IV) for which R represents a methylene or CHOH radical, $R_1$ represents a pyridyl, naphthyl, quinolyl or phenyl radical, $R_2$ represents an alkoxycarbonyl, cycloalkyloxycarbonyl, cyclalkylalkyloxycarbonyl or phenyl radical optionally substituted by one or more substituents chosen from among the alkyl, alkoxy or hydroxyl radicals and $R_5$ represents a hydrogen atom may be obtained by reduction of a derivative of formula:

(XVIII)

in which R, $R_1$ and $R_2$ have the same meanings as above.

This reduction is carried out preferably using hydrogen, in the presence of a catalyst such as platinum oxide, in an inert solvent such as ethanol at a temperature in the vicinity of 20° C., or using sodium borohydride and potassium carbonate in a water-alcohol mixture (preferably ethanol), at a temperature between 0° and 20° C.

The derivatives of formula XVIII may be obtained by application or adaptation of the methods described by A. MKAIRI and J. HAMELIN, Tetrahedron Letters, 28 1397 (1987), A. VANDER WERF and R. M. KELLOGG, Tetrahedron Letters, 32 3727 (1991), E. KATO et al., Chem. Pharm. Bull. 33 4836 (1985), J. ACKERMANN et al., Helv. Chim. Acta 73 122 (1990).

The derivatives of formula (XVIII) may also be obtained by deprotection and dehydration of a derivative of formula:

(XIX)

or (XX)

in which R, $R_1$ and $R_2$ have the same meanings as above or of a mixture of these derivatives.

These deprotection and dehydration operations are generally carried out using trifluoroacetic acid or iodotrimethylsilane, in an inert solvent such as a chlorinated solvent (dichloromethane for example), at a temperature in the vicinity of 20° C.

The derivatives of formula (XIX) and (XX) may be obtained by the action of a derivative of formula:

$$R_1\text{---}M \quad \text{(XXI)}$$

in which $R_1$ has the same meaning as above and $R_1$—M represents an organomagnesium or organolithium derivative or a cuprate, on a carbonyl derivative of formula:

(XXII)

in which R and $R_2$ have the same meanings as above.

This reaction is carried out in an inert solvent such as tetrahydrofuran at a temperature between −78° and 20° C.

The derivatives of formula (XXII) may be obtained by application or adaptation of the methods described by J. ACKERMANN et al., Helv. Chim. Acta, 73, 122 (1990), T. OHTA, Chem. Lett., 2091 (1987) or T. OHTA et al., Tetrahedron Letters 29 329 (1988). Preferably, ditert-butyl dicarbonate is reacted with a derivative of formula:

(XXIII)

in which R and $R_2$ have the same meanings as above.

This reaction is generally carried out in the presence of triethylamine and 4-dimethylaminopyridine in a chlorinated solvent such as dichloromethane at a temperature in the vicinity of 20° C.

The derivatives of formula (XXIII) may be obtained by application or adaptation of the methods described by T. KOLASA et al., J. Org. Chem., 55, 1711 (1990), A. L.

JOHNSON et al., J. Med. Chem., 28, 1596 (1985)and B. RIGO et al., J. Het. Chem., 25, 49 (1988), R. W. ROSENMUND and P. ENGELS, Arch. Pharm. 284 16 (1951), C. F. KOELSCH and C. H. STRATTON, J. Am. Chem. Soc. 66 1883 (1944), S. WIDEQUIST, ArK. Kemi, Mineral. Geol. 26 1 (1948), J. SINNREICH and D. ELAD, Tetrahedron Letters, 24 4509 (1968), G. R. BROWN et al., J. Chem. Soc. Chem Commun. 1973 (1984).

The derivatives of formula (IV), for which R represents a methylene radical, $R_1$ represents an optionally substituted pyridyl radical, an optionally substituted quinolyl radical, an optionally substituted naphthyl radical or a phenyl radical optionally substituted by one or more substituents chosen from among the halogen atoms and the alkyl, alkoxy, hydroxyl, amino, monoalkylamino, dialkylamino, alkoxycarbonyl, —CO—$NR_7R_8$ or —NH—CO—$CH_3$ radicals, $R_2$ represents an alkoxycarbonyl, cycloalkyloxycarbonyl or a cycloalkylalkyloxycarbonyl radical and $R_5$ represents a hydrogen atom may also be obtained by reduction of a derivative of formula:

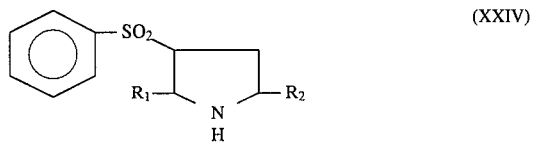

(XXIV)

in which $R_1$ and $R_2$ have the same meanings as above.

This reduction is generally carried out using a mercury-sodium amalgam, in the presence of sodium dihydrogen phosphate or disodium hydrogen phosphate, in a solvent such as an alcohol (methanol for example), tetrahydrofuran, water-ora mixture of these solvents, at a temperature between −10° and 40° C., or using magnesium in an inert solvent such as an alcohol (methanol for example), at a temperature between 20° C. and the boiling point of the reaction mixture.

The derivatives of formula (XXIV) may be obtained by the action of a derivative of formula (XVI) in which $R_1$ and $R_2$ have the same meanings as above on phenyl vinyl sulphone.

This reaction is generally carried out in the presence of a metallic salt such as lithium bromide or silver acetate and a trialkylamine such as triethylamine in an inert solvent such as acetonitrile at a temperature in the vicinity of 20° C.

The derivatives of formula (IV) for which R represents a sulphur atom, $R_1$ is defined as in formula (I), $R_2$ represents a phenyl radical and $R_5$ represents a hydrogen atom may be obtained by the action of a derivative of formula (VIII) on a 2-amino-2-phenylethanethiol, the phenyl ring of which is optionally substituted by one or more substituents chosen from among the alkyl, alkoxy or hydroxyl radicals.

This reaction is generally carried out in an inert solvent such as an alcohol at the boiling point of the reaction mixture.

The 2-amino-2-phenylethanethiols, the phenyl ring of which is optionally substituted, may be prepared by application or adaptation of the method described in the Patent JP 57 197 447 which makes use of 2-amino-2-phenylethanols which are prepared by application or adaptation of the methods described by Z. L. KIS and J. MORLY, EP 258 191, J. PLESS, CH 590 820, S. MIYAMOTO et al., EP 432 661, J. SUZUKI et al., EP 345 775.

The derivatives of formula (IV) for which $R_2$ represents a phenyl optionally substituted by one or more substituents chosen from among the alkyl, alkoxy or hydroxyl radicals, R represents a methylene radical, $R_1$ represents a hydrogen atom and $R_5$ represents a phenyl radical may be prepared by application or adaptation of the methods described by W. H. PEARSON et al., J. Am. Chem. Soc. 114 1329 (1992), O. TSUGE et al., Bull. Chem. Soc. Japan 59 2537 (1986).

These derivatives may also be prepared by reduction of the corresponding pyrroles and pyrrolines by application or adaptation of the methods described by C. G. OVERBERGER et al., J. Am. Chem. Soc. 91 687 (1969).

These pyrroles and these pyrrolines may be prepared by application or adaptation of the methods described by M. OHNO et al., Tetrahedron Letters 32 5093 (1991), S. C. CHERKOFSKY, U.S. Pat. No. 4 267 184, S. C. CHERKOFSKY and G. A. BOSWELL Jr., EP 25884, O. TSUGE et al., Bull. Chem. Soc. Japan 59 1809 (1986).

The derivatives of formula (IV) for which R represents an ethylene radical, $R_2$ represents a phenyl radical optionally substituted by one or more substituents chosen from among the alkyl, alkoxy or hydroxyl radicals, $R_5$ represents a hydrogen atom and $R_1$ has the same meaning as in formula (I) may be prepared by application or adaptation of the methods described by C. G. OVERBERGER et al., J. Am. Chem. Soc. 79 6430 (1957), J. THESING and H. MEYER, Ann. 609 46 (1957), D. Y. JACKSON and P. G. SCHULTZ, J. Am. Chem. Soc. 113 2319 (1991), C. G. OVERBERGER and L. P. HERIN, J. Org. Chem. 27 2423 (1962).

Some of these methods involve reductions of tetrahydropyridines which may also be obtained by application or adaptation of the methods described by H. QUAST and B. MUELLER Chem. Ber. 116 3931 (1983), R. WEIL and N. COLLIGNON, C. Rend. Acad. Sci. Ser. C 275 299 (19 72)and Bull. Soc. Chim. Fr. 258 (1974).

The derivatives of formula (IV) for which $R_2$ represents a phenyl optionally substituted by one or more substituents chosen from among the alkyl, alkoxy or hydroxyl radicals, R represents a radical $CHR_6$, $R_1$ and $R_5$ each represent a hydrogen atom and $R_6$ represents a phenyl radical may be prepared by application or adaptation of the methods described by M. C. KLOEZEL, J. Am. Chem. Soc. 69 2271 (1947), W. H. PEARSON et al., J. Am. Chem. Soc. 114 1329 (1992), O. TSUGE et al., Bull. Soc. Japan 59 2537 (1986), M. CARRIOU et al., Can. J. Chem. 61 2359 (1983), E. BREWER and D. MELUMAD, J. Org. Chem. 37 3949 (1972).

Some of these methods involve reductions of pyrroles and pyrrolines which may also be obtained by application or adaptation of the methods described by C. F. H. ALLEN and C. V. WILSON, Org. Synth. Coll. Vol. III 358 (1955), W. DAVEY and D. J. TIVEY, J. Chem. Soc. 2276 (1958), W. CHEN et al., Chin. Chem. Lett. 2 439 (1991), S. M. BLOOM and P. P. GARCIA, U.S. Pat. Nos. 3,883,555 and 3,691,161.

The derivatives of formula (III) for which $R_2$ represents an alkoxycarbonyl, cycloalkyloxycarbonyl or cycloalkylalkyloxycarbonyl radical may also be obtained by esterification of an acid of formula:

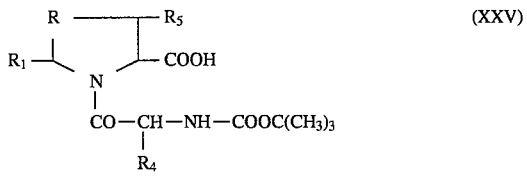

(XXV)

in which R, $R_1$, $R_4$, $R_5$ and $R_6$ have the same meanings as in formula (I).

This reaction is preferably carried out under the same conditions as those described above for the esterification of compounds of formula (V).

The acids of formula (XXV) may be obtained by hydrolysis of the corresponding methyl or ethyl esters of formula (III).

This hydrolysis is generally carried out in an inert solvent such as water, dioxan or a mixture of these solvents, using a base such as an alkali metal hydroxide (sodium hydroxide, potassium hydroxide) at a temperature in the vicinity of 20° C.

The derivatives of formula (III) for which R represents a methylene radical, $R_1$ represents a pyridyl radical which is optionally substituted, a quinoline radical which is optionally substituted, a naphthyl radical which is optionally substituted or a phenyl radical which is optionally substituted by one or more substituents chosen from among the halogen atoms and the alkyl, alkoxy, hydroxyl, amino, monoalkylamino, dialkylamino, alkoxycarbonyl, —CO—$NR_7R_8$ or —NH—CO—$CH_3$ radicals, $R_2$ represents an alkoxycarbonyl, cycloalkyloxycarbonyl or cycloalkylalkyloxycarbonyl radical and $R_5$ represents a hydrogen atom may be obtained by reduction of the derivatives of formula:

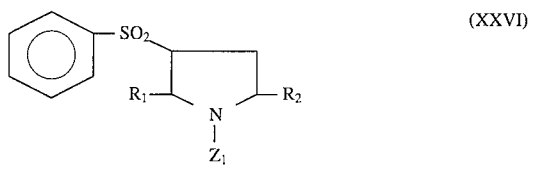

(XXVI)

in which $Z_1$ represents a tert-butoxycarbonyl radical or a CO—CH($R_4$)—NH—COOC($CH_3$)$_3$ radical, $R_1$ and $R_2$ have the same meanings as above and $R_4$ has the same meaning as in formula (I).

This reaction is carried out under the same conditions as those described previously for the reduction of the derivatives of formula (XXIV).

The derivatives of formula (XXVI) may be obtained by the action of an acid of formula (V) or of di-tert-butyl dicarbonate, whichever is appropriate, on a derivative of formula (XXIV).

This reaction is carried out in an inert solvent such as acetonitrile, tetrahydrofuran or a chlorinated solvent, in the presence of a condensation agent used in peptide chemistry such as a carbodiimide (N,N'-dicyclohexylcarbodiimide for example) or an alkyl chloroformate at a temperature between 10° and 40° C.

The optionally substituted anilines are commercially available or may be obtained by application or adaptation of the methods described by R. SCHRÖTER, Methoden der organischen Chemie, Houben Weil, Volume XI/1, p. 360; G. J. ESSELEN et al., J. Am. Chem. Soc., 36, 322 (1914); G. ADRIANT et al., Bull. Soc. Chim. FR, 1511 (1970); W. A. JACOBS et al., J. Am. Chem. Soc., 39, 2438 (1917) and J. Am. Chem. Soc., 39, 1438 (1917) and in the examples therein.

The compounds of formula (I) for which R represents a methylene, ethylene, CHOH or $CHR_6$ radical or a sulphur atom and $R_3$ represents a phenylamino radical, the phenyl ring of which is optionally substituted by one or more substituents chosen from among the halogen atoms and the alkyl, alkoxy, alkylthio, trifluoromethyl, nitro, acyl, cyano, sulphamoyl, alkoxycarbonyl, -alk-O-alk, trifluoromethylsulphonamido, alk-$SO_3H$, in the form of a salt, alk-COOX or alk'-COOX radicals, in which X is other than a hydrogen atom, may also be prepared by the action of a derivative of formula (II) on a phenyl isocyanate, the phenyl ring of which is optionally substituted by one or more substituents chosen from among the halogen atoms and the alkyl, alkoxy, alkylthio, trifluoromethyl, nitro, acyl, cyano, sulphamoyl, alkoxycarbonyl, -alk-O-alk, trifluoromethylsulphonamido or alk-$SO_3H$ radicals, in the form of a salt.

This reaction is generally carried out in an inert solvent such as tetrahydrofuran, dimethylformamide, a chlorinated solvent (chloroform, 1,2-dichloroethane for example), an aromatic solvent (benzene, toluene for example) at a temperature between 10° C. and the boiling point of the solvent.

The phenyl isocyanates are commercially available or may be obtained by application or adaptation of the methods described by R. RICHTER et al., The Chemistry of Cyanate and their thio derivatives, S. PATAI, part 2, Wiley New York (1977) and in the examples therein.

The compounds of formula (I) for which R represents a methylene, ethylene, CHOH or $CHR_6$ radical or a sulphur atom and $R_3$ represents a phenylamino radical, the phenyl ring of which is substituted by a carboxyl, -alk-COOH, —O-alk-COOH, -alk'-COOH, —CH═CH—COOH, —CO—COOH, —S-alk-COOH, —C(═NOH)—COOH, $OCH_2$alk'COOH or CX═N—O-alk-COOH radical and $R_1$, $R_2$, $R_5$ and $R_6$ are defined as in formula (I) may also be prepared by hydrolysis or, where appropriate, by hydrogenolysis of the corresponding esters.

When using alkyl or phenylalkyl esters, it is advantageous to carry out the hydrolysis using a base such as sodium hydroxide, potassium hydroxide or lithium hydroxide in an inert solvent such as tetrahydrofuran, dioxan, water or a mixture of these solvents, at a temperature between 20° C. and 40° C. When using trimethylsilylethyl ester, it is advantageous to carry out the operation in an inert solvent such as tetrahydrofuran, using a fluoride such as tetrabutylammonium fluoride, at a temperature between 10° and 40° C. When using phenylalkyl esters, it may also be advantageous to carry out a hydrogenolysis using hydrogen or ammonium formate in the presence of a catalyst such as palladinized charcoal in a solvent such as methanol or ethyl acetate.

The trimethylsilylethyl esters may be obtained by application or adaptation of the method described in the examples.

The compounds of formula (I) for which R represents a methylene, ethylene, CHOH or $CHR_6$ radical or a sulphur atom, $R_3$ represents a phenylamino radical, the phenyl ring of which is optionally substituted by a hydroxyiminoalkyl or alkoxyiminoalkyl radical and $R_1$, $R_2$, $R_5$ and $R_6$ are defined as in formula (I) may also be prepared by the action of the corresponding acylated derivative on a derivative of formula:

$$H_2N—OR_{12}$$ (XXVII)

in which $R_{12}$ represents a hydrogen atom or an alkyl radical.

This reaction is generally carried out in an inert solvent such as an alcohol (methanol, ethanol for example), water or a mixture of these solvents, at the boiling point of the solvent and optionally in the presence of a base such as pyridine.

The compounds of formula (I) for which R represents a methylene, ethylene, CHOH or $CHR_6$ radical or a sulphur atom and $R_3$ represents an optionally substituted phenyl radical, a naphthyl radical, an indolyl radical, an optionally substituted quinolyl radical or a phenylamino radical, the phenyl ring of which is optionally substituted by one or more substituents chosen from among the halogen atoms and the alkyl, alkoxy, alkylthio, trifluoromethyl, nitro, acyl, cyano, sulphamoyl, alkoxycarbonyl, trifluoromethylsulphonamido, -alk-O-alk, alk-COOX or alk'-COOX radicals, in which X is other than a hydrogen atom and $R_1$, $R_2$, $R_5$ and $R_6$ are defined as in formula (I), may also be prepared by the action of a derivative of formula (IV) on an acid of formula:

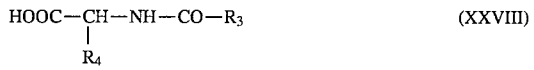

(XXVIII)

in which $R_3$ has the same meaning as above or a reactive derivative of this acid, and $R_4$ has the same meaning as in formula (I).

This reaction is preferably carried out in the presence of a condensation agent used in peptide chemistry such as a carbodimide in a solvent such as acetonitrile, tetrahydrofuran or a chlorinated solvent or using thionyl chloride in dichloromethane at a temperature between 10° C. and the boiling point of the solvent.

The acids of formula (XXVIII) may be obtained by application or adaptation of the method described by J. R. JOHNSON et al., J. Am. Chem. Soc., 69, 2370 (1947) or for the compounds for which R3 represents a phenylamino radical which is optionally substituted, by the action of a phenyl isocyanate, the phenyl ring of which is optionally substituted by one or more substituents chosen from among the halogen atoms and the alkyl, alkoxy, alkylthio, trifluoromethyl, nitro, acyl, cyano, sulphamoyl, alkoxycarbonyl, -alk-O-alk, alk-COOX or alk'-COOX radicals, in which X is other than a hydrogen atom, or a trifluoromethylsulphonamido radical on a derivative of formula:

(XXIX)

in which $R_4$ has the same meaning as in formula (I).

This reaction is generally carried out in aqueous solution in the presence of a base such as an alkali metal bicarbonate or in aqueous dioxan, at a temperature in the vicinity of 20° C.

The compounds of formula (I) for which R represents an SO or $SO_2$ radical and $R_1$, $R_2$ and $R_5$ are defined as in the general formula (I) may be prepared by oxidation of the corresponding compounds of formula (I) for which R represents a sulphur atom, it being understood that the other radicals and the other substituents are chosen in such a way that they are insensitive to the reaction conditions.

This oxidation is generally carried out using oxone® (potassium peroxymonosulphate) marketed by Aldrich, in an alcohol such as methanol or a methanol-water mixture, at a temperature in the vicinity of 25° C.

It is taken for granted by a person skilled in the art that, to implement the processes according to the invention described above, it may be necessary to introduce protecting groups of the amino, hydroxyl and carboxyl functions in order to avoid secondary reactions. The amino functions may for example be blocked in the form of tert-butyl or methyl carbamates, then regenerated using iodotrimethylsilane or benzyl carbamates, then regenerated by hydrogenation after implementing the process according to the invention. The hydroxyl functions may for example be blocked in the form of benzoate, then regenerated by hydrolysis in alkaline medium after implementation of the process according to the invention.

The enantiomers of the compounds of formula (I), containing at least one asymmetric site, may be obtained by resolution of the racemic mixtures, for example by chiral chromatography on a chiral column or by synthesis starting from chiral precursors.

As chiral phase, it is preferable to use a phase whose chiral selector, which is, preferably, 3,5-dinitrobenzoyl-D-phenylglycine, is removed from the silica by an aminoalkyl arm, which contains 3 to 14 carbon atoms, which is fixed on the amine functions of an aminopropyl silica and whose free silanol functions are blocked by trialkylsilyl radicals.

This chiral phase, which constitutes another subject of the present invention, may be defined by the following structure:

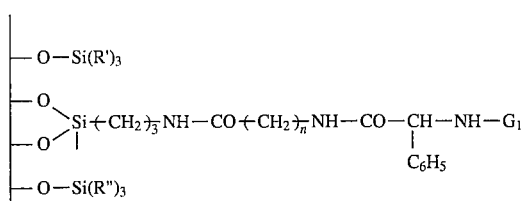
(XXX)

in which the symbols R', which may be identical or different, and R", which may be identical or different, represent alkyl radicals containing 1 to 10 carbon atoms, $G_1$ represents an electro-attracting group and n represents an integer between 3 and 13 inclusive.

Preferably, one of the symbols R' represents an alkyl radical containing 7 to 10 carbon atoms and the other two represent an alkyl radical containing 1 to 2 carbon atoms and preferably a methyl radical, the symbols R" are identical and represent a methyl or ethyl radical, $G_1$ represents a benzoyl radical which is optionally substituted, preferably by one or more nitro radicals such as the 3,5-dinitrobenzoyl radical, and n is equal to 10.

The new chiral phase according to the invention may be prepared by the action, on an aminopropyl silica, of the anhydride of an aminoalkanoic acid which contains 3 to 14 carbon atoms, the amine function of which is protected by a protecting group such as the tert-butoxycarbonyl radical, followed by the blocking of a portion of the silanol functions by $Si(R')_3$ radicals as defined above, then, after elimination of the protecting group of the amine function, by the amidation using D-phenylglycine, the amine function of which is protected by an electro-attracting group $G_1$ as defined above, and finally by the blocking of the residual silanol functions by $Si(R")_3$ radicals as defined above.

Generally, the action of the aminoalkanoic acid anhydride protected on the aminopropyl silica is carried out in an anhydrous organic solvent such as dimethylformamide at a temperature in the vicinity of 20° C.

The blocking of the silanol functions by $—Si(R_3)$ groups as defined above is carried out by the action of a halogenotrialkylsilane on aminopropyl silica grafted on aminoalkanoyl residues by operating in an organic solvent such as methylene chloride in the presence of a basic agent such as pyridine.

The elimination of the protecting groups of the aminoalkanoyl residues is generally carried out, when the protecting group is a tert-butoxycarbonyl radical, by the action of trifluoroacetic acid in an organic solvent such as methylene chloride.

The amidation using D-phenylglycine, the amine function of which is protected, is carried out in the presence of a condensation agent such as N-ethoxy-carbonyl-2-ethoxy-1, 2-dihydroquinoline by operating in an anhydrous organic solvent such as dimethylformamide.

The blocking of the residual silanol functions by $—Si(R")_3$ radicals as defined above is generally carried out using trialkylsilylimidazole in an organic solvent such as methylene chloride.

The compounds of formula (I) may be purified by the usual known methods, for example by crystallization, chromatography or extractions.

The compounds of formula (I) may optionally be converted into addition salts with a mineral or organic acid by the action of such an acid in an organic solvent such as an alcohol, a ketone, an ether or a chlorinated solvent.

The compounds of formula (I) having a carboxyl, sulpho or alk-$SO_3H$ residue may also be converted into metallic salts or into addition salts with nitrogen-containing bases by methods known per se. These salts may be obtained by the action of a metallic base (alkali metal or alkaline earth metal for example), of ammonia, of an amine or of a salt of an organic acid on a compound of formula (I) in a solvent. The salt formed is separated by the usual methods.

These salts also form part of the invention.

The addition salts with inorganic or organic acids (such as acetate, propionate, succinate, benzoate, fumarate, maleate, oxalate, methanesulphonate, isethionate, theophyllinacetate, salicylate, methylene-bis-β-oxynaphthoate, hydrochloride, sulphate, nitrate and phosphate), the salts with alkali metals (sodium, potassium, lithium) or with alkaline earth metals (calcium, magnesium), the ammoniums salt, the salts of nitrogen-containing bases (ethanolamine, trimethylamine, methylamine, benzylamine, N-benzyl-β-phenethylamine, choline, arginine, leucine, lysine, N-methylglucamine) may be cited as examples of pharmaceutically acceptable salts.

The compounds of formula (I) have advantageous pharmacological properties. These compounds possess a strong affinity for the receptors of cholecystokinin (CCK) and of gastrin and are therefore useful in the treatment and the prevention of the disorders linked to CCK and to gastrin at the level of the nervous system and of the gastrointestinal apparatus.

It thus follows that these compounds may be used for the treatment or the prevention of psychoses, of anxiety disorders, of Parkinson's Disease, of tardive dyskinesia, of the irritable colon syndrome, of acute pancreatitis, of ulcers, of intestinal motility disorders, of certain tumours sensitive to CCK and as appetite regulator.

These compounds also have a potentiator effect on analgesic activity of narcotic and non-narcotic medicaments. Moreover, they may have an inherent analgesic effect.

Since the compounds have strong affinity for the CCK receptors, they furthermore modify the capacity for memorization. As a consequence, these compounds may be effective for memory disorders.

The affinity of compounds of formula (I) for the CCK receptors has been determined by a technique inspired by that of A. SAITO et al., (J. Neuro. Chem., 37, 483–490 (1981)) at the level of the cerebral cortex and at the level of the pancreas.

In those tests, the $IC_{50}$ of the compounds of formula (I) is generally smaller than or equal to 1000 nM.

It is furthermore known that the products which recognize the central CCK receptors have a similar specificity for the gastrin receptors in the gastrointestinal tract (BOCK et al., J. Med. Chem., 32, 16–23 (1989); REYFELD et al., Am. J. Physiol., 240, G255–266 (1981); BEINFELD et al., Neuropeptides, 3, 411–427 (1983)).

The compounds of formula (I) have a low toxicity. Their $LD_{50}$ is generally greater than 40 mg/kg subcutaneously in mice.

Of particular interest are the compounds of formula (I) for which R represents a methylene radical, a sulphur atom or an SO radical, $R_1$ represents a phenyl radical which is optionally substituted, $R_2$ represents a phenyl or alkoxycarbonyl radical, $R_4$ and $R_5$ represent a hydrogen atom, $R_3$ represents a phenylamino radical, the phenyl ring of which is substituted by a carboxyl, -alk-COOH, —S-alk-COOH, hydroxyalkyl, alk'-COOH, alkSO$_3$— or hydroxyiminoalkyl radical. More particularly interesting are the products of formula (I) in which $R_1$ and $R_2$ are in the cis position with respect to one another.

Of particular interest are the following compounds:

tert-butyl (2RS,5SR)-1-{2-[3-(3-((RS)-1-hydroxyethyl)phenyl)ureido]acetyl}-5-phenylprolinate, 2-{3-{3-[2-(2S,5R)-2-tert-butoxycarbonyl-5-phenyl-1-pyrrolidinyl)-2-oxoethyl]ureido}phenyl}propionic acid (B form), (2RS,5SR)-{3-{3-[2-(2-tert-butoxycarbonyl-5-phenyl-1-pyrrolidinyl)-2-oxoethyl]ureido}phenylthio}acetic acid, (2R,4R)-3-{3-[2-(4-tert-butoxycarbonyl-2-(2-fluoro-3-thiazolidinyl)-2-oxoethyl]ureido}phenylacetic acid, 2-{3-{3-[2-((2R,4R)-2-tert-butoxycarbonyl-2-(2-fluorophenyl)-3-thiazolidinyl)-2-oxoethyl] ureido}phenyl}propionic acid (B form), potassium (RS)-1-{3-{3-[2-((2R,4R)-4-tert-butoxycarbonyl-2-phenyl-3-thiazolidinyl))-2-oxoethyl] ureido}phenyl}ethanesulphonate, mixture of A and B forms, potassium (RS)-1-{3-{3-[2-((2S,5R)-2-tert-butoxycarbonyl-5-phenyl-1-pyrrolidinyl)-2-oxoethyl] ureido}phenyl}ethanesulphonate, potassium (2S,SR)-1-{3-{3-[2-2-tert-butoxycarbonyl-5-phenyl-1-pyrrolidinyl)-2-oxoethyl] ureido}phenyl}methanesulphonate, (2S,SR)-3-{3-[2-(2-tert-butoxycarbonyl-5-phenyl-1-pyrrolidinyl)-2-oxoethyl]ureido}benzoic acid, (2RS,5SR)-3-{3-{2-[2-tert-butoxycarbonyl-5-(2-fluorophenyl)-1-pyrrolidinyl]-2-oxoethyl}ureido}benzoic acid, cis-3-{3-[2-(2,5-diphenyl-1-pyrrolidinyl)-2-oxoethyl] ureido}benzoic acid, (2RS,5SR)-3-{2-[2-(2-hydroxyphenyl)-5-phenyl-1-pyrrolidinyl]-2-oxoureido}phenylacetic acid, (2R,4R)-3-{3-[2-(4-tert-butoxycarbonyl-2-phenyl-3-thiazolidinyl)-2-oxoethyl]ureido}phenylacetic acid, (2R,4R)-3-{3-[2-(4-tert-butoxycarbonyl-2-phenyl-3-thiazolidinyl)-2-oxoethyl]ureido}benzoic acid, 2-{3-{3-[2-((1RS,2R,4R)-4-tert-butoxycarbonyl-2-(2-fluorophenyl)-1-oxide-3-thiazolidinyl)-2-oxoethyl}ureido}phenyl}propionic acid (A form), (2R,4R)-3-{3-[2-(4-tert-butoxycarbonyl-2-(2,3-difluorophenyl)-3-thiazolidinyl)-2-oxoethyl] ureido}phenylacetic acid, tert-butyl (2RS,5SR)-1-{2-{3-[(E)-3-(1-hydroxyiminoethyl)phenyl]ureido}acetyl}-5-phenylprolinate.

EXAMPLES

The following examples illustrate the invention without any implied limitation.

EXAMPLE 1

0.9 cm$^3$ of sulphinyl chloride is added slowly to a suspension of 3.1 g of tert-butyl (2RS,5SR)-5-phenylprolinate and 2.6 g of 2-[3-(3-methylphenyl)ureido]acetic acid in 100 cm$^3$ of anhydrous 1,2-dichloroethane heated to reflux. The reaction mixture is then heated under reflux for 15 minutes, then cooled to 50° C. and neutralized to a pH of 7–8 by addition of a 10% aqueous sodium bicarbonate solution. The organic phase is washed with 3 times 50 cm$^3$ of water, dried over magnesium sulphate, filtered and concentrated to dryness under reduced pressure. The crude product obtained is purified by chromatography on silica [eluent: dichloromethane/methanol (98/2 by volume)]. The fractions containing the expected product are combined and concentrated to dryness under reduced pressure at a temperature in the vicinity of 45° C. After recrystallization in acetonitrile, 1 g of tert-butyl (2RS,5SR)-1-{2-[3-(3-methylphenyl)ureido]acetyl}-5-phenylprolinate, melting at 156° C., is obtained.

A—2-[3-(3-Methylphenyl)ureido]acetic acid may be prepared as follows: 53.2 g of 3-methylphenyl isocyanate are added in the space of 15 minutes to a solution of 30 g of glycine and 53 g of sodium bicarbonate in 600 cm$^3$ of water. The reaction mixture is stirred for 4 hours at a temperature in the vicinity of 25° C., then washed with 200 cm³ of ethyl acetate and acidified to a pH of 1 with 200 cm³ of a 4N aqueous hydrochloric acid solution. The insoluble product is separated by filtration, washed with 3 times 80 cm³ of water and dried in air. 72 g of 2-[3-(3-methylphenyl)ureido]acetic acid, melting at 208° C., are thus obtained.

B—tert-Butyl (2RS,5SR)-5-phenylprolinate may be prepared as follows: a suspension of 45 g of (2RS,5SR)-5-phenylproline hydrochloride in 500 cm³ of anhydrous chloroform is stirred and cooled to a temperature in the vicinity of 5° C. 5.5 cm³ of concentrated sulphuric acid are added dropwise, and the reaction mixture is saturated with isobutene for 2 hours while stirring and maintaining the temperature at 5° C. After returning to a temperature in the vicinity of 20° C., stirring is continued for 20 hours. The reaction mixture is then brought to a pH of 8 with a 4N aqueous sodium hydroxide solution. The organic phase is decanted, washed with 3 times 100 cm³ of water, dried over magnesium. sulphate and concentrated to dryness under reduced pressure at a temperature in the vicinity of 40° C. 40 g of tert-butyl (2RS,5SR)-5-phenylprolinate are obtained in the form of an orange oil, used as it is in subsequent syntheses.

(2RS,5SR)-5-phenylproline hydrochloride may be prepared according to the method described by H. GERSHON and A. SCALA, J. Org. Chem., 26, 2347–50 (1961).

EXAMPLE 2

0.9 cm³ of 3-methoxyphenyl isocyanate is added to a solution of 2 g of tert-butyl (2RS,5SR)-1-(2-aminoacetyl)-5-phenylprolinate in 20 cm³ of anhydrous tetrahydrofuran. The reaction mixture is stirred for 20 hours at a temperature in the vicinity of 25° C. After evaporation of the solvent under reduced pressure at a temperature in the vicinity of 45° C., the crude product obtained is purified by chromatography on silica [eluent: dichloromethane/methanol (95/5 by volume)]. The fractions containing the expected product are combined, then concentrated to dryness under reduced pressure. After recrystallization in acetonitrile, 1.9 g of tert-butyl (2RS,5SR)-1-{2-[3-(3-methoxyphenyl)ureido]acetyl}-5-phenylprolinate melting at 174° C., are obtained.

A—tert-Butyl (2RS,5SR)-1-(2-aminoacetyl)-5-phenylprolinate may be prepared as follows: at a temperature in the vicinity of 25° C. 5.6 cm³ of iodotrimethylsilane are added dropwise to a solution of 16 g of tert-butyl (2RS, 5SR)-1-(2-tert-butoxycarbonylaminoacetyl)-5-phenylprolinate in 150 cm³ of chloroform. The reaction mixture is stirred for 20 hours at this temperature, then concentrated to dryness under reduced pressure at a temperature in the vicinity of 45° C. The crude product obtained is purified by chromatography on silica [eluent: dichloromethane/methanol (90/10 by volume)]. The fractions containing the expected product are combined and then concentrated to dryness under reduced pressure. 10 g of tert-Butyl (2RS,5SR)-1-(2-aminoacetyl)-5-phenylprolinate are thus obtained in the form of an amorphous white product, used as it is in subsequent syntheses.

Proton NMR (250 MHz, DMSO $D_6$, δ in ppm), 2 rotamers at room temperature, 1.5 (s, 9H, C(CH$_3$)$_3$, 1.8 to 2.4 (bm, 4H, CH$_2$—CH$_2$); 2.7, 3.25, 3.45 and 3.6 (bd, 2H, AB, CH$_2$CO$_2$); 4.3 (bt, 1H, CHN); 5.05 (bm, 1H, CHN); 7.2 to 7.8 (m, 5H, aromatic).

B—tert-Butyl (2RS,5SR)-1-(2-tert-butoxycarbonylaminoacetyl)-5-phenylprolinate may be prepared as follows: in the space of 30 minutes a solution of 9.6 g of N,N'-dicyclohexylcarbodiimide in 50 cm³ of anhydrous acetonitrile is added to a solution of 11.5 g of tert-butyl (2RS,5SR)-5-phenylprolinate and 8.2 g of 2-tertbutoxycarbonylaminoacetic acid in 150 cm³ of anhydrous acetonitrile kept at a temperature in the vicinity of 0° C. The reaction mixture is stirred for 16 hours at a temperature in the vicinity of 25° C., then the insoluble product is separated by filtration and washed with three times 30 cm³ of dichloromethane. The filtrate is concentrated to dryness under reduced pressure at a temperature in the vicinity of 45° C. After recrystallization in pentane, 16 g of tert-butyl (2RS,5SR)-1-(2-tert-butoxycarbonylaminoacetyl)-5-phenylprolinate, melting at 112° C., are obtained.

EXAMPLE 3

A solution of 3.1 g of tert-butyl (2RS,5SR)-1-(2-aminoacetyl)-5-phenylprolinate in 50 cm³ of anhydrous 1,2-dichloroethane is slowly added to a solution of 1.8 g of N,N'-diimidazole-carbonyl in 50 cm³ of anhydrous 1,2-dichloroethane. The reaction mixture is stirred for 1 hour at a temperature in the vicinity of 25° C., followed by the addition of 1.4 g of (RS)-1-(3-aminophenyl)ethanol. The reaction mixture is then heated under reflux while stirring for 4 hours. After cooling, the mixture is washed with 3 times 50 cm³ of water; the organic phase is dried over magnesium sulphate and the solvent is evaporated to dryness under reduced pressure at a temperature of 45° C. The oily residue obtained is purified by chromatography on silica [eluent: dichloromethane/methanol (95/5 by volume)] and the fractions containing the expected product are combined and then concentrated to dryness under reduced pressure. After recrystallization in acetonitrile, 1.8 g of tert-butyl (2RS,5SR)-1-{2-[3-(3-(RS)-1-hydroxyethyl)phenyl)ureido]acetyl}-5phenylprolinate, melting at 160° C., are obtained.

EXAMPLE 4

By proceeding in a fashion similar to that described in Example 3, but starting from 1.8 g of N,N'-diimidazole-carbonyl, 3.1 g of tert-butyl (2RS,5SR)-1-(2-aminoacetyl)-5-phenylprolinate in solution in 100 cm³ of anhydrous 1,2-dichloroethane and 1.3 cm³ of 3-methyl-thioaniline, after recrystallization in acetonitrile, 1.8 g of tert-butyl (2RS,5SR)-1-{2-[3-(3-methylthiophenyl)ureido]acetyl}-5-phenylprolinate, melting at 163° C., are obtained.

EXAMPLE 5

By proceeding in a fashion similar to that described in Example 3, but starting from 1.8 g of N,N'-diimidazole-carbonyl, 3.1 g of tert-butyl (2RS,5SR)-1-(2-aminoacetyl)-5-phenylprolinate in solution in 100 cm³ of anhydrous 1,2-dichloroethane and 1.25 g of 3-aminophenylmethanol, after recrystallization in acetonitrile, 1.8 g of tert-butyl (2RS,5SR)-1-{2-[3-(3-hydroxymethylphenyl)ureido] acetyl}-5-phenylprolinate, melting at 168° C., are obtained.

EXAMPLE 6

By proceeding in a fashion similar to that described in Example 3, but starting from 1.8 g of N,N'-diimidazole-carbonyl, 3.1 g of tert-butyl (2RS,5SR)-1-(2-aminoacetyl)-5-phenylprolinate in solution in 100 cm³ of anhydrous 1,2-dichloroethane and 1.5 g of 3-aminoacetophenone, after recrystallization in a cyclohexane-methanol (9/1 by volume) mixture, 1.1 g of tert-butyl (2RS,5SR)-1-{2-[3-(3-acetylphenyl)ureido]acetyl}-5-phenylprolinate, melting at 122° C., are obtained.

EXAMPLE 7

0.5 g of hydroxylamine hydrochloride in solution in 6 cm$^3$ of water is added to a solution of 3 g of tert-butyl (2RS, 5SR)-1-{2-[3-(3-acetylphenyl)ureido]acetyl}-5-phenylprolinate in 12 cm$^3$ of methanol and 6 cm$^3$ of pyridine. The reaction mixture is heated under reflux for 2 hours. After evaporation of the solvents under reduced pressure at a temperature in the vicinity of 45° C., the residue is taken up in 100 cm$^3$ of ethyl acetate and the organic phase is washed with 3 times 50 cm$^3$ of water, dried over magnesium sulphate, filtered and concentrated to dryness under reduced pressure. The crude product obtained is purified by chromatography on silica [eluent: dichloromethane/methanol (95/5 by volume)]. The fractions containing the expected product are combined and concentrated to dryness under reduced pressure at a temperature in the vicinity of 40° C. After recrystallization in acetonitrile, 1.1 g of tert-butyl (E)-(2RS, 5SR)-1-{2-{3-[3-(1-hydroxyiminoethyl)phenyl]ureido}acetyl}-5-phenylprolinate, melting at 118° C., are obtained.

EXAMPLE 8

By proceeding in a fashion similar to that described in Example 3, but starting from 12.5 g of N,N'-diimidazolecarbonyl, 21.3 g of (2RS,5SR)-1-(2-aminoacetyl)-5-phenylprolinate in solution in 400 cm$^3$ of anhydrous 1,2-dichloroethane and 10.5 cm$^3$ of ethyl 3-aminobenzoate, 24.8 g of tert-butyl (2RS,5SR)-1-{2-[3-(3-ethoxycarbonylphenyl)ureido]acetyl}-5-phenylprolinate are obtained in the form of a meringue-like white product [proton NMR (250 MHz, DMSO D$_6$, δ in ppm), 2 rotamers at room temperature, peak coalescence at 120° C., general description valid for the other products of the seriesi 1.35 (t, 3H, ethyl CH$_3$); 1.50 (bs, 9H, (CH$_3$)$_3$); 1.90 to 2.5 (m, 4H, H in position 3 and 4 on pyrrolidine); 3.9 and 3.5 (ABX, 2H, CH$_2$N); 4.3 (q, 2H, CH$_2$O); 4.5 (vbdd, 1H, H in position 2 on pyrrolidine); 5.15 (dd, 1H, H in position 5 on pyrrolidine); 6.2 (bdd, 1H, NH); 7.2 to 7.6 (m, 8H, aromatic); 8 (bs, 1H, H in position 2 on urea phenyl); 8.7 (bs, 1H, NH).

Infrared spectrum (KBr), characteristic bands in cm$^{-1}$: 3375, 3150, 3090, 3065, 3030, 2980, 2930, 2870, 1720, 1635, 1610, 1595, 1555, 1490, 1450, 1430, 1390, 1365, 1300, 1285, 1235, 1180, 1150, 1105, 1030, 860, 840, 755, 700, 685].

EXAMPLE 9

0.9 g of potassium hydroxide dissolved in 60 cm$^3$ of distilled water is added to a solution of 8 g of tert-butyl (2RS,5SR)-1-{2-[3-(3-ethoxycarbonylphenyl)ureido]acetyl}-5-phenylprolinate in 120 cm$^3$ of methanol. The reaction mixture is stirred for 3 hours at a temperature in the vicinity of 25° C. then concentrated to 50 cm$^3$ under reduced pressure. The solution obtained is diluted with 30 cm$^3$ of water, washed with 2 times 50 cm$^3$ of ethyl acetate, acidified to a pH of 2 with a 4N aqueous hydrochloric acid solution and extracted with 3 times 100 cm$^3$ of dichloromethane. The organic phases are combined, washed with 2 times 50 cm$^3$ of water, dried over magnesium sulphate and concentrated to dryness under reduced pressure at a temperature in the vicinity of 40° C. The crude product obtained is purified by chromatography on silica [eluent: dichloromethane/methanol (90/10 by volume)]. The fractions containing the expected product are combined and concentrated to dryness under reduced pressure. After recrystallization in ethyl acetate, 4.5 g of (2RS,5SR)-3-{2-[2-(2-tert-butyoxycarbonyl-5-phenyl-1-pyrrolidinyl)-2-oxoethyl]ureido}benzoic acid, melting at 236° C., are obtained.

EXAMPLE 10

By proceeding in a fashion similar to that described in Example 3, but starting from 1.8 g of N,N'-diimidazolecarbonyl, 3.1 g of tert-butyl (2RS,5SR)-1-(2-aminoacetyl)-5-phenylprolinate in solution in 100 cm$^3$ of anhydrous 1,2-dichloroethane and 1.4 g of 2-(3-aminophenyl)ethanol, after recrystallization in acetonitrile, 1.5 g of tert-butyl (2RS,5SR)-1-({2-{3-[3-(2-hydroxyethyl)phenyl]ureido}acetyl}-5-phenylprolinate, melting at 162° C., are obtained.

A—2-(3-Aminophenyl)ethanol may be prepared as follows: 0.75 g of 5% palladinized charcoal is added to a solution of 15 g of 2-(3-nitrophenyl)ethanol in 250 cm$^3$ of ethanol. The suspension is stirred for 2 hours at a temperature in the vicinity of 25° C. under a hydrogen atmosphere (130 kPa). The catalyst is separated by filtration and the filtrate is concentrated to dryness under reduced pressure at 45° C. 12 g of 2-(3-aminophenyl)ethanol thus obtained in the form of an orange oil, used as it is in subsequent syntheses.

EXAMPLE 11

By proceeding in a fashion similar to that described in Example 3, but starting from 3.6 g of N,N'-carbonyldiimidazole, 6.2 g of tert-butyl (2RS,5SR)-1-(2-aminoacetyl)-5-phenylprolinate in solution in 150 cm$^3$ of anhydrous 1,2-dichloroethane and 3.9 g of ethyl (E)-3-aminocinnamate, 4.8 g of ethyl (E)-3-{3-[2-((2RS,5SR)-2-tert-butoxycarbonyl-5-phenyl-1-pyrrolidinyl)-2-oxoethyl]ureido}cinnamate are obtained [proton NMR (250 MHz, DMSO D$_6$, δ in ppm, J in Hz), 2 rotamers at room temperature, peak coalescence at 120° C.: 1.3 (t, 3H, CH$_3$); 1.5 (bs, 9H, (CH$_3$)$_3$); 4.25 (q, 2H, CH$_2$O); 6.4 (d, 1H, J=15, CH= trans); 7.10 to 7.70 (m, 10H, aromatic and CH= trans). Infrared spectrum (KBr), characteristic bands in cm$^{-1}$: 3375, 3150, 3070, 3035, 2980, 2940, 2880, 1740, 1700, 1640, 1610, 1590, 1560, 1495, 1490, 1455, 1430, 1395, 1370, 1310, 1270, 1220, 1180, 1160, 1040, 990, 860, 840, 790, 760, 705, 685].

Ethyl (E)-3-aminocinnamate may be prepared according to the method described in the Patent Application NL 7416449 (C.A. 84,58882q).

EXAMPLE 12

By proceeding in a fashion similar to that described in Example 9, but starting from 3.7 g of ethyl (E)-3-{3-[2-((2RS,5SR)-2-tert-butoxycarbonyl-5-phenyl-1-pyrrolidinyl)-2-oxoethyl]ureido}cinnamate in solution in 60 cm$^3$ of methanol and 0.4 g of potassium hydroxide dissolved in 20 cm$^3$ of water and after treatment, 1 g of (E)-3-{3-[2-((2RS, 5SR)-2-tert-butoxycarbonyl-5-phenyl-1-pyrrolidinyl)-2-oxoethyl]ureido}cinnamic-acid is obtained [proton NMR (250 MHz, DMSO D$_6$, δ in ppm, J in Hz), 2 rotamers at room temperature, preponderant rotamer description, general description valid for the other products of the series: 1.5 (bs, 9H, (CH$_3$)$_3$; 1.9 and 2.2 (2m, 4H, H in position 3 and 4 on pyrrolidine); 3.2 and 3.9 (ABX, 2H, CH$_2$N); 4.35 (dd, 1H, H in position 2 on pyrrolidine); 5.20 (dd, 1H, H in position 5 on pyrrolidine); 6.30 (dd, 1H, NH); 6.4 (bd, 1H, J=15, CH= trans); 7.1 to 7.7 (m, 10H, aromatic and CH= trans); (s, 1H, NH). Infrared spectrum (KBr), characteristic bands in cm$^{-1}$: 3380, 3075, 3030, 3700 to 2250 with a maximum at 2475, 2980, 2935, 2875, 1735, 1705, 1695, 1640, 1610, 1590, 1560, 1495, 1450, 1430, 1395, 1370, 1315, 1250, 1225, 1155, 985, 910, 890, 860, 840, 790, 760, 705, 685].

EXAMPLE 13

By proceeding in a fashion similar to that described in Example 3, but starting from 3.6 g of N,N'-carbonyldiimidazole, 6.2 g of tert-butyl (2RS,5SR)-1-(2-aminoacetyl)-5-phenylprolinate in solution in 125 cm³ of anhydrous 1,2-dichloroethane and 3.9 of ethyl 3-(3-aminophenyl)propionate, after crystallization in a mixture of pentane/isopropanol (60/40 by volume), 5.3 g of ethyl (2RS,5SR)-3-{3-[2-(2-tert-butoxycarbonyl-5-phenyl-1-pyrrolidinyl)-2oxoethyl]ureido}-3-phenylpropionate, melting at 96° C., are obtained.

Ethyl 3-(3-aminophenyl)propionate may be prepared in a fashion similar to that described in Example 10 §A, but starting from 16.8 g of ethyl (E)-3-nitrocinnamate in solution in 500 cm³ of ethanol and 0.9 g of 5% palladinized charcoal. 14.2 g of ethyl 3-(3-aminophenyl)propionate are thus obtained in the form of an oil, used as it is in subsequent syntheses.

Ethyl (E)-3-nitrocinnamate may be prepared as follows: 5 cm³ of pure sulphuric acid are added to a solution of 31 g of (E)-3-nitrocinnamic acid in 300 cm³ of ethanol. The reaction mixture is stirred under reflux for 3 hours. After cooling and addition of 50 cm³ of water, the solution is concentrated to about 60 cm³ under reduced pressure at 40° C. 250 cm³ of ethyl acetate are added, the organic phase is then washed successively with 2 times 100 cm³ of a 2N aqueous sodium hydroxide solution, with 2 times 100 cm³ of water, then dried over magnesium sulphate and concentrated to dryness under reduced pressure at 40° C. 32 g of ethyl (E)-3-nitrocinnamate, melting at 70° C., are thus obtained.

(E)-3-Nitrocinnamic acid may be prepared as follows: a mixture of 30.2 g of 3-nitrobenzaldehyde, of 20.8 g malonic acid, of 15.8 g of pyridine and of 0.15 cm³ of piperidine is heated under reflux for 1 hour. After cooling, 50 cm³ of water are added and the insoluble product is separated by filtration, washed with 3 times 50 cm³ of water and dried in the air. 31 g of (E)-3-nitrocinnamic acid, melting at 205° C., are thus obtained.

EXAMPLE 14

By proceeding in a fashion similar to that described in Example 9, but starting from 3.9 g of ethyl (2RS,5SR)-3-{3-[2-(2-tert-butoxycarbonyl-5-phenyl-1-pyrrolidinyl)-2-oxoethyl]ureido}-3-phenylpropionate in solution in 60 cm³ of methanol and 0.45 g of potassium hydroxide dissolved in 20 cm³ of water and after treatment, 2.1 g of (2RS,5SR)-3-{3-[2-(2-tert-butoxycarbonyl-5-phenyl-1-pyrrolidinyl)-2oxoethyl]ureido}-3-phenylpropionic acid are obtained [proton NMR (250 MHz, DMSO D$_6$, δ in ppm), 2 rotamers at room temperature, peak coalescence at 120° C.; 15. (bs, 9H, (CH$_3$)$_3$); 2.5 (t, 2H, CH$_2$); 2.8 (t, 2H, CH$_2$); 6.8 to 7.60 (m, 9H, aromatic). Infrared spectrum (KBr), characteristic bands in cm$^{-1}$: 3380, 3700 to 2250 with a maximum at 2625, 3160, 3060, 3030, 2980, 2930, 2880, 1735, 1635, 1610, 1595, 1560, 1495, 1450, 1440, 1395, 1370, 1310, 1225, 1155, 905, 890, 865, 840, 790, 760, 705].

EXAMPLE 15

By proceeding in a fashion similar to that described in Example 3, but starting from 2.9 g of N,N'-carbonyldiimiidazole, 5 g of tert-butyl (2RS,5SR)-1-(2-aminoacetyl)-5-phenylprolinate insolution in 100 cm³ of anhydrous 1,2-dichloroethane and 3.2 g of ethyl 3-aminophenoxypropionate, 4.9 g of ethyl (2RS,5SR)-3-{3-[2-(2-tert-butoxycarbonyl-5-phenyl-1-pyrrolidinyl)-2-oxoethyl]ureido}phenoxyacetate are obtained [proton NMR (200 MHz, DMSO D$_6$, δ in ppm), 2 rotamers at room temperature, preponderant rotamer description: 1.15 (bt, 3H, ethyl CH$_3$); 1.50 (bs, 9H, (CH$_3$)$_3$); 4.2 (q, 2H, ethyl CH$_2$); 4.5 (bs, 2H, OCH$_2$CO); 6.4 (bd, 1H, H in position 6 on urea phenyl); 6.8 to 7.75 (m, 8H, aromatic). Infrared spectrum (KBr), characteristic bands in cm$^{-1}$: 3375, 3150, 3090, 3060, 3030, 2980, 2930, 2930, 2875, 1758, 1735, 1700, 1638, 1600, 1550, 1495, 1450, 1430, 1390, 1365, 1295, 1220, 1190, 1155, 1085, 1030, 860, 840, 760, 700, 690].

Ethyl 3-aminophenoxyacetate may be prepared as described in Example 10 §A, but starting from 18 g of ethyl 3-nitrophenoxyacetate in solution in 250 cm³ of ethanol and 0.2 g of 5% palladinized charcoal. 15 g of ethyl 3-aminophenoxyacetate are thus obtained in the form of an oil, used as it is in subsequent syntheses.

Ethyl 3-nitrophenoxyacetate may be prepared as follows: in the space of 20 minutes, 4.8 g of an oily suspension (50% by weight) of sodium hydride are added to a solution of 13.9 g of 3-nitrophenol in 125 cm³ of anhydrous dimethylformamide. The mixture obtained is stirred at a temperature in the vicinity of 25° C. for 30 minutes, then, in the space of 10 minutes, 10.8 cm³ of ethyl chloroacetate are added. The reaction mixture is stirred for 20 hours at a temperature in the vicinity of 20° C., then poured into 400 cm³ of water and extracted with 3 times 200 cm³ of ethyl acetate. The combined organic phases are dried over magnesium sulphate and concentrated to dryness under reduced pressure at a temperature of 35° C. 18 g of ethyl 3-nitrophenoxyacetate are obtained in the form of an orange oil, used as it is in subsequent syntheses.

EXAMPLE 16

By proceeding in a fashion similar to that described in Example 9, but starting from 3.7 g of ethyl (2RS,5SR)-3-{3-[2-(2-tert-butoxycarbonyl-5-phenyl-1-pyrrolidinyl)-2-oxoethyl]ureido}phenoxyacetate in solution in 80 cm³ of methanol and 0.4 g of potassium hydroxide dissolved in 40 cm³ of water. After treatment and recrystallization in isopropyl acetate, 1.4 g of (2RS,5SR)-3-{3-[2-(2-tert-butoxycarbonyl-5-phenyl-1-pyrrolidinyl)-2-oxoethyl]ureido}phenoxyacetic acid, melting at 192° C., are obtained.

EXAMPLE 17

By proceeding in a fashion similar to that described in Example 3, but starting from 3.6 g of N,N'-carbonyldiimidazole, 6.2 g of tert-butyl (2RS,5SR)-1-(2-aminoacetyl)-5-phenylprolinate in solution in 150 cm³ of anhydrous 1,2-dichloroethane and 4.2 g of ethyl 3-(aminophenylthio)acetate, 4.9 g of ethyl (2RS,5SR)-{3-{3-[2-(2-tert-butoxycarbonyl-5-phenyl-1-pyrrolidinyl)-2-oxoethyl]ureido}phenylthio}acetate are obtained [proton NMR (300 MHz, DMSO D$_6$, δ in ppm), 2 rotamers at room temperature, preponderant rotamer description: 1.2 (t, 3H, ethyl CH$_3$); 1.5 (bs, 9H, (CH$_3$)$_3$); 3.8 (bs, 2H, CH$_2$S); 4.2 (q, 2H, ethyl CH$_2$O); 6.9 to 7.7 (m, 9H, aromatic). Infrared spectrum (KBr), characteristic bands in cm$^{-1}$: 3365, 3130, 3085, 3065, 3030, 2980, 2930, 2875, 1735, 1700, 1635, 1585, 1545, 1480, 1498, 1425, 1450, 1395, 1365, 1305, 1295, 1275, 1220, 1150, 1030, 885, 865, 840, 780, 760, 700, 690].

Ethyl (3-aminophenylthio)acetate may be prepared as follows: in the space of 5 minutes, 16.7 g of ethyl bromoacetate are added to a solution of 12.5 g of 3-aminothiophenol in 250 cm³ of ethanol. The mixture is stirred at a temperature in the vicinity of 20° C. for 3 hours, then concentrated to dryness under reduced pressure at 40° C. The product obtained is dissolved in 100 cm³ of ethyl acetate and washed in 100 cm³ of a 1N aqueous sodium hydroxide solution. The organic phase is separated, washed with 2 times 50 cm³ of water, dried over magnesium sulphate and concentrated to dryness under reduced pressure. The product obtained is purified by chromatography on silica [eluent: ethyl acetate/cyclohexane (70/30 by volume)]. The fractions containing the expected product are combined and concentrated to dryness under reduced pressure at 40° C. 13 g of ethyl (3-aminophenylthio)acetate are thus obtained in the form of an oil, used as it is in subsequent syntheses.

EXAMPLE 18

By proceeding in a fashion similar to that described in Example 9, but starting from 4 g of ethyl (2RS,5SR)-{3-{3-[2-(2-tert-butoxycarbonyl-5-phenyl-1-pyrrolidinyl)-2-oxoethyl]ureido}phenylthio}acetate in solution in 80 cm³ of methanol and 0.45 g of potassium hydroxide dissolved in 40 cm³ of water and after treatment and crystallization in an isopropyl ether/isopropyl acetate mixture (50/50 by volume), 2 g of (2RS,5SR)-{3-{3-[2-(2-tert-butoxycarbonyl-5-phenyl-1-pyrrolidinyl)-2-oxoethyl] ureido}phenylthio}acetic acid, melting at 136° C., are obtained .

EXAMPLE 19

By proceeding in a fashion similar to that described in Example 3, but starting from 3.6 g of N,N'-carbonyldiimidazole, 6.2 g of tert-butyl (2RS,5SR)-1-(2-aminoacetyl)-5-phenylprolinate in solution in 150 cm³ of anhydrous 1,2-dichloroethane and 3.7 g of ethyl 5-aminosalicylate, 3.1 g of ethyl (2RS,5SR)-5-{3-[2-(2-tert-butoxycarbonyl-5-phenyl-1-pyrrolidinyl)-2-oxoethyl]ureido}salicylate, melting at 150° C., are obtained.

Ethyl 5-aminosalicylate may be prepared in a fashion similar to that described in Example 10 §A, but starting from 10 g of ethyl 5-nitrosalicylate in solution in 200 cm³ of ethanol and 0.5 g of 5% palladinized charcoal. 8.5 g of ethyl 5-aminosalicylate are thus obtained in the form of an orange oil, used as it is in subsequent syntheses.

Ethyl 5-nitrosalicylate may be prepared as follows: 3 cm³ of concentrated sulphuric acid are added to a solution of 10 g of 5-nitrosalicylic acid in 250 cm³ of ethanol. The reaction mixture is stirred to reflux for 70 hours. After cooling and addition of 50 cm³ of water, the solution is concentrated to about 60 cm³ under reduced pressure at 40° C. 250 cm³ of ethyl acetate are added, the organic phase is then washed with 2 times 100 cm³ of distilled water, dried over magnesium sulphate and concentrated to dryness under reduced pressure. The crude product obtained is purified by chromatography on silica [eluent: dichloromethane]. The fractions containing the expected product are combined and concentrated to dryness under reduced pressure at 40° C. 10 g of ethyl 5-nitrosalicylate, melting at 97° C., are thus obtained.

EXAMPLE 20

By proceeding in a fashion similar to that described in Example 9, but starting from 4.7 g of ethyl (2RS,5SR)-5-{3-[2-(2-tert-butoxycarbonyl-5-phenyl-1-pyrrolidinyl)-2-oxoethyl]ureido}salicylate in solution in 80 cm³ of methanol and 1.04 g of potassium hydroxide dissolved in 40 cm³ of water and after treatment, 2.3 g of (2RS,5SR)-5-{3-[2-(2-tert-butoxycarbonyl-5-phenyl-1-pyrrolidinyl)-2-oxoethyl]ureido}salicylic acid, melting at 190° C., are obtained.

EXAMPLE 21

By proceeding in a fashion similar to that described in Example 2, but starting from 6.2 g of tert-butyl (2RS,5SR)-1-(2-aminoacetyl)-5-phenylprolinate in solution in 150 cm³ of anhydrous tetrahydrofuran and 4.2 g of methyl 3-isocyanatophenylacetate, 6 g of methyl (2RS,5SR)-3-{3-[2-(2-tert-butoxycarbonyl-5-phenyl-1-pyrrolidinyl)-2-oxoethyl] ureido}phenylacetate are obtained [proton NMR (200 MHz, DMSO $D_6$, δ in ppm), 2 rotamers at room temperature, peak coalescence at 120° C.: 1.5 (s, 9H, $(CH_3)_3$); 3.6 (s, 2H, $CH_2CO$); 3.65 (s, 3H, $OCH_3$); 6.8 to 7.7 (m, 9H, aromatic). Infrared spectrum (KBr), characteristic bands in $cm^{-1}$: 3365, 3155, 3110, 3090, 3060, 3030, 2975, 2950, 2930, 2875, 1738, 1700, 1650, 1610, 1595, 1560, 1495, 1435, 1395, 1365, 1315, 1250, 1220, 1155, 1015, 905, 890, 860, 845, 780, 760, 700].

Methyl 3-isocyanatophenylacetate is prepared as follows: at a temperature in the vicinity of −20° C. and under argon, 8.25 g of methyl 3-aminophenylacetate in solution in 100 cm³ of toluene are added to a suspension of 1 g of charcoal and 6 cm³ of diphosgene in 70 cm³ of toluene. The reaction mixture is stirred and maintained at −20° C. for 15 minutes, then, after returning to a temperature in the vicinity of 20° C., heated under reflux for 2 hours and 30 minutes. The mixture is then degassed by bubbling through argon for 30 minutes, filtered on Celite, rinsed with 50 cm³ of dichloromethane and concentrated under reduced pressure at a temperature in the vicinity of 50° C. 9.30 g of methyl 3-isocyanatophenylacetate are thus obtained in the form of a yellow liquid stored under argon and used as it is in subsequent syntheses.

Methyl 3-aminophenylacetate may be prepared in a fashion similar to that described in Example 10 §A, but starting from 37.1 g of methyl 3-nitrophenylacetate in solution in 550 cm³ of methanol and 2 g of palladinized charcoal. 28.2 g of methyl 3-aminophenylacetate are thus obtained in the form of a dark yellow liquid used as it is in subsequent syntheses.

Methyl 3-nitrophenylacetate may be prepared according to the method described by SEGERS and A. BRUYLANTS, Bul. Soc. Chim. Belg., 64, 87, (1955).

EXAMPLE 22

By proceeding in a fashion similar to that described in Example 9, but starting from 4.9 g of methyl (2RS,5SR)-3-{3-[2-(2-tert-butoxycarbonyl-5-phenyl-1-pyrrolidinyl)-2-oxoethyl]ureido}phenylacetate in solution in 80 cm³ of methanol and 0.56 g of potassium hydroxide dissolved in 40 cm³ of water and after treatment, 1 g of (2RS,5SR)-3-{3-[2-(2-tert-butoxycarbonyl-5-phenyl-1-pyrrolidinyl)-2-oxoethyl]ureido}phenylacetic acid is obtained [proton NMR (200 MHz, DMSO $D_6$, δ in ppm), 2 rotamers at room temperature, peak coalescence at 120° C.: 1.5 (bs, 9H, $(CH_3)_3$); 3.5 (s, 2H, $CH_2CO$); 6.8 to 7.7 (m, 9H, aromatic). Infrared spectrum (KBr), characteristic bands in $cm^{-1}$: 3380, 3700 to 2250 with a maximum at 2625, 3155, 3110, 3090, 3060, 3030, 2975, 2930, 2880, 1735, 1635, 1610, 1595, 1560, 1495, 1450, 1395, 1365, 1310, 1225, 1155, 905, 890, 860, 840, 780, 760, 705].

EXAMPLE 23

By proceeding in a fashion similar to that described in Example 1 but starting from 2.2 g of ethyl (2RS,5SR)-5-phenylprolinate, 2.1 g of 2-[3-(3-methylphenyl)ureido]acetic acid in suspension in 50 cm³ of anhydrous 1,2-dichloroethane and 0.72 cm³ of sulphinyl chloride, 1.2 g of ethyl (2RS,5SR)-1-{2-[3-(3-methylphenyl)ureido]acetyl}-5-phenylprolinate, melting at 115° C., are obtained after recrystallization in acetonitrile.

Ethyl (2RS,5SR)-5-phenylprolinate may be prepared according to the method described by F. LEONARD, GB Patent 997097, [C.A., 62P, 9109● (1965)].

EXAMPLE 24

By proceeding in a fashion similar to that described in Example 3, but starting from 4.1 g of N,N'-carbonyldiimidazole, 7 g of ethyl (2RS,5SR)-1-(2-aminoacetyl)-5-phenylprolinate in solution in 135 cm³ of anhydrous 1,2-dichloroethane and 4.1 g of ethyl 3-aminobenzoate, 1.5 g of ethyl (2RS,5SR)-1-{2-[3-(3-ethoxycarbonylphenyl)ureido]acetyl}-5-phenylprolinate, melting at 136° C., are obtained.

Ethyl (2RS,5SR)-1-(2-aminoacetyl)-5-phenylprolinate may be prepared in a fashion similar to that described in Example 2 §A, but starting from 11.1 g of ethyl (2RS,5SR)-1-(2-tert-butoxycarbonylaminoacetyl)-5-phenylprolinate and 4.3 cm³ of iodotrimethylsilane in solution in 150 cm³ of anhydrous chloroform. 7 g of ethyl (2RS,5SR)-1-(2-aminoacetyl)-5-phenylprolinate, used as it is in subsequent syntheses, are thus obtained.

Ethyl (2RS,5SR)-1-(2-tert-butoxycarbonylaminoacetyl)-5-phenylprolinate may be prepared as described in Example 2 §B, but starting from a solution containing 7 g of ethyl (2RS,5SR)-5phenylprolinate, 5.6 g of 2-tert-butoxycarbonylaminoacetic acid and 6.6 g of N,N'-dicyclohexylcarbodiimide in 65 cm³ of anhydrous acetonitrile. 11.1 g of ethyl (2RS,5SR)-1-(2-tert-butoxycarbonylaminoacetyl)-5-phenylprolinate are thus obtained in the form of an orange oil, used as it is in subsequent syntheses.

EXAMPLE 25

By proceeding in a fashion similar to that described in Example 1, but starting from 2 g of cyclopropyl-methyl (2RS,5SR)-5-phenylprolinate, 1.7 g of 2-[3-(3-methylphenyl)ureido]acetic acid in suspension in 50 cm³ of anhydrous 1,2-dichloroethane and 0.6 cm³ of sulphinyl chloride, 1.1 g of cyclopropylmethyl (2RS,5SR)-1-{2-[3-(3-methylphenyl)ureido}acetyl-5-phenylprolinate, melting at 130° C., are obtained after recrystallization in acetonitrile.

A—Cyclopropylmethyl (2RS,5SR)-5-phenylprolinate may be prepared as follows: 1.5 cm³ of iodotrimethylsilane are added dropwise to a solution of 3.5 g of cyclopropylmethyl (2RS,5SR)-1-(tert-butoxycarbonyl)-5-phenylprolinate in 50 cm³ of anhydrous chloroform. The reaction mixture is stirred for 20 hours at a temperature in the vicinity of 25° C., then concentrated to dryness under reduced pressure at temperature of 45° C. The crude product obtained is purified by chromatography on silica [eluent: dichloromethane/methanol (97/3 by volume)]. The fractions containing the expected product are combined, then concentrated to dryness under reduced pressure. 2 g of cyclopropylmethyl (2RS,5SR)-5-phenylprolinate are thus obtained in the form of an orange oil, used as it is in subsequent syntheses.

B—Cyclopropylmethyl (2RS,5SR)-1-(tert-butoxycarbonyl)-5-phenylprolinate may be prepared as follows: 1.8 g of cyclopropylmethanol are added dropwise while stirring at a temperature in the vicinity of 0° C. to a solution of 7 g of (2RS,5SR)-1-(tert-butoxycarbonyl)-5-phenylproline and 4.6 g of para-toluenesulphonyl chloride in 40 cm³ of anhydrous pyridine. After returning to a temperature of 20° C., stirring is continued for 20 hours, the mixture is then poured into 100 cm³ of water and the product extracted with 3 times 100 cm³ of ethyl acetate. The combined organic phases are washed with 2 times 100 cm³ of water, with 2 times 100 cm³ of an N aqueous hydrochloric acid solution, with 2 times 100 cm³ of an N aqueous sodium hydroxide solution, then with 3 times 100 cm³ of water, dried over magnesium sulphate and concentrated to dryness under reduced pressure at a temperature in the vicinity of 45° C. The crude product obtained is purified by chromatography on silica [eluent: dichloromethane/methanol (97/3 by volume)]. The fractions containing the expected product are combined and concentrated to dryness under reduced pressure at a temperature in the vicinity of 45° C. 3.6 g of cyclopropylmethyl (2RS,5SR)-1-(tert-butoxycarbonyl-5-phenylprolinate are thus obtained in the form of an orange oil, used as it is in subsequent syntheses.

C—(2RS,5SR)-1-(tert-butoxycarbonyl)-5phenylproline may be prepared as follows: 21.8 g of di-tert-butyl dicarbonate in solution in 120 cm³ of dioxane are added dropwise to a solution of 22.8 g of (2RS,5SR)-5-phenyl-proline hydrochloride and 22 g of sodium carbonate in 160 cm³ of water with stirring. The reaction mixture is stirred for 20 hours at a temperature in the vicinity of 20° C. and then the precipitate formed is removed by filtration. The filtrate is washed with 2 times 100 cm³ of ethyl acetate and acidified to a pH of 1 by a 4N aqueous hydrochloric acid solution. The acid aqueous phase is extracted with 3 times 150 cm³ of dichloromethane. The combined organic extracts are washed with 2 times 50 cm³ of water, dried over magnesium sulphate and concentrated to dryness under reduced pressure at a temperature in the vicinity of 40° C. After recrystallization in acetonitrile, 24 g of (2RS,5SR)-1-(tert-butoxycarbonyl)-5-phenyl-proline, melting at 170° C., are obtained.

EXAMPLE 26

By proceeding in a fashion similar to that described in Example 1, but starting from 3 g of isopropyl (2RS,5SR)-5-phenylprolinate, 2.7 g of 2-[3-(3-methylphenyl)ureido] acetic acid in a suspension in 75 cm³ of anhydrous 1,2-dichloroethane and 1 cm³ of sulphinyl chloride, 1.2 g of isopropyl (2RS,5SR)-1-{2-[3-(3-methylphenyl)ureido] acetyl}-5-phenylprolinate are obtained after purification [proton NMR (200 MHz, CDCl₃, δ in ppm), 2 rotamers at room temperature, preponderant rotamer description: 1.1 (d, 6H, (CH₃)₂); 1.7 to 2.5 (m, 4H, H in position 3 and 4 on pyrrolidine); 2.15 (s, 3H, CH₃); 3 and 4.1 (2bd, 2H, CH₂N); 4.4 (bt, 1H, H in position 2 on pyrrolidine); 4.9 (m, 2H, isopropyl CH and H in position 5 on pyrrolidine); 6.6 to 7.5 (m, 9H, aromatic). Infrared spectrum (KBr), characteristic bands in cm⁻¹: 3365, 3150, 3060, 3030, 2980, 2935, 2875, 1738, 1700, 1645, 1615, 1595, 1560, 1495, 1450, 1430, 1375, 1305, 1295, 1280, 1210, 1190, 1145, 1120, 915, 890, 860, 780, 755 705].

Isopropyl (2RS,5SR)-5-phenylprolinate may be prepared in a fashion similar to that described in Example 25 §A, but starting from 5 g of isopropyl (2RS,5SR)-1-(tert-butoxycarbonyl)-5-phenylprolinate and 2.4 cm³ of iodotrimethylsilane in solution in 50 cm³ of anhydrous chloroform. 3 g of isopropyl (2RS,5SR)-5-phenylprolinate are thus obtained in the form of a yellow oil, used as it is in subsequent syntheses.

Isopropyl (2RS,5SR)-1-(tert-butoxycarbonyl)-5-phenylprolinate may be prepared as described in Example 25 §B, but starting from 5.85 g of (2RS,5SR)-1-(tert-butoxycarbonyl)-5-phenylproline, 3.85 g of paratoluenesulphonyl chloride and 1.6 g of 2-propanol in 30 cm³ of anhydrous pyridine. After treatment, 5 g of isopropyl (2RS,5SR)-1-(tert-butoxycarbonyl)-5-phenylprolinate are obtained in the form of a yellow oil, used as it is in subsequent syntheses.

EXAMPLE 27

The enantiomers of tert-butyl (2RS,5SR)-1-{2-[3-(3-methylphenyl)ureido]-acetyl}-5-phenylprolinate were separated by PIRCKLE-type chiral phase high performance liquid chromatography, using 400 g of (D)-N-3,5-dinitrobenzoylphenylglycine, grafted on aminopropyl silica as the stationary phase packed in a 200 mm long column of 80 mm diameter with, as the mobile phase, a hexane/2-propanol/methylene chloride mixture (85/7.5/7.5). 1 g of racemic mixture yields: 0.48 g of tert-butyl (2S,5R)-1-{2-[3-(3-methylphenyl)ureido]-acetyl}-5-phenylprolinate, melting at 79° C., $[\alpha]_D^{20}=+33.4°\pm0.9°$ (c=1; methanol) [proton NMR (300 MHz, DMSO $D_6$, δ in ppm), 2 rotamers at room temperature, preponderant rotamer description: 1.5 (s, 9H, $(CH_3)_3$); 1.9 and 2.2 (2m, 4H, H in position 3 and 4 on pyrrolidine); 2.2 (s, 3H, $CH_3$); 3.2 and 3.9 (ABX, 2H, $CH_2N$; 4.35 (dd, 1H, H in position 2 on pyrrolidine); 5.20 (dd, 1H, H in position 5 on pyrrolidine; 6.30 (dd, 1H, NH); 6.70 (bd, 1H, H in position 4 on urea phenyl); 7.1 to 7.7 (m, 8H, aromatic); 8.7 (s, 1H, NH)].

0.48 g of tert-butyl (2R,5S)-1-{2-[3-(3-methylphenyl)ureido]-acetyl}-5-phenylprolinate, melting at 79° C., $[\alpha]_D^{20}=-31.6°\pm0.8°$ (c=1; methanol). The support may be prepared as follows: 600 g of aminopropyl silica (100 Å—10 μm—$NH_2$; Macherey-Nagel) in 2 l of dimethylformamide are suspended in a six liter three-necked flask. 95 g of N-11-tert-butoxycarbonylaminoundecanoic acid anhydride are added and the reaction mixture is stirred for 18 hours at a temperature in the vicinity of 20° C. The silica is separated by filtration and washed successively with two times 1500 cm³ of dichloromethane, then with two times 1500 cm³ of dimethylformamide. The silica washed in this fashion is resuspended in 2 l of dimethylformamide and 95 g of N-11-tertbutoxycarbonylaminoundecanoic acid anhydride are added, and the reaction mixture is then stirred for 18 hours at a temperature in the vicinity of 20° C. The silica is separated by filtration, washed successively with two times 600 cm³ of dichloromethane, with two times 600 cm³ of tetrahydrofuran, with methanol and with two times 600 cm³ of diethyl ether and then dried under reduced pressure at a temperature in the vicinity of 20° C. 610 g of silica referred to by the designation "BOC-$C_{11}$-$C_3$-silica" are thus obtained in the form of a white powder, the structure of which is confirmed by the infrared spectrum and for which the elemental analysis (found) is: C %=8.8; H %=1.7; N %=1.2.

607 g of "BOC-$C_{11}$-$C_3$-silica" silica are suspended in a six liter three-necked flask in 2 l of dichloromethane and 69 cm³ of pyridine. 530 cm³ of dimethyloctylchlorosilane are added dropwise and the reaction mixture is stirred for 16 hours at a temperature in the vicinity of 20° C. The solid obtained is separated by filtration and washed successively with two times 1 l of dichloromethane, with two times 1 l of methanol, with two times 1 l of tetrahydrofuran, with two times 1 l of dichloromethane and with two times 1 l of diethyl ether, then dried under reduced pressure at a temperature in the vicinity of 20° C. 712 g of silica referred to by the designation "BOC-$C_{11}$-$C_3$-silica-O—$Si(CH_3)_2(CH_2)_7CH_3$" are thus obtained in the form of a white powder, the structure of which is confirmed by the infrared spectrum and for which the elemental analysis (found) is: C %=12.1; H %=2.4; N %=1.0.

711 g of "BOC-$C_{11}$-$C_3$-silica-O—$Si(CH_3)_2(CH_2)_7CH_3$" silica are suspended in a six liter three-necked flask in 2200 cm³ of a 6% by volume solution of trifluoroacetic acid in dichloromethane. The reaction mixture is stirred for 5 hours at a temperature in the vicinity of 20° C. The silica is separated by filtration and washed successively with two times 1 l of dichloromethane, with two times 1 l of a dichloromethane/diisopropylethylamine (70/30 by volume) mixture, with 1 l of dichloromethane, with two times 1 l of tetrahydrofuran, with two times 1 l of methanol and with 2 times 1 l of diethyl ether, then dried under reduced pressure at a temperature in the vicinity of 50° C. The silica washed and dried in this fashion is resuspended in 2 l of a 6% by volume solution of trifluoroacetic acid in dichloromethane. The reaction mixture is stirred for 16 hours at a temperature in the vicinity of 20° C. The silica is separated by filtration and washed successively with two times 1.5 l of dichloromethane, with two times 1 l of a dichloromethane/diisopropylethylamine (70/30 by volume) mixture, with 1.5 l of dichloromethane, with two times 2 l of tetrahydrofuran, with two times 2 l of methanol and with two times 2 l of diethyl ether, then dried under reduced pressure at a temperature in the vicinity of 50° C. 607 g of silica referred to by the designation "$C_{11}$-$C_3$-silica-O—$Si(CH_3)_2(CH_2)_7CH_3$" are thus obtained in the form of a white powder, the structure of which is confirmed by the infrared spectrum and for which the elemental analysis (found) is: C %=8.8; H %=1.7; N %=1.3.

400 g of "$C_{11}$-$C_3$-silica-O—$Si(CH_3)_2(CH_2)_7CH_3$" silica are suspended in a four liter three-necked flask in 1800 cm³ of dimethylformamide. 42 g of 3,5-dinitrobenzoyl-D-phenylglycine and 30 g of 2-ethoxy-1-ethoxycarbonyl-1,2-dihydroquinoline are added and the reaction mixture is stirred for 16 hours at a temperature in the vicinity of 20° C. The silica is separated by filtration and washed successively with two times 1 l of dichloromethane, with two times 1 l of tetrahydrofuran, with two times 1 l of methanol and with two times 1 l of diethyl ether. The silica washed in this way is resuspended in 2 l of dimethylformamide and 30 g of 2-ethoxy-1-ethoxycarbonyl-1,2-dihydroquinoline and 42 g of 3,5-dinitrobenzoyl-D-phenylglycine are added, then the reaction mixture is stirred for 5 hours at a temperature in the vicinity of 20° C. The silica is separated by filtration, washed successively with two times 1 l of dimethylformamide, with two times 1 l of dichloromethane, with two times 1 l of tetrahydrofuran, with two times 1 l of methanol and with two times 1 l of diethyl ether, and then dried under reduced pressure at a temperature in the vicinity of 140° C. 434 g of silica referred to by the designation "DNB-D-Phg-$C_{11}$-$C_3$-silica-O($CH_3)_2$—$(CH_2)_7CH_3$" are thus obtained in the form of a white powder, the structure of which is confirmed by the infrared spectrum and for which the elemental analysis (found) is: C %=12.3; H %=1.8; N %=2.1.

434 g of "DNB-D-Phg-$C_{11}$-$C_3$-silica-O—$Si(CH_3)_2(CH_2)_7CH_3$" silica are suspended in a four liter three-necked flask in 1.3 l of dichloromethane and 100 cm³ of dimethyloctylmethoxysilane are added, and then the reaction mixture is stirred for 54 hours at a temperature in the vicinity of 20° C. The silica is separated by filtration, washed successively with two times 1 l of dichloromethane, with two times 1 l of methanol, with two times 1 l tetrahydrofuran and with two times 1 l of dichloromethane, then dried under reduced pressure at a temperature in the vicinity of 140° C. 425 g of silica referred to by the designation "reoctylated DNB-D-Phg-C$_{11}$-C$_3$-silica-OSi(CH$_3$)$_2$(CH$_2$)$_7$CH$_3$" are is thus obtained in the form of a white powder, the structure of which is confirmed by the infrared spectrum and for which the elemental analysis (found) is: C %=12.7; H %=1.9; N %=2.0.

425 g of "Reoctylated DNB-D-Phg-C$_{11}$-C$_3$-silica-OSi(CH$_3$)$_2$—(CH$_2$)$_7$CH$_3$" silica are suspended in a four liter three-necked flask in 1.3 l of dichloromethane. 545 cm$^3$ of trimethylsilylimidazole are added dropwise and the reaction mixture is stirred for 15 hours at a temperature in the vicinity of 20° C. The solid obtained is separated by filtration and washed successively with two times 1 l of tetrahydrofuran, with two times 1 l of methanol, with two times 1 l of acetone and with two times 1 l of dichloromethane, then dried under reduced pressure at a temperature in the vicinity of 20° C. 431 g of silica referred to by the designation "DNB-D-Phg-C$_{11}$-C$_3$-silica-[OSi(CH$_3$)$_2$(CH$_2$)$_7$CH$_3$]—[O—Si(CH$_3$)$_3$]" are thus obtained in the form of a white powder, the structure of which is confirmed by the infrared spectrum and for which the elemental analysis (found) is: C %=13.7; H %=2.2; N %=2.0.

N-11-tert-Butoxycarbonylaminoundecanoic acid anhydride may be prepared as follows: in the space of 10 minutes, a solution of 10.63 g of N,N'-dicyclohexylcarbodiimide in 120 cm$^3$ of ethyl acetate are added to a solution of 30.1 g of N-11-tertbutoxycarbonylaminoundecanoic acid in 480 cm$^3$ of ethyl acetate, kept at a temperature in the vicinity of 5° C. The reaction mixture is stirred for 1 hour at a temperature in the vicinity of 5° C., then for 16 hours at a temperature in the vicinity of 20° C. The precipitate formed is separated by filtration and washed with 30 cm$^3$ of ethyl acetate. The filtrate is concentrated under reduced pressure at 30° C. The solid obtained is dried under vacuum at a temperature in the vicinity of 30° C. 31 g of N-11-tertbutoxycarbonylaminoundecanoic acid anhydride, melting at 58° C., are thus obtained.

N-11-tert-Buxotycarbonylaminoundecanoic acid may be prepared according to the method described by J. T. SPARROW, J. Org. Chem., 41, 1350 (1976).

EXAMPLE 28

0.05 cm$^3$ of 3-methylphenyl isocyanate is added to a solution of 0.08 g of tert-butyl (2S,5R)-1-(2-aminoacetyl)-5-phenylprolinate in 10 cm$^3$ of anhydrous tetrahydrofuran. The reaction mixture is stirred for 3 hours at a temperature in the vicinity of 25° C., the solvent is then evaporated under reduced pressure at 45° C. The crude product obtained is purified by chromatography on silica [eluent: dichloromethane/methanol (98/2 by volume)]. The fractions containing the expected product are combined and concentrated to dryness under reduced pressure. 0.04 g of tert-butyl (2S,5R)-1-{2-[3-(3-methylphenyl)ureido]acetyl}-5-phenylprolinate is thus obtained, the analytical data for which are in agreement with those for the dextrorotatory enantiomer prepared by chiral stationary phase chromatography of the racemic product, ([α]$_D^{20}$=±35.6°±0.8° (C=0.11%; MeOH)).

tert-Butyl (2S,5R)-1-(2-aminoacetyl)-5-phenylprolinate may be prepared as follows: 0.1 cm$^3$ of concentrated sulphuric acid is added to a solution of 0.08 g of (2S,5R)-1-(2-tert-butoxycarbonylaminoacetyl)-5-phenylpyrrolidine-2-carboxylic acid in 20 cm$^3$ of chloroform cooled to 5° C. The reaction mixture is saturated with isobutene for 2 hours while stirring and maintaining the temperature at 5° C. After returning to a temperature in the vicinity of 20° C., stirring is continued for 20 hours. The solution is brought to a pH of 8 by addition of a 10% aqueous sodium bicarbonate solution and the aqueous phase is separated, then extracted with 3 times 30 cm$^3$ of chloroform. The combined organic phases are washed with 2 times 10 cm$^3$ of water, dried over magnesium sulphate and concentrated to dryness under reduced pressure at 40° C. 0.08 g of tert-butyl (2S,5R)-1-(2-aminoacetyl)-5-phenylprolinate is thus obtained in the form of a yellow-orange oil, used as it is in subsequent syntheses.

(2S,5R)-1-(2-tert-Butoxycarbonylaminoacetyl)-5-phenylpyrrolidine-2-carboxylic acid may be prepared as follows: 0.5 cm$^3$ of a 1N aqueous sodium hydroxide solution is added to a solution of 0.16 g of methyl (2S,5R)-1-(2-tert-butoxycarbonylaminoacetyl)-5-phenylprolinate in 15 cm of a dioxane/water (70/30 by volume) mixture cooled to 5° C. After returning to a temperature in the vicinity of 20° C. stirring is continued for 12 hours, then 0.5 cm$^3$ of a 1N aqueous sodium hydroxide solution is added again. After stirring for 3 hours at a temperature in the vicinity of 20° C., the reaction mixture is washed with 2 times 10 cm$^3$ of ether, then brought to a pH in the vicinity of 2 by addition of 20 cm$^3$ of a 0.1N aqueous hydrochloric acid solution. The reaction mixture is extracted with 3 times 40 cm$^3$ of ethyl acetate. The combined organic phases are dried over magnesium sulphate and concentrated to dryness under reduced pressure at 35° C. 0.09 g of (2S,5R)-1-(2-tert-butoxycarbonylaminoacetyl)5-phenylpyrrolidine-2-carboxylic acid is thus obtained in the form of a colorless resin, used as it is in subsequent syntheses.

Methyl (2S,5R)-1-(2-tert-butoxycarbonylaminoacetyl)-5-phenylprolinate may be prepared as follows: 0.12 g of N,N'-dicyclohexylcarbodiimide is added in one portion to a solution of 0.1 g of methyl (2S,5R)-5-phenylprolinate and 0.1 g 2-tertbutoxycarbonylaminoacetic acid in 10 cm$^3$ of anhydrous acetonitrile kept at a temperature in the vicinity of 0° C. The reaction mixture is stirred for 16 hours at a temperature in the vicinity of 25° C., then the insoluble product is separated by filtration and washed with three times 5 cm$^3$ of dichloromethane. The filtrate is concentrated to dryness under reduced pressure at 40° C. The oily residue obtained is purified by chromatography on silica [eluent: ethyl acetate/cyclohexane (30/70 by volume)]. The fractions containing the expected product are combined and concentrated to dryness under reduced pressure at 40° C. 0.16 g of methyl (2S,5R)-1-(2-tert-butoxycarbonylaminoacetyl)-5-phenylprolinate is thus obtained in the form of a colorless oil, used as it is in subsequent syntheses.

Methyl (2S,5R)-5-phenylprolinate may be prepared as follows: 0.45 cm$^3$ of iodotrimethylsilane is added dropwise at a temperature in the vicinity of 25° C. to a solution of 0.6 g of methyl (2S,5RS)-1-methoxycarbonyl-5-phenylprolinate in 15 cm$^3$ of chloroform. The mixture is heated under reflux for 18 hours. After cooling to a temperature in the vicinity of 25° C., 20 cm$^3$ of water are added. The aqueous phase is separated, then extracted with 2 times 20 cm$^3$ of chloroform. The organic phases are combined, washed with 2 times 10 cm$^3$ of water, dried over magnesium sulphate and concentrated to dryness under reduced pressure at 40° C. The mixture of the two diastereoisomers obtained is purified by chromatography on silica [eluent: ethyl acetate/cyclohexane (30/70 by volume)]. The fractions containing the expected product are combined and concentrated to dryness under reduced pressure at 40° C. 0.12 g of methyl (2S,5R)-5-phenylprolinate is thus obtained in the form of an oil used as it is in subsequent syntheses.

Methyl (2S,5RS)-1-methoxycarbonyl-5-phenylprolinate may be prepared as follows: 3.1 g of aluminium trichloride are added to a solution of 5.1 g of methyl (2S,5RS)-5-methoxy-1-methoxycarbonylprolinate in 400 cm$^3$ of benzene cooled to a temperature in the vicinity of 5° C. The reaction mixture is kept at a temperature in the vicinity of 25° C. for 12 hours while stirring, then 50 cm$^3$ of saturated aqueous sodium bicarbonate solution are added. The aluminium hydroxides are separated by filtration and washed with times 20 cm$^3$ of methylene chloride. The combined organic phases are washed with 2 times 50 cm$^3$ of water, dried over magnesium sulphate and concentrated to dryness under reduced pressure at 40° C. The oily residue obtained is purified by cbxomatography on silica [eluent: ethyl acetate/cyclohexane (20/80 by volume)]. The fractions containing the expected product are combined and concentrated to dryness under reduced pressure at 40° C. 0.6 g of methyl (2S,5RS)-1-methoxycarbonyl-5-phenylprolinate is thus obtained in the form of a pale yellow oil, a (40/60 by weight) mixture of the (2S,5R) and (2S,5S) isomers used as it is in subsequent syntheses.

Methyl (2S,5RS)-5-methoxy-1-methoxycarbonylprolinate may be prepared according to the method described by T. SHONO et al., J. Am. Chem. Soc., 104, 6697 (1982).

EXAMPLE 29

The enantiomers of (2RS,5SR)-3-{3-[2-(2-tertbutoxycarbonyl-5-phenyl-1-pyrrolidinyl)-2-oxoethyl]ureido}benzoic acid were separated by PIRCKLE-type chiral phase high performance liquid chromatography, using 400 g of (D)-N-3,5-dinitrobenzoylphenyl-glycine, grafted on aminopropyl silica, as the stationary phase, packed in a 220 mm long column of 70 mm diameter with, as the mobile phase, a heptane/2-propanol/trifluoroacetic acid (80/20/0.05 by volume) mixture. 3.5 g of the racemic mixture yield:

0.72 g of (2S,5R)-3-{3-[2-(2-tert-butoxycarbonyl-5-phenyl-1-pyrrolidinyl)-2-oxoethyl]ureido}benzoic acid, melting at 204° C., $[\alpha]_D^{20}$=+32.3°±0.7° (c=1.08; methanol).

0.54 g of (2R,5S)-3-{3-[2-(2-tert-butoxycarbonyl-5-phenyl-1-pyrrolidinyl)-2-oxoethyl]ureido}benzoic acid, melting at 140° C., $[\alpha]_D^{20}$=33.1°±0.8° (c=1.03; methanol).

EXAMPLE 30

By proceeding in a fashion similar to that described in Example 2, but starting from 2 g of cis-1-(2-aminoacetyl)-2,5-diphenylpyrrolidine and 0.9 cm$^3$ of 3-methylphenyl isocyanate in solution in 25 cm$^3$ of anhydrous tetrahydrofuran, 1.4 g of (2RS,5SR)-1-[2-(2,5-diphenyl-1-pyrrolidinyl)-2-oxoethyl]-3-(3-methylphenyl)urea, melting at 168° C., are obtained after recrystallization in 2-propanol.

cis-1-(2-Aminoacetyl)-2,5-diphenylpyrrolidine may be prepared in a fashion similar to that described in Example 2 §A, but starting from 6.6 g of cis-1-(2-tert-butoxycarbonylaminoacetyl)-2,5-diphenylpyrrolidine and 2.5 cm$^3$ of iodotrimethylsilane in solution in 70 cm$^3$ of anhydrous chloroform. 4.8 g of cis-1-(2-aminoacetyl)-2,5-diphenylpyrrolidine are thus obtained in the form of an orange oil, used as it is in subsequent syntheses.

Proton NMR (300 MHz, DMSO D$_6$, δ in ppm), 2 rotamers at room temperature, 1.8 to 2.4 (bm, 4H, CH$_2$—CH$_2$); 2.7 and 3.3 (bd, 2H, AB, CH$_2$CO$_2$); 5.0 (bm, 1H, CHN); 5.2 (bm, 1H, CHN); 7.2 to 7.5 (m, 10H, aromatic).

Mass (electron impact, 70 eV, m/z), 280 (M$^+$), 263 (M$^+$—NH$_2$), 222 (M$^+$—COCH$_2$NH$_2$), 91 (C$_6$H$_5$CH$_2^+$).

cis-1-(2-tert-Butoxycarbonylaminoacetyl)-2,5-diphenylpyrrolidine may be prepared as described in Example 2 §B, but starting from a solution of 6.6 g of 2,5-diphenylpyrrolidine (mixture of the cis/trans isomers), 5.2 g of 2-(tert-butoxycarbonylamino)acetic acid and 6.1 g of N,N'-dicyclohexylcarbodiimide in 50 cm$^3$ of anhydrous acetonitrile. After separation by chromatography on silica [eluent: dichloromethane/methanol (98/2 by volume)], 3.6 g of cis-1-(2-tert-butoxycarbonylaminoacetyl)-2,5-diphenylpyrrolidine are obtained in the form of an orange oil, used as it is in subsequent syntheses.

2,5-Diphenylpyrrolidine (mixture of the cis/trans isomers) may be prepared according to the method described by C. G. OVERBERGER, M. VALENTINE and J-P. ANSELME, J. Amer. Chem. Soc., 91, 687–94 (1969).

EXAMPLE 31

By proceeding in a fashion similar to that described in Example 9, but starting from 3 g of ethyl (cis)-3-{3-[2-(2,5-diphenyl-1-pyrrolidinyl)-2-oxoethyl]ureido}benzoate in solution in 50 cm$^3$ of methanol and 0.7 g of potassium hydroxide dissolved in 20 cm$^3$ of water and after treatment and recrystallization in ethanol, 2 g of (cis)-3-{3-[2-(2,5-diphenyl-1-pyrrolidinyl)-2-oxoethyl]ureido}benzoic acid, melting at 255° C., are obtained.

Ethyl (cis)-3-{3-[2-(2,5-diphenyl-1-pyrrolidinyl)-2-oxoethyl]ureido}benzoate may be prepared in a fashion similar to that described in Example 3, but starting from 3.4 g of cis-1-(2-aminoacetyl)-2,5-diphenylpyrrolidine, 2.2 g of N,N'-carbonyldiimidazole in solution in 75 cm$^3$ of anhydrous 1,2-dichoroethane and 2 g of ethyl 3-aminobenzoate. After purification, 3 g of ethyl (cis)-3-{3-[2-(2,5-diphenyl-1-pyrrolidinyl)-2-oxoethyl]ureido}benzoate are obtained in the form of a white meringue-like product, used as it is in subsequent syntheses.

EXAMPLE 32

Proceeding in a fashion similar to that described in Example 2, but starting from 1.8 g of tert-butyl (2RS,5SR)-1-(2-aminoacetyl)-6-phenyl-2-piperidinecarboxylate in solution in 30 cm$^3$ of anhydrous tetrahydrofuran, 0.7 cm$^3$ of 3-methylphenyl isocyanate is added. After recrystallization in diisopropyl ether, 0.7 g of tert-butyl (2RS,5SR)-1-{2-[3-(3-methylphenyl)ureido]acetyl}-6-phenyl-2piperidinecarboxylate, melting at 123° C., is obtained.

tert-Butyl (2RS,5SR)-1-(2-aminoacetyl)-6-phenyl-2-piperidinecarboxylate may be prepared in a fashion similar to that described in Example 2 §A, but starting from 5.9 g of tert-butyl (2RS,5SR)-1-(2-tert-butoxycarbonylaminoacetyl)-6-phenyl-2-piperidinecarboxylate and 2 cm$^3$ of iodotrimethylsilane in solution in 50 cm$^3$ of anhydrous chloroform. 1.8 g of tert-butyl (2RS,5SR)-1-(2-aminoacetyl)-6-phenyl-2-piperidinecarboxylate are obtained in the form of an orange oil, used as it is in subsequent syntheses.

Mass (electron impact, 70 eV, m/z), 318 (M$^+$), 159 (M$^+$—COCH$_2$NH$_2$ and —CO$_2$tBu).

tert-Butyl (2RS,5SR)-1-(2-tert-butoxycarbonylaminoacetyl)-6-phenyl-2-piperidinecarboxylate may be prepared as described in Example 2 §B, but starting from a solution of 5.1 g of tert-butyl (2RS,5SR)-6-phenyl-2-piperidinecarboxylate, 3.4 g of 2-(tert-butoxycarbonyl-amino)acetic acid and 4 g of N,N'-dicyclohexylcarbo-diimide in solution in 90 cm³ of anhydrous acetonitrile. 5.9 g of tert-butyl (2RS,5SR)-1-(2-tert-butoxycarbonyl-aminoacetyl)-6-phenyl-2-piperidinecarboxylate are obtained in the form of an orange oil, used as it is in subsequent syntheses.

tert-Butyl (2RS,5SR)-6-phenyl-2-piperidinecarboxylate may be prepared in a fashion similar to that described in Example 1 §B, but starting from 14 g of (2RS,5SR)-6-phenyl-2-piperidinecarboxylic acid hydrochloride in suspension in a mixture of 5 cm³ of concentrated sulphuric acid in 250 cm³ of anhydrous chloroform. The mixture is saturated with isobutene. After treatment, 5.2 g of tert-butyl (2RS,5SR)-6-phenyl-2-piperidinecarboxylate, melting at 68° C., are obtained.

(2RS,5SR)-6-phenyl-2-piperidinecarboxylic acid hydrochloride may be prepared as follows: 14 g of 6-phenyl-2,3,4,5-tetrahydro-2-pyridinecarboxylic acid hydrochloride and 0.7 g of platinum oxide in suspension in 200 cm³ of ethanol are stirred for 3 hours at a temperature in the vicinity of 20° C. under a hydrogen atmosphere (130 kPa). The catalyst is removed by filtration and the filtrate is concentrated to dryness under reduced pressure at 45° C. After recrystallization in acetonitrile, 14 g of (2RS,5SR)-6-phenyl-2-piperidinecarboxylic acid hydrochloride, melting at 184° C., are obtained.

6-Phenyl-2,3,4,5-tetrahydro-2-pyridinecarboxylic acid hydrochloride may be prepared as follows: 38.3 g of ethyl acetamidomalonate are added to a solution of sodium ethylate, prepared from 4.1 g of sodium in 180 cm³ anhydrous ethanol. After stirring for 1 hour at a temperature in the vicinity of 20° C., 40 g of 2-(3-chloropropyl)-2-phenyl-1,3-dioxolane and 2.1 g of potassium iodide are poured into the mixture. The reaction mixture is heated under reflux for 24 hours, then concentrated to dryness under reduced pressure at a temperature in the vicinity of 45° C. The pasty residue is taken up in 400 cm³ of dichloromethane, washed with 3 times 100 cm³ of water, dried over magnesium sulphate and concentrated to dryness under reduced pressure. The crude product is purified by chromatography on silica [eluent: dichloromethane]. The fractions containing the expected product are combined and concentrated to dryness under reduced pressure. 25 g of an orange oil which are suspended in 102 cm³ of water and in 102 cm³ of 12N hydrochloric acid are thus obtained. The reaction mixture is heated under reflux while stirring for 5 hours. After cooling, the acid solution is washed with 3 times 100 cm³ of diethyl ether, then concentrated to dryness under reduced pressure at a temperature in the vicinity of 50° C. After recrystallization in acetonitrile, 14 g of 6-phenyl-2,3,4,5-tetrahydro-2-pyridinecarboxylic acid hydrochloride, melting at 146° C., are obtained.

2-(3-Chloropropyl)-2-phenyl-1,3-dioxolane may be prepared according to the method described by M. T. WILLS, J. E. WILLS, L. Von DOLLEN, B. L. BUTLER and J. PORTER. J. Org. Chem., 45 (12), 2495 (1980)

EXAMPLE 33

In the space of 10 minutes, a solution of 0.48 g of N,N'-dicyclohexylcarbodiimide in 10 cm³ of anhydrous acetonitrile is added to a suspension of 0.5 g of tert-butyl (2S,5R)-5-(2-furyl)prolinate and 0.48 g of 2-[3-(3-methylphenyl)ureido]acetic acid in 50 cm³ of an anhydrous mixture of acetonitrile/1,2-dichloroethane (80/20 by volume) kept at a temperature in the vicinity of 0° C. The reaction mixture is stirred for 16 hours at a temperature in the vicinity of 25° C., then the insoluble product is separated by filtration and washed with three times 5 cm³ of dichloromethane. The filtrate is concentrated to dryness under reduced pressure at 40° C. The oily residue obtained is purified by chromatography on silica [eluent: ethyl acetate/cyclohexane (40/60 by volume)]. The fractions containing the expected product are combined, then concentrated to dryness under reduced pressure at 40° C. After recrystallization in an ethyl acetate/cyclohexane (50/50 by volume) mixture, 0.15 g of tert-butyl (2S,5R)-5-(2-furyl)-1-{2-[3-(3-methylphenyl)ureido]acetyl}prolinate, melting at 144° C., is obtained ($[\alpha]_D^{20}$=+4.8°±0.8° (C=0.51%; MeOH)) [proton NMR (250 MHz, DMSO D$_6$, δ in ppm), 2 rotamers at room temperature, coalescence at 120° C., description at 120° C.: 1.50 (bs, 9H, (CH$_3$)$_3$); 2.10 (bm, 2H, CH$_2$); 2.30 (bm, 2H, CH$_2$); 2.30 (s, 3H, CH$_3$); 3.8 and 4.0 (ABX, 2H, CH2N); 4.45 (bt, 1H, NCHCOO); 5.20 (bdd, 1H, NCHC); 6.15 (bt, 1H, NH); 6.40 (bdd, 1H, C$_4$H$_4$O, in position 4); 6.50 (bd, 1H, C$_4$H$_4$O in position 3); 6.70 (bd, 1H, N—C$_6$H$_4$—C in position 4); 7.15 to 7.25 (m, 3H, aromatic); 7.50 (bs, 1H, C$_4$H$_4$O in position 5); 8.40 (bs, 1H, NH). Infrared spectrum (KBr), characteristic bands in cm$^{-1}$: 3365, 2975, 2930, 2850, 1735, 1640, 1615, 1595, 1560, 1490, 1390, 1365, 1150, 780, 745, 695.

tert-Butyl (2S,5R)-5-(2-furyl)prolinate may be prepared as follows: 1.77 cm³ of iodotrimethylsilane are added dropwise at a temperature in the vicinity of 25° C. to a solution of 3.8 g of tert-butyl (2S,5RS)-1-tert-butoxycarbonyl-5-(2-furyl)prolinate in 50 cm³ of chloroform. Stirring is continued for 30 minutes, and then 20 cm³ of water are added. The aqueous phase is separated, then extracted with 2 times 20 cm³ of chloroform. The organic phases are combined, washed successively with 30 cm³ of a saturated aqueous sodium bicarbonate solution and with 2 times 30 cm³ of water, then dried over magnesium sulphate and concentrated to dryness under reduced pressure at 40° C. The mixture of the two diastereoisomers obtained is separated by chromatography on silica [eluent: ethyl acetate/cyclohexane (20/80 by volume)]. The fractions containing the expected product are combined and concentrated to dryness under reduced pressure at 40° C. 0.50 g of tert-butyl (2S,5R)-5-(2-furyl)prolinate is thus obtained in the form of a yellow-orange oil, used as it is in subsequent syntheses.

tert-Butyl (2S,5RS)-1-tert-butoxycarbonyl-5-(2-furyl)prolinate may be prepared as follows: 0.42 g of para-toluenesulphonic acid is added to a solution of 9.6 g of tert-butyl (2S,5RS)-1-tert-butoxycarbonyl-5-methoxyprolinate in 100 cm³ of furan. The reaction mixture is stirred for 24 hours at a temperature in the vicinity of 25° C., with subsequent addition of 1 g of sodium bicarbonate. The heterogeneous medium is concentrated to dryness under reduced pressure at a temperature in the vicinity of 30° C. The residue obtained is taken up in 250 cm³ of ethyl acetate and washed with 2 times 50 cm³ of water. The organic phase is dried over magnesium sulphate and concentrated to dryness under reduced pressure at 30° C. The oily residue obtained is purified by chromatography on silica [eluent: ethyl acetate/cyclohexane (5/95 by volume)]. The fractions containing the expected product are combined and concentrated to dryness under reduced pressure at 35° C. 3.8 g of tert-butyl (2S,5RS)-1-tert-butoxycarbonyl-5-(2-furyl)prolinate, melting at 70° C., are thus obtained as a (30/70 by weight) mixture of the (2S,5R) and (2S,5S) isomers, used as it is in subsequent syntheses.

tert-Butyl (2S,5RS)-1-tert-butoxycarbonyl-5-methoxy prolinate may be prepared according to the method described by T. SHONO et al., J. Am. Chem. Soc., 104, 6697 (1982), but starting from tert-butyl (2S)-1-tert-butoxycarbonylprolinate.

tert-Butyl (2S)-1-tert-butoxycarbonylprolinate may be prepared according to the method described by S. YOSHI-FUJI et al., Chem. Pharm., Bull., 34, 3873 (1986).

EXAMPLE 34

0.8 cm$^3$ of 3-methylphenyl isocyanate is added to a solution of 2.0 g of tert-butyl (2R,4R)-3-(2-aminoacetyl)-2-phenyl-4-thiazolidinecarboxylate in 25 cm$^3$ of anhydrous tetrahydrofuran. The reaction mixture is stirred for 12 hours at a temperature in the vicinity of 25° C., then diluted with 100 cm$^3$ of ethyl acetate. The organic phase is washed with 2 times 40 cm$^3$ of water, dried over magnesium sulphate and concentrated to dryness under reduced pressure at 40° C. The crude product obtained is purified by chromatography on silica [eluent: methylene chloride/methanol (98/2 by volume)]. The fractions containing the expected product are combined and concentrated to dryness under reduced pressure at 40° C. After vigorous stirring in heptane, 0.5 g of tert-butyl (2R,4R)-3-{2-[3-(3-methylphenyl)ureido]acetyl}-2-phenyl-4-thiazolidinecarboxylate is thus obtained in the form of a white amorphous powder ($[\alpha]_D^{20}$=+70.0°±1.3° (C=1.02%; CHCl$_3$)) [proton NMR (200 MHz, CDCl$_3$, δ in ppm), 2 rotamers at room temperature, description for the preponderant rotamer at 25° C.: 1.45 (bs, 9H, (CH$_3$)$_3$); 2.2 (s, 3H, CH$_3$); 3.2 (A$_2$X, 2H, CH$_2$S); 3.2 and 4.3 (ABX, 2H, CH$_2$N); 4.9 (t, 1H, CHN); 6.1 (bdd, 1H, NH); 6.2 (s, 1H, SCHN); 6.8 to 7,7 (m, 9H, aromatic). Infrared spectrum (KBr), characteristic bands in cm$^{-1}$: 3375, 2975, 2930, 1735, 1650, 1610, 1595, 1560, 1490, 1455, 1370, 1150, 780, 730, 695].

A—tert-Butyl (2R,4R)-3-(2-aminoacetyl)-2-phenyl-4-thiazolidinecarboxylate may be prepared as follows: 0.9 cm$^3$ of iodotrimethylsilane is added dropwise at a temperature in the vicinity of 25° C. to a solution of 2.5 g of tert-butyl (2R,4R)-3-(2-tert-butoxycarbonylamino-acetyl)-2-phenyl-4-thiazolidinecarboxylate in 15 cm$^3$ of chloroform. The reaction mixture is stirred for 1 hour at a temperature in the vicinity of 25° C. with subsequent addition of 15 cm$^3$ of water. The aqueous phase is separated, then extracted with 2 times 10 cm$^3$ of chloroform. The organic phases are combined, washed successively with 20 cm$^3$ of water, with 20 cm$^3$ of a saturated aqueous sodium bicarbonate solution and with 20 cm$^3$ of water, then dried over magnesium sulphate and concentrated to dryness under reduced pressure at 40° C. 2 g of tert-butyl (2R,4R)-3-(2-aminoacetyl)-2-phenyl-4-thiazolidinecarboxylate are thus obtained in the form of a pale yellow oil, used as it is in subsequent syntheses.

Proton NMR (200 MHz, DMSO D$_6$, δ in ppm), 2 rotamers at room temperature. 1.5 (s, 9H, C(CH$_3$)$_3$), 2.9 to 4.2 (vbm, 4H, 2 CH$_2$); 4.8 and 5.4 (2m, 1H, NCHCO); 6.2 and 6.55 (2s, 1H, NCHS); 7.2 to 7.8 (m, 5H, aromatic); 8.3 (vbs, 1H, NH$_3^+$).

B—tert-Butyl (2R,4R)-3-(2-tert-butoxycarbonylaminoacetyl)-2-phenyl-4-thiazolidinecarboxylate may be prepared as follows: in the space of 30 minutes, a solution of 29.1 g of N,N'-dicyclohexylcarbodiimide in 80 cm$^3$ of anhydrous acetonitrile is added to a solution of 37.4 g of tert-butyl (2RS,4R)-2-phenyl-4-thiazolidinecarboxylate and 24.7 g of 2-tert-butoxycarbonylaminoacetic acid in 150 cm$^3$ of anhydrous acetonitrile, kept at a temperature in the vicinity of 0° C. The reaction mixture is stirred for 16 hours at a temperature in the vicinity of 25° C., then the insoluble product is separated by filtration and washed with 3 times 20 cm$^3$ of acetonitrile. The filtrate is concentrated to dryness under reduced pressure at 45° C. The crude product is purified by chromatography on silica [eluent: ethyl acetate/cyclohexane (30/70 by volume)]. The fractions containing the expected product are combined and concentrated to dryness under reduced pressure, 39.6 g of tert-butyl (2R, 4R)-3-(2-tert-butoxycarbonylaminoacetyl)-2-phenyl-4-thiazolidinecarboxylate are thus obtained in the form of a thick yellow oil, used as it is in subsequent syntheses, ($[\alpha]_D^{20}$= +60.3°±1.1° (C=0.98%; CHCl$_3$)).

C—tert-Butyl (2RS,4R)-2-phenyl-4-thiazolidinecarboxylate may be prepared as follows: 15 cm$^3$ of concentrated sulphuric acid are added dropwise to a suspension of 53.7 g of (2RS,4R)-2-phenyl-4-thiazolidinecarboxylic acid in 590 cm$^3$ of chloroform cooled to a temperature in the vicinity of 5° C. The reaction mixture is saturated with isobutene for 5 hours while stirring and while maintaining the temperature at 5° C. After returning to a temperature in the vicinity of 20° C., stirring is continued for 20 hours. The solution is brought to a pH of 8 by addition of a saturated aqueous sodium bicarbonate solution, then the aqueous phase is separated and extracted with 2 times 300 cm$^3$ of chloroform. The combined organic phases are washed with 2 times 300 cm$^3$ of water, dried over magnesium sulphate and concentrated to dryness under reduced pressure at 40° C. The oily residue obtained is purified by chromatography on silica [eluent: ethyl acetate/cyclohexane (20/80 by volume)]. The fractions containing the expected product are combined, then concentrated to dryness under reduced pressure. 42.8 g of tert-butyl (2RS,4R)-2-phenyl-4thiazolidinecarboxylate are thus obtained in the form of a pale yellow oil, a (40/60 by weight) mixture of the (2R,4R) and (2S,4R) isomers, used as it is in subsequent syntheses.

D—(2RS,4R)-2-Phenyl-4-thiazolidinecarboxylic acid may be prepared as follows: at a temperature in the vicinity of 50° C., 2.3 cm$^3$ of benzaldehyde are added dropwise to a suspension of 2.4 g of L-cysteine in 35 cm$^3$ of ethanol. The reaction mixture is heated under reflux for 2 hours. After cooling to a temperature in the vicinity of 25° C., the insoluble product is separated by filtration and washed successively with 20 cm$^3$ of ethanol and with 20 cm$^3$ of diethyl ether. 3.7 g of (2RS,4R)-2-phenyl-4-thiazolidinecarboxylic acid, melting at 190° C., used as it is in subsequent syntheses, are thus obtained.

EXAMPLE 35

The operation is carried out in a fashion similar to that described in Example 34, but starting from 0.3 g of tert-butyl (2S,4S)-3-(2 aminoacetyl)-2-phenyl-4-thiazolidinecarboxylate and 0.12 cm$^3$ of 3-methylphenyl isocyanate. After vigorous stirring in cyclohexane, 0.16 g of tert-butyl (2S, 4S)-3-{2-[3-(3-methylphenyl)ureido]acetyl}-2-phenyl-4-thiazolidinecarboxylate is thus obtained in the form of an amorphous pale yellow powder ($[\alpha]_D^{20}$=−62.0°±1.1° (C=1.02%; CHCl$_3$)). [Proton NMR (250 MHz, DMSO D$_6$, δ in ppm), 2 rotamers at room temperature, peak coalescence at 120° C., general description valid for the other products of the thiazolidine family (at 120° C.): 1.50 (bs, 9H, (CH$_3$)$_3$); 2.3 (s, 3H, CH$_3$); 3.25 and 3.5 (ABX, 2H, CH$_2$S); 3.7 and 4.05 (ABX, 2H, CH$_2$N); 5.0 (bd, 1H, CHN); 6.2 (bds, 1H, NH); 6.4 (bs, 1H, SCHN); 6.7 (bd, 1H, N—C$_6$H$_4$—C in position 4 or 6); 7.05 to 7.2 (m, 3H, N—C$_6$H$_4$—C in position 2, 4 and 5); 7.35 (m, 3H, C$_6$H$_5$); (bd, 2H, C$_6$H$_5$); 8.35 (bs, 1H, NH). Infrared spectrum (KBr), characteristic bands in cm$^{-1}$: 3380, 2990, 2940, 2860, 1745, 1650, 1615, 1600, 1560, 1495, 1460, 1375, 1155, 785, 735, 700].

tert-Butyl (2S,4S)-3-(2-aminoacetyl)-2-phenyl-4-thiazolidinecarboxylate may be prepared as in example 34 §A, but starting from 0.53 g of tert-butyl (2S,4S)-3-(2-tert-butoxycarbonylaminoacetyl)-2-phenyl-4-thiazolidinecarboxylate in 0.18 cm$^3$ of iodotrimethylsilane. 0.31 g of tert-butyl (2S,4S)-3-(2-aminoacetyl)-2-phenyl-4-thiazolidinecarboxylate is thus obtained in the form of a pale yellow oil, used as it is in subsequent syntheses.

tert-Butyl (2S,4S)-3-(2-tert-butoxycarbonylaminoacetyl)-2-phenyl-4-thiazolidinecarboxylate may be prepared as described in Example 34 §B, but starting from 0.75 g of tert-butyl (2RS,4S)-2-phenyl-4-thiazolidinecarboxylate, 0.53 g of 2-tert-butoxycarbonylaminoacetic acid and 0.62 g of N,N'-dicyclohexylcarbodiimide. 0.56 g of tert-butyl (2S,4S)-3-(2-tert-butoxycarbonylaminoacetyl)-2-phenyl-4-thiazolidinecarboxylate is thus obtained in the form of a beige amorphous powder, used as it is in subsequent syntheses ($[\alpha]_D^{20}$=−52.4°±1.1° (C=1.01%; CHCl$_3$)).

tert-Butyl (2RS,4S)-2-phenyl-4-thiazolidinecarboxylate may be prepared as in Example 34 §C, but starting from 4.5 g of (2RS,4S)-2-phenyl-4-thiazolidinecarboxylic acid, 1.3 cm$^3$ of concentrated sulphuric acid and an excess of isobutene. 1.5 g of tert-butyl (2RS,4S)-2-phenyl-4-thiazolidinecarboxylate are thus obtained in the form of a pale yellow oil, a (50/50 by weight) mixture of the (2R,4S) and (2S,4S) isomers, used as it is in subsequent syntheses.

(2RS,4S)-2-phenyl-4-thiazolidinecarboxylic acid may be prepared as in example 34 §D, but starting from 3.0 g of D-cysteine and 2.85 cm$^3$ of benzaldehyde. 4.5 g of (2RS,4S)-2-phenyl-4-thiazolidinecarboxylic acid, melting at 190° C., used as it is in subsequent syntheses, are thus obtained.

EXAMPLE 36

A solution of 0.97 g of ethyl 3-aminobenzoate in 10 cm$^3$ of chloroform is added to a solution of 1.1 g of N,N'-carbonyldiimidazole in 30 cm$^3$ of chloroform. The reaction mixture is stirred for 6 hours at a temperature in the vicinity of 25° C., with the subsequent addition of 1.3 g of tert-butyl (2R,4R)-3-(2-aminoacetyl)-2-phenyl-4-thiazolidinecarboxylate in solution in 10 cm$^3$ of chloroform. The reaction mixture is stirred for 24 hours at a temperature in the vicinity of 25° C., then washed successively with 50 cm$^3$ of water, with 40 cm$^3$ of a 0.5N aqueous hydrochloric acid solution and with 50 cm$^3$ of water. The organic phase is separated, dried over magnesium sulphate and concentrated to dryness under reduced pressure at 40° C. The oily residue obtained is purified by chromatography on silica [eluent: ethyl acetate/cyclohexane (35/65 by volume)] and the fractions containing the expected product are combined and concentrated to dryness under reduced pressure at 40° C. After vigorous stirring in heptane, 1.0 g of tert-butyl (2R,4R)-3-{2-[3-(3-ethoxycarbonylphenyl)ureido]acetyl}-2-phenyl-4-thiazolidinecarboxylate is thus obtained in the form of an amorphous white powder, melting at 85° C. ($[\alpha]_D^{20}$=+61.5°±1.2° (C=0.97%; CHCl$_3$)) [proton NMR (200 MHz, DMSO D$_6$, δ in ppm), 2 rotamers at room temperature, peak coalescence at 120° C., characteristic chemical shifts at 120° C.: 1.3 (s, 3H, CH$_3$); 4.3 (q, 2H, CH$_2$O); 7.3 to 7.7 (m, 8H, aromatic); 8.0 (bs, 1H, N—C$_6$H$_4$—C in position 2). Infrared spectrum (KBr), characteristic bands in cm$^{-1}$: 3375, 2980, 2930, 1720, 1655, 1610, 1600, 1560, 1490, 1370, 1240, 1155, 760, 735, 700, 690].

EXAMPLE 37

A solution of 1.0 g of tert-butyl (2R,4R)-3-(2-aminoacetyl)-2-phenyl-4-thiazolidinecarboxylate in 10 cm$^3$ of chloroform is added to a solution of 0.6 g of N,N'-carbonyldiimidazole in 15 cm$^3$ of chloroform. The reaction mixture is stirred for 2 hours at a temperature in the vicinity of 25° C., followed by the addition of 0.44 g of 2-(3-aminophenyl)ethanol in solution in 5 cm$^3$ of chloroform. The reaction mixture is stirred for 12 hours at a temperature in the vicinity of 25° C., then concentrated to dryness under reduced pressure at 40° C. The oily residue obtained is purified by chromatography on silica [eluent: ethyl acetate] and the fractions containing the expected product are combined and concentrated to dryness under reduced pressure at 40° C. After recrystallization in acetonitrile, 0.18 g of tert-butyl (2R,4R)-3-{2-[3-(3-(2-hydroxyethyl)phenyl)ureido]acetyl}-2-phenyl-4-thiazolidinecarboxylate is thus obtained in the form of white crystals, melting at 164° C. ($[\alpha]_D^{20}$=+59.6°±1.8° (C=0.50%; DMF) [proton NMR (300 MHz, DMSO D$_6$, δ in ppm), 2 rotamers at room temperature, peak coalescence at 120° C., characteristic chemical shifts at 120° C.: 2.7 and 3.60 (2t, 4H, CH$_2$CH$_2$O); 6.8 (bd, 1H, N—C$_6$H$_4$—C in position 4 or 6); 7.05 to 7.20 (m, 3H, N—C$_6$H$_4$—C in position 2, 5 and 6); 7.3 (m, 3H, C$_6$H$_5$); 7.6 (d, 2H, C$_6$H$_5$). Infra-red spectrum (KBr), characteristic bands in cm$^{-1}$): 3320, 2975, 2930, 2880, 2850, 1740, 1660, 1610, 1590, 1560, 1510, 1480, 1450, 1365, 1150, 1060, 790, 730, 695].

EXAMPLE 38

In the space of 2 hours, a solution of 2.6 g of tert-butyl (2R,4R)-3-(2-aminoacetyl)-2-phenyl-4-thiazolidinecarboxylate in 15 cm$^3$ of anhydrous tetrahydrofuran is added to a solution of 1.3 g of N,N'-carbonyldiimidazole in 15 cm$^3$ of anhydrous tetrahydrofuran. The reaction mixture is stirred at a temperature in the vicinity of 25° C. for 12 hours, then concentrated to dryness under reduced pressure at 40° C. The oily residue obtained is purified by chromatography on silica [eluent: ethyl acetate]. A solution of 2.8 g of tert-butyl (2R,4R)-3-[2-(1-imidazolylcarboxamido)acetyl]-2-phenyl-4-thiazolidinecarboxylate thus obtained and of 2.7 g of methyl 3-aminophenylacetate in 100 cm$^3$ of toluene is heated under reflux for 4 hours. After cooling to a temperature in the vicinity of 25° C., the reaction mixture is washed successively with 50 cm$^3$ of water, with 50 cm$^3$ of a 1N aqueous hydrochloric acid solution and with 2 times 50 cm$^3$ of water. The organic phase is separated, dried over magnesium sulphate and concentrated to dryness under reduced pressure at 40° C.

The oily residue obtained is purified by chromatography on silica [eluent: ethyl acetate/cyclohexane (50/50 by volume)]. The fractions containing the expected product are combined, then concentrated to dryness under reduced pressure at 30° C. After vigorous stirring in heptane, 1.9 g of methyl (2R,4R)-3-{3-[2-(4-tert-butoxycarbonyl-2-phenyl-3-thiazolidinyl)-2-oxoethyl]ureido}phenylacetate are thus obtained in the form of a pale beige powder, melting at 69° C. ($[\alpha]_D^{20}$=+59.1°±1.2° (C=0.55%; CHCl$_3$)) [proton NMR (200 MHz, DMSO D$_6$, δ in ppm), 2 rotamers at room temperature, peak coalescence at 120° C., characteristic chemical shifts at 120° C.: 3.7 (2s, 5H, CH$_2$CO$_2$CH$_3$); 6.8 (d, 1H, N—C$_6$H$_4$—C in position 4 or 6); 7.1 to 7.7 (m, 8H, aromatic). Infrared spectrum (KBr), characteristics bands in cm$^{-1}$: 3370, 2980, 2950, 2930, 1740, 1650, 1610, 1595, 1560, 1495, 1370, 1240, 1155, 780, 735, 700].

EXAMPLE 39

At a temperature in the vicinity of 5° C., 0.1 g of lithium hydroxide is added to a solution of 1.2 g of methyl (2R, 4R)-3-{3-[2-(4-tert-butoxycarbonyl-2-phenyl-3-thiazolidinyl)-2-oxoethyl]ureido}phenylacetate in 25 cm³ of a water/tetrahydrofuran (30/70 by volume) mixture. The reaction mixture is stirred for 12 hours at a temperature in the vicinity of 25° C., then concentrated to 5 cm³ under reduced pressure at 40° C.

The solution obtained is diluted with 50 cm³ of water, washed with 2 times 30 cm³ of ethyl ether, then acidified to a pH of 2 with 2.8 cm³ of a 1N aqueous hydrochloric acid solution. The insoluble product is separated by filtration, washed with 3 times 10 cm³ of water, then dried in air. 0.7 g of (2R,4R)-3-{3-[2-(4-tert-butoxycarbonyl-2-phenyl-3-thiazolidinyl)-2-oxoethyl]ureido}phenylacetic acid, melting at 140° C., is thus obtained ($[\alpha]_D^{20}$=+62.6°±1.6° (C=0.64%; DMF)) [proton NMR (200 MHz, DMSO $D_6$, δ in ppm), 2 rotamers at room temperature, peak coalescence at 120° C., characteristic chemical shifts at 120° C.: 3.60 (bs, 2H, $CH_2CO_2H$); 6.8 (bd, 1H, N—$C_6H_4$—C in position 6); 7.15 to 7.80 (m, 8H, aromatic). Infrared spectrum (KBr), characteristics bands in cm$^{-1}$: 3385, 2985, 2945, 2625, 1735, 1650, 1615, 1600, 1560, 1500, 1375, 1240, 1155, 785, 735, 705].

EXAMPLE 40

The operation is carried out in a fashion similar to that described in Example 33, but starting from 3.5 g of tert-butyl-(2RS,4R)-2-(2-fluorophenyl)-4-thiazolidinecarboxylate, 2.3 g of 2-[3-(3-methylphenyl)ureido]acetic acid and 2.3 g of N,N'-dicyclohexylcarbodiimide. After vigorous stirring in heptane, 1.05 g of tert-butyl (2R,4R)-3-{2-[3-(3-methylphenyl)ureido]acetyl}-2-(2-fluorophenyl)-4-thiazolidinecarboxylate are thus obtained in the form of a white solid, melting at 107° C. ($[\alpha]_D^{20}$=+61.8°±1.5° (C=0.66%; DMF)) [proton NMR (200 MHz, DMSO $D_6$, δ in ppm), 2 rotamers at room temperature, peak coalescence at 120° C., characteristic chemical shifts at 120° C.: 2.2 (bs, 3H, $CH_3$); 6.7 (bd, 1H, N—$C_6H_4$—C in position 4 or 6); 7.1 to 7.40 (m, 6H, aromatic); 7.9 (bm, 1H, $C_6H_4F$ in position 3). Infrared spectrum (KBr), characteristics bands in cm$^{-1}$: 3370, 2975, 2925, 1735, 1645, 1615, 1590, 1560, 1490, 1460, 1370, 1150, 775, 760, 690].

tert-Butyl (2RS,4R)-2-(2-fluorophenyl)-4-thiazolidinecarboxylate may be prepared as described in Example 34 §C, but starting from 5.7 g of (2RS,4R)-2-(2-fluorophenyl)-4-thiazolidinecarboxylic acid in solution in 60 cm³ of chloroform, 1.5 cm³ of concentrated sulphuric acid and an excess of isobutene. 5.8 g of tert-butyl (2RS,4R)-2-(2-fluorophenyl)-4-thiazolidinecarboxylate are thus obtained in the form of a yellow oil, a (50/50 by weight) mixture of the (2R,4R) and (2S,4R) isomers, used as it is in subsequent syntheses.

(2RS, 4R)-2-(2-fluorophenyl)-4-thiazolidinecarboxylic acid may be prepared as described in Example 34 §D, but starting from 21.2 g of L-cysteine and 19.2 cm³ of 2-fluorobenzaldehyde. 28.2 g of (2RS,4R)-2-(2-fluorophenyl)-4-thiazolidinecarboxylic acid, melting at 147° C., used as it is in subsequent syntheses, are thus obtained.

EXAMPLE 41

At a temperature in the vicinity of 25° C., 13.7 cm³ of a 1M solution of tetrabutylammonium fluoride in tetrahydrofuran are added to a solution of 4.2 g of 2-trimethylsilylethyl (2R,4R)-3-{3-{2-[4-tert-butoxycarbonyl-2-(3-methoxyphenyl)-3-thiazolidinyl]-2-oxoethyl}ureido}benzoate in 80 cm³ of tetrahydrofuran. The reaction mixture is stirred for 12 hours at a temperature in the vicinity of 25° C., then acidified with 15 cm³ of a 1N aqueous sulphuric acid solution. After extraction with 3 times 50 cm³ of ethyl acetate, the combined organic phases are washed with 60 cm³ of water, then extracted with 2 times 20 cm³ of a 1N aqueous sodium hydroxide solution. The aqueous phases are separated, washed with 2 times 40 cm³ of ethyl ether, acidified to a pH of 4 with a 4N aqueous sulphuric acid solution and extracted with 3 times 50 cm³ of ethyl ether. The organic phases are combined, dried over magnesium sulphate and concentrated to dryness under reduced pressure at 30° C. The solid obtained is dissolved in 10 cm³ of a 0.5N aqueous sodium hydroxide solution. The solution obtained is filtered and acidified with 5 cm³ of a 1N aqueous hydrochloric acid solution. The insoluble product is separated by filtration, washed with 2 times 5 cm³ of water and dried in air. 1.48 g of (2R,4R)-3-{3-{2-[4-tert-butoxycarbonyl-2-(3-methoxyphenyl)-3-thiazolidinyl]-2-oxoethyl}ureido}benzoic acid, melting at 125°, are thus obtained, ($[\alpha]_D^{20}$=+74°±2° (C=0.32%; DMF)) [proton NMR (200 MHz, DMSO $D_6$, δ in ppm), 2 rotamers at room temperature, peak coalescence at 120° C., characteristic chemical shifts at 120° C.: 3.8 (s, 3H, $OCH_3$); 6.85 (bd, 1H, O—$C_6H_4$—C in position 4); 7.2 to 7.6 (m, 6H, aromatic); 8.0 (bs, 1H, N—$C_6H_4$— in position 2). Infrared spectrum (KBr), characteristic bands in cm$^{-1}$: 3380, 2975, 2930, 2830, 2600, 1715, 1690, 1655, 1600, 1555, 1490, 1370, 1230, 1150, 1050, 755, 690, 680].

A—2-Trimethylsilylethyl (2R,4R)-3-{3-{2-[4-tert-butoxycarbonyl-2-(3-methoxyphenyl)-3-thiazolidinyl]-2-oxoethyl}ureido}benzoate may be prepared as follows: in the space of 10 minutes, a solution of 2.45 g of N,N'-dicyclohexylcarbodiimide in 10 cm³ of anhydrous tetrahydrofuran are added to a solution of 3.5 g of tert-butyl (2RS,4R)-2-(3-methoxyphenyl)-4-thiazolidinecarboxylate and 4.0 g of 2-{3-[3-(2trimethylsilylethoxycarbonyl)phenyl]ureido}acetic acid in 20 cm³ of anhydrous tetrahydrofuran cooled to a temperature in the vicinity of 5° C. The reaction mixture is stirred for 16 hours at a temperature in the vicinity of 25° C. The insoluble product is separated by filtration and washed with 2 times 10 cm³ of tetrahydrofuran. The filtrate is concentrated to dryness under reduced pressure at 40° C. The oily residue obtained is purified by chromatography on silica [eluent: ethyl acetate/cyclohexane (30/70 by volume)]. The fractions containing the expected product are combined and concentrated to dryness under reduced pressure at 40° C. 4.85 g of 2-trimethylsilylethyl (2R,4R)-3-{3-{2-[4-tert-butoxycarbonyl-2-(3-methoxyphenyl)-3-thiazolidinyl]-2-oxoethyl}ureido}benzoate are thus obtained in the form of an amorphous beige powder, used as it is in subsequent syntheses, ($[\alpha]_D^{20}$=+67.2°±1.3° (C=0.52%; $CHCl_3$)).

B—tert-Butyl (2RS,4R)-2-(3-methoxyphenyl)-4-thiazolidinecarboxylate may be prepared in a fashion similar to that described in Example 34 §C, but starting from 14.0 g of (2RS,4R)-2-(3-methoxyphenyl)-4-thiazolidinecarboxylic acid, 3.0 cm³ of concentrated sulphuric acid and an excess of isobutene. The crude product obtained is purified by chromatography on silica [eluent: ethyl acetate/cyclohexane (30/70 by volume)]. The fractions containing the expected product are combined and concentrated to dryness under reduced pressure at 40° C. 11.0 g of tert-butyl (2RS,4R)-2-(3-methoxyphenyl)-4-thiazolidinecarboxylate are thus obtained in the form of a yellow oil, a (40/60 by weight) mixture of the (2R,4R) and (2S,4R) isomers, used as it is in subsequent syntheses.

C—(2RS,4R)-2-(3-Methoxyphenyl)-4-thiazolidinecarboxylic acid may be prepared as described in Example 34 §D, but starting from 21.2 g of L-cysteine and 23 cm³ of 3-methoxybenzaldehyde. 38.0 g of (2RS,4R)-2-(3-methoxyphenyl)-4-thiazolidinecarboxylic acid, melting at 171° C., used as it is in subsequent syntheses, are thus obtained.

D 2-{3-[3-(2-Trimethylsilylethoxycarbonyl)phenyl]ureido}acetic acid may be prepared as follows: a solution of 4.45 g of potassium hydroxide in 160 cm³ of water is added to a solution of 24.7 g of 2-trimethylsilylethyl 3-(3-ethoxycarbonylmethylureido)benzoate in 500 cm³ of tetrahydrofuran. The reaction mixture is stirred for 12 hours at a temperature in the vicinity of 25° C., then concentrated to 150 cm³ under reduced pressure at 40° C. The solution obtained is diluted with 200 cm³ of water, washed with 2 times 50 cm³ of ethyl acetate, acidified with 68 cm³ of a 1N aqueous hydrochloric acid solution and extracted with 3 times 100 cm³ of ethyl ether. The organic phases are combined, dried over magnesium sulphate and concentrated to dryness under reduced pressure. After recrystallization in diisopropyl ether, 17.2 g of 2-{3-[3-(2-trimethylsilylethoxycarbonyl)phenyl]ureido}acetic acid, melting at 173° C., are obtained.

E—2-Trimethylsilylethyl 3-(3-ethoxycarbonylmethylureido)benzoate may be prepared as follows: a solution of 29.5 g of ethyl 2-(1-imidazolylcarboxamido)acetate and 36.2 g of 2-trimethylsilylethyl 3-aminobenzoate in 1000 cm³ of toluene is stirred under reflux for 3 hours. After cooling to a temperature in the vicinity of 25° C., the reaction mixture is washed with 3 times 50 cm³ of water, dried over magnesium sulphate and concentrated to dryness under reduced pressure at 40° C. The oily residue obtained is purified by chromatography on silica [eluent: ethyl acetate/cyclohexane (40/60 by volume)]. The fractions containing the expected product are combined and concentrated to dryness under reduced pressure at 40° C. 24.7 g of 2-trimethylsilylethyl 3-(3-ethoxycarbonylmethylureido)benzoate are thus obtained in the form of a thick yellow oil, used as it is in subsequent syntheses.

F—Ethyl 2-(1-imidazolylcarboxamido)acetate may be prepared as follows: in the space of 2 hours, 42.3 g of ethyl 2-aminoacetate hydrochloride are added to a solution of 50.0 g of N,N'-carbonyldiimidazole and 43 cm³ of triethylamine in 800 cm³ of anhydrous tetrahydrofuran. The mixture is stirred for 24 hours at a temperature in the vicinity of 25° C., then the insoluble product is separated by filtration and washed with 2 times 50 cm³ of tetrahydrofuran. The filtrate is concentrated to dryness under reduced pressure at 40° C. The oily residue obtained is purified by chromatography on silica [eluent: ethyl acetate]. The fractions containing the expected product are combined and concentrated to dryness under reduced pressure. 36.7 g of ethyl 2-(1-imidazolylcarboxamido)acetate, melting at 103° C., are thus obtained.

G—2-Trimethylsilylethyl 3-aminobenzoate may be prepared as follows: 2.1 g of 5% palladium on charcoal are added to a solution of 42.7 g of 2-trimethylsilylethyl 3-nitrobenzoate in 600 cm³ of ethanol. The suspension is stirred for 2 hours at a temperature in the vicinity of 25° C. under a hydrogen atmosphere (100 kPa). The catalyst is then separated by filtration and the filtrate is concentrated to dryness under reduced pressure at 40° C. 36.2 g of 2-trimethylsilylethyl 3-aminobenzoate are thus obtained in the form of an oil used as it is in subsequent syntheses.

H—2-Trimethylsilylethyl 3-nitrobenzoate may be prepared as follows: a solution of 41.8 g of 2- trimethylsilylethanol in 200 cm³ of 1,2-dichloroethane and 51 cm³ of triethylamine is added to a solution of 66.0 g of 3-nitrobenzoyl chloride in 1000 cm³ of 1,2-dichloroethane cooled to 5° C. The reaction mixture is stirred for 12 hours at a temperature in the vicinity of 25° C., then the insoluble product is separated by filtration and washed with 2 times 50 cm³ of 1,2-dichloroethane. The filtrate is concentrated to dryness under reduced pressure at 40° C. The oily residue obtained is purified by chromatography on silica [eluent: ethyl acetate/cyclohexane (30/70 by volume)]. The fractions containing the expected product are combined and concentrated to dryness under reduced pressure at 40° C. 76.9 g of 2-trimethylsilylethyl 3-nitrobenzoate are thus obtained in the form of an oil used as it is in subsequent syntheses.

EXAMPLE 42

The operation is carried out in a fashion similar to that described in Example 41, but starting from 2.3 g of 2-trimethylsilylethyl (2R,4R)-3-{3-{2-[4-tert-butoxycarbonyl-2-(2-fluorophenyl)-3-thiazolidinyl]-2-oxoethyl}ureido}benzoate and 7.6 cm³ of 1M tetrabutylammonium fluoride solution. The crude product is purified by chromatography on silica [eluent: ethyl acetate/methanol (90/10 by volume)]. The fractions containing the expected product are combined and concentrated to dryness under reduced pressure at 40° C. After vigorous stirring in diisopropyl ether, 0.4 g of (2R,4R)-3-{2-{2-[4-tert-butoxycarbonyl-2-(2-fluorophenyl)-3-thiazolidinyl]-1-oxoethyl}ureido}benzoic acid is thus obtained in the form of an amorphous solid ($[\alpha]_D^{20}$=+68.3°±1.8° (C=0.57%; CHCl$_3$)) [proton NMR (200 MHz, DMSO D$_6$, δ in ppm), 2 rotamers at room temperature, peak coalescence at 120° C., characteristic chemical shifts at 120° C.: 7.2 to 7.6 (m, 6H, aromatic); 7.9 (bt, 1H, F—C$_6$H$_4$ in position 3, $J_{HF}$=9 Hz); 8.0 (bs, 1H, N—C$_6$H$_4$— in position 2). Infrared spectrum (KBr), characteristic bands in cm⁻¹: 3380, 2980, 2930, 2600, 1735, 1690, 1655, 1610, 1590, 1555, 1490, 1455, 1370, 1230, 1150, 760, 680].

2-Trimethylsilylethyl (2R,4R)-3-{3-{2-[4-tertbutoxycarbonyl]-2-(2-fluorophenyl)-3-thiazolidinyl]-2-oxoethyl}ureido}benzoate may be prepared in a fashion similar to that described in Example 41 §A, but starting from 3.35 g of tert-butyl (2RS,4R)-2-(2-fluorophenyl)-4-thiazolidinecarboxylate, 4.0 g of 2-{3-[3-(2-trimethylsilylethoxycarbonyl)phenyl]ureido}acetic acid and 2.45 g of N,N'-dicyclohexylcarbodiimide. The crude product is purified by chromatography on silica [eluent: ethyl acetate/cyclohexane (30/70 by volume)]. The fractions containing the expected product are combined and concentrated to dryness under reduced pressure at 40° C. 2.4 g of 2-trimethylsilylethyl (2R,4R)-3-{3-{2-[4-tert-butoxycarbonyl-2-(2-fluorophenyl)-3-thiazolidinyl]-2-oxoethyl}ureido}benzoate are thus obtained in the form of an amorphous beige solid, used as it is in subsequent syntheses ($[\alpha]_D^{20}$=±50.2°+1.6° (C=0.38%; CHCl$_3$))

EXAMPLE 43

The operation is carried out in a fashion similar to that described in Example 41, but starting from 1.6 g of 2-trimethylsilylethyl (2R,4R)-3-{3-{2-[4-tert-butoxycarbonyl-2-(3-fluorophenyl)-3-thiazolidinyl]-2-oxoethyl}ureido}benzoate in 5.3 cm³ of 1M tetrabutylammonium fluoride solution. The crude product is purified by chromatography on silica [eluent: ethyl acetate/methanol (90/10 by volume)]. The fractions containing the expected product are combined and concentrated to dryness under reduced pressure at 40° C. After vigorous stirring in diisopropyl ether, 0.22 g of (2R,4R)-3-{3-{2-[4-tert-butoxycarbonyl-2-(3-fluorophenyl)-3-thiazolidinyl]-2- oxoethyl}ureido}benzoic acid is thus obtained in the form of an amorphous solid ($[\alpha]_D^{20}$=+79.0°±2.0° (C=0.43%; CHCl$_3$)) [proton NMR (250 MHz, DMSO D$_6$, δ in ppm), 2 rotamers at room temperature, characteristic chemical shifts at 25° C.: 1.5 (bs, 9H, (CH$_3$)$_3$); 7.1 to 7.6 (m, 7H, aromatic); 8.0 (bs, 1H, N—C$_6$H$_4$— in position 2). Infrared spectrum (KBr), characteristic bands in cm$^{-1}$: 3380, 2975, 2930, 2600, 1715, 1695, 1650, 1610, 1590, 1560, 1490, 1450, 1370, 1240, 1150, 780, 755, 685].

2-Trimethylsilylethyl (2R,4R)-3-{3-{2-[4-tert-butoxycarbonyl-2-(3-fluorophenyl)-3-thiazolidinyl]-2-oxoethyl}ureido}benzoate may be prepared in a fashion similar to that described in Example 41 §A, but starting from 1.68 g of tert-butyl (2RS,4R)-2-(3-fluorophenyl)-4-thiazolidinecarboxylate, 2.0 g of 2-{3-[3-(2-trimethylsilylethoxycarbonyl)phenyl]ureido}acetic acid and 1.23 g of N,N'-dicyclohexylcarbodiimide. The crude product is purified by chromatography on silica [eluent: ethyl acetate/cyclohexane (30/70 by volume)]. The fractions containing the expected product are combined and concentrated to dryness under reduced pressure at 40° C. 1.6 g of 2-trimethylsilylethyl (2R,4R)-3-{3-{2-[4-tert-butoxycarbonyl-2-(3-fluorophenyl)-3-thiazolidinyl]-2-oxoethyl}ureido}benzoate are thus obtained in the form of an amorphous beige solid, used as it is in subsequent syntheses ($[\alpha]_D^{20}$=+45.7°±1.5° (C=0.53%; CHCl$_3$))

tert-Butyl (2RS,4R)-2-(3-fluorophenyl)-4-thiazolidinecarboxylate may be prepared in a fashion similar to that described in Example 34 §C, but starting from 11.4 g of (2RS,4R)-2-(3-fluorophenyl)-4-thiazolidinecarboxylic acid in solution in 200 cm$^3$ of chloroform, 3 cm$^3$ of concentrated sulphuric acid and an excess of isobutane. The crude product obtained is purified by chromatography on silica [eluent: ethyl acetate/cyclohexane (30/70 by volume)]. The fractions containing the expected product are combined and concentrated to dryness under reduced pressure at 40° C. 10.3 g of tert-butyl (2RS,4R)-2-(3-fluorophenyl)-4-thiazolidinecarboxylate are thus obtained in the form of a yellow oil, a (30/70 by weight) mixture of the (2R,4R) and (2S,4R) isomers, used as it is in subsequent syntheses.

(2RS,4R)-2-(3-fluorophenyl)-4-thiazolidinecarboxylic acid may be prepared as described in Example 34 §D, but starting from 21.2 g of L-cysteine and 20 cm$^3$ of 3fluorobenzaldehyde. 30.2 g of (2RS,4R)-2-(3-fluorophenyl)-4-thiazolidinecarboxylic acid, melting at 178° C., used as it is in subsequent syntheses, are thus obtained.

EXAMPLE 44

The operation is carried out in a fashion similar to that described in Example 41, but starting from 2.0 g of 2-trimethylsilylethyl (2R,4R)-3-{3-{2-[4-tert-butoxycarbonyl-2-(4-fluorophenyl)-3-thiazolidinyl]-2-oxoethyl}ureido}benzoate and 6.6 cm$^3$ of 1M tetrabutylammonium fluoride solution. The crude product is purified by chromatography on silica [eluent: ethyl acetate]. The fractions containing the expected product are combined and concentrated to dryness under reduced pressure at 40° C. After vigorous stirring in diisopropyl ether, 0.74 g of (2R, 4R)-3-{2-{2-[4-tert-butoxycarbonyl-2-(4-fluorophenyl)-3-thiazolidinyl]-1-oxoethyl}ureido}benzoic acid, melting at 154° C., is thus obtained ($[\alpha]_D^{20}$=+49.7°±1.3° (C=0.46%; DMF)) [proton NMR (250 MHz, DMSO D$_6$, δ in ppm), 2 rotamers at room temperature, characteristic chemical shifts at 25° C.: 1.5 (bs, 9H, (CH$_3$)$_3$); 7.1 to 7.8 (m, 7H, aromatic); 8.0 (bs, 1H, N—C$_6$H$_4$— in position 2). Infrared spectrum (KBr), characteristic bands in cm$^{-1}$: 3380, 2985, 2945, 2625, 1695, 1650, 1610, 1560, 1510, 1490, 1375, 1235, 1155, 800, 760, 685].

2-Trimethylsilylethyl (2R,4R)-3-{3-{2-[4-tert-butoxycarbonyl-2-(4-fluorophenyl)-3-thiazolidinyl]-2-oxoethyl}ureido}benzoate may be prepared in a fashion similar to that described in Example 41 §A, but starting from: 1.68 g of tert-butyl (2RS,4R)-2-(4-fluorophenyl)-4-thiazolidinecarboxylate, 2.0 g of 2-{3-[3-(2-trimethylsilylethoxycarbonyl)phenyl]ureido}acetic acid and 1.23 g of N,N'-dicyclohexylcarbodiimide. The crude product is purified by chromatography on silica [eluent: ethyl acetate/cyclohexane (30/70 by volume)]. The fractions containing the expected product are combined and concentrated to dryness under reduced pressure at 40° C. 2.0 g of 2-trimethylsilylethyl (2R,4R)-3-{3-{2-[4-tert-butoxycarbonyl-2-(4-fluorophenyl)-3-thiazolidinyl]-2-oxoethyl}ureido}benzoate are thus obtained in the form of an amorphous beige solid, used as it is in subsequent syntheses ($[\alpha]_D^{20}$=+46.6°+1° (C=0.50%; CHCl$_3$)).

tert-Butyl (2RS,4R)-2-(4-fluorophenyl)-4-thiazolidinecarboxylate may be prepared in a fashion similar to that described in Example 34 §C, but starting from 11.4 g of (2RS,4R)-2-(4-fluorophenyl)-4-thiazolidinecarboxylic acid, 3.0 cm$^3$ of concentrated sulphuric acid and an excess of isobutene. The crude product obtained is purified by chromatography on silica gel [eluent: ethyl acetate/cyclohexane (30/70 by volume)]. The fractions containing the expected product are combined and concentrated to dryness under reduced pressure at 40° C. 10.0 g of tert-butyl (2RS,4R)-2-(4-fluorophenyl)-4-thiazolidinecarboxylate are thus obtained in the form of a yellow oil, a (40/60 by weight) mixture of the (2R,4R) and (2S,4R) isomers, used as it is in subsequent syntheses.

(2RS,4R)-2-(4-Fluorophenyl)-4-thiazolidinecarboxylic acid may be prepared as described in Example 34 §D, but starting from 21.2 g of L-cysteine and 20 cm$^3$ of 4-fluorobenzaldehyde. 34.3 g of (2RS,4R)-2-(4-fluorophenyl)-4-thiazolidinecarboxylic acid, melting at 186° C., used as it is in subsequent syntheses, are thus obtained.

EXAMPLE 45

The operation is carried out in a fashion similar to that described in Example 41, but starting from 2.0 g of 2-trimethylsilylethyl (2R,4R)-3-{3-{2-[4-tert-butoxycarbonyl-2-(2-chlorophenyl)-3-thiazolidinyl]-2-oxoethyl}ureido}benzoate and 6.5 cm$^3$ of 1M tetrabutylammonium fluoride solution. The crude product is purified by chromatography on silica [eluent: ethyl 0.65 g of acetate/methanol (90/10 by volume)]. The fractions containing the expected product are combined and concentrated to dryness under reduced pressure at 40° C. After vigorous stirring in diisopropyl ether, 0.65 g of (2R,4R)-3-{3-{2-[4-tert-butoxycarbonyl-2-(2-chlorophenyl)-3-thiazolidinyl]-2-oxoethyl}ureido}benzoic acid is thus obtained in the form of an amorphous solid ($[\alpha]_D^{20}$=+88°±2° (C=0.39%; CHCl$_3$)) [proton NMR (200 MHz, DMSO D$_6$, δ in ppm), 2 rotamers at room temperature, peak coalescence at 120° C., characteristic chemical shifts at 120° C.: 7.3 to 7.6 (m, 7H, aromatic); 7.95 (bs, 1H, N—C$_6$H$_4$— in position 2). Infrared spectrum (KBr), characteristic bands in cm$^{-1}$: 3390, 2985, 2940, 2600, 1735, 1660, 1610, 1560, 1375, 1240, 1155, 755, 685].

2-Trimethylsilylethyl (2R,4R)-3-{3-{2-[4-tert-butoxycarbonyl-2-(2-chlorophenyl)-3-thiazolidinyl]-2-oxoethyl)ureido}benzoate may be prepared in a fashion similar to that described in Example 41 §A, but starting from 1.6 g of tert-butyl (2RS,4R)-2-(2-chlorophenyl)-4-thiazolidinecarboxylate, 2.0 g of 2-{3-3-(2-trimethylsilylethoxycarbonyl)phenyl]ureido}acetic acid and 1.23 g of N,N'-dicyclohexylcarbodiimide. The crude product is purified by chromatography on silica [eluent: ethyl acetate/cyclohexane (30/70 by volume)]. The fractions containing the expected product are combined and concentrated to dryness under reduced pressure at 40° C. 2.0 g of 2-trimethylsilylethyl (2R,4R)-3-{3-{2-[4-tert-butoxycarbonyl-2-(2-chlorophenyl)-3-thiazolidinyl]-2-oxoethyl}ureido}benzoate are thus obtained in the form of an amorphous beige solid, used as it is in subsequent syntheses, ($[\alpha]_D^{20}$=+87.0°±2.0° (C=0.46%; $CHCl_3$)).

tert-Butyl (2RS,4R)-2-(2-chlorophenyl)-4-thiazolidinecarboxylate may be prepared in a fashion similar to that described in Example 34 §C, but starting from 12.2 g of (2RS,4R)-2-(2-chlorophenyl)-4-thiazolidinecarboxylic acid, 3.0 $cm^3$ of concentrated sulphuric acid and an excess of isobutene. The crude product obtained is purified by chromatography on silica [eluent: ethyl acetate/cyclohexane (30/70 by volume)]. The fractions containing the expected product are combined and concentrated to dryness under reduced pressure at 40° C. 11.0 g of tert-butyl (2RS,4R)-2-(2-chlorophenyl)-4-thiazolidinecarboxylate are thus obtained in the form of a yellow oil, a (40/60 by weight) mixture of the (2R,4R) and (2S,4R) isomers, used as it is in subsequent syntheses.

(2RS,4R)-2-(2-Chlorophenyl)-4-thiazolidinecarboxylic acid may be prepared as in Example 34 §D, but starting from 21.2 g of L-cysteine and 25.8 g of 2-chlorobenzaldehyde. 21.9 g of (2RS,4R)-2-(2-chlorophenyl)-4-thiazolidinecarboxylic acid, melting at 144° C., used as it is in subsequent syntheses, are obtained.

EXAMPLE 46

The operation is carried out in a fashion similar to that described in Example 41, but starting from 4.0 g of 2-trimethylsilylethyl (2R,4R)-3-{3-{2-[4-tert-butoxycarbonyl-2-(3-hydroxyphenyl)-3-thiazolidinyl]-2-oxoethyl}ureido}benzoate and 11.8 $cm^3$ of 1M tetrabutylammonium fluoride solution. The crude product is purified by chromatography on silica [eluent: ethyl acetate]. The fractions containing the expected product are combined and concentrated to dryness under reduced pressure at 40° C. The solid residue is dissolved in 8.0 $cm^3$ of a 0.5N aqueous sodium hydroxide solution. The solution is filtered and acidified with 4.1 $cm^3$ of a 1N aqueous hydrochloric acid solution. The insoluble product is separated by filtration, washed with 2 times 5 $cm^3$ of water and dried in air. 0.65 g of (2R,4R)-3-{3-{2-[4-tert-butoxycarbonyl-2-(3-hydroxyphenyl)-3-thiazolidinyl]-2-oxoethyl}ureido}-benzoic acid, melting at 150° C., is thus obtained. ($[\alpha]_D^{20}$=+62°±2° (C=0.28%; DMF)) [proton NMR (200 MHz, DMSO $D_6$, δ in ppm), 2 rotamers at room temperature, peak coalescence at 120° C., characteristic chemical shifts at 120° C.: 6.8 (bd, 1H, O—$C_6H_4$—C in position 4; 7.0 to 7.6 (m, 6H, aromatic); 8.0 (bs, 1H, N—$C_6H_4$— in position 2). Infrared spectrum (KBr), characteristic bands in $cm^{-1}$: 3380, 2975, 2930, 2625, 1700, 1650, 1590, 1560, 1490, 1370, 1235, 1150, 785, 760, 690, 680].

2-Trimethylsilylethyl (2R,4R)-3-{3-{2-[4-tert-butoxycarbonyl-2-(3-hydroxyphenyl)-3-thiazolidinyl]-2-oxoethyl}ureido}benzoate may be prepared in a fashion similar to that described in Example 41 §A, but starting from 1.66 g of tert-butyl (2RS,4R)-2-(3-hydroxyphenyl)-4-thiazolidinecarboxylate, 2.0 g of 2-{3-[3-(2-trimethylsilylethoxycarbonyl)phenyl]ureido}acetic acid and 1.33 g of N,N'-dicyclohexylcarbodiimide. 4.0 g of 2-trimethylsilylethyl (2R,4R)-3-{3-{2-[4-tert-butoxycarbonyl-2-(3-hydroxyphenyl)-3-thiazolidinyl]-2-oxoethyl}ureido}benzoate are thus obtained in the form of an amorphous yellow powder used as it is in subsequent syntheses.

tert-Butyl (2RS,4R)-2-(3-hydroxyphenyl)-4-thiazolidinecarboxylate may be prepared in a fashion similar to that described in Example 34 §C, but starting from 11.3 g of (2RS,4R)-2-(3-hydroxyphenyl)-4-thiazolidinecarboxylic acid in solution in 200 $cm^3$ of chloroform, 3.0 $cm^3$ of concentrated sulphuric acid and an excess of isobutene. The crude product obtained is purified by chromatography on silica [eluent: ethyl acetate/cyclohexane (30/70 by volume)]. The fractions containing the expected product are combined and concentrated to dryness under reduced pressure at 40° C. 4.5 g of tert-butyl (2RS,4R)-2-(3-hydroxyphenyl)-4-thiazolidinecarboxylate are thus obtained in the form of a yellow oil, a (50/50 by weight) mixture of the (2R,4R) and (2S,4R) isomers, used as it is in subsequent syntheses.

(2RS,4R)-2-(3-hydroxyphenyl)-4-thiazolidinecarboxylic acid may be prepared as in Example 34 §D, but starting from 21.2 g of L-cysteine and from 22.8 g of 3-hydroxybenzaldehyde. 37.5 g of (2RS,4R)-2-(3-hydroxyphenyl)-4-thiazolidinecarboxylic acid, melting at 207° C., used as it is in subsequent syntheses, are thus obtained.

EXAMPLE 47

The operation is carried out in a fashion similar to that described in Example 41, but starting from 1.3 g of 2-trimethylsilylethyl (2R,4R)-3-{3-[2-(4-tert-butoxycarbonyl-2-phenyl-3-thiazolidinyl)-2-oxoethyl]ureido}benzoate and 4.5 $cm^3$ of a molar tetrabutylammonium fluoride solution. The crude product is purified by chromatography on silica [eluent: ethyl acetate/methanol (95/5 by volume)]. The fractions containing the expected product are combined and concentrated to dryness under reduced pressure at 40° C. The solid residue is dissolved in 4.0 $cm^3$ of 0.5N aqueous sodium hydroxide solution. The solution is filtered, and acidified with 2.1 $cm^3$ of a 1N aqueous hydrochloric acid solution. The insoluble product is separated by filtration, washed with 2 times 5 $cm^3$ of water and dried in air. 0.33 g of (2R,4R)-3-{3-[2-(4-tert-butoxycarbonyl-2-phenyl-3-thiazolidinyl)-2-oxoethyl]ureido}benzoic acid, melting at 134° C., is thus obtained. ($[\alpha]_D^{20}$=+85°±3° (C=0.40%; $CHCl_3$)) [proton NMR (250 MHz, DMSO $D_6$, δ in ppm), 2 rotamers at room temperature, peak coalescence at 120° C., characteristic chemical shifts at 120° C.: 7.3 to 7.7 (m, 8H, aromatic); 8.0 (bs, 1H, N—$C_6H_4$—C in position 2). Infrared spectrum (KBr), characteristic bands in $cm^{-1}$: 3380, 2980, 2930, 2600, 1690, 1650, 1610, 1590, 1555, 1490, 1370, 1235, 1150, 760, 730, 700, 680].

2-Trimethylsilylethyl (2R,4R)-3-{3-[2-(4-tert-butoxycarbonyl-2-phenyl-3-thiazolidinyl)-2-oxoethyl] ureido}benzoate may be prepared in a fashion similar to that described in Example 38, but starting from 1.7 g of tert-butyl (2R,4R)-3-[2-(1-imidazolylcarboxamido)acetyl]-2-phenyl-4-thiazolidinecarboxylate and 1.2 g of 2-trimethylsilylethyl 3-aminobenzoate. The crude product is purified by chromatography on silica [eluent: ethyl acetate/cyclohexane (30/70 by volume)]. The fractions containing the expected product are combined and concentrated to dryness under reduced pressure at 40° C. 1.3 g of 2-trimethylsilylethyl (2R,4R)-3-

{3-[2-(4-tert-butoxycarbonyl-2-phenyl-3-thiazolidinyl)-2-oxoethyl]ureido}benzoate are thus obtained in the form of an orange oil, used as such in subsequent syntheses.

EXAMPLE 48

The operation is carried out in a fashion similar to that described in Example 41, but starting from 4.0 g of 2-trimethylsilylethyl (2R,4R)-3-{3-{2-[4-tert-butoxycarbonyl-2-(4-dimethylaminophenyl)-3thiazolidinyl]-2-oxoethyl}ureido}benzoate and 4.2 cm³ of 1M tetrabutylammonium fluoride solution. The crude product is purified by chromatography on silica [eluent: ethyl acetate/methanol (90/10 by volume)]. The fractions containing the expected product are combined and concentrated to dryness under reduced pressure at 40° C. After vigorous stirring in diisopropyl ether, 0.35 g of (2R,4R)-3-{3-{2-[4-tert-butoxycarbonyl-2-(4-dimethylaminophenyl)-3-thiazolidinyl]-2-oxoethyl}ureido}benzoic acid is thus obtained in the form of an amorphous solid. ($[\alpha]_D^{20}$=+138°±3° (C=0.37%; CHCl₃)) [proton NMR (200 MHz, DMSO D₆, δ in ppm), 2 rotamers at room temperature, peak coalescence at 120° C., characteristic chemical shifts at 120° C.: 6.7 (bd, 2H, (Me)₂N—C₆H₄ in position 3 and 5); 7.3 and 7.6 (m, 5H, aromatic); 8.0 (bs, 1H, N—C₆H₄— in position 2). Infrared spectrum (KBr), characteristic bands in cm⁻¹: 3380, 2975, 2930, 2805, 2600, 1715, 1690, 1650, 1610, 1555, 1520, 1485, 1365, 1230, 1150, 815, 760, 685].

A—2-Trimethylsilylethyl (2R,4R)-3-{3-{2-[4-tert-butoxycarbonyl-2-(4-dimethylaminophenyl)-3-thiazolidinyl]-2-oxoethyl}ureido}benzoate may be prepared in a fashion similar to that described in Example 41 §A, but starting from 1.66 g of tert-butyl (2RS,4R)-2-(4-dimethylaminophenyl)-4-thiazolidinecarboxylate, 2.0 g of 2-{3-[3-(2-trimethylsilylethoxycarbonyl)phenyl]ureido}acetic acid and 1.23 g of N,N'-dicyclohexylcarbodiimide. The crude product is purified by chromatography on silica [eluent: ethyl acetate/cyclohexane (30/70 by volume)]. The fractions containing the expected product are combined and concentrated to dryness under reduced pressure at 40° C. 1.3 g of 2-trimethylsilylethyl (2R,4R)-3-{3-{2-[4-tert-butoxycarbonyl-2-(4-dimethylaminophenyl)-3-thiazolidinyl]-2-oxoethyl}ureido}benzoate are thus obtained in the form of an amorphous beige solid, used as it is in subsequent syntheses, ($[\alpha]_D^{20}$+93°±2° (C=0.49%; CHCl₃)).

B—tert-Butyl (2RS,4R)-2-(4-dimethylaminophenyl)-4-thiazolidinecarboxylate may be prepared as follows: 2.95 cm³ of iodotrimethylsilane are introduced dropwise at a temperature in the vicinity of 25° C. to a solution of 8.1 g of tert-butyl (2RS,4R)-3-tert-butoxycarbonyl-2-(4-dimethylaminophenyl)-4-thiazolidinecarboxylate in 100 cm³ of chloroform. The reaction mixture is stirred for 18 hours at this temperature, followed by the addition of 50 cm³ of water. The organic phase is separated, washed with 2 times 30 cm³ of a saturated aqueous sodium bicarbonate solution and with 2 times 30 cm³ of water, then extracted with 3 times 30 cm³ of a 1N aqueous hydrochloric acid solution. The aqueous phases are combined, washed with 2 times 20 cm³ of dichloromethane, brought to a pH of 7 with a 4N aqueous sodium hydroxide solution and extracted with 3 times 30 cm³ of dichloromethane. The combined organic phases are dried over magnesium sulphate and concentrated to dryness under reduced pressure at 40° C. The oily residue obtained is purified by chromatography on silica [eluent:diisopropyl ether]. The fractions containing the expected product are combined and concentrated to dryness under reduced pressure. 2.3 g of tert-butyl (2RS,4R)-2-(4-dimethylaminophenyl)-4-thiazolidinecarboxylate, melting at 142° C., a (50/50 by weight) mixture of the (2R,4R) and (2S,4R) isomers, used as it is in subsequent syntheses, are thus obtained.

C—tert-Butyl (2RS,4R)-3-tert-butoxycarbonyl-2-(4-dimethylaminophenyl)-4-thiazolidinecarboxylate may be prepared as follows: 3.1 g of tert-butanol are added to a solution of 14.8 g of 3-tert-butoxycarbonyl-2-(4-dimethylaminophenyl)-4-thiazolidinecarboxylic acid and 16.0 g of para-toluenesulphonyl chloride in 70 cm³ of anhydrous pyridine, cooled to a temperature in the vicinity of 0° C. After returning to a temperature of 20° C., stirring is continued for 20 hours, then the mixture is poured into 200 cm³ of water and extracted with 3 times 100 cm³ of ethyl acetate. The combined organic phases are washed successively with 2 times 100 cm³ of water, with 2 times 100 cm³ of 1N aqueous sodium hydroxide solution and with 2 times 100 cm³ of water, then dried over magnesium sulphate and concentrated to dryness under reduced pressure at 40° C. The crude product obtained is purified by chromatography on silica [eluent:diisopropyl ether]. The fractions containing the expected product are combined and concentrated to dryness under reduced pressure at a temperature in the vicinity of 45° C. 8.1 g of tert-butyl (2RS, 4R)-3-tert-butoxycarbonyl-2-(4-dimethylaminophenyl)-4-thiazolidinecarboxylate are thus obtained in the form of an orange oil, used as it is in subsequent syntheses.

D—(2RS,4R)-3-tert-Butoxycarbonyl-2-(4-dimethylaminophenyl)-4-thiazolidinecarboxylic acid may be prepared as follows: 10.9 g of di-tert-butyl dicarbonate in solution in 50 cm³ of dioxane are added dropwise while stirring to a solution of 12.6 g of (2RS,4R)-2-(4-dimethylaminophenyl)-4-thiazolidinecarboxylic acid and 5.25 g of sodium carbonate in 100 cm³ of water. The reaction mixture is stirred for 20 hours at a temperature in the vicinity of 20° C., then the precipitate formed is separated by filtration. The filtrate is washed with 2 times 100 cm³ of ethyl acetate, acidified to a pH of 4 with a 4N aqueous hydrochloric acid solution, then extracted with 3 times 100 cm³ of ethyl acetate. The combined organic phases are washed with 2 times 50 cm³ of water, dried over magnesium sulphate and concentrated to dryness under reduced pressure at 40° C. After recrystallization in diisopropyl ether, 14.8 g of (2RS,4R)-3-tert-butoxycarbonyl-2-(4-dimethylaminophenyl)-4-thiazolidinecarboxylic acid, melting at 175° C., are thus obtained.

(2RS,4R)-2-(4-Dimethylaminophenyl)-4-thiazolidinecarboxylic acid may be prepared as in Example 34 §D, but starting from 21.2 g of L-cysteine and 27.5 g of 4-dimethylaminobenzaldehyde. 41.5 g of (2RS,4R)-2-(4-dimethylaminophenyl)-4-thiazolidinecarboxylic acid, melting at 184° C., used as it is in subsequent syntheses, are thus obtained.

EXAMPLE 49

The operation is carried out in a fashion similar to that described in Example 41, but starting from 0.95 g of 2-trimethylsilylethyl (2R,4R)-3-{3-{2-[4-tert-butoxycarbonyl-2-(3-pyridyl)-3-thiazolidinyl]-2-oxoethyl}ureido}benzoate in 3.2 cm³ of 1M tetrabutylammonium fluoride solution. The crude product is purified by chromatography on silica [eluent: ethyl acetate]. The fractions containing the expected product are combined and concentrated to dryness under reduced pressure at 40° C. After vigorous stirring in diisopropyl ether, 0.36 g of (2R, 4R)-3-{3-{2-[4-tert-butoxycarbonyl-2-(3-pyridyl)-3-thiazolidinyl]-2-oxoethyl}ureido}benzoic acid, melting at 147° C., is thus obtained ($[\alpha]_D^{20}$=+51.1°±17° (C=0.49%; DMF))

[proton NMR (200 MHz, DMSO D$_6$, δ in ppm), 2 rotamers at room temperature, peak coalescence at 120° C., characteristic chemical shifts at 120° C.: 7.3 to 7.6 (m, 5H, aromatic); 8.0 (bs, 1H, N—C$_6$H$_4$—C in position 2); 8.5 (bs, 1H, H in position 2 of pyridyl); 8.8 (bs, 1H, H in position 6 of pyridyl). Infrared spectrum (KBr), characteristic bands in cm$^{-1}$: 3385, 2975, 2930, 2600, 2500, 1730, 1660, 1610, 1590, 1560, 1485, 1370, 1240, 1150, 760, 710, 685].

2-Trimethylsilylethyl (2R,4R)-3-{3-{2-[4-tert-butoxycarbonyl-2-(3-pyridyl)-3-thiazolidinyl]-2-oxoethyl}ureido}benzoate may be prepared in a fashion similar to that described in Example 41 §A, but starting from 2.0 g of tert-butyl (2RS,4R)-2-(3-pyridyl)-4-thiazolidinecarboxylate, 2.5 g of 2-{3-[3-(2-trimethylsilylethoxycarbonyl)phenyl]ureido}acetic acid and 1.8 g of N,N'-dicyclohexylcarbodiimide. The crude product is purified by chromatography on silica [eluent: ethyl acetate/cyclohexane (40/60 by volume)]. The fractions containing the expected product are combined and concentrated to dryness under reduced pressure at 40° C. 1.0 g of 2-trimethylsilylethyl (2R,4R)-3-{3-{2-[4-tert-butoxycarbonyl-2-(3-pyridyl)-3-thiazolidinyl]-2-oxoethyl}ureido}benzoate is thus obtained in the form of a yellow oil, used as it is in subsequent syntheses.

tert-Butyl (2RS,4R)-2-(3-pyridyl)-4-thiazolidinecarboxylate may be prepared in a fashion similar to that described in Example 48 §B, but starting from 3.4 g of tert-butyl (2RS,4R)-3-tert-butoxycarbonyl-2-(3-pyridyl)-4-thiazolidinecarboxylate and 1.7 cm$^3$ of iodotrimethylsilane. 2.1 g of tert-butyl (2RS,4R)-2-(3-pyridyl)-4-thiazolidinecarboxylate are thus obtained in the form of a yellow oil, used as it is in subsequent syntheses.

tert-Butyl (2RS,4R)-3-tert-butoxycarbonyl-2(3-pyridyl)-4-thiazolidinecarboxylate may be prepared in a fashion similar to that described in Example 48 §C, but starting from 9.0 g of (2RS,4R)-3-tert-butoxycarbonyl-2-(3-pyridyl)-4-thiazolidinecarboxylic acid, 5.7 g of para-toluenesulphonyl chloride and 2.2 g of tert-butanol. The crude product obtained is purified by chromatography on silica [eluent: ethyl acetate/cyclohexane (50/50 by volume)]. The fractions containing the expected product are combined and concentrated to dryness under reduced pressure at 40° C. 1.25 g of tert-butyl (2RS,4R)-3-tert-butoxycarbonyl-2-(3-pyridyl)-4-thiazolidinecarboxylate are thus obtained in the form of an orange oil, used as it is in subsequent syntheses.

(2RS,4R)-3-tert-Butoxycarbonyl-2-(3-pyridyl)-4-thiazolidinecarboxylic acid may be prepared in a fashion similar to that described in Example 48 §D, but starting from 26.5 g of (2RS,4R)-2-(3-pyridyl)-4-thiazolidine-carboxylic acid, 130 cm$^3$ of 1N sodium hydroxide solution and 28.4 g of di-tert-butyl dicarbonate. 31.6 g of (2RS, 4R)-3-tert-butoxycarbonyl-2-(3-pyridyl)-4-thiazolidinecarboxylic acid are thus obtained in the form of a yellow amorphous powder, used as it is in subsequent syntheses.

(2RS,4R)-2-(3-Pyridyl)-4-thiazolidinecarboxylic acid may be prepared as in Example 34 §D, but starting from 25.0 g of L-cysteine and 22 cm$^3$ of nicotinaldehyde. 26.6 g of (2RS,4R)-2-(3-pyridyl)-4-thiazolidinecarboxylic acid, melting at 149° C., used as it is in subsequent syntheses, are thus obtained.

EXAMPLE 50

The operation is carried out in a fashion similar to that described in Example 39, but starting from 2.5 g of ethyl (2R,4R)-3-{3-{3-[2-(4-tert-butoxycarbonyl-2-phenyl-3-thiazolidinyl)-2-oxoethyl]ureido}phenyl}propionate and 0.2 g of lithium hydroxide. The crude product is purified by chromatography on silica [eluent: ethyl acetate/methanol (90/10 by volume)]. The fractions containing the expected product are combined and concentrated to dryness under reduced pressure at 40° C. 0.25 g of (2R,4R)-3-{3-{3-[2-(4-tert-butoxycarbonyl-2-phenyl-3-thiazolidinyl)-2-oxoethyl]ureido}phenyl}propionic acid is thus obtained in the form of an amorphous beige solid ([α]$_D^{20}$=+58.4°±1.6° (C=0.61%; CHCl$_3$)) [proton NMR (200 MHz, DMSO D$_6$, δ in ppm), 2 rotamers at room temperature, characteristic chemical shifts at 25° C.: 1.5 (bs, 9H, (CH$_3$)$_3$); 2.5 (bt, 2H, CH$_2$); 2.8 (bt, 2H, CH$_2$); 6.8 (bd, 1H, N—C$_6$H$_4$—C in position 4); 7.1 to 7.5 (m, 7H, aromatic); 7.7 (bd, 2H, aromatic). Infrared spectrum (KBr), characteristic bands in cm$^{-1}$: 3380, 2975, 2930, 2620, 1730, 1645, 1610, 1590, 1555, 1490, 1370, 1235, 1150, 785, 730, 695].

Ethyl (2R,4R)-3-{3-{3-[2-(4-tert-butoxycarbonyl-2-phenyl-3-thiazolidinyl)-2-oxoethyl]ureido}phenyl}propionate may be prepared in a fashion similar to that described in Example 38, but starting from 3.75 g of tert-butyl (2R,4R)-3-[2-(1-imidazolylcarboxamido)-acetyl]-2-phenyl-4-thiazolidinecarboxylate and 3.5 g of ethyl 3-(3aminophenyl)propionate. The oily residue obtained is purified by chromatography on silica [eluent: ethyl acetate/cyclohexane (30/70 by volume)]and the fractions containing the expected product are combined, then concentrated to dryness under reduced pressure at 40° C. 2.5 g of ethyl (2R,4R)-3-{3-{3-[2-(4-tert-butoxycarbonyl-2-phenyl-3-thiazolidinyl)-2-oxoethyl]ureido}phenyl}propionate are thus obtained in the form of an oil used as it is in subsequent syntheses.

EXAMPLE 51

The operation is carried out in a fashion similar to that described in Example 39, but starting from 2.4 g of ethyl (2R,4R)-3-{3-[2-(4-tert-butoxycarbonyl-2-phenyl-3-thiazolidinyl)-2-oxoethyl]ureido}phenoxyacetate and 0.2 g of lithium hydroxide. The crude product is purified by chromatography on silica [eluent: ethyl acetate]. The fractions containing the expected product are combined and concentrated to dryness under reduced pressure at 40° C. After vigorous stirring in diisopropyl ether, 1.3 g of (2R,4R)-3-{3-[2-(4-tert-butoxycarbonyl-2-phenyl-3-thiazolidinyl)-2-oxoethyl]ureido}phenoxyacetic acid are thus obtained in the form of an amorphous solid ([α]$_D^{20}$=+63.7°±1.2° (C=0.96%; CHCl$_3$)) [proton NMR (200 MHz, DMSO D$_6$, δ in ppm), 2 rotamers at room temperature, peak coalescence at 120° C., characteristic chemical shifts at 120° C.: 4.5 (bs, 2H, OCH$_2$CO$_2$); 6.5 (ddd, 1H, N—C$_6$H$_4$—C in position 4); 6.9 (d, 1H aromatic); 7.1 to 7.7 (m, 7H, aromatic). Infrared spectrum (KBr), characteristic bands in cm$^{-1}$: 3380, 2975, 2930, 2630, 2550, 1735, 1640, 1600, 1555, 1490, 1370, 1240, 1150, 770, 730, 695].

Ethyl (2R,4R)-3-{3-[2-(4-tert-butoxycarbonyl-2-phenyl-3-thiazolidinyl)-2-oxoethyl]ureido}phenoxyacetate may be prepared in a fashion similar to that described in Example 38, but starting from 4.4 g of tert-butyl (2R,4R)-3-[2-(1-imidazolylcarboxamido)acetyl]-2-phenyl-4-thiazolidinecarboxylate and 4.1 g of ethyl 3-aminophenoxyacetate. The oily residue obtained is purified by chromatography on silica [eluent: ethyl acetate/cyclohexane (35/65 by volume)]. The fractions containing the expected product are combined and concentrated to dryness under reduced pressure at 40° C. 2.5 g of ethyl (2R,4R)-3-{3-[2-(4-tert-butoxycarbonyl-2-phenyl-3-thiazolidinyl)-2-oxoethyl]ureido}phenoxyacetate are thus obtained in the form of an amorphous beige powder used as it is in subsequent syntheses.

EXAMPLE 52

0.4 g of hydroxylamine hydrochloride in 5 cm³ of solution in water is added to a solution of 2.5 g of tert-butyl (2R,4R)-3-{2-[3-(3-acetylphenyl)ureido]acetyl}-2-phenyl-4-thiazolidinecarboxylate in 10 cm³ of methanol and 5 cm³ of pyridine. The reaction mixture is stirred under reflux for 2 hours. After evaporation of the solvents under reduced pressure at 45° C. the residue is taken up in 100 cm³ of ethyl acetate. The organic phase is washed with 3 times 50 cm³ of water, dried over magnesium sulphate and concentrated to dryness under reduced pressure. The crude product obtained is purified by chromatography on silica [eluent: ethyl acetate/cyclohexane (50/50 by volume)]. The fractions containing the expected product are combined and concentrated to dryness under reduced pressure at 40° C. After vigorous stirring in diisopropyl ether, 0.5 g of tert-butyl (2R,4R)-3-{2-{3-[3-(1-hydroxyiminoethyl)-(E)-phenyl]ureido}acetyl}-2-phenyl-4-thiazolidinecarboxylate is obtained in the form of an amorphous solid ([α]$_D^{20}$=+54°±1.5° (C=0.61%; CHCl₃)) [proton NMR (300 MHz, DMSO D₆, δ in ppm), 2 rotamers at room temperature, peak coalescence at 120° C., characteristic chemical shifts at 120° C.: 2.1 (s, 3H, CH₃); 7.2 to 7.6 (m, 8H, aromatic); 7.7 (bs, 1H, N—C₆H₄—C in position 2); 10.8 (bs, 1H, NOH). An NOE effect has been observed between the methyl group at 2.1 ppm and the NOH oxime group at 10.8 ppm. Infrared spectrum (KBr), characteristic bands in cm⁻¹: 3350, 2975, 2930, 1740, 1650, 1610, 1590, 1560, 1370, 1240, 1150, 1005, 790, 730, 695].

tert-Butyl (2R,4R)-3-{2-[3-(3-acetylphenyl)ureido]acetyl}-2-phenyl-4-thiazolidinecarboxylate may be prepared in a fashion similar to that described in Example 38, but starting from 3.75 g of tert-butyl (2R,4R)-3-[2-(1-imidazolylcarboxamido)acetyl]-2-phenyl4-thiazolidinecarboxylate and 1.46 g of 3-aminoacetophenone. The oily residue obtained is purified by chromatography on silica [eluent: ethyl acetate/cyclohexane (50/50 by volume)]. The fractions containing the expected product are combined and concentrated to dryness under reduced pressure at 40° C. 2.5 g of tert-butyl (2R,4R)-3-{2-[3-(3-acetylphenyl)ureido]acetyl}-2-phenyl-4-thiazolidinecarboxylate are thus obtained in the form of an amorphous yellow powder used as it is in subsequent syntheses.

EXAMPLE 53

The operation is carried out in a fashion similar to that described in Example 38, but starting from 2.3 g of tert-butyl (2R,4R)-3-[2-(1-imidazolylcarboxamido)-acetyl]-2-phenyl-4-thiazolidinecarboxylate and 4.7 g of tetra-n-butylammonium 3-aminobenzylsulphonate. The crude product obtained is dissolved in 20 cm³ of acetone and a solution of 1.86 g of potassium nonafluorobutanesulphonate in 20 cm³ of acetone is added. The reaction mixture is stirred for 18 hours at a temperature in the vicinity of 25° C., followed by the addition of 80 cm³ of diisopropyl ether. The insoluble product is separated by filtration, washed with 2 times 3 cm³ of a mixture of acetone and diisopropyl ether (30/70 by volume). After vigorous stirring in acetonitrile, 0.75 g of potassium (2R,4R)-3-{3-[2-(4-tert-butoxycarbonyl-2-phenyl-3-thiazolidinyl)-2-oxoethyl]ureido}benzyl-sulphonate, melting at 185° C., is thus obtained ([α]$_D^{20}$=+37.3°±1.4° (C=0.38%; CHCl₃)) [proton NMR (300 MHz, DMSO, D₆, δ in ppm), 2 rotamers at room temperature, peak coalescence at 120° C., characteristic chemical shifts at 120° C.: 3.7 (AB, 2H, CH₂SO₃); 6.9 (bd, 1H, N—C₆H₄—C in 6 position); 7.1 to 7.6 (m, 8H, aromatic). Infrared spectrum (KBr), characteristic bands in cm⁻¹: 3400, 2980, 2945, 1740, 1660, 1615, 1600, 1560, 1500, 1375, 1220, 1200, 1160, 1050, 800, 735, 700].

Tetra-n-butylammonium 3-aminobenzylsulphonate may be prepared in a fashion similar to that described in Example 41 §G, but starting from 11.6 g of tetra-n-butylammonium 3-nitrobenzylsulphonate and 0.3 g of 5% palladium on charcoal. 10.5 g of tetra-n-butylammonium 3-aminobenzylsulphonate are thus obtained in the form of an oil used as it is in subsequent syntheses.

Tetra-n-butylammonium 3-nitrobenzylsulphonate may be prepared as follows: 6.9 g of sodium 3-nitro-benzylsulphonate and then 9.9 g of tetra-n-butyl-ammonium hydrogenosulphonate are added to 800 cm³ of a 0.5M aqueous solution of potassium dihydrogen phosphate. The mixture is extracted with 500 cm³ of methylene chloride. The organic phase is dried over magnesium sulphate and concentrated to dryness under reduced pressure at 40° C. 13 g of tetra-n-butylammonium 3-nitrobenzylsulphonate are thus obtained in the form of an oil used as it is in subsequent syntheses.

Sodium 3-nitrobenzylsulphonate may be prepared according to the method described by PURGOTTI and MONTI, Gazz. Chim. Ital. 30, II, 247.

EXAMPLE 54

The operation is carried out in a fashion similar to that described in Example 39, but starting from 1.5 g of methyl (RS)-2-{{3-[3-(2-(2R,4R)-4-tert-butoxycarbonyl-2-phenyl-3-thiazolidinyl)-2-oxoethyl]ureido}phenyl}propionate and 0.11 g of lithium hydroxide. The crude product is purified by chromatography on silica [eluent: ethyl acetate]. The fractions containing the expected product are combined and concentrated to dryness under reduced pressure at 40° C. After vigorous stirring in diisopropyl ether, 0.25 g of (RS)-2-{{3-[3-(2-(2R,4R)-4-tert-butoxycarbonyl-2-phenyl-3-thiazolidinyl)-2-oxoethyl]ureido}phenyl}propionic acid is obtained in the form of an amorphous solid [proton NMR (200 MHz, DMSO D₆, δ in ppm), 2 rotamers at room temperature, peak coalescence at 120° C., characteristic chemical shifts at 120° C.: 1.4 (d, 3H, CH₃); 3.5 (bm, 1H, Ph—CH—CO₂); 6.9 (bd, 1H, N—C₆H₄—C in position 4); 7.1 to 7.4 (m, 6H, aromatic); 7.7 (bd, 2H, aromatic). Infrared spectrum (KBr), characteristic bands in cm⁻¹: 3385, 2975, 2935, 1735, 1650, 1610, 1560, 1495, 1455, 1370, 1240, 1155, 785, 730, 700].

Methyl (RS)-2-{{3-[3-(2-(2R,4R)-4-tert-butoxycarbonyl-2-phenyl-3-thiazolidinyl)-2-oxoethyl]ureido}phenyl}propionate may be prepared in a fashion similar to that described in Example 38, but starting from 3.75 g of tert-butyl (2R,4R)-3-[2-(1-imidazolylcarboxamido)-acetyl]-2-phenyl-4-thiazolidinecarboxylate and 3.22 g of methyl (RS)-2-(3-aminophenyl)propionate. The oily residue obtained is purified by chromatography on silica gel [eluent: ethyl acetate]and the fractions containing the expected product are combined and concentrated to dryness under reduced pressure at 40° C. 3.1 g of methyl (RS)-2-{{3-[3-(2-(2R,4R)-4-tert-butoxycarbonyl-2-phenyl-3-thiazolidinyl)-2-oxoethyl]ureido}phenyl}propionate are thus obtained in the form of an amorphous beige powder used as it is in subsequent syntheses.

Methyl (RS)-2-(3-aminophenyl)propionate may be prepared in a fashion similar to that described in Example 41

§G, but starting from 4 g of methyl (RS)-3-(3-nitrophenyl) propionate and 0.3 g of 5% palladium on charcoal. 3.3 g of methyol (RS)-2-(3-aminophenyl)propionate are thus obtained in the form of an oil used as it is in subsequent syntheses.

Methyl (RS)-3-(3-nitrophenyl)propionate may be prepared as follows: gaseous hydrochloric acid is bubbled for 3 hours through a solution of 5 g of (RS)-2-(3-nitrophenyl) propionitrile in 40 cm³ of methanol. The mixture obtained is stirred under reflux for 30 minutes, and the insoluble product is separated by filtration. The filtrate is concentrated to dryness under reduced pressure at 40° C. The crude product is purified by chromatography on silica [eluent:petroleum ether/ethyl acetate (80/20 by volume)]. The fractions containing the expected product are combined and concentrated to dryness under reduced pressure at 40° C. 4 g of methyl (RS)-3-(3-nitrophenyl)propionate are thus obtained in the form of an oil used as it is in subsequent syntheses.

(RS)-2-(3-Nitrophenyl)propionitrile may be prepared according to the method described by E. Felder et al., J. Med. Chem., 13, 559 (1970).

EXAMPLE 55

By proceeding in a fashion similar to that described in Example 41 §A, but starting from 1.7 g of tert-butyl (2R, 4R)-2-(4-fluorophenyl)-4-thiazolidinecarboxylate in solution in 20 cm³ of anhydrous acetonitrile, 1.24 g of N,N'-dicyclohexylcarbodiimide and 1.3 g of 2-(2-indolylcarboxamido)acetic acid in a mixture of 40 cm³ of anhydrous acetonitrile and 40 cm³ of dichloromethane, after recrystallization in diisopropyl ether, 1.7 g of tert-butyl (2R,4R)-2-(4-fluorophenyl)-3-[2-(2-indolylcarboxamido)acetyl]-4-thiazolidinecarboxylate, melting at 176° C., are obtained.

2-(2-Indolylcarboxamido)acetic acid may be obtained according to the method described by J. R. JOHNSON et al., J. Am. Chem. Soc., 69, 2370 (1947).

EXAMPLE 56

By proceeding in a fashion similar to that described in Example 1, but starting from 1.2 g of (2RS,5SR)-N-methyl-N-phenyl-5-phenylprolinamide, 0.94 g of 2-[3-(3-methylphenyl)ureido]acetic acid in suspension in 25 cm³ of 1,2-dichloroethane and 0.33 cm³ of sulphinyl chloride, after recrystallization in acetonitrile, 1 g of (2RS,5SR)-N-methyl-1-[3-(3-methylphenyl)ureidoacetyl]-N-phenyl-5-phenylprolinamide, melting at 210° C., is obtained.

(2RS,5SR)-N-Methyl-N-phenyl-5-phenylprolinamide may be prepared in a fashion similar to that described in Example 25 §A, but starting from 2.2 g of (2RS,5SR)-1-(tert-butoxycarbonyl-N-methyl-N-phenyl-5-phenylprolinamide in 25 cm³ of anhydrous chloroform and 0.85 cm³ of iodotrimethylsilane. 1.2 g of (2RS,5SR)-N-methyl-N-phenyl-5-phenylprolinamide are obtained in the form of an orange oil, used as it is in the subsequent syntheses.

A (2RS,5SR)-1-(tert-Butoxycarbonyl)-N-methyl-N-phenyl-5-phenylprolinamide may be prepared as follows: at a temperature in the vicinity of 0° C. a solution of 2.1 g of N,N'-dicyclohexylcarbodiimide in 15 cm³ of anhydrous acetonitrile is added dropwise to a suspension of 2.9 g of (2RS,5SR)-1-(tert-butoxycarbonyl)-5-phenylproline and 1.1 cm³ of N-methylaniline in 25 cm³ of anhydrous acetonitrile. The reaction mixture is stirred for 30 minutes at a temperature in the vicinity of 0° C., then for 20 hours at a temperature in the vicinity of 20° C. The insoluble product is then separated by filtration and washed with 2 times 20 cm³ of dichloromethane. The filtrate is concentrated to dryness without reduced pressure at a temperature in the vicinity of of 40° C. The product obtained is purified by chromatography on silica [eluent:dichloromethane/methanol (99/1 by volume)]. The fractions containing the expected product are combined, then concentrated to dryness under reduced pressure. After recrystallization in pentane, 2.2 g of (2RS,5SR)-1-(tert-butoxycarbonyl)-N-methyl-N-phenyl-5-phenylprolinamide, melting at 132° C., are thus obtained.

EXAMPLE 57

By proceeding in a fashion similar to that described in Example 1, but starting from 3 g of (2RS,5SR)-5-phenyl-(1,2,3,4-tetrahydro-1-quinolyl)-2-carbonyl-pyrrolidine, 2 g of 2-[3-(3-methylphenyl)ureido]acetic acid in suspension in 100 cm³ of 1,2-dichloroethane and 0.7 cm³ of sulphinyl chloride, after recrystallization in acetonitrile, 1.5 g of (2RS,5SR)-1-{2-[3-(3-methylphenyl)ureido]acetyl}-5-phenyl-(1,2,3,4-tetrahydro-1-quinolyl)-2-carbonylpyrrolidine, melting at 158° C., are obtained.

(2RS,5SR)-5-Phenyl-(1,2,3,4-tetrahydro-1-quinolyl)-2-carbonylpyrrolidine may be prepared in a fashion similar to that described in Example 25 §A, but starting from 4.1 g of (2RS,5SR)-1-(tert-butoxycarbonyl)-5-phenyl-(1,2,3,4-tetrahydro-1-quinolyl)-2-carbonylpyrrolidine in 50 cm³ of anhydrous chloroform and 1.4 cm³ of iodotrimethylsilane. 3 g of (2RS,5SR)-5-phenyl-(1,2,3,4-tetrahydro-1-quinolyl)-2-carbonylpyrrolidine are obtained in the form of an orange oil used as it is in subsequent syntheses.

(2RS,5SR)-1-(tert-Butoxycarbonyl)-5-phenyl-(1,2,3,4-tetrahydro-1-quinolyl)-2-carbonylpyrrolidine may be prepared in a fashion similar to that described in Example 56 §A but starting from 8.7 g of (2RS,5SR)-1-(tert-butoxycarbonyl)-5-phenylproline, 3.8 cm³ of 1,2,3,4-tetra-hydroquinoline in 75 cm³ of anhydrous acetonitrile and 6.2 g of N,N'-dicylohexylcarbodiimide in 45 cm³ of anhydrous acetonitrile. After crystallization in hexane, 4.1 g of (2RS, 5SR)-1-(tert-butoxycarbonyl)-5-phenyl-(1,2,3,4-tetrahydro-1-quinolyl)-2-carbonylpyrrolidine, melting at 132° C., are obtained.

EXAMPLE 58

By proceeding in a fashion similar to that described in Example 1, but starting from 1.8 g of (2RS,5SR)-3,3-dimethylpiperidino-2-carbonyl-5-phenylpyrrolidine, 1.3 g of 2-[3-(3-methylphenyl)ureido]acetic acid in 75 cm³ of 1,2-dichloroethane, and 0.5 cm³ of sulphinyl chloride, after recrystallization in acetonitrile, 0.7 g of (2RS,5SR)-3,3-dimethylpiperidino)-2-carbonyl-1-{2-[3-(3-methylphenyl)ureido]acetyl}-5-phenylpyrrolidine, melting at 150° C., is obtained.

(2RS,5SR)-3,3-dimethylpiperidino-2-carbonyl-5-phenylpyrrolidine may be prepared in a fashion similar to that described in Example 25 §A, but starting from 5.0 g of 1-tert-butoxycarbonyl-3,3-dimethyl-piperidino-2-carbonyl-5-phenylpyrrolidine in 50 cm³ of anhydrous chloroform and 1.9 cm³ of iodotrimethylsilane. After recrystallization in diisopropyl ether, 1.8 g of (2RS,5SR)-(3,3-dimethylpiperidino)-2-carbonyl-5-phenylpyrrolidine, melting at 163° C., are obtained.

(2RS,5SR)-1-(tert-butoxycarbonyl)-(3,3-dimethylpiperidino)-2-carbonyl-5-phenylpyrrolidine may be prepared in a fashion similar to that described in Example 56 §A, but starting from 5.8 g of (2RS,5SR)-1-(tert-butoxycarbonyl)-

5-phenylproline, 2.6 cm³ of 3,3-dimethylpiperidine in 50 cm³ of anhydrous acetonitrile and 4.1 g of N,N'-dicyclo-hexylcarbodiimide in 30 cm³ of anhydrous acetonitrile. After recrystallization in hexane, 4 g of (2RS,5SR)-1-(tert-butoxycarbonyl)-(3,3-dimethylpiperidino)-2-carbonyl-5-phenylpyrrolidine, melting at 110° C., are obtained.

EXAMPLE 59

By proceeding in a fashion similar to that described in Example 2, but starting from 1.9 g of (2RS,5SR)-1-(2-aminoacetyl)-5-phenyl-N-tert-butylprolinamide in solution in 20 cm³ of anhydrous tetrahydrofuran and 0.82 cm³ of 3-methylphenyl isocyanate, after recrystallistion in acetonitrile, 0.7 g of (2RS,5SR)-N-tert-butyl-1-[3-(3-methylphenyl)ureidoacetyl]-5-phenylprolinamide, melting at 169° C., is obtained.

(2RS,5SR)-1-(2-Aminoacetyl)-5-phenyl-N-tert-butylprolinamide may be prepared in a fashion similar to that described in Example 2 §A, but starting from 2.7 g of (2RS,5SR)-1-(2-tert-butoxycarbonylaminoacetyl)-N-tert-butyl-5-phenylprolinamide in solution in 50 cm³ of anhydrous chloroform and 0.95 cm³ of iodotrimethylsilane. 1.9 g of (2RS,5SR)-1-(2-aminoacetyl)-5-phenyl-N-tert-butylprolinamide are obtained in the form of an amorphous powder used as it is in subsequent syntheses.

Proton MMR (250 MHz, DMSO $D_6$, $\delta$ in ppm), 2 rotamers at room temperature, 1.35 (s, 9H, C(CH$_3$)$_3$), 1.8 to 2.4 (bm, 4H, CH$_2$—CH$_2$); 2.7, 3.25 and 3.8 (d, 2H, AB, CH$_2$CO$_2$); 4.45 (bm, 1H, CHN); 5.1 (bm, 1H, CHN); 7.2 to 8 (m, 6H, aromatic and NH).

1-(2-tert-Butoxycarbonylaminoacetyl)-N-tert-butyl-5-phenylprolinamide may be prepared in a fashion similar to that described in Example 2 §B, but starting from 1.8 g of (2RS,5SR)-N-tert-butyl-5-phenylprolinamide, 1.28 g of 2-tert-butoxycarbonylaminoacetic acid in 50 cm³ of anhydrous acetonitrile and 1.5 g of N,N'-dicyclo-hexylcarbodiimide in 25 cm³ of anhydrous acetonitrile. After crystallization in petroleum ether, 2.7 g of 1-(2-tert-butoxycarbonylaminoacetyl)-N-tert-butyl-5-phenylprolinamide, melting at 117° C., are obtained.

(2RS,5SR)-N-tert-Butyl-5-phenylprolinamide may be prepared in a fashion similar to that described in Example 25 §A, but starting from 3.5 g of (2RS,5SR)-1-(tert-butoxycarbonyl)-N-tert-butyl-5-phenylprolinamide in 50 cm³ of anhydrous chloroform and 2.1 cm³ of iodotrimethylsilane. 1.8 g of (2RS,5SR)-N-tert-butyl-5-phenyl-prolinamide are obtained in the form of a yellow oil used as it is in subsequent syntheses.

(2RS,5SR)-1-tert-butoxycarbonyl-N-tert-butyl-5-phenyl-prolinamide may be obtained as follows: at a temperature in the vicinity of 20° C., 1.8 g of N,N'-carbonyl-diimidazole are added to a solution of 2.9 g of (2RS,5SR)-1-tert-butoxycarbonyl-5-phenylproline in 50 cm³ of 1,2-dichloroethane. The reaction mixture is stirred for 2 hours at a temperature in the vicinity of 20° C., then 1 cm³ of tert-butylamine is added and the mixture is heated under reflux for for 5 hours while stirring. After cooling, the reaction mixture is diluted with 100 cm³ of dichloromethane and washed successively with 2 times 50 cm³ of a normal aqueous hydrochloric acid solution, then with 3 times 50 cm³ of water. The organic phase is dried over magnesium sulphate, then evaporated to dryness under reduced pressure. The residue obtained is purified by chromatography on silica [eluent:dichloromethane/methanol (97.5/2.5 by volume)] and the fractions containing the expected product are combined and concentrated to dryness under reduced pressure. 3 g of (2RS,5SR)-1-tert-butoxycarbonyl-N-tert-butylphenylprolinamide are thus obtained in the form of a yellow oil used as it is in subsequent syntheses.

EXAMPLE 60

By proceeding in a fashion similar to that described in Example 9, but starting from 10.6 g of methyl cis-3-{3-[2-(2,5-diphenyl-1-pyrrolidinyl)-2-oxoethyl]ureido}phenylacetate in solution in 150 cm³ of methanol and 1.7 g of potassium hydroxide dissolved in 30 cm³ of water and after treatment and recrystallization in ethanol, 1.2 g of cis-3-{3-[2-(2,5-diphenyl-1-pyrrolidinyl)-2-oxoethyl]ureido}phenylacetic acid, melting at 152° C., are obtained.

Methyl cis-3-{3-[2-(2,5-diphenyl-1-pyrrolidinyl)-2-oxoethyl]ureido}phenylacetate may be prepared in a fashion similar to that described in Example 41 §A, but starting from 4.45 g of cis-2,5-diphenyl-pyrrolidine, 5.32 g of 2-[3-(3-methoxycarbonylmethyl-phenyl)ureido]acetic acid and 4.2 g of N,N'-dicyclo-hexylcarbodiimide in 40 cm³ of acetonitrile. After treatment, 10.6 g of methyl cis-3-{3-[2-(2,5-diphenyl-1-pyrrolidinyl)-2-oxoethyl]ureido}phenylacetate are obtained in the form of an oil used as it is in subsequent syntheses.

2-[3-(3-Methoxycarbonylmethylphenyl)ureido]acetic acid may be prepared in a fashion similar to that described in Example 1 §A, but starting from 9.42 g of glycine, 34.69 g of potassium carbonate in 220 cm³ of water and 24 g of methyl 3-isocyanatophenylacetate dissolved in 170 cm³ of 1,4-dioxane. After treatment and recrystallization in ethyl acetate, 46.85 g of 2-[3-(3-methoxycarbonylmethylphenyl)ureido]acetic acid, melting at 136° C., are obtained.

EXAMPLE 61

By proceeding in a fashion similar to that described in Example 9, but starting from 4.8 g of ethyl cis-3-{3-[2-(2,5-diphenyl-1-pyrrolidinyl)-2-oxoethyl]ureido}-phenyl}propionate in solution in 25 cm³ of methanol and 0.25 g of potassium hydroxide dissolved in 5 cm³ of water and after treatment, 0.9 g of cis-3-{3-[2-(2,5-diphenyl-1-pyrrolidinyl)-2-oxoethyl]ureido}phenyl}propionic acid, melting at 170° C., is obtained.

Ethyl cis-3-{3-[2-(2,5-diphenyl-1-pyrrolidinyl)-2-oxoethyl]ureido}phenyl}propionate may be prepared in a fashion similar to that described in Example 41 §A, but starting from 0.68 g of cis-2,5-diphenyl-pyrrolidine, 0.9 g of 2-{3-[3-(2-ethoxycarbonylethyl)-phenyl}ureido}acetic acid and 0.63 g of N,N'-dicyclo-hexylcarbodiimide in 6 cm³ of acetonitrile. After treatment, 1.8 g of ethyl cis-3-{3-[2-(2,5-diphenyl-1-pyrrolidinyl)-2-oxoethyl]ureido}phenyl}propionate are obtained in the form of an oil used as it is in subsequent syntheses.

2-{3-[3-(2-Ethoxycarbonylethyl)phenyl]ureido}acetic acid may be prepared in a fashion similar to that described in Example 1 §A, but starting from 0.44 g of glycine, 1.63 g of potassium carbonate in 10 cm³ of water and 1.3 g of ethyl 3-(3-isocyanatophenyl)propionate in solution in 8 cm³ of 1,4-dioxane. After treatment, 0.9 g of 2-{3-[3-(2-ethoxycarbonylethyl)phenyl]-ureido}acetic acid is obtained in the form of an amorphous solid used as it is in subsequent syntheses.

Ethyl 3-(3-isocyanatophenyl)propionate may be prepared as follows: in the space of 30 minutes at a temperature in the vicinity of −20° C. a solution of 2.36 g of bis(trichloromethyl)carbonate in 20 cm³ of toluene is added to a suspension of 0.45 g of charcoal in 3 g of ethyl 3-(3-aminophenyl)propionate in solution in 60 cm³ of toluene. The reaction mixture is heated at a temperature in the vicinity of 110° C. for 2 hours and 30 minutes, cooled to a temperature in the vicinity of 20° C., filtered over Celite and concentrated under reduced pressure. 3.5 g of ethyl 3-(3-isocyanatophenyl)-propionate are thus obtained in the form of an oil used as it is in subsequent syntheses.

EXAMPLE 62

By proceeding in a fashion similar to that described in Example 9, but starting from 1.2 g of methyl (2RS,5SR)-3-{3-{2-[2-(2-methoxyphenyl)-5-phenyl-1-pyrrolidinyl]-2-oxoethyl}ureido}phenylacetate in solution in 20 cm³ of methanol and 0.19 g of potassium hydroxide in solution in 4 cm³ of water, and after treatment and recrystallization in diethyl ether, 0.6 g of (2RS,5SR)-3-{3-{2-[2-(2-methoxyphenyl)-5-phenyl-1-pyrrolidinyl]-2-oxoethyl}ureido}phenylacetic acid, melting at 140° C., is obtained.

Methyl cis-3-{3-{2-[2-(2-methoxyphenyl)-5-phenyl-1-pyrrolidinyl]-2-oxoethyl}ureido}phenylacetate may be prepared in a fashion similar to that described in Example 41 §A, but starting from 0.57 g of (2RS,5SR)-2-(2-methoxyphenyl)-5-phenyl-pyrrolidine, 0.6 g of 2-[3-(3-methoxycarbonylmethylphenyl)ureido]acetic acid and 0.46 g of N,N'-dicyclohexylcarbodiimide in 4.5 cm³ of acetonitrile. After treatment, 1.2 g of methyl (2RS,5SR)-3-{3-{2-[2-(2-methoxyphenyl)-5-phenyl-1-pyrrolidinyl]-2-oxoethyl}ureido}phenylacetate are obtained in the form of an oil used as it is in subsequent syntheses.

A—(2RS,5SR)-2-(2-methoxyphenyl)-5-phenylpyrrolidine may be prepared as follows: 12.8 cm³ of a 1.6M solution of butyllithium in hexane is added dropwise at a temperature in the vicinity of −78° C. while stirring to a solution of 2.25 g of N-benzyl-o-methoxybenzaldimine in 20 cm³ of tetrahydrofuran. After returning to a temperature in the vicinity of 20° C., stirring is continued for 40 hours, then the reaction mixture is poured into 100 cm³ of a saturated aqueous solution of ammonium chloride and the product is extracted with 50 cm³ then two times 25 cm³ of diisopropyl ether. The combined organic phases are dried over magnesium sulphate and concentrated to dryness under reduced pressure at a temperature in the vicinity of 35° C. The residue is dissolved in 25 cm³ of a normal aqueous hydrochloric acid solution and the solution is heated under reflux for 1 minute. After cooling to a temperature in the vicinity of 20° C., the solution is washed with three times 25 cm³ of diisopropyl ether, then the pH is adjusted to 9 using an N aqueous sodium hydroxide solution and the product is extracted with three times 25 cm³ of diisopropyl ether. The organic extracts are combined, washed with two times 25 cm³ of water, dried over magnesium sulphate and concentrated to dryness under reduced pressure at a temperature in the vicinity of 35° C. The product obtained is purified by chromatography on silica (eluent:petroleum ether/diisopropyl ether (50/50 by volume)]. The fractions containing the expected product are combined and concentrated to dryness under reduced pressure at a temperature in the vicinity of 45° C. 0.9 g of (2RS,5SR)-2-(2-methoxyphenyl)-5-phenylpyrrolidine is thus obtained in the form of an amorphous solid used as it is in subsequent syntheses.

B—N-Benzyl-o-methoxybenzaldimine may be prepared as follows: a solution of 60 cm³ of orthomethoxybenzaldehyde, 55 cm³ of benzylamine and 50 mg of para-toluenesulphonic acid in 150 cm³ of toluene is heated for three hours under reflux while collecting the water formed using a Dean-Stark apparatus. After returning to a temperature in the vicinity of 200° C., the organic phase is washed with 100 cm³ of a saturated aqueous sodium bicarbonate solution, then with 100 cm³ of water, dried over magnesium sulphate and concentrated under reduced pressure. After distillation, 57.3 g of N-benzyl-o-methoxybenzaldimine, distilling in the range from 155° to 159° C. at a pressure of 130 Pa, are obtained.

EXAMPLE 63

By proceeding in a fashion similar to that described in Example 9, but starting from 0.46 g of methyl (2RS,5SR)-3-{3-{2-[2-(3-hydroxyphenyl)-5-phenyl-1-pyrrolidinyl]-2-oxoethyl}ureido}phenylacetate in solution in 10 cm³ of methanol and 0.1 g of potassium hydroxide in solution in 2 cm³ of water, and after treatment and recrystallization in ethanol, 0.2 g of (2RS,5SR)-3-{3-{2-[2-(3-hydroxyphenyl)-5-phenyl-1-pyrrolidinyl]-2-oxoethyl}ureido}phenylacetic acid, melting at 166° C., is obtained.

Methyl (2RS,5SR)-3-{3-{2-[2-(3-hydroxyphenyl)-5-phenyl-1-pyrrolidinyl]-2-oxoethyl}ureido}phenylacetate may be prepared in a fashion similar to that described in Example 41 §A, but starting from 0.48 g of (2RS,5SR)-2-(3-hydroxyphenyl)-5-phenylpyrrolidine, 0.54 g of 2-[3-(3-methoxycarbonylmethylphenyl)ureido]acetic acid and 0.42 g of N,N'-dicyclohexylcarbodiimide in 5 cm³ of acetonitrile. After treatment, 0.73 g of methyl (2RS,5SR)-3-{3-{2-[2-(3-hydroxyphenyl)-5-phenyl-1-pyrrolidinyl]-2-oxoethyl}ureido}phenylacetate is obtained in the form of a meringue-like product used as it is in subsequent syntheses.

(2RS,5SR)-2-(3-Hydroxyphenyl)-5-phenylpyrrolidine may be prepared in a fashion similar to that described in Example 62 §A, but starting from 4.22 g of N-benzyl-m-hydroxybenzaldimine in solution in 40 cm³ of tetrahydrofuran and 33.6 cm³ of a 2.5M solution of butyllithium in hexane. After treatment, 3.3 g of (2RS,5SR)-2-(3-hydroxyphenyl)-5-phenylpyrrolidine are obtained in the form of an oil used as it is in subsequent syntheses.

N-Benzyl-m-hydroxybenzaldimine may be prepared in a fashion similar to that described in Example 62 §A, but starting from 61.1 g of 3-hydroxybenzaldehyde and 55 cm³ of benzylamine in 450 cm³ of toluene. After treatment, 100.3 g of N-benzyl-m-hydroxybenzaldimine, melting at 151° C., are obtained.

EXAMPLE 64

By proceeding in a fashion similar to that described in Example 9, but starting from 4 g of benzyl cis-4-{3-[2-(2,5-diphenyl-1-pyrrolidinyl)-2-oxoethyl]ureido}phenylacetate in solution in 65 cm³ of methanol and 0.61 g of potassium hydroxide in solution in 12 cm³ of water, and after treatment, 1.8 g of cis-4-{3-[2-(2,5-diphenyl-1-pyrrolidinyl)-2-oxoethyl]ureido}phenylacetic acid, melting at 221° C., are obtained [proton NMR (200 MHz, DMSO $D_6$, δ in ppm), 1.4 to 2.4 (m, 4H, $CH_2$—$CH_2$); 3.3 (s, 2H, $CH_2CO_2$); 3.2 and 3.8 (ABX, 2H, $CH_2NH$); 5.1 (m, 2H, 2 CHN); 6.1 (t, 1H exchangeable, NH); 6.9 (d, 2H, aromatic in para position); 7.1 to 7.4 (m, 12H, aromatic); 8.6 (s, 1H exchangeable, NH)], [infrared spectrum (KBr), characteristic bands in $cm^{-1}$ 3375, 3095, 3070, 3035, 2980, 2880, 1735, 1700, 1630, 1610, 1515, 1450, 1560, 805, 760, 705].

Benzyl cis-4-{3-[2-(2,5-diphenyl-1-pyrrolidinyl)-2-oxoethyl]ureido}phenylacetate may be prepared in a fashion similar to that described in Example 41 §A, but starting from 1.7 g of cis-2,5-diphenyl-pyrrolidine, 2.6 g of 2-[3-(4-benzyloxycarbonylmethylphenyl)ureido]acetic acid and 1.6 g of N,N'-dicyclohexylcarbodiimide in 15 cm³ of acetonitrile. After treatment, 4 g of benzyl cis-4-{3-[2-(2,5-diphenyl-1-pyrrolidinyl)-2-oxoethyl]ureido}phenylacetate are obtained in the form of a meringue-like product used as it is in subsequent syntheses.

2-[3-(4-Benzyloxycarbonylmethylphenyl)ureido]acetic acid may be prepared in a fashion similar to that described in Example 1 §A, but starting from 3.68 g of glycine, 4.1 g of sodium bicarbonate in 150 cm³ of water and 13 g of benzyl 4-isocyanatophenylacetate in solution in 60 cm³ of 1,4-dioxane. After treatment, 5.2 g of 2-[3-(4-benzyloxycarbonylmethylphenyl)ureido]acetic acid, melting at 192° C., are obtained.

A—Benzyl 4-isocyanatophenylacetate may be prepared as follows: in the space of 15 minutes at a temperature in the vicinity of −25° C., a solution of 11.8 g of benzyl 4-aminophenylacetate in 150 cm³ of toluene is added to a suspension of 1 g of charcoal in a mixture of 5.9 cm³ of trichloromethyl chloroformate and 50 cm³ of toluene. The reaction mixture is stirred at a temperature in the vicinity of 25° C. for two hours, then heated at a temperature in the vicinity of 110° C. for 2 hours. After cooling to a temperature in the vicinity of 25° C., the reaction mixture is degassed by bubbling through nitrogen, filtered on filter paper and concentrated under reduced pressure at a temperature in the vicinity of 52° C. 15.4 g of benzyl 4-isocyanatophenylacetate are thus obtained in the form of an oil used as it is in subsequent syntheses.

Benzyl 4-aminophenylacetate may be prepared according to the method described by E. ZURABYAN et al., Izv. Akad. Nauk. SSSR, Ser. Khim., (11) 2036 (1964).

EXAMPLE 65

By proceeding in a fashion similar to that described in Example 9, but starting from 3.5 g of methyl (2RS,5SR)-3-{3-{2-[2-(2-methylphenyl)-5-phenyl-1-pyrrolidinyl]-2-oxoethyl}ureido}phenylacetate in solution in 60 cm³ of methanol and 0.56 g of potassium hydroxide in solution in 11 cm³ of water, and after treatment and recrystallization in ethyl acetate, 2.2 g of (2RS,5SR)-3-{3-{2-[2-(2-methylphenyl)-5-phenyl-1-pyrrolidinyl]-2-oxoethyl}ureido}phenylacetic acid, melting at 133° C., are obtained.

Methyl (2RS,5SR)-3-{3-{2-[2-(2-methylphenyl)-5-phenyl-1-pyrrolidinyl]-2-oxoethyl}ureido}phenylacetate may be prepared in a fashion similar to that described in Example 41 §A, but starting from 1.6 g of (2RS,5SR)-2-(2-methylphenyl)-5-phenylpyrrolidine, 1.8 g of 2-[3-(3-methoxycarbonyimethylphenyl)ureido]-acetic acid and 1.4 g of N,N'-dicyclohexylcarbodiimide in 15 cm³ of acetonitrile. After treatment, 3.5 g of methyl (2RS,5SR)-3-{3-{2-[2-(2-methylphenyl)-5-phenyl-1-pyrrolidinyl]-2-oxoethyl}ureido}phenylacetate are obtained in the form of a meringue-like product used as it is in subsequent syntheses.

(2RS,5SR)-2-(2-Methylphenyl)-5-phenylpyrrolidine may be prepared in a fashion similar to that described in Example 62 §A, but starting from 4.18 g of N-benzyl-o-methylbenzaldimine in solution in 40 cm³ of tetrahydrofuran and 25.6 cm³ of a 2.5M solution of butyllithium in hexane. After treatment, 1.7 g of (2RS,5SR)-2-(2-methylphenyl)-5-phenylpyrrolidine are obtained in the form of an oil used as it is in subsequent syntheses.

N-Benzyl-o-methylbenzaldimine may be prepared according to the method described by A. PADVA et al., J. Amer. Chem. Soc., 91 2653 (1969).

EXAMPLE 66

By proceeding in a fashion similar to that described in Example 9, but starting from 1.8 g of ethyl (2RS,5SR)-3-{3-{2-[2-(3-hydroxyphenyl)-5-(3-methoxyphenyl)-1-pyrrolidinyl]-2-oxoethyl}ureido}benzoate in solution in 30 cm³ of methanol and 0.29 g of potassium hydroxide in solution in 6 cm³ of water and after treatment and recrystallization in diethyl ether, 1 g of (2R*,5S*)-3-{3-{2-[2-(3-hydroxyphenyl)-5-(3-methoxy-phenyl)-1-pyrrolidinyl]-2-oxoethyl}ureido}benzoic acid, melting at 172° C., is obtained.

Ethyl (2RS,5SR)-3-{3-{2-[2-(3-hydroxyphenyl)-5-(3-methoxyphenyl)-1-pyrrolidinyl]-2-oxoethyl}ureido}benzoate may be prepared in a fashion similar to that described in Example 41 §A, but starting from 1.3 g of (2RS,5SR)-2-(3-hydroxyphenyl)-5-(3-methoxyphenyl)-pyrrolidine, 1.3 g of 2-[3-(3-ethoxycarbonylphenyl)-ureido]acetic acid and 1 g of N,N'-dicyclohexylcarbo-diimide in 11 cm³ of acetonitrile. After treatment, 1.8 g of ethyl (2RS,5SR)-3-{3-{2-[2-(3-hydroxyphenyl)-5-(3-methoxyphenyl)-1-pyrrolidinyl]-2-oxoethyl}ureido}benzoate are obtained in the form of a meringue-like product used as it is in subsequent syntheses.

(2RS,5SR)-2-(3-Hydroxyphenyl)-5-(3-methoxyphenyl)pyrrolidine may be prepared in a fashion similar to that described in Example 62 §A, but starting from 7.2 g of N-[(3-hydroxyphenyl)methylene](3-methoxyphenyl)methylamine in 60 cm³ of tetrahydrofuran and 50.4 cm³ of a 2.5M solution of butyllithium in hexane. After treatment, 4.5 g of (2RS,5SR)-2-(3-hydroxyphenyl)-5-(3-methoxy-phenyl)pyrrolidine are obtained in the form of an oil used as it is in subsequent syntheses. N-[(3-hydroxyphenyl)methylene](3-methoxyphenyl)methylamine may be prepared in a fashion similar to that described in Example 62 §B, but starting from 13.2 g of 3-hydroxybenzal-dehyde and 13.7 g of m-methoxybenzylamine in 90 cm³ of toluene. After treatment, 20.7 g of N-[(3-hydroxyphenyl)methylene](3-methoxy-phenyl)methylamine, melting at 103° C., are obtained.

2-[3-(3-Ethoxycarbonylphenyl)ureido]acetic acid may be prepared as described in Example 1 §A, but starting from 9.85 g of glycine, 11 g of sodium bicarbonate in solution in 150 cm³ of water, and 25 g of ethyl 3-isocyanatobenzoate. After treatment, 16 g of 2-[3-(3-ethoxycarbonylphenyl)ureido]acetic acid, melting at 174° C., are obtained.

EXAMPLE 67

By proceeding in a fashion similar to that described in Example 9, but starting from 1.8 g of benzyl (2RS,5SR)-4-{3-{2-[2-(3-hydroxyphenyl)-5-phenyl-1-pyrrolidinyl]-2-oxoethyl}ureido}phenylacetate in solution in 30 cm³ of methanol and 0.27 g of potassium hydroxide in solution in 6 cm³ of water, and after treatment and crystallization in diethyl ether, 0.5 g of (2RS,5SR)-4-{3-{2-[2-(3-hydroxyphenyl)-5-phenyl-1-pyrrolidinyl]-2-oxoethyl}ureido}phenylacetic acid, melting at 260° C., is obtained.

Benzyl (2RS,5SR)-4-{3-{2-[2-(3-hydroxyphenyl)-5-phenyl-1-pyrrolidinyl]-2-oxoethyl}ureido}phenylacetate may be prepared in a fashion similar to that described in Example 41 §A, but starting from 1.4 g of (2RS,5SR)-2-(3-hydroxyphenyl)-5-phenylpyrrolidine, 2.0 g of 2-[3-(3-methoxycarbonylmethylphenyl)ureido]acetic acid and 1.2 g of N,N'-dicyclohexylcarbodiimide in 11 cm³ of acetonitrile. After treatment, 1.8 g of benzyl (2RS,5SR)-4-{3-{2-[2-(3-hydroxyphenyl)-5-phenyl-1-pyrrolidinyl]-2-oxoethyl}ureido}phenylacetate are obtained in the form of a meringue-like product used as it is in subsequent syntheses.

EXAMPLE 68

By proceeding in a fashion similar to that described in Example 9, but starting from 1.3 g of tert-butyl cis-{4-{3-[2-(2,5-diphenyl-1-pyrrolidinyl)-2-oxoethyl]ureido}-phenylthio}acetate in solution in 20 cm³ of methanol and 0.17 g of potassium hydroxide in solution in 4 cm³ of water, and after treatment, 0.5 g of cis-{4-{3-[2-(2,5-diphenyl-1-pyrrolidinyl)-2-oxoethyl]ureido}phenylthio}-acetic acid, melting at about 200° C., is obtained [proton NMR (200 MHz, DMSO $D_6$, δ in ppm), 1.8 to 2.4 (m, 4H, $CH_2$—$CH_2$); 3.35 (s, 2H, $CH_2S$); 3.3 and 3.85 (ABX, 2H, $CH_2N$): 5.1 (m, 2H, 2 CHN); 6.5 (t, 1H exchangeable, NH); 7.1 to 7.4 (m, 14H, aromatic); 9 (s, 1H exchangeable, NH)], [infrared spectrum (KBr), characteristic bands in $cm^{-1}$ 3400, 3090, 3060, 3030, 2975, 2875, 1640, 1595, 1540, 1495, 1450, 1400, 825, 760, 700].

tert-Butyl cis-{4-{3-[2-(2,5-diphenyl-1-pyrrolidinyl)-2-oxoethyl]ureido}phenylthio}acetate may be prepared in a fashion similar to that described in Example 41 §A, but starting from 0.46 g of 2,5-diphenylpyrrolidine, 0.7 g of 2-[3-(4-tertbutoxycarbonylmethylthiophenyl)ureido]-acetic acid and 0.42 g of N,N'-dicyclohexylcarbodiimide in 5 cm³ of acetonitrile. After treatment, 1.3 g of tert-butyl cis-{4-{3-[2-(2,5-diphenyl-1-pyrrolidinyl)-2-oxoethyl]ureido}phenylthio}acetate are obtained in the form of a meringue-like product used as it is in subsequent syntheses.

2-[3-(4-tert-Butoxycarbonylmethylthiophenyl)ureido]acetic acid may be prepared in a fashion similar to that described in Example 1 §A, but starting from 0.65 g of glycine, 2.4 g of potassium carbonate in 15 cm³ of water and 2.3 g of tert-butyl (4-isocyanatophenylthio)acetate in 12 cm³ of 1,4-dioxane. After treatment, 1.7 g of 2-[3-(4-tertbutoxycarbonylmethylthiophenyl)ureido]acetic acid are obtained in the form of a meringue-like product used as it is in subsequent syntheses.

tert-Butyl (4-isocyanatophenylthio)acetate may be prepared in a fashion similar to that described in Example 64 §A, but starting from 3.1 g of tert-butyl (4-aminophenylthio)acetate in 117 cm³ of toluene, 0.26 g of charcoal and 1.56 cm³ of trichloromethyl chloroformate in 30 cm³ of toluene. After treatment, 2.3 g of tert-butyl (4-isocyanatophenylthio)acetate are obtained in the form of an oil used as it is in subsequent syntheses.

tert-Butyl (4-aminophenylthio)acetate may be prepared in a fashion similar to that described in Example 17 for the preparation of ethyl (3-aminophenylthio)acetate, but starting from 5 g of 4aminothiophenol and 6.4 cm³ of tert-butyl bromoacetate in 80 cm³ of ethanol. 7.45 g of tert-butyl (4-aminophenylthio)acetate are thus obtained in the form of an oil used as it is in subsequent syntheses.

EXAMPLE 69

By proceeding in a fashion similar to that described in Example 9, but starting from 0.8 g of ethyl (2RS,5SR)-3-{3-{2-[2-(2-hydroxyphenyl)-5-phenyl-1-pyrrolidinyl]-2-oxoethyl}ureido}benzoate in solution in 15 cm³ of methanol and 0.27 g of potassium hydroxide in solution in 3 cm³ of water, and after treatment and recrystallization in diisopropyl ether, 0.21 g of (2RS,5SR)-3-{3-{2-[2-(2-hydroxyphenyl)-5-phenyl-1-pyrrolidinyl]-2-oxoethyl}ureido}benzoic acid, melting at about 160° C., is obtained [proton NMR (200 MHz, DMSO $D_6$, δ in ppm), 1.8 to 2.5 (2m, 4H, $CH_2$—$CH_2$); 3.3 and 4 (ABX, 2H, $CH_2N$); 5.2 (m, 2H, 2 CHN); 6.7 to 7.4 (m, 13H, aromatic); 6.8 (bt 9(s) 9.8(bs) 12.8(vbs) (4H exchangeable, 1 OH, 1 $CO_2H$ and 2NH)], [Infrared spectrum (KBr), characteristic bands in $cm^{-1}$ 3400, 3070, 2980, 1695, 1630, 1560, 1490, 1460, 760, 700, 685].

Ethyl (2RS,5SR)-3-{3-{2-[2-(2-hydroxyphenyl)-5-phenyl-1-pyrrolidinyl]-2-oxoethyl}ureido}benzoate may be prepared in a fashion similar to that described in Example 41 §A, but starting from 0.5 g of (2RS,5SR)-2-(2-hydroxyphenyl)-5-phenylpyrrolidine, 0.56 g of 2-[3-(3-ethoxycarbonylphenyl)ureido]acetic acid and 0.43 g of N,N'-dicyclohexylcarbodiimide in 7.5 cm³ of acetonitrile. After treatment, 0.85 g of ethyl (2RS,5SR)-3-{3-{2-[2-(hydroxyphenyl)-5-phenyl-1-pyrrolidinyl]-2-oxoethyl}ureido}benzoate is obtained in the form of a meringue-like product used as it is in subsequent syntheses.

(2RS,5SR)-2-(2-Hydroxyphenyl)-5-phenylpyrrolidine may be prepared as follows: in the space of ten minutes at a temperature in the vicinity of –78° C., 24 cm³ of a 2.5M solution of butyllithium are added to a solution of 8.6 cm³ of diisopropylamine in 60 cm³ of tetrahydrofuran. The reaction mixture is then stirred at a temperature in the vicinity of 20° C. for fifteen minutes, then cooled to a temperature in the vicinity of –70° C. In the space of five minutes at a temperature in the vicinity of –70° C., a solution of 4.2 g of N-benzyl-o-hydroxy-benzaldimine in 5 cm³ of tetrahydrofuran is then added. The solution is stirred for ten minutes at a temperature in the vicinity of –70° C., then left to warm up to a temperature of 20° C. The reaction mixture is then saturated by bubbling through ethylene for 40 hours, then poured into 150 cm³ of a saturated aqueous solution of ammonium chloride, and the product is extracted with 100 cm³ and then two times 50 cm³ of ethyl ether. The combined organic phases are dried over magnesium sulphate and concentrated to dryness under reduced pressure at a temperature in the vicinity of 35° C. The residue is dissolved in 150 cm³ of a normal aqueous hydrochloric acid solution and the solution is heated under reflux for 1 minute. After cooling to a temperature in the vicinity of 20° C., the solution is washed with three times 100 cm³ of ethyl ether, then the pH is adjusted to 11 using a 4N aqueous sodium hydroxide solution, and the product is extracted with three times 75 cm³ of ethyl ether. The organic extracts are combined, washed with two times 50 cm³ of water, dried over magnesium sulphate and concentrated to dryness under reduced pressure at a temperature in the vicinity of 35° C. The product obtained is purified by chromatography on silica [eluent:dichloromethane, then dichloromethane/methanol (95/5 by volume)]. The fractions containing the expected product are combined and concentrated to dryness under reduced pressure at a temperature in the vicinity of 45° C. 0.5 g of (2RS,5SR)-2-(2-hydroxyphenyl)-5-phenylpyrrolidine is thus obtained in the form of an oil used as it is in subsequent syntheses.

N-Benzyl-o-hydroxybenzaldimine may be prepared in a fashion similar to that described in Example 62 §B, but starting from 21.2 cm³ of 2-hydroxybenzaldehyde and 22 cm³ of benzylamine in 180 cm³ of toluene. After treatment, 38.2 g of N-benzyl-o-hydroxybenzaldimine are obtained in the form of a solid melting at below 50° C.

EXAMPLE 70

By proceeding in a fashion similar to that described in Example 9, but starting from 1.4 g of methyl (2RS,5SR)-3-{3-{2-[2-(2-hydroxyphenyl)-5-phenyl-1-pyrrolidinyl]-2-oxoethyl}ureido}phenylacetate in 30 cm$^3$ of solution in methanol and 0.49 g of potassium hydroxide in solution in 6 cm$^3$ of water, and after treatment and recrystallization in diisopropyl ether, 0.45 g of (2RS,5SR)-3-{3-{2-[2-(2-hydroxyphenyl)-5-phenyl-1-pyrrolidinyl]-2-oxoethyl}ureido}phenylacetic acid, melting at about 165° C., is obtained.

Methyl (2RS,5SR)-3-{3-{2-[2-(2-hydroxyphenyl)-5-phenyl-1-pyrrolidinyl]-2-oxoethyl}ureido}phenylacetate may be prepared in a fashion similar to that described in Example 41 §A, but starting from 1.8 g of (2RS,5SR)-2-(3-hydroxyphenyl)-5-phenylpyrrolidine, 2 g of 2-[3-(3-methoxycarbonylmethylphenyl)ureido]acetic acid and 1.55 g of N,N'-dicyclohexyl-carbodiimide in 30 cm$^3$ of acetonitrile. After treatment, 1.4 g of methyl (2RS,5SR)-3-{3-{2-[2-(2-hydroxyphenyl)-5-phenyl-1-pyrrolidinyl]-2-oxoethyl}ureido}phenylacetate are obtained in the form of a meringue-like product used as it is in subsequent syntheses.

EXAMPLE 71

The operation is carried out in a fashion similar to that described in Example 41, but starting from 0.2 g of 2-trimethylsilylethyl (2S,5R)-3-{3-{2-[2-tert-butoxycarbonyl-5-(3-indolyl)-1-pyrrolidinyl]-2-oxoethyl}ureido}benzoate and 1.0 cm$^3$ of a 1M solution of tetrabutylammonium fluoride. The crude product is dissolved in 25 cm$^3$ of ethyl acetate and extracted with 2 times 5 cm$^3$ of a 0.1N aqueous sodium hydroxide solution. The aqueous phases are brought to a pH of 2 by addition of a 1N aqueous hydrochloric acid solution. The product precipitated is separated by filtration, washed with 2 times 5 cm$^3$ of distilled water and dried in air. 0.12 g of (2S,5R)-3-{3-{2-[2-tert-butoxycarbonyl-5-(3-indolyl)-1-pyrrolidinyl]-2-oxoethyl}ureido}benzoic acid is thus obtained in the form of a solid melting at 160° C., $[\alpha]_D^{20}$= +10.7°±1.1° (C=0.43%; CH$_3$OH), [proton NMR (300 MHz, DMSO D$_6$, δ in ppm, J in Hz): 1.5 (s, 9H, —C(CH$_3$)$_3$; 1.8 to 2.5 (m, 4H, —CH$_2$—CH$_2$—); 3.6 and 4.1 (2dd, J=17.5 and 5.1, 2H, N—CO—CH$_2$—N); 4.26 (dd, J=9 and 8, 1H, N—CH—COO—); 5.52 (d, J=8.5, 1H, N—CH—Ar); 6.38 (t, J=5, 1H, —NH—CO—); 7.0 to 7.7 (m, 7H, aromatic); 7.68 (s, 1H, N—CH=); 8 (bs, 1H in position 2 on NH—Ph—COO); 9.03 (broad, 1H, Ph—NH—CO—); 11.05 (broad, 1H, —NH—), an NOE effect has been observed between the N—CH= of indole and the proton in position 5 of pyrrolidine], [infrared spectrum (KBr), characteristic bands in cm$^{-1}$: 3380, 2980, 2935, 2700 to 2250 (broad band), 1720 to 1695 (broad band), 1635, 1595, 1560, 1490, 1460, 1370, 1155, 745, 685].

2-Trimethylsilylethyl (2S,5R)-3-{3-{2-[2-tert-butoxycarbonyl-5-(3-indolyl)-1-pyrrolidinyl]-2-oxoethyl}ureido}benzoate may be prepared in a fashion similar to that described in Example 41 §A, but starting from 0.5 g of tert-butyl (2S,5RS)-5-(3-indolyl)-2-pyrrolidinecarboxylate, 0.59 g of 2-{3-[3-(2-trimethyl-silylethoxycarbonyl)phenyl]ureido}acetic acid and 0.36 g of N,N'-dicyclohexylcarbodiimide. After initial chromatography on silica [eluent: ethyl acetate/cyclohexane (40/60 by volume)], the fractions containing the mixture of the diastereoisomers are concentrated to dryness under reduced pressure at 40° C. and the residue obtained is purified in a second chromatographic operation on silica [eluent ethyl acetate/cyclohexane (with an ethyl acetate gradient)]. The fractions containing each of the two diastereoisomers are combined and concentrated to dryness under reduced pressure at 40° C. 0.20 g of 2-trimethylsilylethyl (2S,5R)-3-{3-{2-[4-tert-butoxycarbonyl-5-(3-indolyl)-1-pyrrolidinyl]-2-oxoethyl}ureido}benzoate (first elution product) and 0.26 g of 2-trimethylsilylethyl (2S,5S)-3-{3-{2-[4-tert-butoxycarbonyl-5-(3-indolyl)-1-pyrrolidinyl]-2-oxoethyl}ureido}benzoate (second elution product) are thus obtained.

tert-Butyl (2S,5RS)-5-(3-indolyl)-2-pyrrolidinecarboxylate may be prepared in a fashion similar to that described in Example 48 §B, but starting from 0.7 g of tert-butyl (2S,5R)-1-tert-butoxycarbonyl-5-(3-indolyl)-2-pyrrolidinecarboxylate and 0.25 cm$^3$ of iodotrimethylsilane. 0.50 g of tert-butyl (2S,5RS)-5-(3-indolyl)-5-pyrrolidinecarboxylate is thus obtained in the form of an oil used as it is in subsequent syntheses.

tert-Butyl (2S,5R)-1-tert-butoxycarbonyl-5-(3-indolyl)-2-pyrrolidinecarboxylate may be prepared as follows: a solution of 3.5 g of indole in 30 cm$^3$ of methylene chloride is added to a solution of 10.0 g of tert-butyl (2S,5RS)-1-tert-butyoxycarbonyl-5-methoxy-2-pyrrolidinecarboxylate and 0.6 g of para-toluenesulphonic acid in 100 cm$^3$ of anhydrous methylene chloride, cooled to a temperature in the vicinity of 5° C. At the end of the addition, the reaction mixture is brought to a temperature in the vicinity of 25° C., stirred for 2 hours at that temperature, then hydrolysed by addition of 40 cm$^3$ of a saturated aqueous sodium bicarbonate solution. The organic phase is decanted and the aqueous phase is extracted with 2 times 50 cm$^3$ of methylene chloride. The organic phases are combined, dried over magnesium sulphate and concentrated to dryness under reduced pressure at 30° C. The residue obtained is purified by chromatography on silica [eluent: ethyl acetate/cyclohexane (10/90 by volume)]. The fractions containing the expected product are combined and concentrated to dryness under reduced pressure at 35° C. After vigorous stirring in diisopropyl ether, 1.2 g of tert-butyl (2S,5R)-1-tert-butoxycarbonyl-5-(3-indolyl)-2-pyrrolidinecarboxylate (first elution product), melting at 214° C. and 0.8 g of tert-butyl (2S,5S)-1-tert-butoxycarbonyl-5-(3-indolyl)-2-pyrrolidinecarboxylate (second elution product), melting at 194° C., are thus obtained.

EXAMPLE 72

The operation is carried out in a fashion similar to that described in Example 41, but starting from 0.25 g of 2-trimethylsilylethyl (2S,5S)-3-{3-{2-[2-tert-butoxycarbonyl-5-(3-indolyl)-1-pyrrolidinyl]-2-oxoethyl}ureido}benzoate and 1.5 cm$^3$ of a 1M solution of tetrabutylammonium fluoride. The crude product is dissolved in 25 cm$^3$ of ethyl acetate and extracted with 2 times 10 cm$^3$ of 0.1N aqueous sodium hydroxide solution. The aqueous phases are brought to a pH of 2 by addition of a 1N aqueous hydrochloric acid solution. The product precipitated is separated by filtration, washed with 2 times 5 cm$^3$ of distilled water and dried in air. 0.09 g of (2S,5S)-3-{3-{2-[2-tert-butoxycarbonyl-5-(3-indolyl)-1-pyrrolidinyl]-2-oxoethyl}ureido}benzoic acid is thus obtained in the form of an amorphous product, $[\alpha]_D^{20}$=−42.9°±1.5° (C=0.503%; CH$_3$OH), [proton NMR (300 MHz, DMSO D$_6$, δ in ppm, J in Hz); 1.44 (s, 9H, —C(CH$_3$)$_3$; 1.7 to 2.4 (m, 4H, —CH$_2$—CH$_2$—); 3.59 and 3.99 (2dd, J=18 and 6, 2H, N—CO—CH$_2$—N); 4.55 (d, J=9 Hz, 1H, N—CH—COO—); 5.53 (d, J=8, 1H, N—CH—Ar); 6.3 (t, J=6.1 Hz, 1H, —NH—CO—); 6.9 to 7.6 (m, 7H, aromatic); 7.15 (bs, 1H, N—CH=); 7.94 (broad s, 1H, in position 2 on NH—Ph—

COO); 8.95 (broad, 1H, Ph—NH—CO—); 11.02 (broad, 1H, —NH—), 12.75 (broad, 1H, COOH). Two NOE effects have been observed between N—CH= of indole and the protons in positions 2 and 5 of pyrrolidine], [infrared spectrum (KBr), characteristic bands in cm$^{-1}$: 3385, 2975, 2930, 2700 to 2250 (broad band), 1730, 1690, 1640, 1560, 1490, 1460, 1395, 1370, 1155, 740, 685].

EXAMPLE 73

The operation is carried out in a fashion similar to that described in Example 38, but starting from 4.84 g of tert-butyl (2R,4R)-3-[2-(1-imidazolylcarboxamido)-acetyl]-2-phenyl-4-thiazolidinecarboxylate and 8.85 g of tetra-n-butylammonium (RS)-1-(3-aminophenyl)ethane-sulphonate. A solution of 2.5 g of potassium nonafluorobutanesulphonate in 15 cm$^3$ of acetone is added to the crude product obtained, in the form of the tetra-n-butylammonium salt, dissolved in 20 cm$^3$ of acetone. After stirring for 2 hours at a temperature in the vicinity of 25° C., 220 cm$^3$ of diisopropyl ether are added. The insoluble product is separated by filtration, washed with 2 times 3 cm$^3$ of a mixture of acetone and diisopropyl ether (30/70 by volume) and purified by chromatography on silica [eluent: ethyl acetate/methanol (85/15 by volume)]. The fractions containing the expected product are combined and concentrated to dryness under reduced pressure at 40° C. After vigorous stirring in acetonitrile, 0.40 g of potassium (RS)-1-{3-{3-[2-(2R,4R)-4-tert-butoxycarbonyl-2-phenyl-3-thiazolidinyl-2-oxoethyl]ureido]-phenyl}ethane-sulphonate (mixture of the A and B forms), melting at 240° C., is thus obtained in the form of a solid ([α]$_D^{20}$=+50.1°±1.5° (C=0.57%; CH$_3$OH), [proton NMR (200 MHz, DMSO D$_6$+several drops of CD$_3$COOD, δ in ppm, J in Hz), 2 rotamers at room temperature, peak coalescence at 120° C., characteristic chemical shifts at 120° C.: 1.51 (m, 12H, —C(CH$_3$)$_3$ and CH$_3$); 3.28 and 3.45 (2dd, J=12.5 and 6, 2H, S—CH$_2$—); 3.7 (m, 2H, —CH— and 1H of N—COCH$_2$—N); 4.05 (d, J=17, 1H, the other H of N—COCH$_2$—N); 5.0 (t, J=6, 1H, N—CH—COO); 6.4 (s, 1H, S—CH—N); 6.97 (broad d, J=8, 1H, in position 4 on CO—NH—Ph); 7.08 (t, J=8, 1H, in position 5 on CO—NH—Ph); 7.2 to 7.5 (m, 5H, aromatic); 7.64 (bd, J=8, 2H, aromatic)] [Infrared spectrum (KBr), characteristic bands in cm$^{-1}$: 3370, 2970, 2920, 2870, 1725, 1655, 1610, 1590, 1555, 1490, 1450, 1365, 1205, 1150, 1025, 725, 695].

Tetra-n-butylammonium (RS)-1-(3-aminophenyl)ethane-sulphonate may be prepared in a fashion similar to that described in Example 41 §G, but starting from 22.4 g of tetra-n-butylammonium (RS)-1-(3-nitro-phenyl)ethane-sulphonate and 0.8 g of 5% palladinised charcoal. 20.7 g of tetra-n-butylammonium 1-(3-amino-phenyl)ethanesulphonate are thus obtained in the form of an oil used as it is in subsequent syntheses.

Tetra-n-butylammonium (RS)-1-(3-nitrophenyl)ethane-sulphonate may be prepared as follows: 11.5 g of 3-(1-bromoethyl)-5-nitrobenzene are added to a solution of 9.45 g of sodium sulphite in 125 cm$^3$ of distilled water. The reaction mixture is heated for 3 hours at a temperature in the vicinity of 70° C., cooled to a temperature in the vicinity of 25° C. then transferred into 1450 cm$^3$ of a 0.5M aqueous potassium dihydrogen phosphate solution. 17.8 g of tetra-n-butylammonium hydrogen sulphate are then added and the mixture is extracted with 300 cm$^3$ of methylene chloride. The organic phase is washed successively with 3 times 300 cm$^3$ of water and with 300 cm$^3$ of a saturated aqueous sodium chloride solution, dried over magnesium sulphate and concentrated to dryness under reduced pressure at 40° C. 22.4 g of tetra-n-butylammonium (RS)-1-(3-nitrophenyl)ethane-sulphonate (22.4 g) are thus obtained in the form of an oil used as it is in subsequent syntheses.

(RS)-3-(1-bromoethyl)nitrobenzene may be prepared according to the method described by E. FELDER et al., J. Med. Chem., 13, 559 (1970).

EXAMPLE 74

The operation is carried out in a fashion similar to that described in Example 38, but starting from 2.42 g of tert-butyl (2R,4R) 3-[2-(1-imidazolylcarboxamido)-acetyl]-2-phenyl-4-thiazolidinecarboxylate and 1.4 g of 1-(3-aminophenyl)ethanol. The crude product is purified by chromatography on silica [eluent: ethyl acetate/cyclohexane (75/25 by volume)]. The fractions containing the expected product are combined and concentrated to dryness under reduced pressure. After recrystallization in acetonitrile, 0.62 g of tert-butyl (2R,4R)-3-{2-{3-[(RS)-3-(1-hydroxyethyl)phenyl]ureido}acetyl}-2-phenyl-4-thiazolidinecarboxylate (mixture of the A and B forms), melting at 160° C., is thus obtained ([α]$_D^{20}$=+60.7°±1.3° (C=0.51%; DMF), [proton NMR (200 MHz, plus several drops of CD$_3$COOD, δ in ppm, J in Hz), 2 rotamers at room temperature, peak coalescence at 120° C., characteristic chemical shifts at 120° C.: 1.35 (d, J=6.5, 3H, —CH$_3$); 1.5 (s, 9H, —C(CH$_3$)$_3$; 3.29 and 3.45 (2dd, J=12.5 and 6, 2H, S—CH$_2$—); 3.72 (bd, 1H of N—COCH$_2$—N); 4.06 (d, J=17, 1H, the other H of N—COCH$_2$—N); 4.68 (q, J=6.5, 1H, —CH—O—); 5.0 (t, J=6, 1H, N—CH—COO); 6.4 (s, 1H, S—CH—N); 6.93 (broad d, J=8, 1H, in position 4 on CO—NH—Ph); 7.14 (t, J=8, 1H, in position 5 on CO—NH—Ph); 7.22 (dd, J=3 and 2.5, 1H, in position 2 on CO—NH—Ph); 7.2 to 7.5 (m, 4H, aromatic); 7.64 (bd, J=8, 2H, aromatic)], [infrared spectrum (KBr), characteristic bands in cm$^{-1}$: 3350, 2975, 2930, 1740, 1660, 1615, 1590, 1560, 1480, 1445, 1365, 1155, 1060, 730, 705, 700].

EXAMPLE 75

The operation is carried out in a fashion similar to that described in Example 34, but starting from 2.0 g of tert-butyl (2R,4R) 3-(2-aminoacetyl)-2-phenyl-4-thiazolidinecarboxylate and 1.6 g of 4-chloro-3-trifluoromethylphenyl isocyanate. The crude product obtained is purified by chromatography on silica [eluent: ethyl acetate/cyclohexane (30/70 by volume)]. The fractions containing the expected product are combined and concentrated to dryness under reduced pressure at 40° C. After vigorous stirring in 20 cm$^3$ of hexane, 0.7 g of tert-butyl (2R,4R)-3-{2-[3-(4-chloro-3-tri-fluoromethylphenyl)ureido]acetyl}-2-phenyl-4-thiazolidinecarboxylate is thus obtained in the form of an amorphous powder, ([α]$_D^{20}$=+58.2°±1.3° (C=0.49%; CH$_3$OH), [proton NMR (250 MHz, DMSO D$_6$, δ in ppm, J in Hz), 2 rotamers at room temperature, peak coalescence at 130° C., characteristic chemical shifts at 130° C.: 1.53 (s, 9H, —C(CH$_3$)$_3$); 3.29 and 3.47 (2dd, J=12.5 and 6.5, 2H, S—CH$_2$—); 3.73 (broad, 1H, of N—COCH$_2$—N); 4.10 (dd, J=17.5 and 4, 1H, the other H of N—COCH$_2$—N); 5.0 (broad, 1H, N—CH—COO); 6.33 (broad, 1H, —NHCO—); 6.4 (s, 1H, S—CH—N); 7.2 to 7.8 (m, 7H, aromatic); 7.97 (bs, 1H, in position 2 on CO—NH—Ph); 8.98 (broad, 1H, —CO—NH—Ph), [infrared spectrum (KBr), characteristic bands in cm$^{-1}$: 3375, 2980, 2930, 2875, 1740, 1640, 1595, 1550, 1485, 1455, 1370, 1325, 1175, 1150, 895, 730, 695].

EXAMPLE 76

The operation is carried out in a fashion similar to that described in Example 41, but starting from 1.37 g of 2-trimethylsilylethyl (2R,4R)-3-{3-{2-[4-tert-butoxycarbonyl-2-(2-methylphenyl)-3-thiazolidinyl]-2-oxoethyl}ureido}benzoate and 4.6 cm³ of 1M tetrabutylammonium fluoride solution. The crude product is dissolved in 25 cm³ of a saturated sodium bicarbonate solution and washed with 25 cm³ of ethyl acetate. The aqueous phase is brought to a pH of 2 by addition of a 4N aqueous hydrochloric acid solution. The product precipitated is separated by filtration, washed with distilled water until the washing water becomes neutral, and dried in air. 0.89 g of (2R,4R)-3-{2-{2-[4-tert-butoxycarbonyl-1-(2-methylphenyl)-3-thiazolidinyl]-1-oxoethyl}ureido}benzoic acid is thus obtained in the form of a solid, melting at 152° C. ($[\alpha]_D^{20}$=+70.3°±1.9° (C=0.53%; DMF), [proton NMR (200 MHz, DMSO $D_6$ plus several drops of $CD_3COOD$, δ in ppm, J in Hz), 2 rotamers at room temperature, peak coalescence at 110° C., characteristic chemical shifts at 110° C.: 1.56, (s, 9H, —C(CH₃)₃); 2.42 (s, 3H, Ar—CH₃); 3.28 and 3.48 (2dd, J=12 and 6.5, 2H, S—CH₂—); 3.65 (broad, 1H of N—COCH₂—N); 4.05 (d, J=17.5, 1H, the other H of N—COCH₂—N—); 4.98 (t, J=6.5, 1H, N—CH—COO); 6.24 (broad, 1H, —NH—CO—); 6.46 (s, 1H, S—CH—N); 7.10 to 7.65 (m, 5H, aromatic); 7.33 (t, J=8, 1H, in position 5 on CO—NH—Ph); 7.94 (broad, 1H, in position 6 on S—CH—Ph); 8.0 (dd, J=2 and 3, 1H, in position 2 on CO—NH—Ph); 8.67 (broad, 1H, —CO—NH—Ph)], [infrared spectrum (KBr), characteristic bands in cm⁻¹: 3380, 2980, 2935, 2700 to 2250 (wide band), 1715 to 1695 (wide band), 1655, 1610, 1595, 1560, 1490, 1370, 1155, 760, 745, 685].

2-Trimethylsilylethyl (2R,4R)-3-{3-{2-[4-tert-butoxycarbonyl-2-(2-methylphenyl)-3-thiazolidinyl]-2-oxoethyl}ureido}benzoate may be prepared in a fashion similar to that described in Example 41 §A, but starting from 2.1 g of tert-butyl (2RS,4R)-2-(2-methylphenyl)-4-thiazolidinecarboxylate, 2.5 g of 2-{3-[3-(2-trimethylsilylethoxycarbonyl)phenyl]ureido}acetic acid and 1.6 g of N,N'-dicyclohexyl-carbodiimide. The crude product is purified by chromatography on silica [eluent: ethyl acetate/cyclohexane (40/60 by volume)]. The fractions containing the expected product are combined and concentrated to dryness under reduced pressure at 40° C. 1.7 g of 2-trimethylsilylethyl (2R,4R)-3-{2-{2-[4-tert-butoxycarbonyl-2-(2-methylphenyl)-3-thiazolidinyl]-1-oxoethyl}ureido}benzoate are thus obtained in the form of an amorphous solid used as it is in subsequent syntheses.

tert-Butyl (2RS,4R)-2-(2-methylphenyl)-4-thiazolidinecarboxylate may be prepared in a fashion similar to that described in Example 34 §C, but starting from 10.0 g of (2RS,4R)-2-(2-methylphenyl)-4-thiazolidinecarboxylic acid in solution in 130 cm³ of chloroform, 3.0 cm³ of concentrated sulphuric acid and an excess of isobutene. The crude product obtained is purified by chromatography on silica [eluent: ethyl acetate/cyclohexane (10/90 by volume)]. The fractions containing the expected product are combined and concentrated to dryness under reduced pressure at 40° C. 3.8 g of tert-butyl (2RS,4R)-2-(2-methyl-phenyl)-4-thiazolidinecarboxylate are thus obtained in the form of an oil, a mixture of the (2R,4R) and (2S,4R) isomers, used as it is in subsequent syntheses.

(2RS,4R)-2-(2-methylphenyl)-4-thiazolidinecarboxylic acid may be prepared as in Example 34 §D, but starting from 12.5 g of L-cysteine and 12.0 cm³ of 2-methyl-benzaldehyde. 18.4 g of (2RS,4R)-2-(2-methylphenyl)-4-thiazolidinecarboxylic acid, melting at 167° C., used as it is in subsequent syntheses, are thus obtained.

EXAMPLE 77

At a temperature in the vicinity of 25° C., 0.12 g of potassium hydroxide is added to a solution of 0.95 g of methyl (2R,4R)-3-{3-{2-[4-tert-butoxycarbonyl-2-(2-fluorophenyl)-3-thiazolidinyl]-2-oxoethyl}ureido}phenylacetate in 6 cm³ of a water/methanol (30/70 by volume) mixture. The reaction mixture is stirred for 3 hours at a temperature in the vicinity of 25° C. then concentrated to about half under reduced pressure. The solution obtained is diluted with 40 cm³ of water, washed with 2 times 30 cm³ of ethyl ether, then brought to a pH of 2 by addition of 2.1 cm³ of a 1N aqueous sulphuric acid solution. The insoluble product is separated by filtration and purified by chromatography on silica [eluent: ethyl acetate/methanol (90/10 by volume)]. The fractions containing the expected product are combined and concentrated to dryness under reduced pressure at 40° C. The amorphous product thus obtained (0.26 g) is dissolved in a 1N aqueous sodium hydroxide solution. This solution is filtered, then acidified by addition of a 1N aqueous sulphuric acid solution. The product thus precipitated is separated by filtration, washed with 3 times 10 cm³ of water, then dried in air. 0.26 g of (2R,4R)-3-{3-{2-[4-tert-butoxycarbonyl-2-(2-fluorophenyl)-3-thiazolidinyl]-2-oxoethyl}ureido}phenylacetic acid, melting at 110° C., is thus obtained ($[\alpha]_D^{20}$=+51.1°±1.6° (C=0.528%; DMF), [proton NMR (200 MHz, DMSO $D_6$ plus several drops of $CD_3COOD$, δ in ppm, J in Hz), 2 rotamers at room temperature, peak coalescence at 120° C., characteristic chemical shifts at 120° C.: 1.55 (s, 9H, —C(CH₃)₃); 3.34 and 3.52 (2dd, J=12.5 and 6.5, 2H, S—CH₂—); 3.51 (s, 2H, ArCH₂COO—); 3.8 and 4.07 (2d, J=17.5, 2H, N—COCH₂—N); 5.02 (t, J=6.5, N—CH—COO); 6.55 (s, 1H, S—CH—N); 6.85 (bd, J=8, 1H, in position 4 on CO—NH—Ph); 7.05 to 7.4 (m, 6H, aromatic); 7.93 (bt, J=8.5, 1H, in position 6 on S—CH—Ph—)], [infrared spectrum (KBr), characteristic bands in cm⁻¹: 3380, 2980, 2930, 2700 to 2250 (broad band), 1735, 1610, 1615, 1595, 1560, 1490, 1460, 1370, 1230, 1155, 760, 705].

Methyl (2R,4R)-3-{3-{2-[4-tert-butoxycarbonyl-2-(2-fluorophenyl)-3-thiazolidinyl]-2-oxoethyl}ureido}phenylacetate may be prepared in a fashion similar to that described in Example 41 §A, but starting from 1.46 g of tert-butyl (2RS,4R)-2-(2-fluorophenyl)-4-thiazolidinecarboxylate, 1.37 g of 2-{3-[3-(methoxy-carbonylmethyl)phenyl]ureido}acetic acid and 1.15 g of N,N'-dicyclohexylcarbodiimide. The crude product is purified by chromatography on silica [eluent: ethyl acetate/cyclohexane (50/50 by volume)]. The fractions containing the expected product are combined and concentrated to dryness under reduced pressure at 40° C. 0.95 g of methyl (2R,4R)-3-{3-{2-[4-tert-butoxycarbonyl-2-(2-fluorophenyl)-3-thiazolidinyl]-2-oxoethyl}ureido}phenylacetate is thus obtained in the form of an amorphous solid, used as it is in subsequent syntheses.

EXAMPLE 78

The operation is carried out in a fashion similar to that described in Example 77, but starting from 0.76 g of methyl (2R,4R)-3-{3-{2-[4-tert-butoxycarbonyl-2-(2-methoxyphenyl)-3-thiazolidinyl]-2-oxoethyl}ureido}phenylacetate in 6 cm³ of a water/methanol (30/70 by volume) mixture and 0.09 g of potassium hydroxide. The crude product (0.45 g) is dissolved in 7.5 cm³ of a 0.1N aqueous sodium hydroxide solution. The solution thus obtained is washed with 2 times 10 cm³ of diethyl ether, brought to a pH of 2 by addition of a 1N aqueous sulphuric acid solution, then extracted with 2 times 20 cm³ of ethyl acetate. The organic phases are combined, dried over magnesium sulphate and concentrated to dryness under reduced pressure at 40° C. After vigorous stirring in diisopropyl ether, 0.25 g of (2R,4R)-3-{3-{2-[4-tert-butoxycarbonyl-2-(2-methoxyphenyl)-3-thiazolidinyl]-2-oxoethyl}ureido}phenylacetic acid is thus obtained in the form of an amorphous product ([α]$_D^{20}$=+6.4°±1.0° (C=0.466%; CHCl₃), [proton NMR (200 MHz, DMSO D₆ plus several drops of CD₃COOD, δ in ppm, J in Hz), 2 rotamers at room temperature, peak coalescence at 120° C., characteristic chemical shifts at 120° C.: 1.55 (s, 9H, —C(CH₃)₃); 3.22 and 3.45 (2dd, J=12.5 and 7, 2H, S—CH₂—); 3.51 (s, 2H, ArCH₂COO—); 3.65 (bd, 1H of N—COCH₂—N); 3.93 (s, 3H, —OCH₃); 4.05 (d, J=17.5, 1H, the other H of N—COCH₂—N); 4.91 (t, J=7, 1H, N—CH—COO); 6.5 (s, 1H, S—CH—N); 6.85 (bd, J=8, 1H, in position 4 on CO—NM—Ph); 6.9 to 7.4 (m, 6H, aromatic); 7.9 (bd, J=8, 1H, in position 6 on S—CH—Ph—)], [infrared spectrum (KBr), characteristic bands in cm⁻¹: 3390, 2975, 2930, 2840, 2700 to 2250 (broad band), 1735, 1645, 1610, 1600, 1595, 1560, 1495, 1370, 1245, 1155, 1025, 760, 705].

Methyl (2R,4R)-3-{3-{2-[4-tert-butoxycarbonyl-2-(2-methoxyphenyl)-3-thiazolidinyl]-2-oxoethyl}ureido}phenylacetate may be prepared in a fashion similar to that described in Example 41 §A, but starting from 1.9 g of tert-butyl (2RS,4R)-2-(2-methoxyphenyl)-4-thiazolidinecarboxylate, 1.73 g of 2-{3-[3-methoxycarbonylmethylphenyl]ureido}acetic acid and 1.4 g of N,N'-dicyclohexylcarbodiimide. The crude product is purified by chromatography on silica [eluent: ethyl acetate/cyclohexane (50/50 by volume)]. The fractions containing the expected product are combined and concentrated to dryness under reduced pressure at 40° C. 1.5 g of methyl (2R,4R)-3-{3-{2-[4-tert-butoxycarbonyl-2-(2-methoxyphenyl)-3-thiazolidinyl]-2-oxoethyl}ureido}phenylacetate are thus obtained in the form of an amorphous white solid, used as it is in subsequent syntheses.

tert-Butyl (2RS,4R)-2-(2-methoxyphenyl)-4-thiazolidinecarboxylate may be prepared in a fashion similar to that described in Example 34 §C, but starting from 3.5 g of (2RS,4R)-2-(2-methoxyphenyl)-4-thiazolidinecarboxylic acid in solution in 50 cm³ of chloroform, 1.0 cm³ of concentrated sulphuric acid and an excess of isobutene. The crude product obtained is purified by chromatography on silica [eluent: ethyl acetate/cyclohexane (30/70 by volume)]. The fractions containing the expected product are combined and concentrated to dryness under reduced pressure at 40° C. 2.0 g of tert-butyl (2RS,4R)-2-(2-methoxyphenyl)-4-thiazolidinecarboxylate are thus obtained in the form of an oil, a mixture of the (2R,4R) and (2S,4R) isomers, used as it is in subsequent syntheses.

(2RS,4R)-2-(2-methoxyphenyl)-4-thiazolidinecarboxylic acid may be prepared as in Example 34 §D, but starting from 7.26 g of L-cysteine and 8.9 g of 2-methoxybenzaldehyde. 3.7 g of (2RS,4R)-2-(2-methoxyphenyl)-4-thiazolidinecarboxylic acid, melting at 170° C., used as it is in subsequent syntheses, are thus obtained.

EXAMPLE 79

The operation is carried out in a fashion similar to that described in Example 77, but starting from 0.70 g of methyl (RS)-3-{3-{2-[(2R,4R)-4-tert-butoxycarbonyl-2-(2-fluorophenyl)-3-thiazolidinyl]-2-oxoethyl}ureido}mandelate in 7 cm³ of a water/methanol (30/70 by volume) mixture and 0.08 g of potassium hydroxide. The crude product (0.45 g) is dissolved in 8.5 cm³ of a 0.1N aqueous sodium hydroxide solution. The solution thus obtained is washed with 2 times 25 cm³ of ethyl acetate, filtered and acidified to a pH of 2 by addition of a 1N aqueous hydrochloric acid solution. The product precipitated is separated by filtration, washed with 2 times 10 cm³ of water and dried in air. 0.15 g of (RS)-3-{3-{2-[(2R,4R)-4-tert-butoxycarbonyl-2-(2-fluorophenyl)-3-thiazolidinyl]-2-oxoethyl}ureido}mandelic acid is thus obtained in the form of a white product, melting at 135° C. [proton NMR (200 MHz, DMSO D₆ plus several drops of CD₃COOD, δ in ppm, J in Hz), 2 rotamers at room temperature, peak coalescence at 110° C.: characteristic chemical shifts at 110° C. 1.55 (s, 9H, —C(CH₃)₃); 3.32 and 3.53 (2dd, J=12.5 and 6.5, 2H, S—CH₂—); 3.8 (bd, 1H of N—COCH₂—N); 4.08 (d, J=17.5, 1H, the other H of N—COCH₂—N); 5 (m and s, 2H in total respectively N—CH—COO and Ar—CH—); 6.2 (broad, 1H, —NHCO—); 6.54 (s, 1H, S—CH—N); 7.02 (bd, J=7.5, 1H, in position 4 on CO—NH—Ph); 7.1 to 7.5 (m, 6H, aromatic); 7.94 (dd, J=7.5 and 9, 1H, in position 6 on S—CH—Ph—); 8.5 (broad, —CONH—Ar)], [infrared spectrum (KBr), characteristic bands in cm⁻¹: 3390, 2980, 2930, 2840, 2700 to 2250 (broad band), 1735, 1650, 1610, 1560, 1490, 1455, 1370, 1230, 1150, 1060, 790, 760, 700].

Methyl (2R,4R)-3-{3-{2-[(2R,4R)-4-tert-butoxycarbonyl-2-(2-fluorophenyl)-3-thiazolidinyl]-2-oxoethyl}ureido}mandelate may be prepared in a fashion similar to that described in Example 38, but starting from 3.2 g of tert-butyl (2R,4R)-3-[2-(1-imidazolylcarboxamido)-acetyl]-2-(2-fluorophenyl)-4-thiazolidinecarboxylate and 2.7 g of methyl (RS)-3aminomandelate. The crude product is purified by two successive chromatographic operations on silica [eluent:methylene chloride/methanol (95/5 by volume) for the first chromatographic operation; eluent: ethyl acetate for the second chromatographic operation]. The fractions containing the expected product are combined and concentrated to dryness under reduced pressure. 1.6 g of methyl (RS)-3-{3-{2-[(2R,4R)-4-tert-butoxycarbonyl-2-(2-fluorophenyl)-3-thiazolidinyl]-2-oxoethyl}ureido}-mandelate are thus obtained in the form of a meringue-like product, used as it is in subsequent syntheses.

tert-Butyl (2R,4R)-3-[2-(1-imidazolylcarboxamido)acetyl]-2-(2-fluorophenyl)-4-thiazolidinecarboxylate may be prepared as follows: at a temperature in the vicinity of 25° C., a solution of 4.8 g of N,N'-carbonyldiimidazole in 50 cm³ of anhydrous tetrahydrofuran is added slowly to a solution of 7 g of tert-butyl (2R,4R)-3-(2-aminoacetyl)-2-(2-fluorophenyl)-4-thiazolidinecarboxylate in 100 cm³ of anhydrous tetrahydrofuran. The reaction medium is stirred for 12 hours at this temperature, and is then concentrated to dryness under reduced pressure at 40° C. The residue obtained is dissolved in 200 cm³ of ethyl acetate and washed with 2 times 50 cm³ of water. The organic phase is dried over magnesium sulphate and evaporated to dryness under reduced pressure at 40° C. 8.7 g of tert-butyl (2R,4R)-3-[2-(1-imidazolylcarboxamido)-acetyl]-2-(2-fluorophenyl)-4-thiazolidinecarboxylate are thus obtained in the form of an oil used as it is in subsequent syntheses. tert-Butyl (2R,4R)-3-(2-aminoacetyl)-2-(2-fluorophenyl)-4-thiazolidinecarboxylate may be prepared in a fashion similar to that described in Example 34 §A, but starting from 15.0 g of tert-butyl (2R,4R)-3-(2-tert-butoxycarbonylaminoacetyl)-2-(2-fluorophenyl)-4-thiazolidinecarboxylate and 5.34 cm³ of iodotrimethylsilane. 10 g of tert-butyl (2R,4R)-3-(2-aminoacetyl)-2-(2-fluorophenyl)-4-thiazolidinecarboxylate are thus obtained in the form of an oil used as it is in subsequent syntheses.

tert-Butyl (2R,4R)-3-(2-tert-butoxycarbonylaminoacetyl)-2-(2-fluorophenyl)-4-thiazolidinecarboxylate may be prepared in a fashion similar to that described in Example 34 §B, but starting from 25.0 g of tert-butyl (2RS,4R)-2-(2-fluorophenyl)-4-thiazolidinecarboxylate, 15.5 g of 2-tert-butoxycarbonylaminoacetic acid and 18.2 g of N,N'-dicyclohexylcarbodiimide. The crude product is purified by chromatography on silica (eluent: ethyl acetate/cyclohexane (30/70 by volume)]. The fractions containing the expected product are combined and concentrated to dryness under reduced pressure. 25.0 g of tert-butyl (2R,4R)-3-(2-tert-butoxycarbonylaminoacetyl)-2-(2-fluorophenyl)-4-thiazolidinecarboxylate are thus obtained in the form of an oil used as it is in subsequent syntheses.

Methyl (RS)-3-aminomandelate may be prepared as follows: 0.5 g of 5% palladinised charcoal is added to solution of 15 g of methyl (RS)-3-nitromandelate in 150 cm$^3$ of ethanol. The suspension is stirred for 2 hours at a temperature in the vicinity of 25° C. under a hydrogen atmosphere (100 kPa). The catalyst is then separated by filtration and the filtrate is concentrated to dryness under reduced pressure at 40° C. 13.1 g of methyl (RS)-3-aminomandelate are thus obtained in the form of an oil used as it is in subsequent syntheses.

Methyl (RS)-3-nitromandelate may be prepared according to the method described by L. S. FOSDICK and J. C. CALANDRA, J. Am. Chem. Soc., 63, 1101 (1941).

EXAMPLE 80

The operation is carried out in a fashion similar to that described in Example 38, but starting from 2.17 g of tert-butyl (2R,4R)-3-[2-(1-imidazolylcarboxamido)acetyl]-2-(2-fluorophenyl)-4-thiazolidinecarboxylate and 1.37 g of 2-(3-aminophenyl)ethanol. The crude product is purified by two successive chromatographic operations on silica [eluent:methylene chloride/methanol (95/5 by volume) for the first chromatographic operation; eluent: ethyl acetate for the second chromatographic operation). The fractions containing the expected product are combined and concentrated to dryness under reduced pressure. 0.5 g of tert-butyl (2R,4R)-3-{2-{3-[3-(2-hydroxyethyl)phenyl]ureido}acetyl]-2-(2-fluorophenyl)-4-thiazolidinecarboxylate is thus obtained in the form of an amorphous product, ([α]$_D^{20}$=+69.0°±2.0° (C=0.48%; CHCl$_3$), [proton NMR (200 MHz, DMSO D$_6$ plus several drops of CD$_3$COOD, δ in ppm, J in Hz), 2 rotamers at room temperature, peak coalescence at 110° C., characteristic chemical shifts at 110° C.: 1.55 (s, 9H, —C(CH$_3$)$_3$); 2.72 (t, J=7, 2H, ARCH$_2$—); 3.31 and 3.52 (2dd, J=12 and 6, 2H, S—CH$_2$); 3.67 (t, J=7, 2H, —CH$_2$O—); 3.8 (bd, 1H, o f N—COCH$_2$—N); 4.1 (d, J=17, 1H, the other H of N—COCH$_2$—N); 5.01 (t, J=6, 1H, N—CH—COO); 6.2 (broad, 1H, —NHCO—); 6.54 (s, 1H, S—CH—N); 6.81 (bd, J=7.5, 1H, in position 4 on CO—NH—Ph); 7.05 to 7.45 (m, 6H, aromatic); 7.93 (bt, J=8.5, 1H, in position 6 on S—CH—Ph); 8.36 (broad, 1H, ArNHCO—)], [infrared spectrum (KBr), characteristic bands in cm$^{-1}$: 3380, 2975, 2930, 2875, 1740, 1655, 1610, 1590, 1560, 1490, 1460, 1370, 1230, 1150, 1050, 760, 700].

2-(3-Aminophenyl)ethanol may be prepared according to the method described by B. CARNMALM et al., Acta Pharm. Suecica, 11, 33 (1974).

EXAMPLE 81

The operation is carried out in a fashion similar to that described in Example 41, but starting from 1.37 g of 2-trimethylsilylethyl (2R,4R)-3-{3-{2-[4-tert-butoxycarbonyl-2-(2-chloro-6-fluorophenyl)-3-thiazolidinyl]-2-oxoethyl}ureido}benzoate and 4.3 cm$^3$ of a 1M solution of tetrabutylammonium fluoride. The crude product is dissolved in 10 cm$^3$ of a 0.5N aqueous sodium hydroxide solution and washed with 2 times 20 cm$^3$ of ethyl acetate. The aqueous phase is brought to a pH of 2 by addition of a 1N aqueous sulphuric acid solution. The product precipitated is separated by filtration, washed with 2 times 5 cm$^3$ of distilled water and dried in air. 0.12 g of (2R,4R)-3-{3-{2-[4-tert-butoxycarbonyl-2-(2-chloro-6-fluorophenyl)-3-thiazolidinyl]-2-oxoethyl}ureido}benzoic acid, melting at 148° C., is thus obtained ([α]$_D^{20}$=+3.1°±0.8° (C=0.518%; DMF), [proton NMR (250 MHz, DMSO D$_6$ d in ppm, J in Hz), 2 rotamers at room temperature, peak coalescence at 120° C., characteristic chemical shifts at 120° C.: 1.5 (s, 9H, —C(CH$_3$)$_3$); 3.48 (dd, J=12.5 and 6.5. 1H, of S—CH$_2$); 3.62 (dd, J=12.5 and 5, 1H, the other H of S—CH$_2$—); 3.96 (dd, J=17.5 and 5, 1H, of N—COCH$_2$—N); 4.18 (dd, J=17.5 and 5.5, 1H, the other H of N—COCH$_2$—N); 5.11 (dd, J=6.5 and 5, N—CH—COO); 6.24 (broad, 1H, —NHCO—); 6.01 (s, 1H, S—CH—N); 7.05 to 7.65 (m, 6H, aromatic); 7.98 (bs, 1H, in position 2 on CO—NH—Ph—); 8.66 (broad, 1H, ArNHCO—)], [infrared spectrum (KBr), characteristic bands in cm$^{-1}$: 3380, 2980, 2930, 2700 to 2250 (broad band), 1715, 1695, 1655, 1605, 1590, 1560, 1490, 1460, 1370, 1150, 785, 760, 680].

2-Trimethylsilylethyl (2R,4R)-3-{3-{2-[4-tert-butoxycarbonyl-2-(2-chloro-6-fluorophenyl)-3-thiazolidinyl]-2-oxoethyl}ureido}benzoate may be prepared in a fashion similar to that described in Example 34, but starting from 1.40 g of tert-butyl (2R,4R)-3-(2-aminoacetyl)-2-(2-chloro-6-fluorophenyl)-4-thiazolidinecarboxylate and 1.4 g of 2-trimethylsilylethyl 3-isocyanatobenzoate. The crude product obtained is purified by chromatography on silica [eluent: ethyl acetate/cyclohexane (30/70 by volume)]. The fractions containing the expected product are combined and concentrated to dryness under reduced pressure at 40° C. 1.44 g of 2-trimethylsilylethyl (2R,4R)-3-{3-{2-[4-tert-butoxycarbonyl-2-(2-chloro-6-fluorophenyl)-3-thiazolidinyl]-2-oxoethyl}ureido}benzoate are thus obtained in the form of a meringue-like product used as it is in subsequent syntheses.

tert-Butyl (2R,4R)-3-(2-aminoacetyl)-2-(2-chloro-6-fluorophenyl)-4-thiazolidinecarboxylate may be prepared in a fashion similar to that described in Example 34 §A, but starting from 1.86 g of tert-butyl (2R,4R)-3-(2-tert-butoxycarbonylaminoacetyl)-2-(2-chloro-6-fluorophenyl)-4-thiazolidinecarboxylate and 0.67 cm$^3$ of iodotrimethylsilane. 1.4 g of tert-butyl (2R,4R)-3-(2-aminoacetyl)-2-(2-chloro-6-fluorophenyl)-4-thiazolidinecarboxylate are thus obtained in the form of a paste used as it is in subsequent syntheses.

tert-Butyl (2R,4R)-3-(2-tert-butoxycarbonylaminoacetyl)-2-(2-chloro-6-fluorophenyl)-4-thiazolidinecarboxylate may be prepared in a fashion similar to that described in Example 34 §B, but starting from 2.2 g of tert-butyl (2RS,4R)-2-(2-chloro-6-fluorophenyl)-4-thiazolidinecarboxylate, 1.22 g of 2-tert-butoxycarbonylaminoacetic acid and 1.45 g of N,N'-dicyclohexylcarbodiimide. The crude product is purified by chromatography on silica (eluent:methylene chloride/methanol (98/2 by volume)]. The fractions containing the expected product are combined and concentrated to dryness under reduced pressure. 1.56 g of tert-butyl (2R,4R)-3-(2-tert-butoxycarbonylaminoacetyl)-2-(2-chloro-6-fluorophenyl)-4-thiazolidinecarboxylate are thus obtained in the form of a solid used as it is in subsequent syntheses.

tert-Butyl (2RS,4R)-2-(2-chloro-6-fluorophenyl)-4-thiazolidinecarboxylate may be prepared in a fashion similar to that described in Example 34 §C, but starting from 6.1 g of (2RS,4R)-2-(2-chloro-6-fluorophenyl)-4-thiazolidinecarboxylic acid in solution in 60 cm³ of chloroform, 1.4 cm³ of concentrated sulphuric acid (1.4 cc) and an excess of isobutene. The crude product obtained is purified by chromatography on silica (eluent: ethyl acetate/cyclohexane (25/75 by volume)]. The fractions containing the expected product are combined and concentrated to dryness under reduced pressure at 40° C. 4.4 g of tert-butyl (2RS,4R) 2-(2-chloro-6-fluorophenyl)-4-thiazolidinecarboxylate are thus obtained in the form of an oil used as it is in subsequent syntheses.

(2RS,4R)-2-(2-Chloro-6-fluorophenyl)-4-thiazolidinecarboxylic acid may be prepared as in Example 34 §D, but starting from 11.4 g of L-cysteine and 16.7 g of 2-chloro-6-fluorobenzaldehyde. 12.3 g of (2RS,4R)-2-(2-chloro-6-fluorophenyl)-4-thiazolidinecarboxylic acid, melting at 148° C., used as it is in subsequent syntheses, are thus obtained.

2-Trimethylsilylethyl 3-isocyanatobenzoate may be prepared as in Example 21, but starting from 2.37 g of 2-trimethylsilylethyl 3-aminobenzoate, 1.32 cm³ of trichloromethyl chloroformate and 0.21 g of charcoal. 2.6 g of 2-trimethylsilylethyl 3-isocyanatobenzoate are thus obtained in the form of an oil used as it is in subsequent syntheses.

EXAMPLE 82

The operation is carried out in a fashion similar to that described in Example 77, but starting from 0.38 g of methyl 3-{3-{(2S)-1-[(2R,4R)-4-tert-butoxycarbonyl-2-(2-fluorophenyl)-3-thiazolidinyl]-1-oxo-2-propyl}ureido}-phenylacetate in 6 cm³ of a water/methanol (30/70 by volume) mixture and 0.05 g of potassium hydroxide. The crude product is dissolved in 3.5 cm³ of 0.1N aqueous sodium hydroxide solution. The solution thus obtained is washed with 2 times 10 cm³ of ethyl acetate, filtered and brought to a pH of 2 by addition of a 1N aqueous sulphuric acid solution. The product precipitated is separated by filtration, washed with 2 times 5 cm³ of water and dried in air. 0.13 g of 3-{3-{(2S)-1-[(2R,4R)-4-tert-butoxycarbonyl-2-(2-fluorophenyl)-3-thiazolidinyl]-1-oxo-2-propyl}ureido}phenylacetic acid, melting at 110° C., is thus obtained ([α]$_D^{20}$=+103°±4° (C=0.244%; DMF), [proton NMR (200 MHz, DMSO D$_6$, δ in ppm, J in Hz), 2 rotamers at room temperature, peak coalescence at 120° C., characteristic chemical shifts at 120° C.: 1.05 (d, J=7, 3H, —CH$_3$): 1.55 (s, 9H, —C(CH$_3$)$_3$); 3.25 (dd, J=12.5 and 7, 1H, of S—CH$_2$); 3.52 (dd, J=12.5 and 6, 1H, the other H of S—CH$_2$—); 3.53 (s, 2H, ArCH$_2$COO); 4.4 (m, 1H, N—COCH—N); 4.86 (dd, J=7 and 6, N—CH—COO); 6.3 (d, J=8, 1H, —NHCO—); 6.83 (s,1H, S—CH—N); 6.89 (bd, J=8, 1H, in position 4 on CO—NH—Ph—); 7.10 to 7.5 (m, 6H, aromatic); 8.0 (bt, J=8.5, 1H, in position 6 on S—CH—Ph—); 8.29 (broad, 1H, ArNHCO—)], [infrared spectrum (KBr), characteristic bands in cm$^{-1}$: 3380, 2980, 2935, 2700 to 2250 (broad band), 1735, 1640, 1615, 1595, 1560, 1490, 1460, 1370, 1235, 1155, 760, 705].

Methyl 3-{3-{(2S)-1-[(2R,4R)-4-tert-butoxycarbonyl-2-(2-fluorophenyl)-3-thiazolidinyl]-1-oxo-2-propyl}ureido}phenylacetate may be prepared in a fashion similar to that described in Example 34, but starting from 0.85 g of tert-butyl (2R,4R)-3-((2S)-2-aminopropionyl)-2-(2-fluorophenyl)-4-thiazolidinecarboxylate and 0.53 g of methyl 3-isocyanatophenylacetate. The crude product obtained is purified by chromatography on silica [eluent: ethyl acetate/cyclohexane (30/70 by volume)]. The fractions containing the expected product are combined and concentrated to dryness under reduced pressure at 40° C. 0.38 g of methyl 3-{3-{(2S)-1-[(2R,4R)-4-tert-butoxycarbonyl-2-(2-fluorophenyl)-3-thiazolidinyl]-1-oxo-2-propyl}ureido}phenylacetate is thus obtained in the form of an oil used as it is in subsequent syntheses.

tert-Butyl (2R,4R)-3-((2S)-2-aminopropionyl)-2-(2-fluorophenyl)-4-thiazolidinecarboxylate may be prepared in a fashion similar to that described in Example 34 §A, but starting from 1.0 g of tert-butyl (2R,4R)-3-((2S)-2-tert-butoxycarbonylaminopropionyl)-2-(2-fluorophenyl)-4-thiazolidinecarboxylate and 0.39 cm³ of iodotrimethylsilane. 0.85 g of tert-butyl (2R,4R)-3-((2S)-2-aminopropionyl)-2-(2-fluorophenyl)-4-thiazolidinecarboxylate is thus obtained in the form of an oil, used as it is in subsequent syntheses.

tert-Butyl (2R,4R)-3-((2S)-2-tert-butoxycarbonylaminopropionyl)-2-(2-fluorophenyl)-4-thiazolidinecarboxylate may be prepared in a fashion similar to that described in Example 34 §B, but starting from 2.0 g of tert-butyl (2RS, 4R)-2-(2-fluorophenyl)-4-thiazolidinecarboxylate, 1.36 g of N-tert-butoxycarbonyl-L-alanine and 1.47 g of N,N'-dicyclohexylcarbodiimide- The crude product is purified by chromatography on silica (eluent: ethyl acetate/cyclohexane (15/85 by volume)]. The fractions containing the expected product are combined and concentrated to dryness under reduced pressure. 1.0 g of tert-butyl (2R,4R)-3-((2S)-2-tert-butoxycarbonylaminopropionyl)-2-(2-fluorophenyl)-4-thiazolidinecarboxylate is thus obtained in the form of an oil, used as it is in subsequent syntheses.

EXAMPLE 83

The operation is carried out in a fashion similar to that described in Example 77, but starting from 0.48 g of methyl 3-{3-{(2R)-1-[(2R,4R)-4-tert-butoxycarbonyl-2-(2-fluorophenyl)-3-thiazolidinyl]-1-oxo-2-propyl}ureido}-phenylacetate in 7 cm³ of a water/methanol (30/70 by volume) mixture and 0.06 g of potassium hydroxide. The product obtained after filtration on silica (eluent: ethyl acetate/methanol (90/10 by volume)]is dissolved in 7.0 cm³ of 0.1N aqueous sodium hydroxide solution. The solution thus obtained is filtered and brought to a pH of 2 by addition of 1N aqueous sulphuric acid solution. The product precipitated is separated by filtration, washed with 2 times 5 cm³ of water and dried in air. 0.25 g of 3-{(2R)-3-{1-[(2R$_{1,4}$R)-4-tert-butoxycarbonyl-2-(2-fluorophenyl)-3-thiazolidinyl]-1-oxo-2propyl}ureido}phenylacetic acid, melting at 200° C., is thus obtained ([α]$_D^{20}$=+83°±2.0° (C=0.48%; DMF), [proton NMR (250 MHz, DMSO D$_6$, d in ppm, J in Hz), 2 rotamers at room temperature, peak coalescence at 120° C., characteristic chemical shifts at 120° C.: 127 (d, J=7.5, 3H, —CH$_3$); 1.54 (s, 9H, —C(CH$_3$)$_3$); 3.40 and 3.56 (2dd, J=12.5 and 6.5, 2H, S—CH$_2$—); 3.50 (s, 2H, —CH$_2$COO—); 4.50 (m, 1H, N—COCH—N); 5.45 (broad, 1H, N—CH—COO); 6.3 (d, J=8.5, 1H, —NHCO—); 6.50 (s, 1H, S—CH—N); 6.9 (bd, J=8, 1H, in position 4 of CO—NH—Ph); 7.0 to 7.45 (m, 6H, aromatic); 7.9 (bt, J=8.5, 1H, in position 6 on S—CH—Ph—); 8.3 (broad, 1H, ArNHCO—)], [infrared spectrum (KBr), characteristic bands in cm$^{-1}$: 3380, 2975, 2930, 2700 to 2250 (broad band), 1730, 1640, 1610, 1595, 1555, 1490, 1455, 1365, 1230, 1150, 755, 700].

Methyl 3-{3-{(2R)-1-[(2R,4R)-4-tert-butoxycarbonyl-2-(2-fluorophenyl)-3-thiazolidinyl]-1-oxo-2-propyl}ureido}phenylacetate may be prepared in a fashion similar to that described in Example 34, but starting from 0.55 g of tert-butyl (2R,4R)-3-((2R)-2-aminopropionyl)-2-(2-fluorophenyl)-4-thiazolidinecarboxylate and 0.37 g of methyl 3-isocyanatophenylacetate. The crude product obtained is purified by chromatography on silica [eluent: ethyl acetate/cyclohexane (40/60 by volume)]. The fractions containing the expected product are combined and concentrated to dryness under reduced pressure at 40° C. 0.48 g of methyl 3-{3-{(2R)-1-[(2R,4R)-4-tert-butoxycarbonyl-2-(2-fluorophenyl)-3-thiazolidinyl]-1-oxo-2-propyl}ureido}phenylacetate is thus obtained in the form of an amorphous product used as it is in subsequent syntheses.

tert-Butyl (2R,4R)-3-((2R)-2-aminopropionyl)-2-(2-fluorophenyl)-4-thiazolidinecarboxylate may be prepared in a fashion similar to that described in Example 34 §A, but starting from 0.8 g of tert-butyl (2R,4R)-3-((2R)-2-tert-butoxycarbonylaminopropionyl)-2-(2-fluorophenyl)-4-thiazolidinecarboxylate and 0.30 cm³ of iodotrimethylsilane. 0.55 g of tert-butyl (2R,4R)-3-((2R)-2-aminopropionyl)-2-(2-fluorophenyl)-4-thiazolidinecarboxylate is thus obtained in the form of an oil used as it is in subsequent syntheses.

tert-Butyl (2R,4R)-3-((2R)-2-tert-butoxycarbonylaminopropionyl)-2-(2-fluorophenyl)]-4-thiazolidinecarboxylate may be prepared in a fashion similar to that described in Example 34 §B, but starting from 2.0 g of tert-butyl (2RS,4R)-2-(2-fluorophenyl)-4-thiazolidinecarboxylate, 1.36 g of N-tert-butoxycarbonyl-D-alanine and 1.47 g of N,N'dicyclohexylcarbodiimide. The crude product is purified by chromatography on silica [eluent: ethyl acetate/cyclohexane (15/85 by volume)]. The fractions containing the expected product are combined and concentrated to dryness under reduced pressure. 1.0 g of tert-butyl (2R,4R)-3-((2R)-2-tert-butoxycarbonylaminopropionyl)-2-(2-fluorophenyl)]-4-thiazolidinecarboxylate is thus obtained in the form of an oil, used as it is in subsequent syntheses.

EXAMPLE 84

0.1 g of 10% palladinised charcoal is added to a solution of 0.35 g of benzyl 2-{3-{3-{2-[(2R,4R)-4-tert-butoxycarbonyl-2-(2-fluorophenyl)-3-thiazolidinyl]-2-oxoethyl}ureido}phenyl}propionate (B form) in 40 cm³ of ethyl acetate. The suspension is stirred for 48 hours at a temperature in the vicinity of 25° C. under a hydrogen atmosphere (100 kPa). The catalyst is then separated by filtration and the filtrate is concentrated to dryness under reduced pressure at 40° C. The residue obtained is dissolved in 10 cm³ of 0.1N aqueous sodium hydroxide solution and washed with 2 times 10 cm³ of ethyl ether. The aqueous phase is brought to a pH of 2 by addition of a 1N aqueous sulphuric acid solution. The product precipitated is separated by filtration, is washed with 2 times 10 cm³ of water and dried in air. 0.12 g of 2-{3-{3-{2-[(2R,4R)-4-tert-butoxycarbonyl-2-(2-fluorophenyl)-3-thiazolidinyl]-2-oxoethyl}ureido}-phenyl}propionic acid (B form), melting at 126° C., is thus obtained.

$[\alpha]_D^{20} = +97° \pm 2°$ (C=0.502%; DMF) Proton NMR (200 MHz, DMSO $D_6$ plus several drops of $CD_3COOD$, δ in ppm, J in Hz), 2 rotamers at room temperature, peak coalescence at 120° C., characteristic chemical shifts at 120° C.: 1.4 (d, J=7.5, 3H, —$CH_3$); 1.54 (s, 9H, —$C(CH_3)_3$); 3.32 (2dd, J=12.5 and 6.5, 1H, of S—$CH_2$); 3.52 (dd, J=12 and 7, 1H, the other H of S—$CH_2$—); 3.62 (q, J=7.5, 1H, Ar—CH—COO); 3.78 (bd, 1H, of N—$COCH_2$—N); 4.07 (d, J=17, 1H, the other H of N—$COCH_2$—N); 5.0 (dd, J=7 and 6.5, 1H, N—CH—COO); 6.17 (broad, 1H, —NHCO—); 6.53 (s, 1H, S—CH—N); 6.86 (bd, J=8, 1H, in position 4 on CO—NH—Ph—); 7.10 to 7.5 (m, 6H, aromatic); 7.92 (bt, J=8.5, 1H, in position 6 on S—CH—Ph—); 8.43 (broad, 1H, ArNHCO—).

Infrared spectrum (KBr), characteristic bands in $cm^{-1}$: 3380, 2975, 2930, 2650 to 2250 (broad band), 1735, 1650, 1610, 1595, 1560, 1490, 1455, 1370, 1230, 1150, 760, 700.

A. Benzyl 2-{3-{3-{2-[(2R,4R)-4-tert-butoxycarbonyl-2-(2-fluorophenyl)-3-thiazolidinyl]-2-oxoethyl}ureido}phenyl}propionate (B form) may be prepared in a fashion similar to that described in Example 34, but starting from 1.02 g of tert-butyl (2R,4R)-3-(2-aminoacetyl)-2-(2-fluorophenyl)-4-thiazolidinecarboxylate and 0.89 g of benzyl 2-(3-isocyanatophenyl)propionate (B form). The crude product is purified by chromatography on silica [eluent: ethyl acetate/cyclohexane (50/50 by volume)]. The fractions containing the expected product are combined and concentrated to dryness under reduced pressure at 40° C. 1.2 g of benzyl 2-{3-{3-{2-[(2R,4R)-4-tert-butoxycarbonyl-2-(2-fluorophenyl)-3-thiazolidinyl]-2-oxoethyl}ureido}phenyl}propionate (B form) are thus obtained in the form of a yellow paste, used as it is in subsequent syntheses.

B. Benzyl 2-(3-isocyanatophenyl)propionate (B form) may be prepared as in Example 21, but starting from 2.85 g of (+)-[benzyl 2-(3-aminophenyl)propionate], 1.48 cm³ of trichloromethyl chloroformate and 0.24 g of charcoal. 3.1 g of benzyl 2-(3-isocyanatophenyl)propionate (B form) are thus obtained in the form of an orange oil used as it is in subsequent syntheses.

C. (+)-[Benzyl 2-(3-aminophenyl)propionate] may be prepared as follows: 75 g of ammonium chloride and 37.0 g of zinc powder are added to a mixture of 8.0 g of (+)-[benzyl 2-(3-nitrophenyl)propionate]in 35 cm³ of methanol and 300 cm³ of water. The reaction medium is heated under reflux for 1 hour, then cooled to 0° C. The insoluble salts are separated by filtration and the filtrate is extracted with 3 times 200 cm³ of ethyl ether. The collected organic phases are washed successively with 100 cm³ of water and with 100 cm³ of a saturated aqueous solution of sodium chloride. After drying over magnesium sulphate concentrating to dryness under reduced pressure at 40° C., 6.7 g of (+)-[benzyl 2-(3-aminophenyl)propionate]are thus obtained in the form of a yellow oil, used as it is in subsequent syntheses.

D. (+)-[Benzyl 2-(3-nitrophenyl)propionate] may be prepared as follows: 4.72 cm³ of oxalyl dichloride are slowly added to a mixture containing 9.75 g of (+)-[2-(3-nitrophenyl)propionic acid] and 0.5 cm³ of dimethylformamide in 100 cm³ of 1,2-dichloroethane. The reaction medium is stirred for 3 hours at a temperature in the vicinity of 25° C., followed by the addition of 5.4 g of benzyl alcohol. Stirring is continued for 12 hours at the same temperature, then the reaction mixture is washed successively with a saturated aqueous solution of 2 times 200 cm³ of sodium bicarbonate, with 100 cm³ of water and with 100 cm³ of a saturated aqueous solution of sodium chloride. The collected organic phases are washed successively with 100 cm³ of water and with 100 cm³ of a saturated aqueous solution of sodium chloride. The collected organic phases are dried over magnesium sulphate and concentrated to dryness under reduced pressure at 40° C. The residue obtained is purified by chromatography on silica [eluent: ethyl acetate/cyclohexane (30/70 by volume)]. The fractions containing the expected product are combined and concentrated to dryness under reduced pressure at 40° C. 11.5 g of (+)-[Benzyl 2-(3-nitrophenyl)propionate] are thus obtained in the form of a yellow oil, used as it is in subsequent syntheses.

E. (+)-[2-(3-Nitrophenyl)propionic acid] may be prepared as follows: 21.5 g of 2-(3-nitrophenyl)-N-[(R)-2-hydroxy-1-phenylethyl]propionamide (B form) in solution in a mixture of 450 cm³ of dioxane and 450 cm³ of 4N aqueous hydrochloric acid solution are heated to a temperature in the vicinity of 80° C. for 5 hours, then stirred for 12 hours at a temperature in the vicinity of 25° C. The reaction mixture is concentrated to half by evaporation under reduced pressure at 40° C., diluted by addition of 500 cm³ of water and extracted with 2 times 500 cm³ of diethyl ether. The collected organic phases are washed successively with 3 times 250 cm³ of water and with 250 cm³ of a saturated aqueous solution of sodium chloride. After drying over magnesium sulphate and concentrating to dryness under reduced pressure at 40° C., 14 g of (+)-[2-(3-nitrophenyl)propionic acid] are thus obtained in the form of a cream-colored solid used as it is in subsequent syntheses.

F. 2-(3-Nitrophenyl)-N-[(R)-2-hydroxy-1-phenylethyl]propionamide (B form) may be prepared as follows: 17.2 cm³ of oxalyl dichloride are added slowly to a mixture containing 39.0 g of (RS)-2-(3-nitrophenyl)propionic acid and 0.5 cm³ of dimethylformamide in 400 cm³ of 1,2-dichloroethane. The reaction medium is stirred for 3 hours at a temperature in the vicinity of 25° C., then concentrated to dryness under reduced pressure at 40° C. The residue obtained is dissolved in 150 cm³ of 1,2-dichloroethane. The acid chloride solution thus obtained is added to a solution of 27.4 g of (2R)-2-phenylglycinol while maintaining the temperature of the reaction medium below 10° C. At the end of the addition, the mixture is stirred for 12 hours at a temperature in the vicinity of 25° C., then washed successively with 1 times 1000 cm³ of water, with 500 cm³ of 1N aqueous hydrochloric acid solution, with 2 times 500 cm³ of water and with 1 times 500 cm³ of a saturated aqueous solution of sodium chloride. The organic phase collected is dried over magnesium sulphate and concentrated to dryness under reduced pressure at 40° C. The two diastereoisomers obtained are separated by chromatography on silica [eluent: methylene chloride/ethyl acetate (70/30 by volume)]. The fractions containing each of the two diastereoisomers are combined and concentrated to dryness under reduced pressure at 40° C. 21.0 g of 2-(3-nitrophenyl)-N-[(R)-2-hydroxy-1-phenylethyl]propionamide (A form) (first elution product, melting at 135° C., and 19.0 g of 2-(3-nitrophenyl)-N-[(R)-2-hydroxy-1-phenylethyl]propionamide (B form) (second elution product), melting at 150° C., are thus obtained.

EXAMPLE 85

The operation is carried out in a fashion similar to that described in Example 84, but starting from 3.8 g of benzyl 2-{3-{3-{2-[(2R,4R)-4-tert-butoxycarbonyl-2-(2-fluorophenyl)-3-thiazolidinyl]-2-oxoethyl}ureido}phenyl}propionate (A form) and 0.8 g of 10% palladinized charcoal. 1.4 g of 2-{3-{3-{2-[(2R,4R)-4-tert-butoxycarbonyl-2-(2-fluorophenyl)-3-thiazolidinyl]-2-oxoethyl}ureido}phenyl}propionic acid (A form), melting at 145° C., are thus obtained. $[\alpha]_D^{20} = +20.0°\pm11°$ (C=0.539%; DMF)

Proton NMR (200 MHz, DMSO $D_6$, δ in ppm, J in Hz), 2 rotamers at room temperature, peak coalescence at 120° C., characteristic chemical shifts at 120° C.: 1.4 (d, J=7, 3H, —CH₃); 1.53 (s, 9H, —C(CH₃)₃); 3.3 and 3.48 (2dd, J=12.5 and 6, 2H, S—CH₂); 3.6 (q, J=7, 1H, Ar—CH—COO); 3.77 and 4.05 (2dd, J=17.5 and 5.5, 2H, N—COCH₂—N); 5.0 (t, J=6, 1H, N—CH—COO); 6.17 (t, J=5.5, 1H, —NHCO—); 6.53 (s, 1H, S—CH—N); 6.85 (bd, J=7.5, 1H, in position 4 on CO—NH—Ph); 7.05 to 7.45 (m, 6H, aromatic); 7.91 (dt, J=8 and 1, 1H, in position 6 on S—CH—Ph); 8.43 (broad, 1H, ArNHCO—).

Infrared spectrum (KBr), characteristic bands in cm⁻¹: 3380, 3100 to 3000, 2975, 2930, 2875, 2750 to 2350 (wide band), 1735, 1650, 1615, 1595, 1555, 1490, 1460, 1420, 1395, 1370, 1155, 760, 700.

Benzyl 2-{3-{3-{2-[(2R,4R)-4-tert-butoxycarbonyl-2-(2-fluorophenyl)-3-thiazolidinyl]-2-oxoethyl}ureido}phenyl}propionate (A form) may be prepared in a fashion similar to that described in Example 34, but starting from 4.0 g of tert-butyl (2R,4R)-3-(2-aminoacetyl)-2-(2-fluorophenyl)-4-thiazolidine-carboxylate and 4.0 g of benzyl 2-(3-isocyanatophenyl)-propionate. The crude product is purified by chromatography on silica [eluent: ethyl acetate/cyclohexane (40/60 by volume)]. The fractions containing the expected product are combined and concentrated to dryness under reduced pressure at 40° C. 3.8 g of benzyl 2-{3-{3-{2-[(2R,4R)-4-tert-butoxycarbonyl-2-(2-fluorophenyl)-3-thiazolidinyl]-2-oxoethyl}ureido}phenyl}propionate are thus obtained in the form of an amorphous product, used as it is in subsequent syntheses.

Benzyl 2-(3-isocyanatophenyl)propionate (A form) may be prepared as in Example 21, but starting from 4.0 g of (−)-[benzyl 2-(3-aminophenyl)propionate], 2.1 cm³ of trichloromethyl chloroformate and 0.33 g of charcoal. 4.7 g of benzyl 2-(3-isocyanatophenyl)propionate are thus obtained in the form of an orange oil, used as it is in subsequent syntheses.

(−)-[Benzyl 2-(3-aminophenyl)propionate] may be prepared in a fashion similar to that described in Example 84C, but starting from 5.3 g of (−)-[benzyl 2-(3-nitrophenyl)propionate], 50 g of ammonium chloride and 24.8 g of zinc powder. 4.2 g of (−)-[benzyl 2-(3-aminophenyl)propionate] are thus obtained in the form of a yellow oil, used as it is in subsequent syntheses.

(−)-[Benzyl 2-(3-nitrophenyl)propionate] may be prepared in a fashion similar to that described in Example 84D, but starting from 4.45 g of (−)-[2-(3-nitrophenyl)propionic acid], 0.3 cm³ of dimethylformamide and 2.15 cm³ of oxalyl dichloride. The crude product is purified by chromatography on silica [eluent: ethyl acetate/cyclohexane (30/70 by volume)]. The fractions containing the expected product are combined and concentrated to dryness under reduced pressure at 40° C. 5.6 g of (−)-[benzyl 2-(3-nitrophenyl)propionate] are thus obtained in the form of a yellow oil, used as it is in subsequent syntheses.

(−)-[2-(3-Nitrophenyl)propionic acid] may be prepared in a fashion similar to that described in Example 84E, but starting from 9.4 g of 2-(3-nitrophenyl)-N-[(R)-2-hydroxy-1-phenylethyl]propionamide (A form) in solution in a mixture of 200 cm³ of dioxane and 200 cm³ of 4N aqueous hydrochloric acid solution. 5.85 g of (−)-[2-(3-nitrophenyl)propionic acid] are thus obtained in the form of a cream-colored solid used as it is in subsequent syntheses.

EXAMPLE 86

The operation is carried out in a fashion similar to that described in Example 77, but starting from 0.68 g of methyl (2R,4R)-3-{3-{2-[4-tert-butoxycarbonyl-2-(2,3-difluorophenyl)-3-thiazolidinyl]-2-oxoethyl}ureido}phenylacetate in 6 cm³ of a water/methanol (30/70 by volume) mixture and 0.08 g of potassium hydroxide. The crude product (0.45 g) is dissolved in 7.5 cm³ of 0.1N aqueous sodium hydroxide solution. The solution thus obtained is washed with 2 times 10 cm³ of diethyl ether, brought to a pH of 2 by addition of a 1N aqueous sulphuric acid solution, then extracted with 2 times 20 cm³ of ethyl acetate. The organic phases are combined, dried over magnesium sulphate and concentrated to dryness under reduced pressure at 40° C. The product obtained is purified by chromatography on silica [eluent:methylene chloride/methanol (80/20 by volume)]. The fractions containing the expected product are combined and concentrated to dryness under reduced pressure at 40° C. 0.05 g of (2R,4R)-3-{3-{2-[4-tert-Butoxycarbonyl-2-(2,3-difluorophenyl)-3-thiazolidinyl]-2-oxoethyl}ureido}phenylacetic acid is thus obtained in the form of an amorphous product.

$[\alpha]_D^{20} = +64° \pm 2°$ (C=0.557%, CHCl₃).

proton NMR (200 MHz, DMSO D₆, plus several drops of CD₃COOD, δ in ppm, J in Hz), 2 rotamers at room temperature, peak coalescence at 120° C., characteristic chemical shifts at 120° C.: 1.52 (s, 9H, —C(CH₃)₃); 3.31 and 3.51 (2dd, J=12.5 and 6, 2H, S—CH₂); 3.46 (s, 2H, Ar—CH₂—COO); 3.82 (bd, 1H, of N—COCH₂—N); 4.05 (d, J=17, 1H, the other H of N—COCH₂—N); 5.0 (t, J=6, 1H, N—CH—COOO); 6.15 (broad, 1H, —NHCO—); 6.5 (s, 1H, S—CH—N); 6.82 (bd, J=7.5, 1H, in position 4 on CO—NH—Ph); 7.05 to 7.45 (m, 5H, aromatic); 7.68 (bt, J=8 and 1, 1H, in position 6 on S—CH—Ph); 8.7 (broad, 1H, ArNHSCO—).

Infrared spectrum (KBr), characteristic bands in cm⁻¹: 3380, 3100 to 3000, 2975, 2930, 2750 to 2350 (wide band), 1735, 1655, 1615, 1595, 1560, 1490, 1405, 1370, 1150, 775, 745.

Methyl (2R,4R)-3-{3-{2-[4-tert-butoxycarbonyl-2-(2,3-difluorophenyl)-3-thiazolidinyl]-2-oxoethyl}ureido}phenylacetate may be prepared in a fashion similar to that described in Example 41 A, but starting from 1.5 g of tert-butyl (2RS,4R)-2-(2,3-difluorophenyl)-4-thiazolidinecarboxylate, 1.33 g of 2-{3-[3-methoxycarbonylmethylphenyl]ureido}acetic acid and 1.0 g of N,N'-dicyclohexylcarbodiimide. The crude product is purified by chromatography on silica [eluent: ethyl acetate/cyclohexane (40/60 by volume)]. The fractions containing the expected product are combined and concentrated to dryness under reduced pressure at 40° C. 0.4 g of methyl (2R,4R)-3-{3-{2-[4-tert-butoxycarbonyl-2-(2,3-difluorophenyl)-3-thiazolidinyl]-2-oxoethyl}ureido}phenylacetate is thus obtained in the form of a colourless oil, used as it is in subsequent syntheses.

tert-Butyl (2RS,4R)-2-(2,3-difluorophenyl)-4-thiazolidinecarboxylate may be prepared in a fashion similar to that described in Example 34 C, but starting from 14.3 g of (2RS,4R)-2-(2,3-difluorophenyl)-4-thiazolidinecarboxylic acid in solution in 50 cm³ of chloroform, 3.5 cm³ of concentrated sulphuric acid and an excess of isobutene. The crude product obtained is purified by chromatography on silica [eluent: ethyl acetate/cyclohexane (10/90 by volume)]. The fractions containing the expected product are combined and concentrated to dryness under reduced pressure at 40° C. 14.0 g of tert-butyl (2RS,4R)-2-(2,3-difluorophenyl)-4-thiazolidinecarboxylate are thus obtained in the form of a thick yellow oil, a mixture of the (2R,4R) and (2S,4R) isomers, used as it is in subsequent syntheses.

(2RS,4R)-2-(2,3-difluorophenyl)-4-thiazolidinecarboxylic acid may be prepared as in Example 34 D, but starting from 8.5 g of L-cysteine and 10.1 g of 2,3-difluoro-benzaldehyde. 3.7 g of (2RS,4R)-2-(2,3-difluorophenyl)-4-thiazolidinecarboxylic acid, melting at 120° C., used as it is in subsequent syntheses, are thus obtained.

EXAMPLE 87

By proceeding in a fashion similar to that described in Example 41 §A, but starting from 1.2 g of (2RS,4R)-2,4-diphenylthiazolidine, 1.04 g of 2-[3-(3-methylphenyl)ureido]acetic acid and 1.03 g of N,N'-dicyclohexylcarbodiimide in 15 cm³ of acetonitrile, and after treatment, 0.98 g of (2RS,4R)-1-{2-[3-(3-methylphenyl)ureido]acetyl}-2,4-diphenylthiazolidine is obtained in the form of a meringue-like product.

Mass (chemical ionization with ammonia 70 eV, m/z), 432 (M⁺).

Infrared spectrum (KBr) characteristic bands in cm⁻¹ 3340, 3085, 3060, 3030, 2920, 1635, 1610, 1490, 1450, 1560, 780, 765, 695.

(2RS,4R)-2,4-diphenylthiazolidine may be prepared as in Example 34 §D, but starting from 1.9 g of (R)-2-amino-2-phenyl-ethanethiol hydrochloride, 2.75 cm³ of triethylamine and 1.15 cm³ of benzaldehyde in 25 cm³ of ethanol. 1.15 g of (2RS,4R)-2,4-diphenylthiazolidine, melting at 120° C., are thus obtained.

(R)-2-amino-2-phenylethanethiol may be prepared according to the method described in the patent application JP 57193447 (C.A. 98, 178924r).

EXAMPLE 88

By proceeding in a fashion similar to that described in Example 9, but starting from 1.35 g of methyl (2RS,4R)-3-{3-{2-(2-fluorophenyl)-4-phenyl-3-thiazolidinyl]-2-oxoethyl}ureido}phenylacetate in solution in 25 cm³ of methanol and 0.22 g of potassium hydroxide dissolved in 5 cm³ of water, and after treatment, 0.45 g of (2RS,4R)-3-{3-{2-(2-fluorophenyl)-4-phenyl-3-thiazolidinyl]-2-oxoethyl}ureido}phenylacetic acid is obtained in the form of a meringue-like product.

Mass (chemical ionization with ammonia, 70 eV, m/z), 494 (M⁺), 343.

Infrared spectrum (KBr), characteristic bands in cm⁻¹ 3375, 3060, 3025, 2930, 2700 to 2250, 1710, 1640, 1610, 1485, 1455, 1560, 760, 700.

Methyl (2RS,4R)-3-{3-{2-(2-fluorophenyl)-4-phenyl-3-thiazolidinyl]-2-oxoethyl}ureido}phenylacetate may be prepared as described in Example 41 §A, but starting from 1.3 g of (2RS,4R)-2-(2-fluorophenyl)-4-phenylthiazolidine, 1.33 g of 2-[3-(3-methoxycarbonylmethylphenyl)ureido]acetic acid and 1.03 g of N,N'-dicyclohexylcarbodiimide in 15 cm³ of acetonitrile. After treatment, 1.5 g of methyl (2RS,4R)-3-{3-{2-(2-fluorophenyl)-4-phenyl-3-thiazolidinyl]-2-oxoethyl}ureido}phenylacetate are obtained in the form of an oil used as it is in subsequent syntheses.

(2RS,4R)-2-(2-Fluorophenyl)-4-phenylthiazolidine may be prepared as in Example 34 §D, but starting from 1.9 g of (R)-2-amino-2-phenylethanethiol, 2.75 cm³ of triethylamine and 1.37 g of 2-fluorobenzaldehyde in 25 cm³ of ethanol. 1.5 g of (2RS,4R)-2-(2-fluorophenyl)-4-phenyl-thiazolidine are thus obtained in the form of an oil, used as it is in subsequent syntheses.

EXAMPLE 89

The operation is carried out in a fashion similar to that described in Example 9, but starting from 0.9 g of tert-butyl (2RS, 5SR)-1-{2-[3-(3-ethoxycarbonylphenyl)ureido]acetyl}-5-(2-methylphenyl)prolinate in solution in 30 cm³ of methanol and 0.1 g of potassium hydroxide dissolved in 15 cm³ of water. After treatment and recrystallization in a diisopropyl ether/isopropyl acetate (9/1 by volume) mixture, 0.35 g of (2RS,5SR)-3-{3-{2-[4-tert-butoxycarbonyl-5-(2-methylphenyl)-1-pyrrolidinyl]-2-oxoethyl}ureido}benzoic acid, melting at 235° C., is obtained.

tert-Butyl (2RS,5RS)-1-{2-[3-(3-ethoxycarbonylphenyl)ureido]acetyl}-5-(2-methylphenyl)prolinate may be prepared as described in Example 41 §A, but starting from 1.3 g of tert-butyl (2RS,5SR)-5-(2-methylphenyl)prolinate, 1.32 g of 2-[3-(3-ethoxycarbonylphenyl)ureido]acetic acid and 1.03 g of N,N'-dicyclohexylcarbodiimide in 50 cm³ of tetrahydrofuran. After treatment, 1.9 g of tert-butyl (2RS, 5RS)-1-{2-[3-(3-ethoxycarbonylphenyl)ureido]acetyl}-5-(2-methylphenyl)prolinate are obtained in the form of a meringue-like product, used as it is in subsequent syntheses.

tert-Butyl (2RS,5SR)-5-(2-methylphenyl)prolinate may be prepared as follows: a suspension of 3 g of magnesium in a solution of 4 g of a mixture of the two 4-position epimers of tert-butyl (2RS,5RS)-5-(2-methylphenyl)-4-phenylsulphonylprolinate in 200 cm³ of methanol is stirred for three hours at a temperature in the vicinity of 20° C. The reaction mixture is then poured into 200 cm³ of a normal aqueous hydrochloric acid solution, then extracted with three times 200 cm³ of dichloromethane. The organic extracts are combined, washed with two times 100 cm³ of a saturated aqueous sodium chloride solution, dried over magnesium sulphate and concentrated under reduced pressure. The residue is subjected to chromatography on silica [eluent: cyclohexane/ethyl acetate (70/30 by volume)]. The fractions containing the expected product are combined and concentrated under reduced pressure. 0.6 g of tert-Butyl (2RS, 5SR)-5-(2-methylphenyl)prolinate is thus obtained in the form of an oil, used as it is in subsequent syntheses.

A—tert-Butyl (2RS,5RS)-5-(2-methylphenyl)-4-phenylsulphonylprolinate may be prepared as follows: 2.8 cm³ of triethylamine at a temperature in the vicinity of 20° C. are added dropwise to a suspension of 5 g of silver acetate in a solution of 3.4 g of phenyl vinyl sulphone and 4.7 g of of tert-butyl N-(orthomethylbenzylidene)-glycinate in 150 cm³ of acetonitrile. The reaction mixture is stirred for two hours at a temperature in the vicinity of 20° C., then poured into 200 cm³ of a saturated aqueous ammonium chloride solution. The aqueous phase is filtered and extracted with three times 100 cm³ of dichloromethane. The organic extracts are combined, washed with 100 cm³ of a saturated aqueous sodium chloride solution, dried over magnesium sulphate and concentrated under reduced pressure. After recrystallization in ethyl ether, 5 g of tert-butyl (2RS,5RS)-5-(2-methylphenyl)-4-phenylsulphonylprolinate (mixture of the two 4-position epimers), melting at 180° C., are thus obtained.

B—tert-Butyl N-(ortho-methylbenzylidene)glycinate may be prepared as follows: 2.8 cm³ of triethylamine at a temperature in the vicinity of 20° C. are added dropwise to a suspension of 3 g of 4 Å molecular sieve in a solution of 3.35 g of tert-butyl glycinate hydrochloride in 2.4 cm³ of ortho-tolualdehyde and 50 cm³ of dichloromethane. The reaction mixture is stirred for twenty hours at a temperature in the vicinity of 20° C., filtered and concentrated under reduced pressure. The residue is taken up in 250 cm³ of diethyl ether, filtered and concentrated under reduced pressure. 4.7 g of tert-butyl N-(orthomethylbenzylidene)glycinate are thus obtained in the form of an oil, used as it is in subsequent syntheses.

EXAMPLE 90

The operation is carried out in a fashion similar to that described in Example 9, but starting from 1.1 g of tert-butyl (2RS,5SR)-1-{2-[3-(3-ethoxycarbonylphenyl)ureido]acetyl}-5-(2-fluorophenyl)-prolinate in solution in 30 cm³ of methanol and 0.12 g of potassium hydroxide dissolved in 15 cm³ of water. After treatment and recrystallization in diisopropyl ether, 0.4 g of (2RS,5SR)-3-{3-{2-[2-tert-butoxycarbonyl-5-(2-fluorophenyl)-1-pyrrolidinyl]-2-oxoethyl}ureido}benzoic acid, melting at 180° C., is obtained.

tert-Butyl (2RS,5SR)-1-{2-[3-(3-ethoxycarbonylphenyl)ureido]acetyl}-5-(2-fluorophenyl)prolinate may be prepared as described in Example 41 §A, but starting from 0.8 g of tert-butyl (2RS,5SR)-5-(2-fluorophenyl)prolinate, 0.8 g of 2-[3-(3ethoxycarbonylphenyl)ureido]acetic acid and 0.62 g of N,N'-dicyclohexylcarbodiimide in 30 cm³ of tetrahydrofuran. After treatment, 1.5 g of tert-butyl (2RS,5SR)-1-{2-[3-(3-ethoxycarbonylphenyl)ureido]acetyl}-5-(2-fluorophenyl)prolinate are obtained in the form of a meringue-like product, used as it is in subsequent syntheses.

A tert-Butyl (2RS,5SR)-5-(2-fluorophenyl)prolinate may be prepared as follows: a suspension of 5.7 g of disodium hydrogen phosphate and of 7.7 g of 6% sodium amalgam (in mercury) in a solution of 4.06 g of a mixture of the two 4-position epimers of tert-butyl (2RS,5RS)-5-(2-fluorophenyl)-4-phenylsulphonylprolinate in 150 cm³ of methanol is stirred for twenty hours at a temperature in the vicinity of 20° C. The reaction mixture is then poured into 200 cm³ of water and the mercury is separated by decantation. The aqueous phase is extracted with three times 100 cm³ of ethyl acetate. The organic extracts are combined, washed with two times 100 cm³ of water, dried over magnesium sulphate and concentrated under reduced pressure. The residue is subjected to chromatography on silica [eluent:cyclohexane/ethyl acetate (70/30 by volume)]. The fractions containing the expected product are combined and concentrated under reduced pressure. 0.4 g of tert-butyl (2RS,5SR)-5-(2-fluorophenyl)prolinate is thus obtained in the form of an oil, used as it is in subsequent syntheses.

tert-Butyl (2RS,5RS)-5-(2-fluorophenyl)-4-phenylsulphonylprolinate may be prepared as described in Example 89 §A, but starting from 4.8 g of tert-butyl N-(ortho-fluorobenzylidene)glycinate, 5 g of silver acetate, 3.4 g of phenyl vinyl sulphone and 2.8 cm³ of triethylamine. After treatment and recrystallization in ethyl ether, 8 g of tert-butyl (2RS,5RS)-5-(2-fluorophenyl)-4-phenylsulphonyl prolinate, mixture of the two 4-position epimers, melting at 200° C., are obtained.

tert-Butyl N-(ortho-fluorobenzylidene)glycinate may be prepared as described in Example 89 §B, but starting from 2 cm³ of ortho-fluorobenzaldehyde, 3.35 g of tert-butyl glycinate hydrochloride, 2.8 cm³ of triethylamine and 3 g of 4 Å molecular sieve in 50 cm³ of dichloromethane. After treatment, 4.8 g of tert-butyl N-(ortho-fluorobenzylidene)glycinate are obtained in the form of an oil, used as it is in subsequent syntheses.

EXAMPLE 91

The operation is carried out in a fashion similar to that described in Example 2, but starting from 1.12 g of tert-butyl (2RS,5SR)-1-(2-aminoacetyl)-5-phenylprolinate and 1.3 cm³ of para-chlorophenyl isocyanate in 50 cm³ of tetrahydrofuran. After treatment, 1.2 g of tert-butyl (2RS,5SR)-1-{2-[3-(4-chlorophenyl)ureido]acetyl}-5-phenylprolinate are obtained in the form of an amorphous solid [proton NMR (250 MHz, DMSO D$_6$, δ in ppm), 1.50 (s, 9H, (CH$_3$)$_3$); 1.85 (m, 2H, CH$_2$); 2.2 and 2.4 (2m, 2H, CH$_2$); 3.25 and 3.85 (ABX, 2H, CH$_2$N); 4.30 (dd, 1H, CHN); 5.20 (dd, 1H, CHN); 6.3 (t, 1H exchangeable, NH); 7.2 to 7.6 (m, 9H, aromatic); 9 (s, 1H exchangeable, NH)], [infrared spectrum (KBr), characteristic bands in cm$^{-1}$ 3370, 3065, 3030, 2980, 2930, 287, 1735, 1595, 1490, 1450, 1545, 1365, 1150, 830, 760, 700].

EXAMPLE 92

The operation is carried out in a fashion similar to that described in Example 3, but starting from 3.05 g of tert-butyl (2RS,5SR)-1-(2-aminoacetyl)-5-phenylprolinate, 1.78 g of N,N'-carbonyldiimidazole and 4.5 g of tetrabutylammonium (RS)-1-(3-aminophenyl)ethanesulphonate in 100 cm$^3$ of 1,2-dichloroethane. After treatment, 0.6 g of potassium (2RS,5SR)-1-{3-{3-[2-(2-tert-butoxycarbonyl-5-phenyl-1-pyrrolidinyl)-2-oxoethyl]ureido}phenyl}ethanesulfonate (mixture of the two 1-position epimers), is obtained in the form of an amorphous solid [proton NMR (200 MHz, DMSO D$_6$, δ in ppm,), 1.6 (s+d, 12H, CCH$_3$ and (CH$_3$)$_3$); 1.8 to 2.4 (m, 4H, 2 CH$_2$); 3.5 (m, 1H, CHSO$_3$); 3.1 and 3.8 (ABX, 2H, CH$_2$N); 4.2 (dd, 1H, CHN); 5.1 (dd, 1H, CHN); 6.2 (t, 1H exchangeable, NH); 6.8 to 7.6 (m, 9H, aromatic); 8.7 (bs, 1H exchangeable, NH)], [infrared spectrum (KBr), characteristic bands in cm$^{-1}$ 3380, 3060, 3025, 2975, 2930, 2875, 1730, 1555, 1490, 1445, 1390, 1360, 1215, 1115, 1030, 790, 755, 700].

EXAMPLE 93

The operation is carried out in a fashion similar to that described in Example 41 §A, but starting from 4.95 g of tert-butyl (2RS,5SR)-5-phenylprolinate, 5.04 g of 2-[3-(3-methoxycarbonylphenyl)ureido]acetic acid and 4.12 g of N,N'-dicyclohexylcarbodiimide in 75 cm$^3$ of tetrahydrofuran. After treatment and recrystallization in a diisopropyl ether/isopropyl acetate (90/10 by volume) mixture, 1.2 g of tert-butyl (2RS,5SR)1-{2-[3-(3-methoxycarbonyl)ureido]acetyl}-5-phenyl-prolinate, melting at 141° C., are obtained.

2-[3-(3-Methoxycarbonylphenyl)ureido]acetic acid may be prepared as described in Example 1 §A, but starting from 7.5 g of glycine, 8.4 g of sodium bicarbonate in 150 cm$^3$ of water and 17.7 g of methyl 3-isocyanatobenzoate. After treatment, 14.5 g of 2-[3-(3-methoxycarbonylphenyl)ureido]acetic acid, melting at 215° C., are obtained.

EXAMPLE 94

The operation is carried out in a fashion similar to that described in Example 9, but starting from 2.6 g of tert-butyl (2S,5R)-1-{2-[3-(3-ethoxycarbonylphenylureido]-acetyl}-5-phenylprolinate in solution in 40 cm$^3$ of methanol and 0.33 g of potassium hydroxide in solution in 20 cm$^3$ of water. After treatment, 1.8 g of (2S,5R)-3-{3-[2-(2-tert-butoxycarbonyl-5-phenyl-1-pyrrolidinyl)-2-oxoethyl]ureido}benzoic acid, its analytical data being in agreement with those of the dextrorotatory enantiomer prepared by chiral stationary phase chromatography of the racemic product, are obtained.

tert-Butyl (2S,5R)-1-{2-[3-(3-ethoxycarbonylphenyl)ureido]acetyl}-5-phenylprolinate may be obtained as follows: starting from 6.6 g of tert-butyl (2RS,5SR)-1-{2-[3-(3-ethoxycarbonylphenyl)ureido]acetyl}-5-phenylprolinate, high performance liquid chromatography on 400 g of a support, the preparation of which is described below, contained in a 26 cm long column of 6 cm diameter with, as mobile phase, a hexane/ethanol (70/30 by volume) mixture, is used to separate, at a rate of 70 cm$^3$ per minute in sequential elution order:

2.9 g of tert-butyl (2S,5R)-1-{2-[3-(3-ethoxycarbonylphenyl)ureido]acetyl}-5-phenylprolinate, the specific rotation of which is [α]$_D^{20}$=+30°±0.8° (c=0.922; methanol)

2.8 g of tert-butyl (2R,5S)-1-{2-[3-(3-ethoxycarbonylphenyl)-ureido]acetyl}-5-phenylprolinate, the specific rotation of which is [α]$_D^{20}$=−27°±0.6° (c=1,213; methanol).

EXAMPLE 95

The operation is carried out in a fashion similar to that described in Example 9, but starting from 3.5 g of tert-butyl (2S,5R)-1-{2-[3-(3-methoxycarbonylphenyl)ureido]-acetyl}-5-phenylprolinate in solution in 60 cm$^3$ of methanol and 0.45 g of potassium hydroxide in solution in 30 cm$^3$ of water. After treatment, 2.0 g of (2S,5R)-3-{3-{2-(2-tert-butoxycarbonyl-5-phenyl-1-pyrrolidinyl)-2-oxoethyl}ureido}benzoic acid, the analytical data of which are in agreement with those of the dextrorotatory enantiomer prepared by chiral stationary phase chromatography of the racemic product, are obtained.

(2S,5R)-1-{2-[3-(3-methoxycarbonylphenyl)ureido]acetyl}-5-phenylprolinate may be prepared as described in Example 41 §A, but starting from 0.1 g of tert-butyl (2S,5R)-5-phenylprolinate, 0.1 g of 2-[3-(3-methoxycarbonylphenyl)ureido]acetic acid and 0.08 g of N,N'-dicyclo-hexylcarbodiimide in 5 cm$^3$ of tetrahydrofuran. After treatment, 0.1 g of (2S,5R)-1-{2-[3-(3-methoxycarbonyl-phenyl)ureido]acetyl}-5-phenylprolinate, the analytical data of which are in agreement with those of the dextrorotatory enantiomer prepared by chiral stationary phase chromatography of the racemic product, is obtained.

tert-Butyl (2S,5R)-5-phenylprolinate may be prepared as follows: in the space of five minutes at a temperature in the vicinity of 2° C., a solution of 0.14 g of sodium borohydride and of 0.07 g of potassium carbonate in 0.8 cm$^3$ of water is added to an emulsion of 0.83 g of tert-butyl (S)-5-phenyl-Δ$_5$-pyrroline-2-carboxylate in a mixture of 0.5 cm$^3$ of ethanol and of 1.5 cm$^3$ of water. The reaction medium is stirred for 20 hours at a temperature in the vicinity of 20° C., followed by the addition of a solution of 0.14 g of sodium borohydride and 0.07 g of potassium carbonate in 0.8 cm$^3$ of water. The reaction medium is stirred again for 70 hours at a temperature in the vicinity of 20° C., then diluted with 25 cm$^3$ of water and extracted with three times 20 cm$^3$ of dichloromethane. The organic extracts are combined, washed with 10 cm$^3$ of water, dried over magnesium sulphate and concentrated to dryness under reduced pressure at 50° C. The residue is purified by chromatography on silica [eluent:dichloromethane]. The fractions containing the expected product are combined and concentrated under reduced pressure. 0.1 g of tert-butyl (2S,5R)-5-phenylprolinate is thus obtained in the form of an oil used as it is in subsequent syntheses.

tert-Butyl (S)-5-phenyl-Δ$^5$-pyrroline-2-carboxylate may be prepared as follows: at a temperature in the vicinity of 20° C. 2.3 cm$^3$ of trifluoroacetic acid are added to a solution of 1.8 g of tert-butyl (S)-2-tert-butoxycarbonyl-amino-5-oxo-5-phenylpentanoate in 25 cm$^3$ of dichloromethane. The reaction mixture is stirred for six hours at a temperature in the vicinity of 20° C., with the subsequent addition of 120 cm$^3$ of a saturated aqueous sodium bicarbonate solution. The organic phase is separated by decantation, washed with 20 cm³ of distilled water, dried over magnesium sulphate and concentrated under reduced pressure. 0.9 g of tert-butyl (S)-5-phenyl-Δ⁵-pyrroline-2-carboxylate is thus obtained in the form of an oil, used as it is in subsequent syntheses.

tert-Butyl (S)-2-tert-butoxycarbonylamino-5-oxo-5-phenylpentanoate may be prepared as follows: in the space of 35 minutes at a temperature of between 20 and 30° C. a solution of 2.8 cm³ of bromobenzene in 60 cm³ of tetrahydrofuran is added to a suspension of 0.72 g of magnesium in 20 cm³ of tetrahydrofuran. The reaction medium is then stirred at a temperature in the vicinity of 24° C. for 145 minutes, with the subsequent addition in the space of 20 minutes of a solution of 5.7 g of tert-butyl (S)-1-tert-butoxycarbonyl-5-oxopyrrolidine-2-carboxylate in 80 cm³ of tetrahydrofuran kept at a temperature in the vicinity of −75° C. The reaction medium is stirred for another three hours at a temperature in the vicinity of −78° C., then reheated to a temperature in the vicinity of −15° C. 100 cm³ of a 10% aqueous ammonium chloride solution are then added in the space of 15 minutes. The aqueous phase is separated by decantation and extracted with three times 100 cm³ of diethyl ether. The organic phases are combined and washed with two times 25 cm³ of water, dried over magnesium sulphate and concentrated under reduced pressure at a temperature in the vicinity of 50° C. The residue is purified by crystallization in 20 cm³ of pentane. 2.5 g of tert-butyl (S)-2-tert-butoxycarbonylamino-5-oxo-5-phenyl-pentanoate, melting at 107° C., are thus obtained. This product may also be present in the form of tert-butyl (2S,5RS)-1-tert-butoxycarbonyl-5-hydroxy-5-phenyl-pyrrolidine-2-carboxylate, melting at 85° C.

tert-Butyl (S)-1-tert-butoxycarbonyl-5-oxopyrrolidine-2-carboxylate may be obtained according to the method described by J. ACKERMANN and M. MATTHES, Helv. Chim. Acta, 73, 122–132, (1990).

tert-Butyl (2S,5R)-1-{2-[3-(3-methoxycarbonylphenyl)ureido]acetyl}-5-phenylprolinate may also be obtained as follows: starting from 7.8 g of tert-butyl (2RS,5SR)-1-{2-[3-(3-methoxycarbonylphenyl)ureido]acetyl}-5-phenyl-prolinate, high performance liquid chromatography on 400 g of a support, the preparation of which is described in the preceding example, contained in a 26 cm long column of 6 cm diameter, with, as mobile phase, a hexane/ethanol (70/30 by volume) mixture, is used to separate at a rate of 70 cm per minute rate in sequential elution order:

3.7 g of tert-butyl (2S,5R)-1-{2-[3-(3-methoxycarbonylphenyl)ureido]acetyl}-5-phenylprolinate, the specific rotation of which is $[\alpha]_D^{20}=+31.4°\pm1.2°$ (c=0.579; methanol)

3.6 g of tert-butyl (2R,5S)-1-{2-[3-(3-methoxycarbonylphenyl)ureido]acetyl}-5-phenylprolinate, the specific rotation of which is $[\alpha]_D^{20}=+28.2°\pm0.8°$ (c=0.949; methanol).

EXAMPLE 96

The operation is carried out in a fashion similar to that described in Example 9, but starting from 2.6 g of tert-butyl (2R,5S)-1-{2-[3-(3-ethoxycarbonylphenyl)ureido]acetyl}-5-phenylprolinate in solution in 60 cm³ of methanol and 0.3 g of potassium hydroxide in solution in 40 cm³ of water. After treatment, 1.3 g of (2R,5S)-3-{3-[2-(2-tert-butoxycarbonyl-5-phenyl)-1-pyrrolidinyl)-2-oxoethyl]ureido}benzoic acid, the analytical data of which are in agreement with those of the levorotatory enantiomer prepared by chiral stationary phase chromatography of the racemic product, are obtained.

EXAMPLE 97

The operation is carried out in a fashion similar to that described in Example 9, but starting from 3.38 g of tert-butyl (2R,5S)-1-{2-[3-(3-methoxycarbonylphenyl)-ureido]acetyl}-5-phenylprolinate in solution in 60 cm³ of methanol and 0.45 g of potassium hydroxide in solution in 20 cm³ of water. After treatment, 2.0 g of (2R,5S)-3-{3-[2-(2-tert-butoxycarbonyl-5-phenyl)-1-pyrrolidinyl)-2-oxoethyl]ureido}benzoic acid, the analytical data of which are in agreement with those of the levorotatory enantiomer prepared by chiral stationary phase chromatography of the racemic product, are obtained.

EXAMPLE 98

The operation is carried out as in Example 9, but starting from 1.9 g of methyl (2S,5R)-3-{3-[2-(2-tert-butoxycarbonyl-5-phenyl-1-pyrrolidinyl)-2-oxoethyl]ureido}phenylacetate in solution in 60 cm³ of methanol and 0.22 g of potassium hydroxide dissolved in 30 cm³ of water. After treatment, 0.65 g of (2S,5R)-3-{3-[2-(2-tert-butoxycarbonyl-5-phenyl-1-pyrrolidinyl)-2-oxoethyl]ureido}phenylacetic acid, melting at 112° C., $[\alpha]_D^{20}=+30.6°\pm0.8°$ (c=1; methanol) is obtained.

Methyl (2S,5R)-3-{3-[2-(2-tert-butoxycarbonyl-5-phenyl-1-pyrrolidinyl)-2-oxoethyl]ureido}phenylacetate may be prepared as described in Example 41 §A, but starting from 1.2 g of tert-butyl (2S,5R)-5-phenylprolinate, 1.29 g of 2-[3-(3-methoxycarbonylmethylphenyl)ureido]acetic acid and 1 g of N,N'-dicyclohexylcarbodiimide in 50 cm³ of acetonitrile. After treatment, 1.9 g of methyl (2S,5R)-3-{3-[2-(2-tert-butoxycarbonyl-5-phenyl-1-pyrrolidinyl)-2-oxoethyl]ureido}phenylacetate are obtained in the form of a meringue-like product, used as it is in subsequent syntheses.

tert-Butyl (2S,5R)-5-phenylprolinate may be prepared as follows: 0.02 g of platinum oxide is added to a solution of 1.25 g of tert-butyl (S)-5-phenyl-Δ⁵-pyrroline-2-carboxylate in 50 cm³ of ethanol. The suspension is stirred for 3 hours at a temperature in the vicinity of 20° C. under a hydrogen atmosphere (130 kPa). The catalyst is separated by filtration and the filtrate is concentrated to dryness under reduced pressure at 45° C. The residue is purified by chromatography on silica [eluent:dichloromethane/methanol (97.5/2.5 by volume)]. The fractions containing the expected product are combined and concentrated under reduced pressure. 1.2 g of tert-butyl (2S,5R)-5-phenylprolinate are thus obtained in the form of an oil used as it is in subsequent syntheses.

tert-Butyl (S)-5-phenyl-Δ⁵-pyrroline-2-carboxylate may be prepared as follows: at a temperature in the vicinity of 20° C., 1.4 cm³ of iodotrimethylsilane are added to a solution of 3.65 g of tert-butyl (S)-2-tert-butoxycarbonylamino-5-oxo-5-phenylpentanoate in 50 cm³ of dichloromethane. The reaction mixture is stirred for 20 hours at a temperature in the vicinity of 20° C., with subsequent addition of 50 cm³ of a saturated aqueous sodium bicarbonate solution. The organic phase is separated by decantation, washed with 20 cm³ of distilled water, dried over magnesium sulphate and concentrated under reduced pressure. 2.0 g of tert-butyl (S)-5-phenyl-Δ⁵-pyrroline-2-carboxylate are thus obtained in the form of an oil used as it is in subsequent syntheses.

EXAMPLE 99

The operation is carried out in a fashion similar to that described in Example 2, but starting from 1.93 g of tert-butyl (2RS,5SR)-1-(2-aminoacetyl)-5-phenylprolinate and 3.61 g of benzyl 3-isocyanatobenzoate in 50 cm³ of tetrahydrofuran. After treatment, 1 g of tert-butyl (2RS,5SR)-1-{2-[3-(3-benzyloxycarbonylphenyl)-ureido]acetyl}-5-phenylprolinate, melting at 75° C., is obtained.

Benzyl 3-isocyanatobenzoate may be prepared as described in Example 64 §A, but starting from 27 g of benzyl 3-aminobenzoate hydrochloride in 200 cm³ of toluene, 14.4 cm³ of triethylamine, 2 g of charcoal and 12.5 cm³ of trichloromethyl chloroformate in 200 cm³ of toluene. After treatment, 27 g of benzyl 3-isocyanatobenzoate are obtained in the form of an oil, used as it is in subsequent syntheses.

Benzyl 3-aminobenzoate may be prepared according to the method described by H. A. SHONLE et al., J. Amer. Chem. Soc., 43, 361 (1921).

EXAMPLE 100

0.5 g of 5% palladinized charcoal is added to a solution of 1.7 g of ethyl (2RS,5SR)-1-{2-[3-(3-benzyloxycarbonylphenyl)-ureido]acetyl}-5-phenylprolinate in 100 cm³ of ethanol. The suspension is stirred for 20 hours at a temperature in the vicinity of 25° C. under a hydrogen atmosphere (130 kPa). The catalyst is separated by filtration and the filtrate is concentrated to dryness under reduced pressure. The residue is recrystallised in 80 cm³ of ethanol. 0.7 g of (2RS,5SR)-3-{3-[2-(2-Ethoxy-carbonyl-5-phenyl-1-pyrrolidinyl)-2-oxoethyl]-ureido}benzoic acid, melting at 240° C., is thus obtained.

Ethyl (2RS,5SR)-1-{2-[3-(3-benzyloxycarbonylphenyl)ureido]acetyl}-5-phenyl-prolinate may be prepared as described in Example 41 §A, but starting from 2 g of ethyl (2RS,5SR)-5-phenylprolinate, 2.99 g of 2-[3-(3-benzyloxycarbonylphenyl]ureido]acetic acid and 2.07 g of N,N'-dicyclohexylcarbodiimide in 180 cm³ of tetrahydrofuran. After treatment, 1.95 g of ethyl (2RS,5SR)-1-{2-[3-(3-benzyloxycarbonylphenyl)ureido]acetyl}-5-phenylprolinate are obtained in the form of a meringue-like product, used as it is in subsequent syntheses.

2-[3-(3-benzyloxycarbonylphenyl)ureido]acetic acid may be prepared as described in Example 1 §A, but starting from 3.97 g of glycine and 14.62 g of potassium carbonate in solution in 90 cm³ of water and 13.4 g of benzyl 3-isocyanato-benzoate in solution in 70 cm³ of 1,4-dioxane. After treatment, 13 g of 2-[3-(3-benzyloxycarbonylphenyl)-ureido]acetic acid, used as it is in subsequent syntheses, are obtained.

Ethyl (2RS,5SR)-5-phenylprolinate may be obtained as follows: 0.5 cm³ of concentrated sulphuric acid is added dropwise to a solution of 5.5 g of (2RS,5SR)-5-phenylproline in 50 cm³ of ethanol. The reaction mixture is then stirred at a temperature in the vicinity of 80° C. for five hours, then cooled to a temperature in the vicinity of 20° C. and concentrated under reduced pressure. The residue is taken up in 50 cm³ of water, brought to a pH in the vicinity of 9 by a normal aqueous sodium hydroxide solution and extracted with 3 times 100 cm³ of ethyl acetate. The combined organic extracts are washed with 50 cm³ of saturated aqueous sodium chloride solution, dried over magnesium sulphate and concentrated under reduced pressure. The residue is subjected to chromatography on silica [eluent cyclohexane/ethyl acetate (90/10 by volume)]. The fractions containing the expected product are combined and concentrated under reduced pressure. 2.16 g of ethyl (2RS,5SR)-5-phenylprolinate are thus obtained in the form of an oil, used as it is in subsequent syntheses.

EXAMPLE 101

The operation is carried out in a fashion similar to that described in Example 100, but starting from 10.2 g of tert-butyl (2RS,5SR)-1-{2-[3-(3-benzyloxycarbonylphenyl)-ureido]acetyl}-5-phenylprolinate and 1 g of 5% palladium on charcoal in 300 cm³ of ethanol. After treatment, 7.1 g of (2RS,5RS)-3-{3-[2-(2-tert-butoxycarbonyl-5-phenyl-1-pyrrolidinyl)-2-oxoethyl]ureido}benzoic acid, melting at 236° C., are obtained.

EXAMPLE 102

The operation is carried out in a fashion similar to that described in Example 100, but starting from 0.8 g of tert-butyl (2RS,5RS)-1-{2-[3-(3-benzyloxycarbonylphenyl)-ureido]acetyl}-5-phenylprolinate in solution in 50 cm³ of ethyl acetate and 0.1 g of 5% palladium on charcoal. After treatment, 0.45 g of (2RS,5SR)-3-{3-{2-[2-tert-butoxy-carbonyl-5-(3-methylphenyl)-1-pyrrolidinyl]-2-oxoethyl}ureido}benzoic acid, melting at 208° C., is obtained.

tert-Butyl (2RS,5SR)-1-{2-[3-(3-benzylcarbonylphenyl)ureido]acetyl}-5-phenylprolinate may be prepared as described in Example 41 §A, but starting from 0.4 g of tert-butyl (2RS,5SR)-5-(3-methylphenyl)-prolinate, 0.5 g of 2-[3-(3-benzyloxycarbonylphenyl)-ureido]acetic acid and 0.31 g of N,N'-dicyclohexyl-carbodiimide in 20 cm³ of acetonitrile. After treatment, 0.8 g of tert-butyl (2RS,5RS)-1-{2-[3-(3-benzyloxycarbonylphenyl)ureido]-acetyl}-5-phenylprolinate is obtained in the form of a meringue-like product, used as it is in the subsequent syntheses.

tert-Butyl (2RS,5SR)-5-(3-methylphenyl)prolinate may be prepared as described in Example 2 §A, but starting from 1 g of tert-butyl (2RS,5SR)-1-tert-butoxycarbonyl-5-(3-methylphenyl)prolinate and 0.4 cm³ of iodotrimethylsilane in 40 cm³ of chloroform. After treatment, 0.4 g of tert-butyl (2RS,5SR)-5-(3-methylphenyl)prolinate is obtained in the form of an oil, used as it is in subsequent syntheses.

tert-Butyl (2RS,5SR)-1-tert-butoxycarbonyl-5-(3-methylphenyl)prolinate may be prepared as described in Example 90 §A, but starting from 2.4 g of sodium dihydrogen phosphate and 7.63 g of 6% sodium amalgam (in mercury) in a solution of 2.5 g of a mixture of the two 4-position epimers of tert-butyl (2RS,5RS)-1-tert-butoxycarbonyl-5-(3-methylphenyl)-4-phenylsulphonylprolinate in a mixture of 20 cm³ of methanol and 40 cm³ of tetrahydrofuran. After treatment, 1 g of tert-butyl (2RS,5SR)-1-tert-butoxycarbonyl-5-(3-methylphenyl)-prolinate is obtained in the form of an oil, used as it is in subsequent syntheses.

tert-Butyl (2RS,5RS)-1-tert-butoxycarbonyl-5-(3-methylphenyl)-4-phenylsulphonylprolinate may be prepared as follows: 0.42 g of sodium bicarbonate and then a solution of 1.09 g of di-tert-butyl dicarbonate in 20 cm³ of dichloromethane are added successively to a solution of 2.01 g of a mixture of the two 4-position epimers of tert-butyl (2RS,5RS)-5-(3-methylphenyl)-4-phenylsulphonylprolinate in 50 cm³ of dichloromethane. The reaction mixture is stirred for 72 hours at a temperature in the vicinity of 20° C., with the subsequent addition of 50 cm³ of water. The organic phase is separated by decantation, dried over magnesium sulphate and concentrated to dryness under reduced pressure. 2.5 g of tert-butyl (2RS,5RS-1-tert-butoxycarbonyl-5-(3-methylphenyl)-4-phenylsulphonylprolinate mixture of the two 4-position epimers), are thus obtained in the form of an oil, used as it is in subsequent syntheses.

tert-Butyl (2RS,5RS)-5-(3-methylphenyl)-4-phenylsulphonylprolinate may be prepared as described in Example 89 §A, but starting from 4.7 g of tert-butyl N-(meta-methylbenzylidene)glycinate, 5 g of silver acetate, 3.4 g of phenyl vinyl sulfone and 2.8 cm³ of triethylamine. After treatment, 6.1 g of tert-butyl (2RS,5RS)-5-(3-methylphenyl)-4-phenylsulphonylprolinate, a mixture of the two 4-position epimers, melting at 139° C., are obtained.

tert-Butyl (N-(meta-methylbenzylidene) glycinate may be prepared as described in Example 89 §B, but starting from 2.4 cm³ of meta-tolualdehyde, 3.35 g of tert-butyl glycinate hydrochloride, 2.8 cm³ of triethylamine and 3 g of 4 Å molecular sieve in 30 cm³ of dichloromethane. After treatment, 4.7 g of tert-butyl (N-(metamethylbenzylidene) glycinate are obtained in the form of an oil, used as it is in subsequent syntheses.

EXAMPLE 103

The operation is carried out in a fashion similar to that of Example 9, but starting from 1.2 g of a mixture of tert-butyl (2RS,3SR)- and (2RS,3RS)-1-{2-[3-(3-ethoxy-carbonylphenyl)ureido]acetyl}-3-phenylprolinate}in a weight ratio of 85 to 15 in solution in 30 cm³ of tetrahydrofuran in 2.4 cm³ of normal sodium hydroxide solution diluted with 15 cm³ of water. After treatment, 0.7 g of a mixture of (2RS, 3SR)- and (2RS,3RS)-3-{3-[2-(2-tert-butoxycarbonyl-3-phenyl-1-pyrrolidinyl)-2-oxoethyl]ureido}benzoic acid, in a weight ratio of 85 to 15, melting at 225° C., is obtained.

tert-Butyl (2RS,3SR)-1-{2-[3-(3-ethoxycarbonylphenyl)ureido]acetyl}-3-phenylprolinate may be prepared as described in Example 41 §A, but starting from 1 g of a mixture of tert-butyl (2RS,3SR)- and (2RS,3RS)-3-phenylprolinate, in a weight ratio of 85 to 15, of 1.1 g of 2-[3-(3-ethoxycarbonylphenyl)ureido]acetic acid and of 0.83 g of N,N'-dicyclohexylcarbodiimide in 30 cm³ tetrahydrofuran. After treatment, a mixture of 1.2 g of tert-butyl (2RS,3SR)- and (2RS,3RS)-1-{2-[3-(3-ethoxycarbonylphenyl)ureido]acetyl}-3-phenylprolinate in a weight ratio of 85 to 15, melting at 154° C., is obtained.

tert-Butyl (2RS,3SR)-3-phenylprolinate and (2RS,3RS)-3-phenylprolinate may be prepared as described in Example 1 §B, but starting from 10 g of a mixture of (2RS,5SR) and (2RS,5RS)-3-phenylproline, isobutene and 3 cm³ of sulphuric acid in 200 cm³ of chloroform. After treatment and chromatography on silica [eluent cyclohexane/ethyl acetate (50/50 by volume)], 1 g of a mixture of tert-butyl (2RS, 3SR)- and (2RS,3RS)-3-phenylprolinate, in a weight ratio of 85 to 15, in the form of an oil used as it is in subsequent syntheses, and 2.5 g of a mixture of tert-butyl (2RS,3RS)- and (2RS,3SR)-3-phenylprolinate, in a weight ratio of 85 to 15, in the form of an oil, used as it is in subsequent syntheses, are obtained.

The (2RS,5SR)- and (2RS,5RS)-3-phenylprolines may be prepared by the methods described by Y. N. BELOKON et al., J. Chem. Soc., Perkin Trans., 1, 2075 (1988) and J. RIVIER., G. R. MARSHALL Peptides, Chemistry, Structure and Biology, Proceedings of the Eleventh American Peptide Symposium, Jul. 9–14 1989, La Jolla, Calif., U.S.A., ESCOM, Leiden, 1990.

EXAMPLE 104

The operation is carried out in a fashion similar to that described in Example 9, but starting from 2.5 g of a mixture of tert-butyl (2RS,3RS)- and (2RS,3SR)-1-{2-[3-(3-ethoxycarbonylphenyl)ureido]acetyl}-3-phenylprolinate, in a weight ratio of 80 to 20, in solution in 30 cm³ of tetrahydrofuran and 5 cm³ of a normal sodium hydroxide solution diluted with 15 cm³ of water. After treatment, a mixture of 1 g of (2RS,3RS)- and (2RS,3SR)-3-{3-[2-(2-tert-butoxycarbonyl-3-phenyl-1-pyrrolidinyl)-2-oxoethyl] ureido}benzoic acid, in a weight ratio of 90 to 10, melting at 200° C., is obtained.

tert-Butyl (2RS,3RS)-1-{2-[3-(3-ethoxycarbonylphenyl)ureido]acetyl}-3-phenylprolinate may be prepared as described in Example 41 §A, but starting from 2.5 g of a mixture of tert-butyl (2RS,3RS)- and (2RS,3SR)-3-phenylprolinate, in a weight ratio of 90 to 10, 2.7 g of 2-[3-(3-ethoxycarbonylphenyl)ureido]acetic acid, and 2.1 g of N,N'-dicyclohexylcarbodiimide in 50 cm³ of tetrahydrofuran. After treatment, a mixture of 1.2 g of tert-butyl (2RS,3RS)- and (2RS, 3SR)-1-{2-[3-(3-ethoxycarbonylphenyl)ureido] acetyl}-3-phenylprolinate, in a weight ratio of 80 to 20, melting at 141° C., is obtained.

EXAMPLE 105

The operation is carried out in a fashion similar to that described in Example 9, but starting from 2.1 g of tert-butyl (2S,4S)-1-{2-[3-(3-methoxycarbonylphenyl)ureido]acetyl}-4-phenylprolinate in solution in 30 cm³ of methanol and 0.5 g of potassium hydroxide dissolved in 15 cm³ of water. After treatment and crystallization in a diisopropyl ether/diisopropyl acetate (90/10 by volume) mixture, 0.65 g of (2S,4S)-3-{3-[2-(2-tert-butoxycarbonyl-4-phenyl-1-pyrrolidinyl)-2-oxoethyl]ureido}benzoic acid, melting at 144° C., is obtained.

tert-Butyl (2S,4S)-1-{2-[3-(3-methoxycarbonylphenyl)ureido]acetyl}-4-phenylprolinate may be prepared as described in Example 41 §A, but starting from 1.2 g of tert-butyl (2S,4S)-4-phenylprolinate, 1.2 g of 2-[3-(3-methoxycarbonylphenyl)ureido]acetic acid and 1 g of N,N'-dicyclohexylcarbodiimide in 30 cm³ of acetonitrile. After treatment, 2.1 g of tert-butyl (2S,4S)-1-{2-[3-(3-methoxycarbonylphenyl)ureido]acetyl}-4-phenylprolinate are obtained in the form of a meringue-like product, used as it is in subsequent syntheses.

tert-Butyl (2S,4S)-4-phenylprolinate may be prepared as described in Example 1 §B, but starting from 3.4 g of (2S,4S)-4-phenylproline, isobutene and 1.5 cm³ of sulphuric acid in 150 cm³ of chloroform. After treatment, 1.2 g of tert-butyl (2S,4S)-4-phenylprolinate are obtained in the form of a meringue-like product, used as it is in subsequent syntheses.

(2S,4S)-4-phenylproline may be prepared according to the methods described by J. K. THOTTATHIL and J. L. MONIOT, Tetrahedron Lett., 27, 151 (1968)and D. R. KRONENTHAL et al., Tetrahedron Lett., 31, 1241 (1990).

EXAMPLE 106

The operation is carried out in a fashion similar to that described in Example 9, but starting from 1.8 g of tert-butyl (2S,4R)-1-{2-[3-(3-methoxycarbonylphenyl)ureido] acetyl}-4-phenylprolinate in solution in 30 cm³ of methanol and 0.21 g of potassium hydroxide dissolved in 15 cm³ of water. After treatment and crystallization in a diisopropyl ether/diisopropyl acetate (90/10 by volume) mixture, 0.55 g of (2S,4R)-3-{3-[2-(2-tert-butoxycarbonyl-4-phenyl-1-pyrrolidinyl)-2-oxoethyl]ureido}benzoic acid, melting at 140° C., is obtained.

tert-Butyl (2S,4R)-1-{2-[3-(3-methoxycarbonylphenyl)ureido]acetyl}-4-phenylprolinate may be prepared as described in Example 41 §A, but starting from 1 g of tert-butyl (2S,4R)-4-phenylprolinate, 1 g of 2-[3-(3methoxycarbonylphenyl)ureido]acetic acid and 0.85 g of N,N'-dicyclohexylcarbodiimide in 30 cm³ of acetonitrile. After treatment, 1.8 g of tert-butyl (2S,4R)-1-{2-[3-(3-methoxycarbonylphenyl)ureido]acetyl}-4-phenylprolinate are obtained in the form of a meringue-like product, used as it is in subsequent syntheses.

tert-Butyl (2S,4R)-4-phenylprolinate may be prepared as described in Example 1 §B, but starting from 4.4 g of (2S,4R)-4-phenylproline, isobutene and 1.5 cm³ of sulphuric acid in 150 cm³ of chloroform. After treatment, 1 g of tert-butyl (2S,4R)-4-phenylprolinate, melting at 62° C., is obtained.

(2S,4R)-4-phenylproline may be prepared according to the methods described by J. K. THOTTATHIL and J. L. MONIOT, Tetrahedron Lett., 27, 151 (1968) and D. R. KRONENTHAL et al., Tetrahedron Lett., 31, 1241 (1990).

EXAMPLE 107

The operation is carried out in a fashion similar to that described in Example 9, but starting from 0.55 g of tert-butyl (2RS,5SR)-1-{2-[3-(3-benzyloxycarbonylphenyl)-ureido]acetyl}-5-(2-pyridyl)prolinate in solution in 20 cm³ of methanol and 10 cm³ of 0.1N aqueous potassium hydroxide solution. After treatment, 0.17 g of (2RS,5SR)-3-{3-[2-(2-tert-butoxycarbonyl-5-(2-pyridyl)-1-pyrrolidinyl)-2-oxoethyl]ureido}benzoic acid, melting at 174° C., is obtained.

tert-Butyl (2RS,5SR)-1-{2-[3-(3-benzyloxycarbonylphenyl)ureido]acetyl}-5-(2-pyridyl)prolinate may be prepared as described in Example 2, but starting from 0.5 g of tert-butyl (2RS,5SR)-1-(2-aminoacetyl)-5-(2-pyridyl)-prolinate and 0.45 g of benzyl 3-isocyanatobenzoate in 25 cm³ of tetrahydrofuran. After treatment, 0.7 g of tert-butyl (2RS,5SR)-1-{2-[3-(3-benzyloxycarbonyl-phenyl)ureido]acetyl}-5-(2-pyridyl)prolinate is obtained in the form of a meringue-like product, used as it is in subsequent syntheses.

tert-Butyl (2RS,5SR)-1-(2-aminoacetyl)-5-(2-pyridyl)prolinate may be prepared as described in Example 2 §A, but starting from 0.7 g of tert-butyl (2RS,5SR)-1-(2-tert-butoxycarbonylaminoacetyl)-5-(2-pyridyl)-prolinate and 0.25 cm³ of iodotrimethylsilane in 30 cm³ of chloroform. After treatment, 0.5 g of tert-butyl (2RS,5SR)-1-(2-aminoacetyl)-5-(2-pyridyl)prolinate is obtained in the form of an oil, used as it is in subsequent syntheses.

tert-Butyl (2RS,5SR)-1-(2-tert-butoxycarbonylaminoacetyl)-5-(2-pyridyl)prolinate may be prepared as described in Example 90 §A, but starting from 4.8 g of sodium dihydrogen phosphate and 15.3 g of 6% sodium amalgam (in mercury) in a solution of 5.5 g of a mixture of the two 4-position epimers of tert-butyl (2RS,5RS)-1-(2-tert-butoxycarbonylaminoacetyl)-4-phenylsulphonyl-5-(2-pyridyl)prolinate in a mixture of 20 cm³ of methanol and of 60 cm³ of tetrahydrofuran. After treatment, 0.7 g of tert-butyl (2RS,5SR)-1-(2-tert-butoxycarbonylaminoacetyl)-5-(2-pyridyl)prolinate is obtained in the form of an oil, used as it is in subsequent syntheses.

tert-Butyl (2RS,5RS)-1-(2-tert-butoxycarbonylaminoacetyl)-4-phenylsulphonyl-5-(2-pyridyl)prolinate may be prepared as follows: 1.5 cm³ of ethyl chloroformate are added to a solution of 2.7 g of 2-tert-butoxycarbonylaminoacetic acid in a mixture of 2.2 cm³ of triethylamine and of 100 cm³ of dichloromethane maintained at a temperature in the vicinity of 0° C. The reaction medium is stirred for thirty minutes at a temperature in the vicinity of 0° C. with a subsequent addition of a solution of 6 g of tert-butyl (2RS, 5RS)-4-phenylsulphonyl-5-(2-pyridyl)prolinate in 50 cm³ of dichloromethane. The reaction mixture is stirred for twenty hours at a temperature in the vicinity of 20° C., with a subsequent addition of 100 cm³ of water. The organic phase is separated by decantation, washed with 25 cm³ of water, dried over magnesium sulphate and concentrated under reduced pressure. The residue is purified by chromatography on silica [eluent: cyclohexane/ethyl acetate (50/50 by volume)]. The fractions containing the expected product are combined and concentrated under reduced pressure. 5.6 g of tert-butyl (2RS,5RS)-1-(2-tert-butoxycarbonylaminoacetyl)-4-phenylsulphonyl-5-(2-pyridyl)prolinate (mixture of the two 4-position epimers) are thus obtained in the form of an oil, used as it is in subsequent syntheses.

tert-Butyl (2RS,5RS)-4-phenylsulphonyl-5-(2-pyridyl)prolinate may be prepared as described in Example 89 §A, but starting from 4.4 g of tert-butyl N-[(2-pyridyl)methylene]glycinate, 5 g of silver acetate, 3.4 g of phenyl vinyl sulphone and 2.8 cm³ of triethylamine in 200 cm³ of acetonitrile. After treatment, 6 g of tert-butyl (2RS,5RS)-4-phenylsulphonyl-5-(2-pyridyl)prolinate (mixture of the two 4-position epimers) are obtained in the form of an oil, used as it is in the subsequent syntheses.

tert-Butyl N-[(2-pyridyl)methylene]glycinate may be prepared as described in Example 89 §B, but starting from 1.4 cm³ of 2-pyridylcarboxaldehyde, 3.35 g of tert-butyl glycinate hydrochloride, 2.8 cm³ of triethylamine and 3 g of 4 Å molecular sieve in 30 cm³ of dichloromethane. After treatment, 4.8 g of tert-butyl N-[(2-pyridyl)methylene]glycinate are obtained in the form of an oil, used as it is in subsequent syntheses.

EXAMPLE 108

1.3 g of oxone® in solution in 8 cm³ of distilled water are added to a solution of 0.65 g of 2-{3-{3-{2-[(2R,4R)-4-tert-butoxycarbonyl-2-(2-fluorophenyl)-3-thiazolidinyl]-2-oxoethyl}ureido}phenyl}-propionic acid (A form) in 6 cm³ of methanol. The reaction medium is stirred for 12 hours at a temperature in the vicinity of 25° C., then concentrated under reduced pressure at 40° C. The product obtained is purified by chromatography on silica [eluent:methylene chloride/methanol (90/10 by volume)]. The fractions containing the expected product are combined and concentrated to dryness under reduced pressure at 40° C. 0.4 g of 2-{3-{3-{2-[(1RS,2R,4R)-4-tert-butoxycarbonyl-2-(2-fluorophenyl)-1-oxide-3-thiazolidinyl]-2-oxoethyl}ureido}phenyl}-propionic acid (A form) is thus obtained in the form of an amorphous product.

Proton NMR (200 MHz, DMSO D$_6$, δ in ppm, J in Hz); at 120° C. the mixture of the two diastereoisomers in the proportions 85–15 is observed, characteristic chemical shifts at 120° C.: 1.32 (d, J=7.5, 3H, —CH$_3$); 1.50 and 1.58 (2s, 9H in total, —C(CH$_3$)$_3$ of the preponderant isomer, then of the less abundant isomer); 2.85 (t, J=12.5, 0.85H, 1H of —S—CH$_2$ for the preponderant isomer); 3.4 to 4.4 (m, 6.15H, —CH—COO, the other H of —S—CH$_2$ for the preponderant isomer, the —S—CH$_2$ of the less abundant isomer and N—COCH$_2$—N); 4.8 (t, J=8, 0,15H, S—CH—N of the less abundant isomer); 4.97 (dd, J=12.5 and 5.0, 0.85H, S—CH—N of the preponderant isomer); 6.3 to 6.45 (m, 1H, —NHCO—); 6.5 and 6.6 (2s, 0.15H and 0.85H, S—CH—N of the less abundant isomer and of the preponderant isomer); 6.8 (bd, J=8, 1H, in position 4 on CO—NH—Ph—); 7.0 to 7.6 (m, 6H, aromatic); 7.77 and 8.10 (t, J=8, 0.15H and 0.85H, in position 6 on S—CH—Ph— for the less abundant isomer and for the preponderant isomer); 8.84 and 8.96 (2s, 0.85H and 0.15H, ArNHCO— for the preponderant isomer and for the less abundant isomer).

Infrared spectrum (KBr), characteristic bands in cm$^{-1}$: 3390, 3100 to 3000, 2975, 2930, 2875 to 2300 (wide band), 1735, 1670, 1615, 1595, 1555, 1490, 1460, 1400, 1395, 1370, 1150, 760, 700.

EXAMPLE 109

The operation is carried out in a fashion similar to that described in Example 41, but starting from 1.85 g of 2-trimethylsilylethyl (2R,4R)-3-{3-{2-[4-tert-butoxycarbonyl-2-(1-naphthyl)-3-thiazolidinyl]-2-oxoethyl}ureido}benzoate and 5.82 cm$^3$ of a 1M tetrabutylammonium fluoride solution. 0.47 g of (2R,4R)-3-{2-{2-[4-tert-butoxycarbonyl-2-(1-naphthyl)-3-thiazolidinyl]-1-oxoethyl}ureido}benzoic acid is thus obtained in the form of a beige solid, melting at 210° C. $[\alpha]_D^{20}=+222°\pm5°$ (C=0.5%; CHCl$_3$).

Proton NMR (200 MHz, DMSO D$_6$ plus several drops of CD$_3$COOD, δ in ppm, J in Hz), 2 rotamers at room temperature, characteristic chemical shifts at 120° C.: 1.53 (s, 9H, —C(CH$_3$)$_3$); 3.25 (dd, J=12 and 7, 1H, 1H of S—CH$_2$); 3.49 (dd, J=12 and 6.5, 1H, the other H of S—CH$_2$); 3.7 (bd, J=17.5, 1H, 1H of N—COCH$_2$—N); 4.08 (d, J=17.5, 1H, the other H of N—COCH$_2$—N); 5.02 (dd, J=7.0 and 6.5, 1H, N—CH—COO); 7.08 (s, 1H, S—CH—N); 7.15 to 8.15 (m, 11H, aromatic).

Infrared spectrum (KBr), characteristic bands in cm$^{-1}$: 3390, 3100 to 3000, 2975, 2930, 1735, 1655, 1595, 1555, 1510, 1485, 1400, 1370, 1150, 785, 770.

2-Trimethylsilylethyl (2R,4R)-3-{3-{2-[4-tert-butoxycarbonyl-2-(1-naphthyl)-3-thiazolidinyl]-2-oxoethyl}ureido}benzoate may be prepared in a fashion similar to that described in Example 34, but starting from 2.4 g of tert-butyl (2R,4R)-3-(2-aminoacetyl)-2-(1-naphthyl)-4-thiazolidinecarboxylate and 2.1 g of 2-trimethylsilylethyl 3-isocyanatobenzoate. The crude product is purified by chromatography on silica [eluent: ethyl acetate/cyclohexane (30/70 by volume)]. The fractions containing the expected product are combined and concentrated to dryness under reduced pressure at 40° C. 1.85 g of 2-trimethylsilyl (4R)-3-{3-{2-[4-tert-butoxycarbonyl-2-(1-naphthyl)-3-thiazolidinyl]-2-oxoethyl}ureido}benzoate (A form) are thus obtained in the form of a beige paste, used as it is in subsequent syntheses.

tert-Butyl (2R,4R)-3-(2-aminoacetyl)-2-(1-naphthyl)-4-thiazolidinecarboxylate may be prepared in a fashion similar to that described in Example 34 A, but starting from 3.65 g of tert-butyl (2R,4R)-3-(2-tert-butoxycarbonylaminoacetyl)-2-(1-naphthyl)-4-thiazolidinecarboxylate and 1.13 cm$^3$ of iodotrimethylsilane. 2.43 g of (2R,4R)-3-(2-aminoacetyl)-2-(1-naphthyl)-4-thiazolidinecarboxylate are thus obtained in the form of a yellow solid, used as it is in subsequent syntheses.

tert-Butyl (2R,4R)-3-(2-tert-butoxycarbonylaminoacetyl)-2-(1-naphthyl)-4-thiazolidinecarboxylate may be prepared in a fashion similar to that described in Example 34 B, but starting from 7.54 g of tert-butyl (2RS,4R)-2-(1-naphthyl)-4-thiazolidinecarboxylate, 4.23 g of 2-tert-butoxycarbonylaminoacetic acid and 4.98 g of N,N'-dicyclohexylcarbodiimide. The crude product is purified by chromatography on silica [eluent: ethyl acetate/cyclohexane (30/70 by volume)]. The fractions containing the expected product are combined and concentrated to dryness under reduced pressure. 13.9 g of tert-butyl (2R,4R)-3-(2-tert-butoxycarbonylaminoacetyl)-2-(1-naphthyl)-4-thiazolidinecarboxylate are thus obtained in the form of an orange oil, used as it is in subsequent syntheses.

tert-Butyl (2RS,4R)-2-(1-naphthyl)-4-thiazolidinecarboxylate may be prepared in a fashion similar to that described in Example 34 C, but starting from 20.0 g of (2RS,4R)-2-(1-naphthyl)-4-thiazolidinecarboxylic acid in solution in 300 cm$^3$ of chloroform, 5.8 cm$^3$ of concentrated sulphuric acid and an excess of isobutene. The crude product obtained is purified by chromatography on silica [eluent: ethyl acetate/cyclo-hexane (30/70 by volume)]. The fractions containing the expected product are combined and concentrated to dryness under reduced pressure at 40° C. 10.15 g of tert-butyl (2RS,4R)-2-(1-naphthyl)-4-thiazolidinecarboxylate are thus obtained in the form of an orange oil, a mixture of the (2R,4R) and (2S,4R) isomers, used as it is in subsequent syntheses.

(2RS,4R)-2-(1-naphthyl)-4-thiazolidinecarboxylic acid may be prepared as in Example 34 D, but starting from 20.0 g of L-cysteine and 28.5 g of 1-naphthyl-carboxaldehyde. 36.3 g of (2RS,4R)-2-(1-naphthyl)-4-thiazolidinecarboxylic acid, melting at 208° C., used as it is in subsequent syntheses, are thus obtained.

EXAMPLE 110

The operation is carried out in a fashion similar to that described in Example 41, but starting from 0.12 g of 2-trimethylsilylethyl (4R)-3-{3-{2-[4-tert-butoxy-carbonyl-2-(5-methyl-2-thienyl)-3-thiazolidinyl]-2-oxoethyl}ureido}benzoate (A form) and 0.4 cm$^3$ of 1M tetrabutylammonium fluoride solution. 0.08 g of (4R)-3-{2-{2-[4-tert-butoxy-carbonyl-2-(5-methyl-2-thienyl)-3-thiazolidinyl]-1-oxoethyl}ureido}benzoic acid (A form) is thus obtained in the form of an orange solid, melting at 85°–90° C.

Proton MMR (300 MHz, DMSO D$_6$ plus several drops of CD$_3$COOD, δ in ppm, J in Hz), 2 rotamers at room temperature, characteristic chemical shifts at 120° C.: 1.5 (s, 9H, —C(CH$_3$)$_3$; 2.46 (s, 3H, —CH$_3$); 3.4 and 3.52 (2dd, J=12 and 6.5, 1H each, —S—CH$_2$); 3.96 (d, J=17.5, 1H, 1H of N—COCH$_2$—N); 4.05 (d, J=17.5, 1H, the other H of N—COCH$_3$—N); 4.96 (t, J=6.5, 1H, OOC—CH—N); 6.65 (s, 1H, S—CH—N); 6.65 (d, J=4, 1H, H in position 4 on thienyl); 7.12 (d, J=4, 1H, H in position 3 on thienyl); 7.55 and 7.62 (2dd, J=8 and 2, 1H each, H in position 4 and 6 on CO—NH—Ph—), 8.02 (t, J=2, 1H, H in position 2 on CO—NH—Ph—).

Infrared spectrum (KBr), characteristic bands in cm$^{-1}$: 3390, 3100 to 3000, 2975, 2930, 2830, 2750–2300 (broad band), 1715, 1695, 1650, 1615, 1595, 1560, 1490, 1425, 1395, 1370, 1150, 800, 785, 755.

2-Trimethylsilylethyl (4R)-3-{3-[4-tert-butoxycarbonyl-2-(5-methyl-2-thienyl)-3-thiazolidinyl]-2-oxoethyl}ureido}benzoate (A form) may be prepared in a fashion similar to that described in Example 41 A, but starting from 0.38 g of tert-butyl (2RS,4R)-2-(5-methyl-2-thienyl)-4-thiazolidinecarboxylate, 0.45 g of 2-{3-[3-(2-trimethylsilylethoxycarbonyl)phenyl]ureido}acetic acid, and 0.30 g of N,N'-dicyclohexylcarbodiimide. The crude product is purified by chromatography on silica [eluent: ethyl acetate/cyclohexane (30/70 by volume)]. The fractions containing the expected product are combined and concentrated to dryness under reduced pressure at 40° C. 0.12 g of 2-trimethylsilylethyl (4R)-3-{3-[4-tert-butoxycarbonyl-2-(5-methyl-2-thienyl)-3-thiazolidinyl]-2-oxoethyl}-ureido}benzoate (A form) is thus obtained in the form of an orange-yellow solid, used as it is in subsequent syntheses.

tert-Butyl (2RS,4R)-2-(5-methyl-2-thienyl)-4-thiazolidinecarboxylate may be prepared in a fashion similar to that described in Example 48 B, but starting from 1.0 g of tert-butyl (4R)-3-tert-butoxycarbonyl-2-(5-methyl-2-thienyl)-4-thiazolidinecarboxylate (A form) and 0.38 cm³ of iodotrimethylsilane. 0.38 g of tert-butyl (2RS,4R)-2-(5-methyl-2-thienyl)-4-thiazolidinecarboxylate is thus obtained in the form of a yellow oil, used as it is in subsequent syntheses.

tert-Butyl (4R)-3-tert-butoxycarbonyl-2-(5-methyl-2-thienyl)-4-thiazolidinecarboxylate (A form) may be prepared in a fashion similar to that described in Example 48 C, but starting from 2.97 g of 3-tert-butoxycarbonyl-2-(5-methyl-2-thienyl)-4-thiazolidinecarboxylic acid (A form), 1.72 g of para-toluenesulphonyl chloride and 0.67 g of tert-butanol. The crude product obtained is purified by chromatography on silica [eluent: ethyl acetate/cyclohexane (30/70 by volume)]. The fractions containing the expected product are combined and concentrated to dryness under reduced pressure at 40° C. 1.0 g of tert-butyl (4R)-3-tert-butoxycarbonyl-2-(5-methyl-2-thienyl)-4-thiazolidinecarboxylate (A form) is thus obtained in the form of an orange oil, used as it is in subsequent syntheses.

3-tert-Butoxycarbonyl-2-(5-methyl-2-thienyl)-4-(4R)-thiazolidinecarboxylic acid (A form) may be prepared in a fashion similar to that described in Example 48 D, but starting from 2.7 g of 2-(5-methyl-2-thienyl)-4-thiazolidinecarboxylic acid, 11.9 cm³ of 1N aqueous sodium hydroxide solution and 2.6 g of di-tert-butyl dicarbonate. 3.0 g of 3-tert-butoxycarbonyl-2-(5-methyl-2-thienyl)-4-(4R)-thiazolidinecarboxylic acid (A form) are thus obtained in the form of a yellow solid, used as it is in subsequent syntheses.

2-(5-Methyl-2-thienyl)-4-(2RS,4R)-thiazolidinecarboxylic acid may be prepared as in Example 34D, but starting from 10.0 g of L-cysteine and 11.3 g of 5-methyl-2-thienylcarboxaldehyde. 7.86 g of 2-(5-methyl-2-thienyl)-4-(2RS,4R)-thiazolidinecarboxylic acid, melting at 178° C., used as it is in subsequent syntheses, are thus obtained.

EXAMPLE 111

The operation is carried out as in Example 84, but starting from 0.88 g of benzyl 2-{3-{3-[2-((2S,5R)-2-tert-butoxycarbonyl-5-phenyl-1-pyrrolidinyl)-2-oxoethyl]ureido}phenyl}propionate (B form) in solution in 50 cm³ of ethyl acetate and 0.22 g of 10% palladium on charcoal. After treatment, 0.5 g of 2-{3-{3-[2-((2S,5R)-2-tert-butoxycarbonyl-5-phenyl-1-pyrrolidinyl)-2-oxoethyl]ureido}phenyl}propionic acid (B form), melting at 120° C., $[\alpha]_D^{20}$=+49.8°±0.8° (c=0.53; methanol), is obtained.

Benzyl 2-{3-{3-[2-((2S,5R)-2-tert-butoxycarbonyl-5-phenyl-1-pyrrolidinyl)-2-oxoethyl]ureido}phenyl}propionate (B form) may be obtained in a fashion similar to that described in Example 2, but starting from 0.79 g of tert-butyl (2S,5R)-1-(2-aminoacetyl)-5-phenylprolinate and 0.8 g of benzyl 2-(3-isocyanato-phenyl)propionate (B form) in 40 cm³ of tetrahydrofuran. After treatment, 0.9 g of benzyl 2-{3-{3-[2-((2S,5R)-2-tert-butoxycarbonyl-5-phenyl-1-pyrrolidinyl)-2-oxoethyl]ureido}phenyl}propionate, melting at 75° C., is obtained.

tert-Butyl (2S,5R)-1-(2-aminoacetyl)-5-phenylprolinate may be obtained in a fashion similar to that described in Example 2 A, but starting from 1.22 g of tert-butyl (2S,5R)-1-(2-tert-butoxycarbonylaminoacetyl)-5-phenylprolinate, 0.45 cm³ of iodotrimethylsilane in solution in 30 cm³ of anhydrous chloroform. 0.79 g of tert-butyl (2S,5R)-1-(2-aminoacetyl)-5-phenylprolinate is thus obtained in the form of an oil, used as it is in subsequent syntheses.

tert-Butyl (2S,5R)-1-(2-tert-butoxycarbonylaminoacetyl)-5-phenylprolinate may be obtained as per Example 2 B, but starting from a solution containing 8 g of tert-butyl (2S,5R)-5-phenylprolinate, 5.7 g of 2-tert-butoxycarbonylaminoacetic acid and 6.7 g of N,N'-dicyclohexylcarbodiimide in 75 cm³ of anhydrous acetonitrile. 10.5 g of tert-butyl (2S,5R)-1-(2-tert-butoxycarbonylaminoacetyl)-5-phenylprolinate, melting at 136° C., $[\alpha]_D^{20}$+19.1°±0.8° (C=0.64; methanol), are thus obtained.

EXAMPLE 112

The operation is carried out in a fashion similar to that described in Example 2, but starting from 2.5 g of tert-butyl (2S,5R)-1-(2-aminoacetyl)-5-phenyl-prolinate, 5 g of tetrabutylammonium (RS)-1-(3-iso-cyanatophenyl)ethanesulphonate in 60 cm³ of tetrahydrofuran. After treatment, 0.23 g of potassium (2S,5R)-1-{3-{3-[2-(2-tert-butoxycarbonyl-5-phenyl-1-pyrrolidinyl)-2-oxoethyl]ureido}phenyl}ethanesulphonate, (mixture of the two 1-position epimers) is obtained in the form of an amorphous beige solid, $[\alpha]_D^{20}$=+20.7°±0.9° (c=0.55; methanol).

Tetrabutylammonium (RS)-1-(3-isocyanatophenyl)ethanesulphonate may be prepared as described in Example 21, but starting from 4.5 g of tetrabutylammonium (RS)-1-(3-aminophenyl)ethanesulphonate in 40 cm³ of toluene (40 cc), 0.2 g of charcoal and 1.21 cm³ of trichloromethyl chloroformate. After treatment, 5 g of tetrabutylammonium (RS)-1-(3-isocyanato-phenyl)ethanesulphonate are obtained in the form of an oil, used as it is in subsequent syntheses.

EXAMPLE 113

The operation is carried out in a fashion similar to that described in Example 2, but starting from 2.6 g of tert-butyl (2S,5R)-1-(2-aminoacetyl)-5-phenylprolinate, 4.8 g of tetrabutylammonium 3-isocyanatophenylmethanesulphonate in 60 cm³ of tetrahydrofuran. After treatment, 0.21 g of potassium (2S,5R)-1-{3-{3-[2-(2-tert-butoxycarbonyl-5-phenyl-1-pyrrolidinyl)-2-oxoethyl}ureido}phenyl}methanesulphonate is obtained in the form of an amorphous beige solid, $[\alpha]_D^{20}$=+18.7°±0.8° (c=0.63; methanol).

Tetrabutylammonium 3-isocyanatophenylmethanesulphonate may be prepared as described in Example 21, but starting from 10 g of tetrabutylammonium (RS)-3-aminophenylmethanesulphonate in 80 cm³ of toluene, 0.49 g of charcoal and 2.85 cm³ of trichloromethyl chloroformate. After treatment, 11 g of tetrabutylammonium 3-isocyanatophenylmethanesulphonate are obtained in the form of an oil, used as it is in subsequent syntheses.

EXAMPLE 114

In an inert atmosphere 20 cm³ of methanol are slowly added to a flask containing 1.38 g of benzyl 2-{3-{3-{2-[(2R,4R)-4-tert-butoxycarbonyl-2-(2,3-difluorophenyl)-3-thiazolidinyl]-2-oxoethyl}ureido}phenyl}propionate (B form), 0.85 g of ammonium formate and 1.38 g of 10% palladium on charcoal. The reaction mixture is heated under reflux for 1 hour, then cooled to a temperature in the vicinity of 25° C. The catalyst is then removed by filtration and the filtrate is concentrated to dryness under reduced pressure at 40° C. The residue obtained is dissolved in 20 cm³ of a 0.1N aqueous sodium hydroxide solution and washed with two times 10 cm³ of diethyl ether. The aqueous phase is brought to a pH of 2 by addition of a 1N aqueous sulphuric acid solution. The precipitated product is separated by filtration, washed with 2 times 10 cm³ of water and dried in air. 1.0 g of 2-{3-{3-{2-[(2R,4R)-4-tert-butoxycarbonyl-2-(2,3-difluorophenyl)-3-thiazolidinyl]-2-oxoethyl}ureido}phenyl}propionic acid (B form), melting at 130° C., is thus obtained. $[\alpha]_D^{20}=+82°\pm2°$ (C=0.707%; DMF)

Benzyl 2-{3-{3-{2-[(2R,4R)-4-tert-butoxycarbonyl-2-(2,3-difluorophenyl)-3-thiazolidinyl]-2-oxoethyl}ureido}phenyl}propionate (B form) may be prepared in a fashion similar to that described in Example 34, but starting from 2.5 g of tert-butyl (2R,4R)-3-(2-aminoaccyl)-2-(2,3-difluorophenyl)-4-thiazolidine-carboxylate and 1.96 g of benzyl 2-(3-isocyanatophenyl)-propionate (B form). The crude product is purified by chromatography on silica [eluent: ethyl acetate/cyclohexane (40/60 by volume)]. The fractions containing the expected product are combined and concentrated to dryness under reduced pressure at 40° C. 1.8 g of benzyl 2-{3-{3-{2-[(2R,4R)-4-tert-butoxycarbonyl-2-(2,3-difluorophenyl)-3-thiazolidinyl]-2-oxoethyl}ureido}phenyl}propionate (B form) are thus obtained in the form of an amorphous product, used as it is in subsequent syntheses.

EXAMPLE 115

A solution of 2.1 g of tert-butyl (cis)-{3-{3-[2-(2,5-diphenyl-1-pyrrolidinyl)-2-oxoethyl]ureido}phenyl}methylene-aminooxyacetate in solution in 10 cm³ of trichloroacetic acid is stirred for two hours at a temperature in the vicinity of 20° C., then the reaction medium is brought to dryness under reduced pressure at a temperature in the vicinity of 40° C. The residue is crystallised in 50 cm³ of water, filtered, washed with three times 15 cm³ of water and dried at a temperature in the vicinity of 20° C. The product thus obtained is purified by chromatography on silica [eluent:dichloromethane/methanol (95/5 by volume)]. The fractions containing the expected product are combined and concentrated to dryness under reduced pressure at a temperature in the vicinity of 35° C. After recrystallization in acetonitrile, 1 g of (cis)-{3-{3-[2-(2,5-diphenyl-1-pyrrolidinyl)-2-oxoethyl]ureido}phenyl}-methylenaminooxyacetic acid, melting at 194° C., is thus obtained.

tert-Butyl (cis)-{3-{3-[2-(2,5-diphenyl-1-pyrrolidinyl)-2-oxoethyl]ureido}phenyl}methylenaminooxyacetate may be obtained in a fashion similar to that described in Example 3, but starting from 4.2 g of (cis)-1-(2-aminoacetyl)-2,5-diphenylpyrrolidine, 1.78 g of N,N'-carbonyldiimidazole and 2.5 g of tert-butyl 3-aminophenylmethyleneaminooxyacetate in 60 cm³ of 1,2-dichloroethane. After treatment, 2.1 g of tert-butyl (cis)-{3-{3-[2-(2,5-diphenyl-1-pyrrolidinyl)-2-oxoethyl]ureido}phenyl}methylenaminooxyacetate are obtained in the form of an amorphous beige solid.

tert-Butyl 3-aminophenylmethyleneaminooxyacetate may be obtained as follows: 0.75 g of platinum oxide is added to a solution of 7.5 g of tert-butyl 3-nitrophenylmethyleneaminooxyacetate in 100 cm³ of ethanol. The suspension is stirred for 1 hour at a temperature in the vicinity of 20° C. under a hydrogen atmosphere (130 kPa). The catalyst is separated by filtration and the filtrate is concentrated to dryness under reduced pressure at 45° C. The residue is dissolved in 50 cm³ of ethyl acetate and the organic phase is washed with 50 cm³ of water, dried over magnesium sulphate and concentrated under reduced pressure. 6.2 g of tert-butyl 3-aminophenylmethyleneaminooxyacetate are thus obtained in the form of an oil, used as it is in subsequent syntheses.

tert-Butyl 3-nitrophenylmethyleneaminooxyacetate may be obtained as follows: 4.3 g of a 60% solution of sodium hydride in Vaseline are degreased by washing with two times 50 cm³ of hexane. After addition of 100 cm³ of tetrahydrofuran, the suspension is cooled to a temperature in the vicinity of 5° C. and a solution of 4.98 g of 3-nitrobenzaldoxime in 20 cm³ of tetrahydrofuran is introduced dropwise. The reaction mixture is stirred for an hour at a temperature in the vicinity of 25° C., with the subsequent addition of 6 g of tert-butyl bromoacetate in solution in 5 cm³ of tetrahydrofuran, and stirring is continued-for an hour at a temperature in the vicinity of 25° C. The reaction medium is then poured into a mixture of 200 cm³ of water and 100 cm³ of ethyl acetate. The organic phase is separated by decantation, dried over magnesium sulphate and concentrated to dryness under reduced pressure at a temperature in the vicinity of 40° C. 7.5 g of tert-butyl 3-nitrophenylmethyleneaminooxy-acetate, melting at 120° C., are thus obtained.

3-Nitrobenzaldoxime may be prepared according to the method described by T. M. Opryshko et al., Izv. Vyssh. Uchebn. Zaved., Khim. Khim. Tekhnol., 31, 53 (1988).

EXAMPLE 116

The operation is carried out as in Example 108, but starting from 0.5 g of 2-{3-{3-{2-[(2R,4R)-4-tert-butoxycarbonyl-2-(2-fluorophenyl)-3-thiazolidinyl]-2-oxoethyl}ureido}-phenyl}propionic acid (B form) and 1.0 g of Oxone®. The crude product obtained is purified by chromatography on silica [eluent:methylene chloride/methanol (90/10 by volume)], collecting 10 cm³ fractions. Fractions 15 to 19 are combined and concentrated to dryness under reduced pressure at 40° C. 0.2 g of 2-{3-{3-{2-[(1RS,2R,4R)-4-tert-butoxycarbonyl-2-(2-fluorophenyl)-1-oxide-3-thiazolidinyl]-2-oxoethyl}ureido}phenyl}propionic acid (B form) is thus obtained in the form of an amorphous product. Fractions 9 to 14 are combined and concentrated to dryness under reduced pressure at 40° C. A mixture of 0.1 g of 2-{3-{3-{2-[(1RS,2R,4R)-4-tert-butoxycarbonyl-2-(2-fluorophenyl)-1-oxide-3-thiazolidinyl]-2-oxoethyl}ureido}phenyl}propionic acid (B form) and of 2-{3-{3-{2-[(2R,4R)-4-tert-butoxycarbonyl-2-(2-fluorophenyl)-1-dioxide-3-thiazolidinyl]-2-oxoethyl}ureido}phenyl}propionic acid (B form) is thus obtained.

Proton NMR (200 MHz, DMSO D₆, δ in ppm, J in Hz): at 120° C. the mixture of the two diastereoisomers in the proportions 88–12 is observed, characteristic chemical shifts at 120° C.: 1.32 (d, J=7.5, 3H, —CH₃); 1.50 and 1.58 (2s, 9H in total, —C(CH₃)₃ of the preponderant isomer then of the less abundant isomer); 2.85 (t, J=12.5, 0.88H, 1H of —S—CH₂ for the preponderant isomer); 3.4 to 4.4 (m, 6,12H, —CH—COO, the other H of —S—CH₂ for the preponderant isomer, the —S—CH₂ of the less abundant isomer and N—COCH₂—N); 4.8 (t, J=8, 0.12H, S—CH—N of the less abundant isomer); 4.97 (dd, J=12.5 and 5.0, 0.88H, S—CH—N of the preponderant isomer); 6.3 to 6.45 (m, 1H, —NHCO—); 6.5 and 6.6 (2s, 0.12H and 0.88H, S—CH—N of the less abundant isomer and of the preponderant isomer); 6.8 (bd, J=8, 1H, in position 4 on CO—NH—Ph—); 7.0 to 7.6 (m, 6H, aromatic); 7.77 and 8.10 (t, J=8, 0.12H and 0.88H, in position 6 on S—CH—Ph— for the less abundant isomer and for the preponderant isomer); 8.84 and 8.96 (2s, 0.88H and 0.12H, ArNHCO— for the preponderant isomer and for the less abundant isomer).

Infrared spectrum (KBr), characteristic bands in cm$^{-1}$: 3380, 2975, 2930, 2650 to 2250 (broad band), 1735, 1650, 1610, 1595, 1560, 1490, 1455, 1370, 1230, 1150, 1050, 760, 700.

2-{3-{3-{2-[(2R,4R)-4-tert-Butoxycarbonyl-2-(2-fluorophenyl)-1-dioxide-3-thiazolidinyl]-2-oxoethyl}ureido}phenyl}propionic acid (B form) was separated from the mixture of 2-{3-{3-{2-[(1RS,2R,4R)-4-tert-butoxycarbonyl-2-(2-fluorophenyl)-1-oxide-3-thiazolidinyl]-2-oxoethyl}ureido}phenyl}propionic acid (B form) and of 2-{3-{3-{2-[(2R,4R)-4-tert-butoxycarbonyl-2-(2-fluorophenyl)-1-dioxide-3-thiazolidinyl]-2-oxoethyl}ureido}phenyl}propionic acid (B form) by chromatography on silica [eluent: ethyl acetate/methanol (95/5 by volume)]. The fractions containing the expected product are combined and concentrated to dryness under reduced pressure at 30° C. 0.02 g of 2-{3-{3-{2-[(2R,4R)-4-tert-butoxycarbonyl-2-(2-fluorophenyl)-1-dioxide-3-thiazolidinyl]-2-oxoethyl}ureido}phenyl}propionic acid (B form) is thus obtained in the form of an amorphous product.

Proton MMR (200 MHz, DMSO $D_6$, δ in ppm): 1.3 (d, 3H, —$C_3$); 1.5 (s, 9H, —$CH_3$)$_3$); 3.6 (m, 2H, $CH_2$—$SO_2$), 4.0 to 43. (m, 3H, Ar—CH—COO and N—$COCH_2$—N); 4.8 (bt, 1H, N—CH—COO); 6.4 (bt, 1H, —NHCO—); 6.5 (s, 1H, S—CH—N); 6.8 (bd, in position 4 on CO—NH—Ph—); 7.1 to 7.8 (m, 6H, aromatic); 8.1 (bt, 1H in position 6 on S—CH—Ph—); 8.8 (bs, 1H, ArNHCO—).

Infrared spectrum (KBr), characteristic bands in cm$^{-1}$: 3380, 2975, 2930, 2650 to 2250 (broad band), 1735, 1650, 1610, 1595, 1560, 1490, 1455, 1370, 1345, 1230, 1150, 760, 700, 550.

The medicaments according to the invention consist of a compound of formula (I) in free form or in the form of an addition salt with a pharmaceutically acceptable acid, in the pure state or in the form of a composition in which it is associated with any other pharmaceutically compatible product, which may be inert or physiologically active. The medicaments according to the invention may be used orally, parenterally, rectally or topically.

Tablets, pills, powders (gelatin capsules, cachets) or granules may be used as solid compositions for oral administration. In these compositions, the active principle according to the invention is mixed with one or more inert diluents, such as starch, cellulose, sucrose, lactose or silica, under an argon stream. These compositions may also contain substances other than diluents, for instance one or more lubricants such as magnesium stearate or talc, a coloring agent, a coating (coated pills) or a glaze.

Pharmaceutically acceptable solutions, suspensions, emulsions, syrups and elixirs containing inert diluents such as water, ethanol, glycerol, vegetable oils or paraffin oil may be used as liquid compositions for oral administration. These compositions may contain substances other than diluents, for example wetting agents, sweetening agents, thickening agents, flavouring agents or stabilizing agents.

Sterile compositions for parenteral administration may preferably be aqueous or nonaqueous solutions, suspensions or emulsions. Water, propylene glycol, a polyethylene glycol, vegetable oils, in particular olive oil, injectable organic esters, for instance ethyl oleate or other appropriate organic solvents may be used as solvent or carrier. These compositions may also contain adJuvants, in particular wetting agents, isotonicity agents, emulsifiers, dispersing and stabilising agents. Sterilisation can be carried out in a variety of ways, for instance by asepticising filtration, by incorporating to the composition sterilizing agents, by irradiation or by heating. They can also be prepared in the form of sterile solid compositions which can be dissolved at the time of use in sterile water or any other injectable sterile medium.

Compositions for rectal administration are suppositories or rectal capsules which contain, besides the active ingredient, excipients such as cocoa butter, semisynthetic glycerides or polyethylene glycols.

Compositions for topical administration may be for instance creams, lotions, eyewashes, mouthwashes, nasal drops or aerosols.

In human therapy, the compounds according to the invention are particularly useful in the treatment and prevention of disorders linked to CCK and to gastrin at the level of the nervous system and of the gastro-intestinal tract. These compounds may therefore be used in the treatment and prevention of psychoses, of anxiety disorders, of Parkinson's disease or tardive dyskinesia, of irritable colon syndrome, of acute pancreatitis, of ulcers, of intestinal motility disorders, of certain tumors sensitive to CCK, of memory disorders, as analgesic agents, as a potentiator of the analgesic activity of narcotic or nonnarcotic analgesic medicaments and as an appetite regulator.

The doses depend on the effect sought, on the duration of the treatment and on the administration route used; they are generally between 0.05 g and 1 g per day for oral administration to an adult with unitary doses ranging from 10 mg to 500 mg of active substance.

Generally speaking, the doctor will determine the appropriate dosage as a function of age, of weight and of all the other factors relevant to the subject to be treated.

The following examples give an illustration of compositions according to the invention:

Example A

Hard gelatin capsules with a 50 mg dosage of active ingredient with the composition shown below are prepared using the usual technique:

| | |
|---|---|
| (2RS,5SR)-3-{3-[2-(2-tert-Butoxycarbonyl-5-phenyl-1-pyrrolidinyl)-2-oxoethyl]-ureido}-3-phenylbenzoic acid | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

Example B

Tablets with a dosage of 50 mg of active ingredient with the composition shown below are prepared using the usual technique:

| | |
|---|---|
| (2R,5S)-3-{3-[2-(2-tert-Butoxycarbonyl-5-phenyl-1-pyrrolidinyl)-2-oxoethyl]-ureidobenzoic acid | 50 mg |
| Lactose | 104 mg |
| Cellulose | 40 mg |
| Povidone | 10 mg |
| Sodium carboxymethyl starch | 22 mg |
| Talc | 10 mg |
| Magnesium stearate | 2 mg |
| Colloidal silica | 2 mg |
| Mixture of hydroxymethylcellulose, glycerine, titanium oxide (72-3.5-24.5) to complete 1 finished coated tablet | 245 mg |

Example C

An injectable solution containing 10 mg of the active product with the following composition is prepared:

| | |
|---|---|
| (2R,4R)-3-{3-[2-(4-tert-Butoxycarbonyl-2-phenyl-3-thiazolidinyl)-2-oxoethyl]-ureido}phenylacetic acid | 10 mg |
| Benzoic acid | 80 mg |
| Benzyl alcohol | 0.06 cm³ |
| Sodium benzoate | 80 mg |
| 95% ethanol | 0.4 cm³ |
| Sodium hydroxide | 24 mg |
| Propylene glycol | 1.6 cm³ |
| Water q.s | 4 cm³ |

Although the invention has been described in conjunction with specific embodiments, it is evidence that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A compound of the formula:

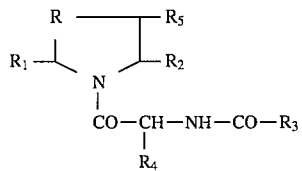

(I)

in which either R represents a methylene, ethylene, SO, SO₂ or CHOH radical or a sulphur atom, $R_1$ represents a pyridyl radical optionally substituted by one or more alkyl radicals, a furyl radical optionally substituted by one or more alkyl radicals, a thienyl radical optionally substituted by one or more alkyl radicals, a quinolyl radical optionally substituted by one or more alkyl radicals, a naphthyl radical optionally substituted by one or more alkyl radicals, an indolyl radical optionally substituted by one or more alkyl radicals, or a phenyl radical optionally substituted by one or more substituents chosen from halogen atoms and alkyl, alkoxy, hydroxyl, nitro, amino, monoalkylamino, dialkylamino, alkoxycarbonyl, —CO—$NR_7R_8$, —NH—CO—$CH_3$, trifluoromethyl and trifluoromethoxy radicals, and $R_5$ represents a hydrogen atom, or R represents a methylene radical, $R_1$ represents a hydrogen atom and $R_5$ represents a phenyl radical, or R represents a radical $CHR_6$ and $R_1$ and $R_5$ each represent a hydrogen atom, $R_2$ represents an alkoxycarbonyl, cycloalkyloxycarbonyl, cycloalkylalkyloxycarbonyl, $CONR_9R_{10}$ or phenyl radical optionally substituted by one or more substituents chosen from alkyl, alkoxy, and hydroxyl radicals, $R_3$ represents a phenyl radical optionally substituted by one or more substituents chosen from halogen atoms and alkyl, alkoxy, and alkylthio radicals; a naphthyl, indolyl, quinolyl or phenylamino radical, the phenyl ring of which is optionally substituted by one or more substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyamino-carbonyl, alkoxyaminocarbonyl, 5-tetrazolyl, 5-tetrazolylalkyl, trifluoromethylsulphonamido, alkyl-sulphinyl, mono- and polyhydroxyalkyl, sulpho, -alk-O—CO-alk, alk-COOX, alk-O-alk, alk'-COOX, —O-alk-COOX, —CH=CH—COOX, —CO—COOX, alk-SO₃H in the form of a salt, —CH=CH-alk', —C(=NOH)—COOX, S-alk-COOX, —O—CH₂-alk'-COOX, CX=N—O-alk-COOX, alk-N(OH)—CO-alk and 2,2-dimethyl-4,6-dioxo-1,3-dioxan-5-yl radicals, $R_4$ represents a hydrogen atom or an alkyl radical, $R_6$ represents a phenyl radical, $R_7$ represents a hydrogen atom or an alkyl, phenylalkyl or phenyl radical optionally substituted by one or more substituents chosen from halogen atoms and alkyl, alkoxy, and alkylthio radicals, $R_8$ represents an alkyl, phenylalkyl or phenyl radical optionally substituted by one or more substituents chosen from halogen atoms and alkyl, alkoxy, and alkylthio radicals, or $R_7$ and $R_8$ form with the nitrogen atom to which they are attached a mono- or polycyclic saturated or unsaturated heterocycle containing 4 to 9 carbon atoms and one or more hetero atoms selected from oxygen and nitrogen and optionally substituted by one or more alkyl radicals, $R_9$ represents a hydrogen atom or an alkyl, cycloalkylalkyl, cycloalkyl, phenylalkyl or phenyl radical optionally substituted by one or more substituents chosen from halogen atoms and alkyl, alkoxy, and alkylthio radicals, $R_{10}$ represents an alkyl, cycloalkylalkyl, cycloalkyl, phenylalkyl or phenyl radical optionally substituted by one or more substituents chosen from halogen atoms and alkyl, alkoxy, and alkylthio radicals, or $R_9$ and $R_{10}$ form with the nitrogen atom to which they are attached a mono- or polycyclic saturated or unsaturated heterocycle containing 4 to 9 carbon atoms and one or more hetero atoms selected from oxygen, nitrogen, and sulfur, and optionally substituted by one or more alkyl radicals, X represents a hydrogen atom, an alkyl, or phenylalkyl radical, alk represents an alkyl or alkylene radical, alk' represents a hydroxyalkyl, hydroxyalkylene, alkoxyalkyl or alkoxyalkylene radical, the alkyl, alkylene and alkoxy radicals and the alkyl, alkylene, and alkoxy moieties containing 124; carbon atoms in a straight or branched chain, the acyl radicals and moieties; containing 2 to 4 carbon atoms and the cycloalkyl radicals and; moieties containing 3 to 6 carbon atoms, or a pharmaceutically acceptable salt of the compound of formula (I).

2. The compounds of formula (I) or the salt thereof according to claim 1 wherein R represents a methylene radical or a sulphur atom, $R_1$ represents a phenyl radical, $R_2$ represents a phenyl or alkoxycarbonyl radical and $R_3$ represents a phenylamino radical, the phenyl ring of which is substituted by a carboxyl, -alk-COOH, —S-alk-COOH, hydroxyalkyl, alk'-COOH, or alk-SO₃⁻ radical, $R_4$ represents a hydrogen atom and $R_5$ represents a hydrogen atom.

3. The compound of formula (I) or the salt thereof according to claim 1 as follows:

tert-butyl (2RS,5SR)-1-{2-[3-(3-((RS)-1-hydroxyethyl)phenyl)ureido]acetyl}-5-phenylprolinate 2-{3-{3-[2-(2S,5R)-2-tert-butoxycarbonyl-5-phenyl-1-pyrrolidinyl)-2-oxoethyl]ureido}phenyl}propionic acid (B form)

(2RS,5SR)-{3-{3-[2-(2-tert-butoxycarbonyl-5-phenyl-1-pyrrolidinyl)-2-oxoethyl]ureido}phenylthio}acetic acid (2R,4R)-3-{3-[2-(4-tert-butoxycarbonyl-2-(2-fluoro-3-thiazolidinyl))-2-oxoethyl]ureido}phenylacetic acid 2-{3-{3-[2-((2R,4R)-2-tert-butoxycarbonyl-2-(2-fluorophenyl)-3-thiazolidinyl)-2-oxoethyl]ureido}phenyl}propionic acid (B form)

potassium (RS)-1-{3-{3-[2-((2R,4R)-4-tert-butoxycarbonyl-2-phenyl-3-thiazolidinyl)-2-oxoethyl]ureido}phenyl}ethanesulphonate, mixture of A and B forms potassium (RS)-1-{3-{3-[2-((2S,5R)-2-tert-butoxycarbonyl-5-phenyl-1-pyrrolidinyl)-2-oxoethyl]ureido}phenyl}ethanesulphonate, potassium (2S,5R)-1-{3-{3-[2-(tert-butoxycarbonyl-5-phenyl-1-pyrrolidinyl)-2-oxoethyl]ureido}phenyl}methanesulphonate (2S,5R)-3-{3-[2-(2-tert-butoxycarbonyl-5-phenyl-1-pyrrolidinyl)-2-oxoethyl]ureido}benzoic acid (2RS,5SR)-3-{3-{2-[2-tert-butoxycarbonyl-5-(2-fluorophenyl)-1-pyrrolidinyl]-2-oxoethyl}ureido}benzoic acid cis-3-{3-[2-(2,5-diphenyl-1-pyrrolidinyl)-2-oxoethyl]ureido}benzoic acid (2RS,5RS)-3-{2-[2-(2-hydroxyphenyl)-5-phenyl-1-pyrrolidinyl]-2-oxoureido}phenylacetic acid (2R,4R)-3-{3-[2-(4-tert-butoxycarbonyl-2-phenyl-3-thiazolidinyl)-2-oxoethyl]ureido}phenylacetic acid (2R,4R)-3-{3-[2-(4-tert-butoxycarbonyl-2-phenyl-3-thiazolidinyl)-2-oxoethyl]ureido}benzoic acid 2-{3-{3-[2-((1RS,2R,4R)-4-tert-butoxycarbonyl-2-(2-fluorophenyl)-1-oxide-3-thiazolidinyl)-2-oxoethyl]ureido}phenyl}propionic acid (A form)

(2R,4R)-3-{3-[2-(4-tert-butoxycarbonyl-2-(2,3-difluorophenyl)-3-thiazolidinyl)-2-oxoethyl]ureido}phenylacetic acid tert-butyl (2RS,5SR)-1-{2-{3-[(E)-3-(1-hydroxyiminoethyl)phenyl]ureido}acetyl}-5-phenylprolinate.

4. A compound or salt according to claim 1, wherein said compound or salt is a racemic mixture.

5. A compound or salt according to claim 1, wherein said compound or salt is an enantiomer.

6. A medicament containing as an active principle at least one compound according to claim 1 or a pharmaceutically acceptable salt.

7. A method of antagonizing cholecystokinin or gastrin in a mammal having a nervous system or gastrointestinal tract disorder linked to cholecystokinin or to gastrin, said method comprising the step of administering to said mammal an amount effective to antagonize cholecystokinin or gastrin of a compound according to claim 1 or a pharmaceutically acceptable salt thereof.

* * * * *

UNITED STATES PATENT AND TRADEMARK OFFICE
CERTIFICATE OF CORRECTION

PATENT NO. : 5,610,144
DATED : March 11, 1997
INVENTOR(S) : Marc CAPET et al.

It is certified that error appears in the above-identified patent and that said Letters Patent is hereby corrected as shown below:

Title page, item, [75], lines 3-4 under "Inventors", "Neuilly Sur Mame"" should read --Neuilly Sur Marne--.

Claim 1, column 102, line 47, "124; carbon atoms" should read --1 to 4 carbon atoms--.

Claim 1, column 102, lines 48-49, "moieties; containing" should read --moieties containing--.

Claim 1, column 102, line 50, "and; moieties" should read --and moieties--.

UNITED STATES PATENT AND TRADEMARK OFFICE
CERTIFICATE OF CORRECTION

PATENT NO. : 5,610,144
DATED : March 11, 1997
INVENTOR(S) : Marc CAPET et al.

It is certified that error appears in the above-identified patent and that said Letters Patent is hereby corrected as shown below:

Claim 2, column 102, line 53, "compounds" should read --compound--.

Signed and Sealed this

Twentieth Day of January, 1998

Attest:

BRUCE LEHMAN

Attesting Officer

Commissioner of Patents and Trademarks